(12) United States Patent
Hughes et al.

(10) Patent No.: US 10,913,784 B2
(45) Date of Patent: Feb. 9, 2021

(54) RAGE FUSION PROTEINS WITH IMPROVED STABILITY AND LIGAND BINDING AFFINITY AND USES THEREOF

(71) Applicant: BioAge Labs, Inc., Richmond, CA (US)

(72) Inventors: Robert Hughes, Berkeley, CA (US); William Strohl, Bridgewater, NJ (US)

(73) Assignee: BIOAGE LABS, INC., Richmond, CA (US)

( * ) Notice: Subject to any disclaimer, the term of this patent is extended or adjusted under 35 U.S.C. 154(b) by 0 days.

(21) Appl. No.: 16/571,011

(22) Filed: Sep. 13, 2019

(65) Prior Publication Data
US 2020/0115435 A1    Apr. 16, 2020

Related U.S. Application Data

(60) Provisional application No. 62/731,663, filed on Sep. 14, 2018.

(51) Int. Cl.
*C07K 14/705*    (2006.01)

(52) U.S. Cl.
CPC .... *C07K 14/70503* (2013.01); *C07K 2319/30* (2013.01)

(58) Field of Classification Search
CPC .......... C07K 14/70503; C07K 2319/30; C07K 14/435; A61P 3/10; A61K 38/00
See application file for complete search history.

(56) References Cited

U.S. PATENT DOCUMENTS

| | | |
|---|---|---|
| 7,470,521 B2 | 12/2008 | O'Keefe et al. |
| 8,043,616 B2 | 10/2011 | Anderson et al. |
| 8,877,192 B2 | 11/2014 | Mjalli et al. |
| 9,399,668 B2 | 7/2016 | Bleck et al. |
| 2006/0078562 A1 | 4/2006 | Mjalli et al. |
| 2007/0087406 A1 | 4/2007 | Shepard |

FOREIGN PATENT DOCUMENTS

| | | |
|---|---|---|
| EP | 2 158 210 B1 | 12/2015 |
| WO | WO 2004/016229 A2 | 2/2004 |
| WO | WO 2008/157378 A3 | 12/2008 |

OTHER PUBLICATIONS

Di Maggio, S. et al., "The Mouse-Specific Splice Variant mRAGE_v4 Encodes a Membrane-Bound RAGE That Is Resistant to Shedding and Does Not Contribute to the Production of Soluble RAGE," PLoS One, vol. 11, No. 9, Sep. 21, 2016, pp. 1-17.
PCT Invitation to Pay Additional Fees, PCT Application No. PCT/US19/51182, Dec. 26, 2019, three pages.
PCT International Search Report and Written Opinion, PCT Application No. PCT/US19/51182, dated Feb. 18, 2020, 18 pages.

*Primary Examiner* — Gregory S Emch
(74) *Attorney, Agent, or Firm* — Fenwick & West LLP; Payal Sud

(57) ABSTRACT

The present invention provides soluble RAGE-Fc fusion proteins with increased stability and extended half-life capable of binding endogenous RAGE ligands with high apparent affinity. The present invention also provides methods of making and using stable, soluble RAGE-Fc fusion proteins. These soluble RAGE-Fc fusion proteins are useful as therapeutics based on their ability to bind endogenous RAGE ligands.

15 Claims, 34 Drawing Sheets

Specification includes a Sequence Listing.

Construct #1

Construct #9

Construct #10

Construct #11

Construct #12

Construct #13

Construct #14

Construct #15

Construct #16

Construct #17

Construct #18

Construct #19

Construct #20

Construct #21

Construct #22

Construct #23

Construct #24

Construct #25

Construct #26

Construct #27

Construct #28

Construct #29

Construct #30

Construct #31

Construct #32

Construct #33

Construct #34

Construct #35

Construct #36

Construct #16ΔK

Construct #12ΔK

Construct #1

Construct #9

Construct #10

Construct #11

Construct #12

Construct #16

Construct #1

Construct #10

Construct #12

Construct #16

SEQUENCE LISTING

<160> NUMBER OF SEQ ID NOS: 75

<210> SEQ ID NO 1
<211> LENGTH: 347
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 1

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270
```

```
Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Glu Gly Phe Asp Lys
                325                 330                 335

Val Arg Glu Ala Glu Asp Ser Pro Gln His Met
            340                 345

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Gly Phe Asp Lys Val Arg Glu Ala Glu Asp Ser Pro Gln His
1               5                   10                  15

<210> SEQ ID NO 3
<211> LENGTH: 671
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
                20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Thr Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
            115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
            195                 200                 205
```

```
Ser Pro Ser Pro Gly Leu Pro Arg Arg Ala Leu His Thr Ala Pro
    210             215             220

Ile Gln Pro Arg Val Trp Glu Pro Val Pro Leu Glu Glu Val Gln Leu
225             230             235             240

Val Val Glu Pro Glu Gly Gly Ala Val Ala Pro Gly Gly Thr Val Thr
                245             250             255

Leu Thr Cys Glu Val Pro Ala Gln Pro Ser Pro Gln Ile His Trp Met
            260             265             270

Lys Asp Gly Val Pro Leu Pro Leu Pro Pro Ser Pro Val Leu Ile Leu
        275             280             285

Pro Glu Ile Gly Pro Gln Asp Gln Gly Thr Tyr Ser Cys Val Ala Thr
    290             295             300

His Ser Ser His Gly Pro Gln Glu Ser Arg Ala Val Ser Ile Ser Ile
305             310             315             320

Ile Glu Pro Gly Glu Glu Gly Pro Thr Ala Gly Ser Val Gly Gly Ser
                325             330             335

Gly Leu Gly Thr Leu Ala Leu Ala Ala Ser Thr Lys Gly Pro Ser Val
            340             345             350

Phe Pro Leu Ala Pro Cys Ser Arg Ser Thr Ser Glu Ser Thr Ala Ala
    355             360             365

Leu Gly Cys Leu Val Lys Asp Tyr Phe Pro Glu Pro Val Thr Val Ser
370             375             380

Trp Asn Ser Gly Ala Leu Thr Ser Gly Val His Thr Phe Pro Ala Val
385             390             395             400

Leu Gln Ser Ser Gly Leu Tyr Ser Leu Ser Ser Val Val Thr Val Pro
                405             410             415

Ser Ser Ser Leu Gly Thr Lys Thr Tyr Thr Cys Asn Val Asp His Lys
            420             425             430

Pro Ser Asn Thr Lys Val Asp Lys Arg Val Glu Ser Lys Tyr Gly Pro
    435             440             445

Pro Cys Pro Ser Cys Pro Ala Pro Glu Phe Leu Gly Gly Pro Ser Val
450             455             460

Phe Leu Phe Pro Pro Lys Pro Lys Asp Thr Leu Met Ile Ser Arg Thr
465             470             475             480

Pro Glu Val Thr Cys Val Val Val Asp Val Ser Gln Glu Asp Pro Glu
                485             490             495

Val Gln Phe Asn Trp Tyr Val Asp Gly Val Glu Val His Asn Ala Lys
            500             505             510

Thr Lys Pro Arg Glu Glu Gln Phe Asn Ser Thr Tyr Arg Val Val Ser
    515             520             525

Val Leu Thr Val Leu His Gln Asp Trp Leu Asn Gly Lys Glu Tyr Lys
530             535             540

Cys Lys Val Ser Asn Lys Gly Leu Pro Ser Ser Thr Glu Lys Thr Ile
545             550             555             560

Ser Lys Ala Lys Gly Gln Pro Arg Glu Pro Gln Val Tyr Thr Leu Pro
                565             570             575

Pro Ser Gln Glu Glu Met Thr Lys Asn Gln Val Ser Leu Thr Cys Leu
            580             585             590

Val Lys Gly Phe Tyr Pro Ser Asp Ile Ala Val Glu Trp Glu Ser Asn
    595             600             605

Gly Gln Pro Glu Asn Asn Tyr Lys Thr Thr Pro Pro Val Leu Asp Ser
610             615             620
```

```
Asp Gly Ser Phe Phe Leu Tyr Ser Arg Leu Thr Val Asp Lys Ser Arg
625                 630                 635                 640

Trp Gln Glu Gly Asn Val Phe Ser Cys Ser Val Met His Glu Ala Leu
                645                 650                 655

His Asn His Tyr Thr Gln Lys Ser Leu Ser Leu Ser Leu Gly Lys
            660                 665                 670

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 4

Xaa Tyr Xaa Thr Xaa Glu
1               5

<210> SEQ ID NO 5
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175
```

```
Gly Gly Asp Pro Arg Pro Thr Phe Ser Cys Ser Phe Ser Pro Gly Leu
            180                 185                 190
Pro Arg His Arg Ala Leu Arg Thr Ala Pro Ile Gln Pro Arg Val Trp
        195                 200                 205
Glu Pro Val Pro Leu Glu Glu Val Gln Leu Val Val Glu Pro Glu Gly
    210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                245                 250                 255
Pro Leu Pro Pro Ser Pro Val Leu Ile Leu Pro Glu Ile Gly Pro Gln
            260                 265                 270
Asp Gln Gly Thr Tyr Ser Cys Val Ala Thr His Ser Ser His Gly Pro
        275                 280                 285
Gln Glu Ser Arg Ala Val Ser Ile Ser Ile Ile Glu Pro Gly Glu Glu
    290                 295                 300
Gly Pro Thr Ala Gly Ser Val Gly Gly Ser Gly Leu Gly Thr Leu Ala
305                 310                 315                 320
Leu Ala Ile Glu Gly Arg Met Pro Lys Ser Cys Asp Lys Thr His Thr
                325                 330                 335
Cys Pro Pro Cys Pro Ala Pro Glu Leu Leu Gly Gly Pro Ser Val Phe
            340                 345                 350
Leu Phe Pro Pro Lys Pro Lys Asp Thr Leu Met Ile Ser Arg Thr Pro
        355                 360                 365
Glu Val Thr Cys Val Val Val Asp Val Ser His Glu Asp Pro Glu Val
    370                 375                 380
Lys Phe Asn Trp Tyr Val Asp Gly Val Glu Val His Asn Ala Lys Thr
385                 390                 395                 400
Lys Pro Arg Glu Glu Gln Tyr Asn Ser Thr Tyr Arg Val Val Ser Val
                405                 410                 415
Leu Thr Val Leu His Gln Asp Trp Leu Asn Gly Lys Glu Tyr Lys Cys
            420                 425                 430
Lys Val Ser Asn Lys Ala Leu Pro Ala Pro Ile Glu Lys Thr Ile Ser
        435                 440                 445
Lys Ala Lys Gly Gln Pro Arg Glu Pro Gln Val Tyr Thr Leu Pro Pro
    450                 455                 460
Ser Arg Asp Glu Leu Thr Lys Asn Gln Val Ser Leu Thr Cys Leu Val
465                 470                 475                 480
Lys Gly Phe Tyr Pro Ser Asp Ile Ala Val Glu Trp Glu Ser Asn Gly
                485                 490                 495
Gln Pro Glu Asn Asn Tyr Lys Thr Thr Pro Pro Val Leu Asp Ser Asp
            500                 505                 510
Gly Ser Phe Phe Leu Tyr Ser Lys Leu Thr Val Asp Lys Ser Arg Trp
        515                 520                 525
Gln Gln Gly Asn Val Phe Ser Cys Ser Val Met His Glu Ala Leu His
    530                 535                 540
Asn His Tyr Thr Gln Lys Ser Leu Ser Leu Ser Pro Gly Lys
545                 550                 555

<210> SEQ ID NO 6
<211> LENGTH: 309
<212> TYPE: PRT
<213> ORGANISM: Homo sapiens

<400> SEQUENCE: 6
```

```
Ala Gln Asn Ile Thr Ala Arg Ile Gly Glu Pro Leu Val Leu Lys Cys
1               5                   10                  15

Lys Gly Ala Pro Lys Pro Pro Gln Arg Leu Glu Trp Lys Leu Asn
            20              25                  30

Thr Gly Arg Thr Glu Ala Trp Lys Val Leu Ser Pro Gln Gly Gly
        35                  40                  45

Pro Trp Asp Ser Val Ala Arg Val Leu Pro Asn Gly Ser Leu Phe Leu
50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly
305

<210> SEQ ID NO 7
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

Gln Glu Asp Pro Glu Val Gln Phe Asn Trp Tyr Val Asp Gly Val Glu
```

```
                35                  40                  45
Val His Asn Ala Lys Thr Lys Pro Arg Glu Glu Gln Phe Asn Ser Thr
 50                  55                  60

Tyr Arg Val Val Ser Val Leu Thr Val Leu His Gln Asp Trp Leu Asn
 65                  70                  75                  80

Gly Lys Glu Tyr Lys Cys Lys Val Ser Asn Lys Gly Leu Pro Ser Ser
                 85                  90                  95

Ile Glu Lys Thr Ile Ser Lys Ala Lys Gly Gln Pro Arg Glu Pro Gln
                100                 105                 110

Val Tyr Thr Leu Pro Pro Ser Gln Glu Glu Met Thr Lys Asn Gln Val
            115                 120                 125

Ser Leu Thr Cys Leu Val Lys Gly Phe Tyr Pro Ser Asp Ile Ala Val
        130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Arg Leu Thr
                165                 170                 175

Val Asp Lys Ser Arg Trp Gln Glu Gly Asn Val Phe Ser Cys Ser Val
            180                 185                 190

Met His Glu Ala Leu His Asn His Tyr Thr Gln Lys Ser Leu Ser Leu
        195                 200                 205

Ser Leu Gly Lys
    210

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Ser Lys Tyr Gly Pro Pro Cys Pro Pro Cys Pro Ala Pro Glu Ala
 1               5                  10                  15

Ala

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Glu Cys Pro Pro Cys Ala Pro Pro Val Ala
 1               5                  10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Arg Lys Cys Cys Val Glu Cys Pro Pro Cys Ala Pro Pro Val Ala
 1               5                  10                  15
```

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Pro Lys Ser Cys Asp Lys Thr His Thr Cys Pro Pro Cys Pro Ala
1               5                   10                  15

Pro Glu Ala Ala
            20

<210> SEQ ID NO 12
<211> LENGTH: 554
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

| | | | | | | | | | | | |
|---|---|---|---|---|---|---|---|---|---|---|---|
|Asp|Gln|Gly|Thr|Tyr|Ser|Cys|Val|Ala|Thr|His|Ser|His|Gly|Pro|
| | |275| | | |280| | | |285| | | | |

Asp Gln Gly Thr Tyr Ser Cys Val Ala Thr His Ser His Gly Pro
            275                 280                 285

Gln Glu Ser Arg Ala Val Ser Ile Ser Ile Glu Pro Gly Glu Glu
    290                 295                 300

Gly Pro Thr Ala Gly Glu Gly Phe Asp Lys Val Arg Glu Ala Glu Asp
305             310                 315                 320

Ser Pro Gln His Ala Glu Ser Lys Tyr Gly Pro Pro Cys Pro Pro Cys
            325                 330                 335

Pro Ala Pro Glu Ala Ala Gly Gly Pro Ser Val Phe Leu Phe Pro Pro
            340                 345                 350

Lys Pro Lys Asp Thr Leu Met Ile Ser Arg Thr Pro Glu Val Thr Cys
            355                 360                 365

Val Val Val Asp Val Ser Gln Glu Asp Pro Glu Val Gln Phe Asn Trp
370                 375                 380

Tyr Val Asp Gly Val Glu Val His Asn Ala Lys Thr Lys Pro Arg Glu
385                 390                 395                 400

Glu Gln Phe Asn Ser Thr Tyr Arg Val Val Ser Val Leu Thr Val Leu
            405                 410                 415

His Gln Asp Trp Leu Asn Gly Lys Glu Tyr Lys Cys Lys Val Ser Asn
            420                 425                 430

Lys Gly Leu Pro Ser Ser Ile Glu Lys Thr Ile Ser Lys Ala Lys Gly
            435                 440                 445

Gln Pro Arg Glu Pro Gln Val Tyr Thr Leu Pro Pro Ser Gln Glu Glu
            450                 455                 460

Met Thr Lys Asn Gln Val Ser Leu Thr Cys Leu Val Lys Gly Phe Tyr
465                 470                 475                 480

Pro Ser Asp Ile Ala Val Glu Trp Glu Ser Asn Gly Gln Pro Glu Asn
            485                 490                 495

Asn Tyr Lys Thr Thr Pro Pro Val Leu Asp Ser Asp Gly Ser Phe Phe
            500                 505                 510

Leu Tyr Ser Arg Leu Thr Val Asp Lys Ser Arg Trp Gln Glu Gly Asn
            515                 520                 525

Val Phe Ser Cys Ser Val Met His Glu Ala Leu His Asn His Tyr Thr
530                 535                 540

Gln Lys Ser Leu Ser Leu Ser Leu Gly Lys
545                 550

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Thr Leu Val Thr Val Ser Ser
1               5

<210> SEQ ID NO 14
<211> LENGTH: 562
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

-continued

```
Ala Gln Asn Ile Thr Ala Arg Ile Gly Glu Pro Leu Val Leu Lys Cys
1               5                   10                  15

Lys Gly Ala Pro Lys Pro Pro Gln Arg Leu Glu Trp Lys Leu Asn
            20              25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
                100                 105                 110

Ala Gly Val Pro Asn Lys Val Gly Thr Cys Val Ser Glu Gly Ser Tyr
            115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly Glu Gly Phe Asp Lys Val Arg Glu Ala Glu Asp
305                 310                 315                 320

Ser Pro Gln His Ala Gly Thr Leu Val Thr Val Ser Ser Glu Ser Lys
                325                 330                 335

Tyr Gly Pro Pro Cys Pro Pro Cys Pro Ala Pro Glu Ala Ala Gly Gly
            340                 345                 350

Pro Ser Val Phe Leu Phe Pro Pro Lys Pro Lys Asp Thr Leu Met Ile
        355                 360                 365

Ser Arg Thr Pro Glu Val Thr Cys Val Val Val Asp Val Ser Gln Glu
    370                 375                 380

Asp Pro Glu Val Gln Phe Asn Trp Tyr Val Asp Gly Val Glu Val His
385                 390                 395                 400

Asn Ala Lys Thr Lys Pro Arg Glu Glu Gln Phe Asn Ser Thr Tyr Arg
                405                 410                 415

Val Val Ser Val Leu Thr Val Leu His Gln Asp Trp Leu Asn Gly Lys
```

```
                    420                 425                 430
Glu Tyr Lys Cys Lys Val Ser Asn Lys Gly Leu Pro Ser Ser Ile Glu
            435                 440                 445

Lys Thr Ile Ser Lys Ala Lys Gly Gln Pro Arg Glu Pro Gln Val Tyr
        450                 455                 460

Thr Leu Pro Pro Ser Gln Glu Glu Met Thr Lys Asn Gln Val Ser Leu
465                 470                 475                 480

Thr Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Arg Leu Thr Val Asp
        515                 520                 525

Lys Ser Arg Trp Gln Glu Gly Asn Val Phe Ser Cys Ser Val Met His
    530                 535                 540

Glu Ala Leu His Asn His Tyr Thr Gln Lys Ser Leu Ser Leu Ser Leu
545                 550                 555                 560

Gly Lys

<210> SEQ ID NO 15
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
```

```
            210                 215                 220
Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
            245                 250                 255

Pro Leu Pro Pro Ser Pro Val Leu Ile Leu Pro Glu Ile Gly Pro Gln
                260                 265                 270

Asp Gln Gly Thr Tyr Ser Cys Val Ala Thr His Ser Ser His Gly Pro
            275                 280                 285

Gln Glu Ser Arg Ala Val Ser Ile Ser Ile Ile Glu Pro Gly Glu Glu
        290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Cys Ala Pro Pro Val Ala
            325                 330                 335

Gly Gly Pro Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
            355                 360                 365

Gln Glu Asp Pro Glu Val Gln Phe Asn Trp Tyr Val Asp Gly Val Glu
        370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
            420                 425                 430

Ile Glu Lys Thr Ile Ser Lys Ala Lys Gly Gln Pro Arg Glu Pro Gln
            435                 440                 445

Val Tyr Thr Leu Pro Pro Ser Gln Glu Glu Met Thr Lys Asn Gln Val
        450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
            500                 505                 510

Val Asp Lys Ser Arg Trp Gln Glu Gly Asn Val Phe Ser Cys Ser Val
            515                 520                 525

Met His Glu Ala Leu His Asn His Tyr Thr Gln Lys Ser Leu Ser Leu
            530                 535                 540

Ser Leu Gly Lys
545

<210> SEQ ID NO 16
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Gln Asn Ile Thr Ala Arg Ile Gly Glu Pro Leu Val Leu Lys Cys
1               5                   10                  15
```

-continued

```
Lys Gly Ala Pro Lys Lys Pro Pro Gln Arg Leu Glu Trp Lys Leu Asn
             20                  25                  30
Thr Gly Arg Thr Glu Ala Trp Lys Val Leu Ser Pro Gln Gly Gly Gly
         35                  40                  45
Pro Trp Asp Ser Val Ala Arg Val Leu Pro Asn Gly Ser Leu Phe Leu
     50                  55                  60
Pro Ala Val Gly Ile Gln Asp Glu Gly Ile Phe Arg Cys Gln Ala Met
 65                  70                  75                  80
Asn Arg Asn Gly Lys Glu Thr Lys Ser Asn Tyr Arg Val Arg Val Tyr
                 85                  90                  95
Gln Ile Pro Gly Lys Pro Glu Ile Val Asp Ser Ala Ser Glu Leu Thr
            100                 105                 110
Ala Gly Val Pro Asn Lys Val Gly Thr Cys Val Ser Glu Gly Ser Tyr
        115                 120                 125
Pro Ala Gly Thr Leu Ser Trp His Leu Asp Gly Lys Pro Leu Val Pro
    130                 135                 140
Asn Glu Lys Gly Val Ser Val Lys Glu Gln Thr Arg Arg His Pro Glu
145                 150                 155                 160
Thr Gly Leu Phe Thr Leu Gln Ser Glu Leu Met Val Thr Pro Ala Arg
                165                 170                 175
Gly Gly Asp Pro Arg Pro Thr Phe Ser Cys Ser Phe Ser Pro Gly Leu
            180                 185                 190
Pro Arg His Arg Ala Leu Arg Thr Ala Pro Ile Gln Pro Arg Val Trp
        195                 200                 205
Glu Pro Val Pro Leu Glu Glu Val Gln Leu Val Val Glu Pro Glu Gly
    210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                245                 250                 255
Pro Leu Pro Pro Ser Pro Val Leu Ile Leu Pro Glu Ile Gly Pro Gln
            260                 265                 270
Asp Gln Gly Thr Tyr Ser Cys Val Ala Thr His Ser Ser His Gly Pro
        275                 280                 285
Gln Glu Ser Arg Ala Val Ser Ile Ser Ile Ile Glu Pro Gly Glu Glu
    290                 295                 300
Gly Pro Thr Ala Gly Glu Gly Phe Asp Lys Val Arg Glu Ala Glu Asp
305                 310                 315                 320
Ser Pro Gln His Ala Val Glu Cys Pro Pro Cys Ala Pro Pro Val Ala
                325                 330                 335
Gly Gly Pro Ser Val Phe Leu Phe Pro Pro Lys Pro Lys Asp Thr Leu
            340                 345                 350
Tyr Ile Thr Arg Glu Pro Glu Val Thr Cys Val Val Val Asp Val Ser
        355                 360                 365
Gln Glu Asp Pro Glu Val Gln Phe Asn Trp Tyr Val Asp Gly Val Glu
    370                 375                 380
Val His Asn Ala Lys Thr Lys Pro Arg Glu Glu Gln Phe Asn Ser Thr
385                 390                 395                 400
Tyr Arg Val Val Ser Val Leu Thr Val Leu His Gln Asp Trp Leu Asn
                405                 410                 415
Gly Lys Glu Tyr Lys Cys Lys Val Ser Asn Lys Gly Leu Pro Ser Ser
            420                 425                 430
Ile Glu Lys Thr Ile Ser Lys Ala Lys Gly Gln Pro Arg Glu Pro Gln
```

-continued

```
                    435                 440                 445
Val Tyr Thr Leu Pro Pro Ser Gln Glu Glu Met Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
                500                 505                 510

Val Asp Lys Ser Arg Trp Gln Glu Gly Asn Val Phe Ser Cys Ser Val
                515                 520                 525

Met His Glu Ala Leu His Asn His Tyr Thr Gln Lys Ser Leu Ser Leu
                530                 535                 540

Ser Leu Gly Lys
545

<210> SEQ ID NO 17
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Gln Glu Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
                20                  25                  30

Thr Gly Arg Thr Glu Ala Trp Lys Val Leu Ser Pro Gln Gly Gly Gly
            35                  40                  45

Pro Trp Asp Ser Val Ala Arg Val Leu Pro Asn Gly Ser Leu Phe Leu
        50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240
```

```
Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
            275                 280                 285

Gln Glu Ser Arg Ala Val Ser Ile Ser Ile Glu Pro Gly Glu Glu
        290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Pro Cys Ala Pro Pro Val Ala
                325                 330                 335

Gly Gly Pro Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
            355                 360                 365

Gln Glu Asp Pro Glu Val Gln Phe Asn Trp Tyr Val Asp Gly Val Glu
        370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Gln Glu Glu Met Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
            500                 505                 510

Val Asp Lys Ser Arg Trp Gln Glu Gly Asn Val Phe Ser Cys Ser Val
        515                 520                 525

Met His Glu Ala Leu His Asn His Tyr Thr Gln Lys Ser Leu Ser Leu
    530                 535                 540

Ser Leu Gly Lys
545

<210> SEQ ID NO 18
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Gln Gln Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45
```

-continued

```
Pro Trp Asp Ser Val Ala Arg Val Leu Pro Asn Gly Ser Leu Phe Leu
 50                  55                  60

Pro Ala Val Gly Ile Gln Asp Glu Gly Ile Phe Arg Cys Gln Ala Met
 65                  70                  75                  80

Asn Arg Asn Gly Lys Glu Thr Lys Ser Asn Tyr Arg Val Arg Val Tyr
                 85                  90                  95

Gln Ile Pro Gly Lys Pro Glu Ile Val Asp Ser Ala Ser Glu Leu Thr
                100                 105                 110

Ala Gly Val Pro Asn Lys Val Gly Thr Cys Val Ser Glu Gly Ser Tyr
            115                 120                 125

Pro Ala Gly Thr Leu Ser Trp His Leu Asp Gly Lys Pro Leu Val Pro
130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Pro Cys Ala Pro Pro Val Ala
                325                 330                 335

Gly Gly Pro Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
        355                 360                 365

Gln Glu Asp Pro Glu Val Gln Phe Asn Trp Tyr Val Asp Gly Val Glu
    370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Gln Glu Glu Met Thr Lys Asn Gln Val
450                 455                 460
```

```
Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
            500                 505                 510

Val Asp Lys Ser Arg Trp Gln Glu Gly Asn Val Phe Ser Cys Ser Val
        515                 520                 525

Met His Glu Ala Leu His Asn His Tyr Thr Gln Lys Ser Leu Ser Leu
    530                 535                 540

Ser Leu Gly Lys
545

<210> SEQ ID NO 19
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Ser Ser Leu Phe Leu
50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270
```

```
Asp Gln Gly Thr Tyr Ser Cys Val Ala Thr His Ser Ser His Gly Pro
            275                 280                 285

Gln Glu Ser Arg Ala Val Ser Ile Ser Ile Ile Glu Pro Gly Glu Glu
        290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Pro Cys Ala Pro Pro Val Ala
                325                 330                 335

Gly Gly Pro Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
        355                 360                 365

Gln Glu Asp Pro Glu Val Gln Phe Asn Trp Tyr Val Asp Gly Val Glu
    370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Gln Glu Glu Met Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
            500                 505                 510

Val Asp Lys Ser Arg Trp Gln Glu Gly Asn Val Phe Ser Cys Ser Val
        515                 520                 525

Met His Glu Ala Leu His Asn His Tyr Thr Gln Lys Ser Leu Ser Leu
    530                 535                 540

Ser Leu Gly Lys
545

<210> SEQ ID NO 20
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Gln Glu Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Ser Ser Leu Phe Leu
    50                  55                  60

Pro Ala Val Gly Ile Gln Asp Glu Gly Ile Phe Arg Cys Gln Ala Met
```

```
            65                  70                  75                  80
Asn Arg Asn Gly Lys Glu Thr Lys Ser Asn Tyr Arg Val Arg Val Tyr
                    85                  90                  95
Gln Ile Pro Gly Lys Pro Glu Ile Val Asp Ser Ala Ser Glu Leu Thr
                    100                 105                 110
Ala Gly Val Pro Asn Lys Val Gly Thr Cys Val Ser Glu Gly Ser Tyr
                    115                 120                 125
Pro Ala Gly Thr Leu Ser Trp His Leu Asp Gly Lys Pro Leu Val Pro
                    130                 135                 140
Asn Glu Lys Gly Val Ser Val Lys Glu Gln Thr Arg Arg His Pro Glu
145                 150                 155                 160
Thr Gly Leu Phe Thr Leu Gln Ser Glu Leu Met Val Thr Pro Ala Arg
                    165                 170                 175
Gly Gly Asp Pro Arg Pro Thr Phe Ser Cys Ser Phe Ser Pro Gly Leu
                    180                 185                 190
Pro Arg His Arg Ala Leu Arg Thr Ala Pro Ile Gln Pro Arg Val Trp
                    195                 200                 205
Glu Pro Val Pro Leu Glu Glu Val Gln Leu Val Val Glu Pro Glu Gly
                    210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                    245                 250                 255
Pro Leu Pro Pro Ser Pro Val Leu Ile Leu Pro Glu Ile Gly Pro Gln
                    260                 265                 270
Asp Gln Gly Thr Tyr Ser Cys Val Ala Thr His Ser Ser His Gly Pro
                    275                 280                 285
Gln Glu Ser Arg Ala Val Ser Ile Ser Ile Ile Glu Pro Gly Glu Glu
                    290                 295                 300
Gly Pro Thr Ala Gly Gly Phe Asp Lys Val Arg Glu Ala Glu Asp
305                 310                 315                 320
Ser Pro Gln His Ala Val Glu Cys Pro Pro Cys Ala Pro Pro Val Ala
                    325                 330                 335
Gly Gly Pro Ser Val Phe Leu Phe Pro Pro Lys Pro Lys Asp Thr Leu
                    340                 345                 350
Met Ile Ser Arg Thr Pro Glu Val Thr Cys Val Val Val Asp Val Ser
                    355                 360                 365
Gln Glu Asp Pro Glu Val Gln Phe Asn Trp Tyr Val Asp Gly Val Glu
                    370                 375                 380
Val His Asn Ala Lys Thr Lys Pro Arg Glu Glu Gln Phe Asn Ser Thr
385                 390                 395                 400
Tyr Arg Val Val Ser Val Leu Thr Val Leu His Gln Asp Trp Leu Asn
                    405                 410                 415
Gly Lys Glu Tyr Lys Cys Lys Val Ser Asn Lys Gly Leu Pro Ser Ser
                    420                 425                 430
Ile Glu Lys Thr Ile Ser Lys Ala Lys Gly Gln Pro Arg Glu Pro Gln
                    435                 440                 445
Val Tyr Thr Leu Pro Pro Ser Gln Glu Glu Met Thr Lys Asn Gln Val
                    450                 455                 460
Ser Leu Thr Cys Leu Val Lys Gly Phe Tyr Pro Ser Asp Ile Ala Val
465                 470                 475                 480
Glu Trp Glu Ser Asn Gly Gln Pro Glu Asn Asn Tyr Lys Thr Thr Pro
                    485                 490                 495
```

```
Pro Val Leu Asp Ser Asp Gly Ser Phe Phe Leu Tyr Ser Arg Leu Thr
            500                 505                 510

Val Asp Lys Ser Arg Trp Gln Glu Gly Asn Val Phe Ser Cys Ser Val
            515                 520                 525

Met His Glu Ala Leu His Asn His Tyr Thr Gln Lys Ser Leu Ser Leu
530                 535                 540

Ser Leu Gly Lys
545

<210> SEQ ID NO 21
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Gln Gln Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Ser Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
```

```
                290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Pro Cys Ala Pro Pro Val Ala
                325                 330                 335

Gly Gly Pro Ser Val Phe Leu Phe Pro Pro Lys Pro Lys Asp Thr Leu
                340                 345                 350

Met Ile Ser Arg Thr Pro Glu Val Thr Cys Val Val Val Asp Val Ser
                355                 360                 365

Gln Glu Asp Pro Glu Val Gln Phe Asn Trp Tyr Val Asp Gly Val Glu
                370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
                420                 425                 430

Ile Glu Lys Thr Ile Ser Lys Ala Lys Gly Gln Pro Arg Glu Pro Gln
                435                 440                 445

Val Tyr Thr Leu Pro Pro Ser Gln Glu Glu Met Thr Lys Asn Gln Val
                450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
                500                 505                 510

Val Asp Lys Ser Arg Trp Gln Gln Gly Asn Val Phe Ser Cys Ser Val
                515                 520                 525

Met His Glu Ala Leu His Asn His Tyr Thr Gln Lys Ser Leu Ser Leu
                530                 535                 540

Ser Leu Gly Lys
545

<210> SEQ ID NO 22
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
                20                  25                  30

Thr Gly Arg Thr Glu Ala Trp Lys Val Leu Ser Pro Gln Gly Gly Gly
                35                  40                  45

Pro Trp Asp Ser Val Ala Arg Val Leu Pro Ala Gly Ser Leu Phe Leu
                50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95
```

-continued

Gln Ile Pro Gly Lys Pro Glu Ile Val Asp Ser Ala Ser Glu Leu Thr
            100                 105                 110
Ala Gly Val Pro Asn Lys Val Gly Thr Cys Val Ser Glu Gly Ser Tyr
            115                 120                 125
Pro Ala Gly Thr Leu Ser Trp His Leu Asp Gly Lys Pro Leu Val Pro
            130                 135                 140
Asn Glu Lys Gly Val Ser Val Lys Glu Gln Thr Arg Arg His Pro Glu
145                 150                 155                 160
Thr Gly Leu Phe Thr Leu Gln Ser Glu Leu Met Val Thr Pro Ala Arg
                165                 170                 175
Gly Gly Asp Pro Arg Pro Thr Phe Ser Cys Ser Phe Ser Pro Gly Leu
            180                 185                 190
Pro Arg His Arg Ala Leu Arg Thr Ala Pro Ile Gln Pro Arg Val Trp
            195                 200                 205
Glu Pro Val Pro Leu Glu Glu Val Gln Leu Val Val Glu Pro Glu Gly
            210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                245                 250                 255
Pro Leu Pro Pro Ser Pro Val Leu Ile Leu Pro Glu Ile Gly Pro Gln
            260                 265                 270
Asp Gln Gly Thr Tyr Ser Cys Val Ala Thr His Ser Ser His Gly Pro
            275                 280                 285
Gln Glu Ser Arg Ala Val Ser Ile Ser Ile Ile Glu Pro Gly Glu Glu
            290                 295                 300
Gly Pro Thr Ala Gly Glu Gly Phe Asp Lys Val Arg Glu Ala Glu Asp
305                 310                 315                 320
Ser Pro Gln His Ala Val Glu Cys Pro Pro Cys Ala Pro Pro Val Ala
                325                 330                 335
Gly Gly Pro Ser Val Phe Leu Phe Pro Pro Lys Pro Lys Asp Thr Leu
            340                 345                 350
Met Ile Ser Arg Thr Pro Glu Val Thr Cys Val Val Val Asp Val Ser
            355                 360                 365
Gln Glu Asp Pro Glu Val Gln Phe Asn Trp Tyr Val Asp Gly Val Glu
            370                 375                 380
Val His Asn Ala Lys Thr Lys Pro Arg Glu Glu Gln Phe Asn Ser Thr
385                 390                 395                 400
Tyr Arg Val Val Ser Val Leu Thr Val Leu His Gln Asp Trp Leu Asn
                405                 410                 415
Gly Lys Glu Tyr Lys Cys Lys Val Ser Asn Lys Gly Leu Pro Ser Ser
            420                 425                 430
Ile Glu Lys Thr Ile Ser Lys Ala Lys Gly Gln Pro Arg Glu Pro Gln
            435                 440                 445
Val Tyr Thr Leu Pro Pro Ser Gln Glu Glu Met Thr Lys Asn Gln Val
            450                 455                 460
Ser Leu Thr Cys Leu Val Lys Gly Phe Tyr Pro Ser Asp Ile Ala Val
465                 470                 475                 480
Glu Trp Glu Ser Asn Gly Gln Pro Glu Asn Asn Tyr Lys Thr Thr Pro
                485                 490                 495
Pro Val Leu Asp Ser Asp Gly Ser Phe Phe Leu Tyr Ser Arg Leu Thr
            500                 505                 510
Val Asp Lys Ser Arg Trp Gln Glu Gly Asn Val Phe Ser Cys Ser Val

```
                515                 520                 525
Met His Glu Ala Leu His Asn His Tyr Thr Gln Lys Ser Leu Ser Leu
    530                 535                 540

Ser Leu Gly Lys
545

<210> SEQ ID NO 23
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Gln Glu Ile Thr Ala Arg Ile Gly Glu Pro Leu Val Leu Lys Cys
1               5                  10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Ala Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly Glu Gly Phe Asp Lys Val Arg Glu Ala Glu Asp
305                 310                 315                 320
```

```
Ser Pro Gln His Ala Val Glu Cys Pro Pro Cys Ala Pro Pro Val Ala
            325                 330                 335

Gly Gly Pro Ser Val Phe Leu Phe Pro Pro Lys Pro Lys Asp Thr Leu
        340                 345                 350

Met Ile Ser Arg Thr Pro Glu Val Thr Cys Val Val Val Asp Val Ser
        355                 360                 365

Gln Glu Asp Pro Glu Val Gln Phe Asn Trp Tyr Val Asp Gly Val Glu
    370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
            420                 425                 430

Ile Glu Lys Thr Ile Ser Lys Ala Lys Gly Gln Pro Arg Glu Pro Gln
            435                 440                 445

Val Tyr Thr Leu Pro Pro Ser Gln Glu Glu Met Thr Lys Asn Gln Val
        450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
                500                 505                 510

Val Asp Lys Ser Arg Trp Gln Glu Gly Asn Val Phe Ser Cys Ser Val
            515                 520                 525

Met His Glu Ala Leu His Asn His Tyr Thr Gln Lys Ser Leu Ser Leu
        530                 535                 540

Ser Leu Gly Lys
545

<210> SEQ ID NO 24
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Gln Gln Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Ala Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125
```

-continued

Pro Ala Gly Thr Leu Ser Trp His Leu Asp Gly Lys Pro Leu Val Pro
        130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
                180                 185                 190

Pro Arg His Arg Ala Leu Arg Thr Ala Pro Ile Gln Pro Arg Val Trp
        195                 200                 205

Glu Pro Val Pro Leu Glu Val Gln Leu Val Val Glu Pro Glu Gly
210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
                260                 265                 270

Asp Gln Gly Thr Tyr Ser Cys Val Ala Thr His Ser Ser His Gly Pro
                275                 280                 285

Gln Glu Ser Arg Ala Val Ser Ile Ser Ile Ile Glu Pro Gly Glu Glu
        290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Cys Ala Pro Pro Val Ala
                325                 330                 335

Gly Gly Pro Ser Val Phe Leu Phe Pro Pro Lys Pro Lys Asp Thr Leu
                340                 345                 350

Met Ile Ser Arg Thr Pro Glu Val Thr Cys Val Val Val Asp Val Ser
                355                 360                 365

Gln Glu Asp Pro Glu Val Gln Phe Asn Trp Tyr Val Asp Gly Val Glu
        370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
                420                 425                 430

Ile Glu Lys Thr Ile Ser Lys Ala Lys Gly Gln Pro Arg Glu Pro Gln
        435                 440                 445

Val Tyr Thr Leu Pro Pro Ser Gln Glu Glu Met Thr Lys Asn Gln Val
450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
                500                 505                 510

Val Asp Lys Ser Arg Trp Gln Glu Gly Asn Val Phe Ser Cys Ser Val
        515                 520                 525

Met His Glu Ala Leu His Asn His Tyr Thr Gln Lys Ser Leu Ser Leu
530                 535                 540

Ser Leu Gly Lys
545

<210> SEQ ID NO 25
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Gln Glu Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Pro Cys Ala Pro Pro Val Ala
                325                 330                 335

Gly Gly Pro Ser Val Phe Leu Phe Pro Pro Lys Pro Lys Asp Thr Leu
            340                 345                 350

-continued

```
Tyr Ile Thr Arg Glu Pro Glu Val Thr Cys Val Val Val Asp Val Ser
            355                 360                 365

Gln Glu Asp Pro Glu Val Gln Phe Asn Trp Tyr Val Asp Gly Val Glu
        370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Gln Glu Glu Met Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
            500                 505                 510

Val Asp Lys Ser Arg Trp Gln Glu Gly Asn Val Phe Ser Cys Ser Val
        515                 520                 525

Met His Glu Ala Leu His Asn His Tyr Thr Gln Lys Ser Leu Ser Leu
    530                 535                 540

Ser Leu Gly Lys
545

<210> SEQ ID NO 26
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Gln Gln Ile Thr Ala Arg Ile Gly Glu Pro Leu Val Leu Lys Cys
1               5                  10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
```

```
            145                 150                 155                 160
Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
                180                 185                 190

Pro Arg His Arg Ala Leu Arg Thr Ala Pro Ile Gln Pro Arg Val Trp
                195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
                260                 265                 270

Asp Gln Gly Thr Tyr Ser Cys Val Ala Thr His Ser His Gly Pro
                275                 280                 285

Gln Glu Ser Arg Ala Val Ser Ile Ser Ile Ile Glu Pro Gly Glu Glu
    290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Cys Ala Pro Pro Val Ala
                325                 330                 335

Gly Gly Pro Ser Val Phe Leu Phe Pro Pro Lys Pro Lys Asp Thr Leu
                340                 345                 350

Tyr Ile Thr Arg Glu Pro Glu Val Thr Cys Val Val Asp Val Ser
                355                 360                 365

Gln Glu Asp Pro Glu Val Gln Phe Asn Trp Tyr Val Asp Gly Val Glu
    370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
                420                 425                 430

Ile Glu Lys Thr Ile Ser Lys Ala Lys Gly Gln Pro Arg Glu Pro Gln
                435                 440                 445

Val Tyr Thr Leu Pro Pro Ser Gln Glu Glu Met Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
                500                 505                 510

Val Asp Lys Ser Arg Trp Gln Glu Gly Asn Val Phe Ser Cys Ser Val
                515                 520                 525

Met His Glu Ala Leu His Asn His Tyr Thr Gln Lys Ser Leu Ser Leu
                530                 535                 540

Ser Leu Gly Lys
545

<210> SEQ ID NO 27
```

<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Ser Ser Leu Phe Leu
50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Pro Cys Ala Pro Pro Val Ala
                325                 330                 335

Gly Gly Pro Ser Val Phe Leu Phe Pro Pro Lys Pro Lys Asp Thr Leu
            340                 345                 350

Tyr Ile Thr Arg Glu Pro Glu Val Thr Cys Val Val Val Asp Val Ser
        355                 360                 365

Gln Glu Asp Pro Glu Val Gln Phe Asn Trp Tyr Val Asp Gly Val Glu

```
                370                 375                 380
Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
                420                 425                 430

Ile Glu Lys Thr Ile Ser Lys Ala Lys Gly Gln Pro Arg Glu Pro Gln
            435                 440                 445

Val Tyr Thr Leu Pro Pro Ser Gln Glu Glu Met Thr Lys Asn Gln Val
        450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
                500                 505                 510

Val Asp Lys Ser Arg Trp Gln Glu Gly Asn Val Phe Ser Cys Ser Val
            515                 520                 525

Met His Glu Ala Leu His Asn His Tyr Thr Gln Lys Ser Leu Ser Leu
        530                 535                 540

Ser Leu Gly Lys
545

<210> SEQ ID NO 28
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Gln Glu Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
                20                  25                  30

Thr Gly Arg Thr Glu Ala Trp Lys Val Leu Ser Pro Gln Gly Gly Gly
            35                  40                  45

Pro Trp Asp Ser Val Ala Arg Val Leu Pro Asn Ser Ser Leu Phe Leu
        50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
                100                 105                 110

Ala Gly Val Pro Asn Lys Val Gly Thr Cys Val Ser Glu Gly Ser Tyr
            115                 120                 125

Pro Ala Gly Thr Leu Ser Trp His Leu Asp Gly Lys Pro Leu Val Pro
        130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175
```

```
Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
            245                 250                 255

Pro Leu Pro Pro Ser Pro Val Leu Ile Leu Pro Glu Ile Gly Pro Gln
        260                 265                 270

Asp Gln Gly Thr Tyr Ser Cys Val Ala Thr His Ser Ser His Gly Pro
    275                 280                 285

Gln Glu Ser Arg Ala Val Ser Ile Ser Ile Ile Glu Pro Gly Glu Glu
    290                 295                 300

Gly Pro Thr Ala Gly Gly Phe Asp Lys Val Arg Glu Ala Glu Asp
305                 310                 315                 320

Ser Pro Gln His Ala Val Glu Cys Pro Pro Cys Ala Pro Pro Val Ala
            325                 330                 335

Gly Gly Pro Ser Val Phe Leu Phe Pro Pro Lys Pro Lys Asp Thr Leu
        340                 345                 350

Tyr Ile Thr Arg Glu Pro Glu Val Thr Cys Val Val Val Asp Val Ser
        355                 360                 365

Gln Glu Asp Pro Glu Val Gln Phe Asn Trp Tyr Val Asp Gly Val Glu
    370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
            405                 410                 415

Gly Lys Glu Tyr Lys Cys Lys Val Ser Asn Lys Gly Leu Pro Ser Ser
        420                 425                 430

Ile Glu Lys Thr Ile Ser Lys Ala Lys Gly Gln Pro Arg Glu Pro Gln
    435                 440                 445

Val Tyr Thr Leu Pro Pro Ser Gln Glu Glu Met Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
            485                 490                 495

Pro Val Leu Asp Ser Asp Gly Ser Phe Phe Leu Tyr Ser Arg Leu Thr
        500                 505                 510

Val Asp Lys Ser Arg Trp Gln Glu Gly Asn Val Phe Ser Cys Ser Val
    515                 520                 525

Met His Glu Ala Leu His Asn His Tyr Thr Gln Lys Ser Leu Ser Leu
    530                 535                 540

Ser Leu Gly Lys
545

<210> SEQ ID NO 29
<211> LENGTH: 548
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 29

```
Ala Gln Gln Ile Thr Ala Arg Ile Gly Glu Pro Leu Val Leu Lys Cys
1               5                   10                  15
Lys Gly Ala Pro Lys Lys Pro Pro Gln Arg Leu Glu Trp Lys Leu Asn
            20                  25                  30
Thr Gly Arg Thr Glu Ala Trp Lys Val Leu Ser Pro Gln Gly Gly Gly
        35                  40                  45
Pro Trp Asp Ser Val Ala Arg Val Leu Pro Asn Ser Ser Leu Phe Leu
50                  55                  60
Pro Ala Val Gly Ile Gln Asp Glu Gly Ile Phe Arg Cys Gln Ala Met
65                  70                  75                  80
Asn Arg Asn Gly Lys Glu Thr Lys Ser Asn Tyr Arg Val Arg Val Tyr
                85                  90                  95
Gln Ile Pro Gly Lys Pro Glu Ile Val Asp Ser Ala Ser Glu Leu Thr
            100                 105                 110
Ala Gly Val Pro Asn Lys Val Gly Thr Cys Val Ser Glu Gly Ser Tyr
        115                 120                 125
Pro Ala Gly Thr Leu Ser Trp His Leu Asp Gly Lys Pro Leu Val Pro
130                 135                 140
Asn Glu Lys Gly Val Ser Val Lys Glu Gln Thr Arg Arg His Pro Glu
145                 150                 155                 160
Thr Gly Leu Phe Thr Leu Gln Ser Glu Leu Met Val Thr Pro Ala Arg
                165                 170                 175
Gly Gly Asp Pro Arg Pro Thr Phe Ser Cys Ser Phe Ser Pro Gly Leu
            180                 185                 190
Pro Arg His Arg Ala Leu Arg Thr Ala Pro Ile Gln Pro Arg Val Trp
        195                 200                 205
Glu Pro Val Pro Leu Glu Glu Val Gln Leu Val Val Glu Pro Glu Gly
210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                245                 250                 255
Pro Leu Pro Pro Ser Pro Val Leu Ile Leu Pro Glu Ile Gly Pro Gln
            260                 265                 270
Asp Gln Gly Thr Tyr Ser Cys Val Ala Thr His Ser Ser His Gly Pro
        275                 280                 285
Gln Glu Ser Arg Ala Val Ser Ile Ser Ile Ile Glu Pro Gly Glu Glu
290                 295                 300
Gly Pro Thr Ala Gly Glu Gly Phe Asp Lys Val Arg Glu Ala Glu Asp
305                 310                 315                 320
Ser Pro Gln His Ala Val Glu Cys Pro Pro Cys Ala Pro Pro Val Ala
                325                 330                 335
Gly Gly Pro Ser Val Phe Leu Phe Pro Pro Lys Pro Lys Asp Thr Leu
            340                 345                 350
Tyr Ile Thr Arg Glu Pro Glu Val Thr Cys Val Val Val Asp Val Ser
        355                 360                 365
Gln Glu Asp Pro Glu Val Gln Phe Asn Trp Tyr Val Asp Gly Val Glu
370                 375                 380
Val His Asn Ala Lys Thr Lys Pro Arg Glu Glu Gln Phe Asn Ser Thr
385                 390                 395                 400
```

```
Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
            420                 425                 430

Ile Glu Lys Thr Ile Ser Lys Ala Lys Gly Gln Pro Arg Glu Pro Gln
            435                 440                 445

Val Tyr Thr Leu Pro Pro Ser Gln Glu Glu Met Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
                500                 505                 510

Val Asp Lys Ser Arg Trp Gln Glu Gly Asn Val Phe Ser Cys Ser Val
            515                 520                 525

Met His Glu Ala Leu His Asn His Tyr Thr Gln Lys Ser Leu Ser Leu
    530                 535                 540

Ser Leu Gly Lys
545

<210> SEQ ID NO 30
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205
```

Glu Pro Val Pro Leu Glu Val Gln Leu Val Glu Pro Glu Gly
    210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                245                 250                 255
Pro Leu Pro Pro Ser Pro Val Leu Ile Leu Pro Glu Ile Gly Pro Gln
            260                 265                 270
Asp Gln Gly Thr Tyr Ser Cys Val Ala Thr His Ser Ser His Gly Pro
        275                 280                 285
Gln Glu Ser Arg Ala Val Ser Ile Ser Ile Ile Glu Pro Gly Glu Glu
    290                 295                 300
Gly Pro Thr Ala Gly Glu Gly Phe Asp Lys Val Arg Glu Ala Glu Asp
305                 310                 315                 320
Ser Pro Gln His Ala Glu Arg Lys Cys Cys Val Glu Cys Pro Pro Cys
                325                 330                 335
Ala Pro Pro Val Ala Gly Gly Pro Ser Val Phe Leu Phe Pro Pro Lys
            340                 345                 350
Pro Lys Asp Thr Leu Tyr Ile Thr Arg Glu Pro Glu Val Thr Cys Val
        355                 360                 365
Val Val Asp Val Ser Gln Glu Asp Pro Glu Val Gln Phe Asn Trp Tyr
    370                 375                 380
Val Asp Gly Val Glu Val His Asn Ala Lys Thr Lys Pro Arg Glu Glu
385                 390                 395                 400
Gln Phe Asn Ser Thr Tyr Arg Val Val Ser Val Leu Thr Val Leu His
                405                 410                 415
Gln Asp Trp Leu Asn Gly Lys Glu Tyr Lys Cys Lys Val Ser Asn Lys
            420                 425                 430
Gly Leu Pro Ser Ser Ile Glu Lys Thr Ile Ser Lys Ala Lys Gly Gln
        435                 440                 445
Pro Arg Glu Pro Gln Val Tyr Thr Leu Pro Pro Ser Gln Glu Glu Met
    450                 455                 460
Thr Lys Asn Gln Val Ser Leu Thr Cys Leu Val Lys Gly Phe Tyr Pro
465                 470                 475                 480
Ser Asp Ile Ala Val Glu Trp Glu Ser Asn Gly Gln Pro Glu Asn Asn
                485                 490                 495
Tyr Lys Thr Thr Pro Pro Val Leu Asp Ser Asp Gly Ser Phe Phe Leu
            500                 505                 510
Tyr Ser Arg Leu Thr Val Asp Lys Ser Arg Trp Gln Glu Gly Asn Val
        515                 520                 525
Phe Ser Cys Ser Val Met His Glu Ala Leu His Asn His Tyr Thr Gln
    530                 535                 540
Lys Ser Leu Ser Leu Ser Leu Gly Lys
545                 550

<210> SEQ ID NO 31
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Gln Asn Ile Thr Ala Arg Ile Gly Glu Pro Leu Val Leu Lys Cys

-continued

```
1               5                   10                  15
Lys Gly Ala Pro Lys Pro Pro Gln Arg Leu Glu Trp Lys Leu Asn
                20                  25                  30
Thr Gly Arg Thr Glu Ala Trp Lys Val Leu Ser Pro Gln Gly Gly
                35                  40                  45
Pro Trp Asp Ser Val Ala Arg Val Leu Pro Asn Gly Ser Leu Phe Leu
50                  55                  60
Pro Ala Val Gly Ile Gln Asp Glu Gly Ile Phe Arg Cys Gln Ala Met
65                  70                  75                  80
Asn Arg Asn Gly Lys Glu Thr Lys Ser Asn Tyr Arg Val Arg Val Tyr
                85                  90                  95
Gln Ile Pro Gly Lys Pro Glu Ile Val Asp Ser Ala Ser Glu Leu Thr
                100                 105                 110
Ala Gly Val Pro Asn Lys Val Gly Thr Cys Val Ser Glu Gly Ser Tyr
                115                 120                 125
Pro Ala Gly Thr Leu Ser Trp His Leu Asp Gly Lys Pro Leu Val Pro
                130                 135                 140
Asn Glu Lys Gly Val Ser Val Lys Glu Gln Thr Arg Arg His Pro Glu
145                 150                 155                 160
Thr Gly Leu Phe Thr Leu Gln Ser Glu Leu Met Val Thr Pro Ala Arg
                165                 170                 175
Gly Gly Asp Pro Arg Pro Thr Phe Ser Cys Ser Phe Ser Pro Gly Leu
                180                 185                 190
Pro Arg His Arg Ala Leu Arg Thr Ala Pro Ile Gln Pro Arg Val Trp
                195                 200                 205
Glu Pro Val Pro Leu Glu Glu Val Gln Leu Val Val Glu Pro Glu Gly
                210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                245                 250                 255
Pro Leu Pro Pro Ser Pro Val Leu Ile Leu Pro Glu Ile Gly Pro Gln
                260                 265                 270
Asp Gln Gly Thr Tyr Ser Cys Val Ala Thr His Ser Ser His Gly Pro
                275                 280                 285
Gln Glu Ser Arg Ala Val Ser Ile Ser Ile Ile Glu Pro Gly Glu Glu
                290                 295                 300
Gly Pro Thr Ala Gly Glu Gly Phe Asp Lys Val Arg Glu Ala Glu Asp
305                 310                 315                 320
Ser Pro Gln His Ala Val Glu Cys Pro Pro Cys Ala Pro Pro Val Ala
                325                 330                 335
Gly Pro Ser Val Phe Leu Phe Pro Pro Lys Pro Lys Asp Thr Leu Tyr
                340                 345                 350
Ile Thr Arg Glu Pro Glu Val Thr Cys Val Val Val Asp Val Ser His
                355                 360                 365
Glu Asp Pro Glu Val Gln Phe Asn Trp Tyr Val Asp Gly Val Glu Val
                370                 375                 380
His Asn Ala Lys Thr Lys Pro Arg Glu Glu Gln Phe Asn Ser Thr Phe
385                 390                 395                 400
Arg Val Val Ser Val Leu Thr Val Val His Gln Asp Trp Leu Asn Gly
                405                 410                 415
Lys Glu Tyr Lys Cys Lys Val Ser Asn Lys Gly Leu Pro Ala Pro Ile
                420                 425                 430
```

```
Glu Lys Thr Ile Ser Lys Thr Lys Gly Gln Pro Arg Glu Pro Gln Val
            435                 440                 445

Tyr Thr Leu Pro Pro Ser Arg Glu Glu Met Thr Lys Asn Gln Val Ser
    450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Met Leu Asp Ser Asp Gly Ser Phe Phe Leu Tyr Ser Lys Leu Thr Val
            500                 505                 510

Asp Lys Ser Arg Trp Gln Gln Gly Asn Val Phe Ser Cys Ser Val Met
            515                 520                 525

His Glu Ala Leu His Asn His Tyr Thr Gln Lys Ser Leu Ser Leu Ser
            530                 535                 540

Pro Gly Lys
545

<210> SEQ ID NO 32
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
```

```
                225                 230                 235                 240
Ala Gln Pro Ser Pro Gln Ile His Trp Met Lys Asp Gly Val Pro Leu
                    245                 250                 255

Pro Leu Pro Pro Ser Pro Val Leu Ile Leu Pro Glu Ile Gly Pro Gln
                260                 265                 270

Asp Gln Gly Thr Tyr Ser Cys Val Ala Thr His Ser Ser His Gly Pro
            275                 280                 285

Gln Glu Ser Arg Ala Val Ser Ile Ser Ile Glu Pro Gly Glu Glu
    290                 295                 300

Gly Pro Thr Ala Gly Glu Gly Phe Asp Lys Val Arg Glu Ala Glu Asp
305                 310                 315                 320

Ser Pro Gln His Ala Val Glu Cys Pro Pro Cys Ala Pro Pro Val Ala
                325                 330                 335

Gly Gly Pro Ser Val Phe Leu Phe Pro Pro Lys Pro Lys Asp Thr Leu
            340                 345                 350

Tyr Ile Thr Arg Glu Pro Glu Val Thr Cys Val Val Val Asp Val Ser
        355                 360                 365

His Glu Asp Pro Glu Val Lys Phe Asn Trp Tyr Val Asp Gly Val Glu
    370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Ala Leu Pro Ala Pro
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Arg Asp Glu Leu Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
        515                 520                 525

Met His Glu Ala Leu His Asn His Tyr Thr Gln Lys Ser Leu Ser Leu
    530                 535                 540

Ser Pro Gly Lys
545

<210> SEQ ID NO 33
<211> LENGTH: 554
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30
```

```
Thr Gly Arg Thr Glu Ala Trp Lys Val Leu Ser Pro Gln Gly Gly
         35                  40                  45

Pro Trp Asp Ser Val Ala Arg Val Leu Pro Asn Gly Ser Leu Phe Leu
 50                  55                  60

Pro Ala Val Gly Ile Gln Asp Glu Gly Ile Phe Arg Cys Gln Ala Met
 65                  70                  75                  80

Asn Arg Asn Gly Lys Glu Thr Lys Ser Asn Tyr Arg Val Arg Val Tyr
                 85                  90                  95

Gln Ile Pro Gly Lys Pro Glu Ile Val Asp Ser Ala Ser Glu Leu Thr
                100                 105                 110

Ala Gly Val Pro Asn Lys Val Gly Thr Cys Val Ser Glu Gly Ser Tyr
                115                 120                 125

Pro Ala Gly Thr Leu Ser Trp His Leu Asp Gly Lys Pro Leu Val Pro
        130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
                180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
        210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
                260                 265                 270

Asp Gln Gly Thr Tyr Ser Cys Val Ala Thr His Ser Ser His Gly Pro
                275                 280                 285

Gln Glu Ser Arg Ala Val Ser Ile Ser Ile Ile Glu Pro Gly Glu Glu
        290                 295                 300

Gly Pro Thr Ala Gly Glu Gly Phe Asp Lys Val Arg Glu Ala Glu Asp
305                 310                 315                 320

Ser Pro Gln His Ala Glu Ser Lys Tyr Gly Pro Cys Pro Pro Cys
                325                 330                 335

Pro Ala Pro Glu Ala Ala Gly Gly Pro Ser Val Phe Leu Phe Pro Pro
                340                 345                 350

Lys Pro Lys Asp Thr Leu Tyr Ile Thr Arg Glu Pro Glu Val Thr Cys
        355                 360                 365

Val Val Val Asp Val Ser His Glu Asp Pro Glu Val Lys Phe Asn Trp
        370                 375                 380

Tyr Val Asp Gly Val Glu Val His Asn Ala Lys Thr Lys Pro Arg Glu
385                 390                 395                 400

Glu Gln Tyr Asn Ser Thr Tyr Arg Val Val Ser Val Leu Thr Val Leu
                405                 410                 415

His Gln Asp Trp Leu Asn Gly Lys Glu Tyr Lys Cys Lys Val Ser Asn
                420                 425                 430

Lys Ala Leu Pro Ala Pro Ile Glu Lys Thr Ile Ser Lys Ala Lys Gly
        435                 440                 445

Gln Pro Arg Glu Pro Gln Val Tyr Thr Leu Pro Pro Ser Arg Asp Glu
```

```
                    450                 455                 460
Leu Thr Lys Asn Gln Val Ser Leu Thr Cys Leu Val Lys Gly Phe Tyr
465                 470                 475                 480

Pro Ser Asp Ile Ala Val Glu Trp Glu Ser Asn Gly Gln Pro Glu Asn
                    485                 490                 495

Asn Tyr Lys Thr Thr Pro Pro Val Leu Asp Ser Asp Gly Ser Phe Phe
                500                 505                 510

Leu Tyr Ser Lys Leu Thr Val Asp Lys Ser Arg Trp Gln Gln Gly Asn
            515                 520                 525

Val Phe Ser Cys Ser Val Met His Glu Ala Leu His Asn His Tyr Thr
        530                 535                 540

Gln Lys Ser Leu Ser Leu Ser Pro Gly Lys
545                 550

<210> SEQ ID NO 34
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
                20                  25                  30

Thr Gly Arg Thr Glu Ala Trp Lys Val Leu Ser Pro Gln Gly Gly Gly
            35                  40                  45

Pro Trp Asp Ser Val Ala Arg Val Leu Pro Asn Gly Ser Leu Phe Leu
        50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
        130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
        210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255
```

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser His Gly Pro
        275                 280                 285

Gln Glu Ser Arg Ala Val Ser Ile Ser Ile Glu Pro Gly Glu Glu
    290                 295                 300

Gly Pro Thr Ala Gly Glu Gly Phe Asp Lys Val Arg Glu Ala Glu Asp
305                 310                 315                 320

Ser Pro Gln His Ala Glu Pro Lys Ser Cys Asp Lys Thr His Thr Cys
                325                 330                 335

Pro Pro Cys Pro Ala Pro Glu Ala Ala Gly Gly Pro Ser Val Phe Leu
            340                 345                 350

Phe Pro Pro Lys Pro Lys Asp Thr Leu Tyr Ile Thr Arg Glu Pro Glu
        355                 360                 365

Val Thr Cys Val Val Val Asp Val Ser His Glu Asp Pro Glu Val Lys
    370                 375                 380

Phe Asn Trp Tyr Val Asp Gly Val Glu Val His Asn Ala Lys Thr Lys
385                 390                 395                 400

Pro Arg Glu Glu Gln Tyr Asn Ser Thr Tyr Arg Val Val Ser Val Leu
                405                 410                 415

Thr Val Leu His Gln Asp Trp Leu Asn Gly Lys Glu Tyr Lys Cys Lys
            420                 425                 430

Val Ser Asn Lys Ala Leu Pro Ala Pro Ile Glu Lys Thr Ile Ser Lys
        435                 440                 445

Ala Lys Gly Gln Pro Arg Glu Pro Gln Val Tyr Thr Leu Pro Pro Ser
    450                 455                 460

Arg Asp Glu Leu Thr Lys Asn Gln Val Ser Leu Thr Cys Leu Val Lys
465                 470                 475                 480

Gly Phe Tyr Pro Ser Asp Ile Ala Val Glu Trp Glu Ser Asn Gly Gln
                485                 490                 495

Pro Glu Asn Asn Tyr Lys Thr Thr Pro Pro Val Leu Asp Ser Asp Gly
            500                 505                 510

Ser Phe Phe Leu Tyr Ser Lys Leu Thr Val Asp Lys Ser Arg Trp Gln
        515                 520                 525

Gln Gly Asn Val Phe Ser Cys Ser Val Met His Glu Ala Leu His Asn
    530                 535                 540

His Tyr Thr Gln Lys Ser Leu Ser Leu Ser Pro Gly Lys
545                 550                 555

<210> SEQ ID NO 35
<211> LENGTH: 554
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

```
Pro Ala Val Gly Ile Gln Asp Glu Gly Ile Phe Arg Cys Gln Ala Met
 65                  70                  75                  80

Asn Arg Asn Gly Lys Glu Thr Lys Ser Asn Tyr Arg Val Arg Val Tyr
                 85                  90                  95

Gln Ile Pro Gly Lys Pro Glu Ile Val Asp Ser Ala Ser Glu Leu Thr
                100                 105                 110

Ala Gly Val Pro Asn Lys Val Gly Thr Cys Val Ser Glu Gly Ser Tyr
                115                 120                 125

Pro Ala Gly Thr Leu Ser Trp His Leu Asp Gly Lys Pro Leu Val Pro
130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
                180                 185                 190

Pro Arg His Arg Ala Leu Arg Thr Ala Pro Ile Gln Pro Arg Val Trp
                195                 200                 205

Glu Pro Val Pro Leu Glu Glu Val Gln Leu Val Val Glu Pro Glu Gly
210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
                260                 265                 270

Asp Gln Gly Thr Tyr Ser Cys Val Ala Thr His Ser Ser His Gly Pro
                275                 280                 285

Gln Glu Ser Arg Ala Val Ser Ile Ser Ile Ile Glu Pro Gly Glu Glu
                290                 295                 300

Gly Pro Thr Ala Gly Glu Gly Phe Asp Lys Val Arg Glu Ala Glu Asp
305                 310                 315                 320

Ser Pro Gln His Ala Glu Ser Lys Tyr Gly Pro Pro Cys Pro Pro Cys
                325                 330                 335

Pro Ala Pro Glu Ala Ala Gly Gly Pro Ser Val Phe Leu Phe Pro Pro
                340                 345                 350

Lys Pro Lys Asp Thr Leu Tyr Ile Thr Arg Glu Pro Glu Val Thr Cys
                355                 360                 365

Val Val Val Asp Val Ser Gln Glu Asp Pro Glu Val Gln Phe Asn Trp
                370                 375                 380

Tyr Val Asp Gly Val Glu Val His Asn Ala Lys Thr Lys Pro Arg Glu
385                 390                 395                 400

Glu Gln Phe Asn Ser Thr Tyr Arg Val Val Ser Val Leu Thr Val Leu
                405                 410                 415

His Gln Asp Trp Leu Asn Gly Lys Glu Tyr Lys Cys Lys Val Ser Asn
                420                 425                 430

Lys Gly Leu Pro Ser Ser Ile Glu Lys Thr Ile Ser Lys Ala Lys Gly
                435                 440                 445

Gln Pro Arg Glu Pro Gln Val Tyr Thr Leu Pro Pro Ser Gln Glu Glu
                450                 455                 460

Met Thr Lys Asn Gln Val Ser Leu Thr Cys Leu Val Lys Gly Phe Tyr
465                 470                 475                 480
```

```
Pro Ser Asp Ile Ala Val Glu Trp Glu Ser Asn Gly Gln Pro Glu Asn
            485                 490                 495

Asn Tyr Lys Thr Thr Pro Pro Val Leu Asp Ser Asp Gly Ser Phe Phe
        500                 505                 510

Leu Tyr Ser Arg Leu Thr Val Asp Lys Ser Arg Trp Gln Glu Gly Asn
        515                 520                 525

Val Phe Ser Cys Ser Val Met His Glu Ala Leu His Asn His Tyr Thr
530                 535                 540

Gln Lys Ser Leu Ser Leu Ser Leu Gly Lys
545                 550

<210> SEQ ID NO 36
<211> LENGTH: 562
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285
```

```
Gln Glu Ser Arg Ala Val Ser Ile Ser Ile Ile Pro Gly Glu Glu
        290                 295                 300

Gly Pro Thr Ala Gly Glu Gly Phe Asp Lys Val Arg Glu Ala Glu Asp
305                 310                 315                 320

Ser Pro Gln His Ala Gly Thr Leu Val Thr Val Ser Glu Ser Lys
            325                 330                 335

Tyr Gly Pro Pro Cys Pro Pro Cys Pro Ala Pro Glu Ala Ala Gly Gly
            340                 345                 350

Pro Ser Val Phe Leu Phe Pro Pro Lys Pro Lys Asp Thr Leu Tyr Ile
            355                 360                 365

Thr Arg Glu Pro Glu Val Thr Cys Val Val Val Asp Val Ser Gln Glu
370                 375                 380

Asp Pro Glu Val Gln Phe Asn Trp Tyr Val Asp Gly Val Glu Val His
385                 390                 395                 400

Asn Ala Lys Thr Lys Pro Arg Glu Glu Gln Phe Asn Ser Thr Tyr Arg
                405                 410                 415

Val Val Ser Val Leu Thr Val Leu His Gln Asp Trp Leu Asn Gly Lys
                420                 425                 430

Glu Tyr Lys Cys Lys Val Ser Asn Lys Gly Leu Pro Ser Ser Ile Glu
            435                 440                 445

Lys Thr Ile Ser Lys Ala Lys Gly Gln Pro Arg Glu Pro Gln Val Tyr
450                 455                 460

Thr Leu Pro Pro Ser Gln Glu Glu Met Thr Lys Asn Gln Val Ser Leu
465                 470                 475                 480

Thr Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Arg Leu Thr Val Asp
            515                 520                 525

Lys Ser Arg Trp Gln Glu Gly Asn Val Phe Ser Cys Ser Val Met His
530                 535                 540

Glu Ala Leu His Asn His Tyr Thr Gln Lys Ser Leu Ser Leu Ser Leu
545                 550                 555                 560

Gly Lys

<210> SEQ ID NO 37
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Gln Glu Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
                20                  25                  30

Thr Gly Arg Thr Glu Ala Trp Lys Val Leu Ser Pro Gln Gly Gly Gly
            35                  40                  45

Pro Trp Asp Ser Val Ala Arg Val Leu Pro Asn Ser Ser Leu Phe Leu
        50                  55                  60

Pro Ala Val Gly Ile Gln Asp Glu Gly Ile Phe Arg Cys Gln Ala Met
65                  70                  75                  80
```

```
Asn Arg Asn Gly Lys Glu Thr Lys Ser Asn Tyr Arg Val Arg Val Tyr
            85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
            115                 120                 125

Pro Ala Gly Thr Leu Ser Trp His Leu Asp Gly Lys Pro Leu Val Pro
            130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
                180                 185                 190

Pro Arg His Arg Ala Leu Arg Thr Ala Pro Ile Gln Pro Arg Val Trp
            195                 200                 205

Glu Pro Val Pro Leu Glu Glu Val Gln Leu Val Val Glu Pro Glu Gly
            210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
                260                 265                 270

Asp Gln Gly Thr Tyr Ser Cys Val Ala Thr His Ser Ser His Gly Pro
            275                 280                 285

Gln Glu Ser Arg Ala Val Ser Ile Ser Ile Ile Glu Pro Gly Glu Glu
            290                 295                 300

Gly Pro Thr Ala Gly Ser Val Gly Gly Ser Gly Leu Gly Thr Leu Ala
305                 310                 315                 320

Leu Ala Ile Glu Gly Arg Met Pro Lys Ser Cys Asp Lys Thr His Thr
                325                 330                 335

Cys Pro Pro Cys Pro Ala Pro Glu Leu Leu Gly Gly Pro Ser Val Phe
                340                 345                 350

Leu Phe Pro Pro Lys Pro Lys Asp Thr Leu Met Ile Ser Arg Thr Pro
            355                 360                 365

Glu Val Thr Cys Val Val Val Asp Val Ser His Glu Asp Pro Glu Val
            370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
                405                 410                 415

Leu Thr Val Leu His Gln Asp Trp Leu Asn Gly Lys Glu Tyr Lys Cys
                420                 425                 430

Lys Val Ser Asn Lys Ala Leu Pro Ala Pro Ile Glu Lys Thr Ile Ser
            435                 440                 445

Lys Ala Lys Gly Gln Pro Arg Glu Pro Gln Val Tyr Thr Leu Pro Pro
            450                 455                 460

Ser Arg Asp Glu Leu Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
                485                 490                 495
```

```
Gln Pro Glu Asn Asn Tyr Lys Thr Thr Pro Pro Val Leu Asp Ser Asp
            500                 505                 510

Gly Ser Phe Phe Leu Tyr Ser Lys Leu Thr Val Asp Lys Ser Arg Trp
        515                 520                 525

Gln Gln Gly Asn Val Phe Ser Cys Ser Val Met His Glu Ala Leu His
    530                 535                 540

Asn His Tyr Thr Gln Lys Ser Leu Ser Leu Ser Pro Gly Lys
545                 550                 555

<210> SEQ ID NO 38
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gctcagaata tcaccgccag aatcggcgag ccctggtgc tgaaatgtaa aggcgcct      60
aagaagcctc ctcagcggct ggaatggaag ctgaacaccg gcagaaccga ggcctggaaa  120
gtgctgtctc ctcaaggcgg aggccttgg gattctgtgg ctagagtgct gcctaacggc   180
tccctgtttc tgcctgctgt gggcatccag gacgagggca tcttcaggtg tcaggccatg   240
aaccggaacg gcaaagagac aaagtccaac taccgcgtca gagtgtatca gatccccggc   300
aagcctgaga tcgtggactc tgcctctgaa ctgacagccg gcgtgcccaa caaagtgggc   360
acttgtgtgt ccgagggcag ctatcctgct ggcaccctgt cttggcatct ggatggaaag   420
cctctggtgc ccaacgagaa aggcgtgtcc gtgaaagagc agaccagacg gcatcctgag   480
actggcctgt tcaccctgca gtccgagctg atggttaccc tgctagagg cggcgatccc    540
agacctacct tcagctgctc cttctctcct ggcctgcctc acatagagc cctgagaacc     600
gctcctatcc agcctagagt gtgggagcct gtgcctctgg aagaggtgca gctggtggtt    660
gaacctgaag gcggagctgt tgctcctggc ggaacagtga ccctgacctg tgaagttccc    720
gctcagccct ctccacagat ccactggatg aaggatggcg tgccactgcc tctgcctcca    780
tctcctgttc tgatcctgcc agagatcggc cctcaggacc agggcaccta ttcttgtgtg    840
gctacccact cctctcacgg ccctcaagag tctagagccg tgtccatctc catcatcgag    900
cctggcgagg aaggccctac agctggttct gttggaggct ctggactggg cacactggcc    960
ctggctattg agggcagaat gcccaagtcc tgcgacaaga cccacacctg tcctccatgt   1020
cctgctccag aactgctcgg cggaccttcc gtgttcctgt ttcctccaaa gcctaaggac   1080
accctgatga tctctcggac ccctgaagtg acctgcgtgg tggtggatgt gtctcacgag   1140
gatcccgaag tgaagttcaa ttggtacgtg acggcgtgg aagtgcacaa cgccaagacc    1200
aagcctagag aggaacagta caactccacc tacagagtgg tgtccgtgct gaccgtgctg   1260
caccaggatt ggctgaatgg caaagagtat aagtgcaagg tgtccaacaa ggcccctgcct  1320
gctcctatcg aaaagaccat ctccaaggcc aagggccagc ctagggaacc ccaggtttac   1380
accttgccac cttctcggga cgagctgacc aagaaccagg tgtccctgac atgcctggtc   1440
aagggcttct accctccga tatcgccgtg gaatgggagt ctaatggcca gcctgagaac    1500
aactacaaga caacccctcc tgtgctggac tccgacggct cattcttcct gtactccaag   1560
ctgacagtgg acaagtccag atggcagcag ggcaacgtgt tctcctgctc cgtgatgcac   1620
gaggccctgc acaatcacta cacccagaag tccctgtctc tgtccctgg caaatga      1677
```

<210> SEQ ID NO 39
<211> LENGTH: 1665
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
gctcagaata tcaccgccag aatcggcgag ccctggtgc tgaaatgtaa aggcgcccct      60
aagaagcctc ctcagcggct ggaatggaag ctgaacaccg gcagaaccga ggcctggaaa    120
gtgctgtctc ctcaaggcgg aggcccttgg gattctgtgg ctagagtgct gcctaacggc    180
tccctgtttc tgcctgctgt gggcatccag gacgagggca tcttcaggtg tcaggccatg    240
aaccggaacg gcaaagagac aaagtccaac taccgcgtca gagtgtatca gatcccggc    300
aagcctgaga tcgtggactc tgcctctgaa ctgacagccg gcgtgcccaa caaagtgggc    360
acttgtgtgt ccgagggcag ctatcctgct ggcaccctgt cttggcatct ggatggaaag    420
cctctggtgc ccaacgagaa aggcgtgtcc gtgaaagagc agaccagacg gcatcctgag    480
actggcctgt tcaccctgca gtccgagctg atggttaccc ctgctagagg cggcgatccc    540
agacctacct tcagctgctc cttctctcct ggcctgcctc gacatagagc cctgagaacc    600
gctcctatcc agcctagagt gtgggagcct gtgcctctgg aagaggtgca gctggtggtt    660
gaacctgaag gcggagctgt tgctcctggc ggaacagtga ccctgacctg tgaagttccc    720
gctcagccct ctccacagat ccactggatg aaggatggcg tgccactgcc tctgcctcca    780
tctcctgttc tgatcctgcc agagatcggc cctcaggacc agggcaccta ttcttgtgtg    840
gctacccact cctctcacgg ccctcaagag tctagagccg tgtccatctc catcatcgag    900
cctggcgagg aaggacctac agctggcgag ggctttgaca agtgcgcga ggccgaggat    960
tctcctcagc atgctgagtc taagtacggc cctccttgtc ctccatgtcc tgctccagaa   1020
gctgctggcg gccttccgt gtttctgttc cctccaaagc ctaaggacac cctgatgatc   1080
tctcggaccc ctgaagtgac ctgcgtggtg gtggatgtgt cccaagagga tcccgaggtg   1140
cagttcaatt ggtacgtgga cggcgtggaa gtgcacaacg ccaagaccaa gcctagagag   1200
gaacagttca actccaccta cagagtggtg tccgtgctga ccgtgctgca ccaggattgg   1260
ctgaatggca aagagtataa gtgcaaggtg tccaacaagg gcctgccttc cagcatcgaa   1320
aagaccatct ccaaggccaa gggccagcct agggaacccc aggtttacac cctgcctcca   1380
agccaagagg aaatgaccaa gaaccaggtg tccctgacat gcctggtcaa gggcttctac   1440
ccctccgata tcgccgtgga atgggagtct aatggccagc ctgagaacaa ctacaagacc   1500
acacctcctg tgctggactc cgacggcagc ttctttctgt actcccgcct gaccgtggac   1560
aagtccaggt ggcaagaggg caacgtgttc tcctgctccg tgatgcacga ggccctgcac   1620
aatcactaca cccagaagtc cctgtctctg tccctgggca atga                    1665
```

<210> SEQ ID NO 40
<211> LENGTH: 1689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
gctcagaata tcaccgccag aatcggcgag ccctggtgc tgaaatgtaa aggcgcccct      60
```

```
aagaagcctc ctcagcggct ggaatggaag ctgaacaccg gcagaaccga ggcctggaaa     120
gtgctgtctc ctcaaggcgg aggcccttgg gattctgtgg ctagagtgct gcctaacggc     180
tccctgtttc tgcctgctgt gggcatccag gacgagggca tcttcaggtg tcaggccatg     240
aaccggaacg gcaaagagac aaagtccaac taccgcgtca gagtgtatca gatccccggc     300
aagcctgaga tcgtggactc tgcctctgaa ctgacagccg gcgtgcccaa caaagtgggc     360
acttgtgtgt ccgagggcag ctatcctgct ggcaccctgt cttggcatct ggatggaaag     420
cctctggtgc ccaacgagaa aggcgtgtcc gtgaaagagc agaccagacg gcatcctgag     480
actggcctgt tcaccctgca gtccgagctg atggttaccc ctgctagagg cggcgatccc     540
agacctacct tcagctgctc cttctctcct ggcctgcctc gacatagagc cctgagaacc     600
gctcctatcc agcctagagt gtgggagcct gtgcctctgg aagaggtgca gctggtggtt     660
gaacctgaag gcggagctgt tgctcctggc ggaacagtga ccctgacctg tgaagttccc     720
gctcagcccc tccacagat ccactggatg aaggatggcg tgccactgcc tctgcctcca     780
tctcctgttc tgatcctgcc agagatcggc cctcaggacc agggcaccta ttcttgtgtg     840
gctacccact cctctcacgg ccctcaagag tctagagccg tgtccatctc catcatcgag     900
cctggcgagg aaggacctac agctggcgag ggctttgaca aagtgcgcga ggctgaggac     960
tctcctcagc atgccggaac actggtcacc gtgtcctccg agtctaagta cggcccctct    1020
tgtcctccat gtcctgctcc agaagctgct ggcggccctt ccgtgtttct gttccctcca    1080
aagcctaagg acaccctgat gatctctcgg accctgaag tgacctgcgt ggtggtggat    1140
gtgtcccaag aggatcccga ggtgcagttc aattggtacg tggacggcgt ggaagtgcac    1200
aacgccaaga ccaagcctag agaggaacag ttcaactcca cctacagagt ggtgtccgtg    1260
ctgaccgtgc tgcaccagga ttggctgaat ggcaaagagt ataagtgcaa ggtgtccaac    1320
aagggcctgc cttccagcat cgaaaagacc atctccaagg ccaagggcca gcctagggaa    1380
ccccaggttt acaccctgcc tccaagccaa gaggaaatga ccaagaacca ggtgtccctg    1440
acatgcctgg tcaagggctt ctaccccctcc gatatcgccg tggaatggga gtctaatggc    1500
cagcctgaga caactacaa gaccacacct cctgtgctgg actccgacgg cagcttcttt    1560
ctgtactccc gcctgaccgt ggacaagtcc aggtggcaag agggcaacgt gttctcctgc    1620
tccgtgatgc acgaggccct gcacaatcac tacacccaga gtccctgtc tctgtccctg    1680 ggcaaatga                                                            1689
```

<210> SEQ ID NO 41
<211> LENGTH: 1647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
gctcagaata tcaccgccag aatcggcgag ccctggtgc tgaaatgtaa aggcgcccct      60
aagaagcctc ctcagcggct ggaatggaag ctgaacaccg gcagaaccga ggcctggaaa    120
gtgctgtctc ctcaaggcgg aggcccttgg gattctgtgg ctagagtgct gcctaacggc    180
tccctgtttc tgcctgctgt gggcatccag gacgagggca tcttcaggtg tcaggccatg    240
aaccggaacg gcaaagagac aaagtccaac taccgcgtca gagtgtatca gatccccggc    300
aagcctgaga tcgtggactc tgcctctgaa ctgacagccg gcgtgcccaa caaagtgggc    360
```

```
acttgtgtgt ccgagggcag ctatcctgct ggcaccctgt cttggcatct ggatggaaag      420
cctctggtgc ccaacgagaa aggcgtgtcc gtgaaagagc agaccagacg gcatcctgag      480
actggcctgt tcaccctgca gtccgagctg atggttaccc ctgctagagg cggcgatccc      540
agacctacct tcagctgctc cttctctcct ggcctgcctc gacatagagc cctgagaacc      600
gctcctatcc agcctagagt gtgggagcct gtgcctctgg aagaggtgca gctggtggtt      660
gaacctgaag gcggagctgt tgctcctggc ggaacagtga ccctgacctg tgaagttccc      720
gctcagccct ctccacagat ccactggatg aaggatggcg tgccactgcc tctgcctcca      780
tctcctgttc tgatcctgcc agagatcggc cctcaggacc agggcaccta ttcttgtgtg      840
gctacccact cctctcacgg ccctcaagag tctagagccg tgtccatctc catcatcgag      900
cctggcgagg aaggacctac agctggcgag ggctttgaca aagtgcgcga ggctgaggac      960
tctcctcagc atgccgtgga atgccctcct tgtgctcctc ctgtggctgg cggcccttcc     1020
gtgtttctgt tccctccaaa gcctaaggac accctgatga tctctcggac ccctgaagtg     1080
acctgcgtgg tggtggatgt gtcccaagag gatcccgagg tgcagttcaa ttggtacgtg     1140
gacggcgtgg aagtgcacaa cgccaagacc aagcctagag aggaacagtt caactccacc     1200
tacagagtgg tgtccgtgct gaccgtgctg caccaggatt ggctgaatgg caaagagtat     1260
aagtgcaagg tgtccaacaa gggcctgcct tccagcatcg aaaagaccat ctccaaggcc     1320
aagggccagc ctagggaacc ccaggtttac accctgcctc caagccaaga ggaaatgacc     1380
aagaaccagg tgtccctgac atgcctggtc aagggcttct accctccgga tatcgccgtg     1440
gaatgggagt ctaatggcca gcctgagaac aactacaaga ccacacctcc tgtgctggac     1500
tccgacggca gcttctttct gtactcccgc ctgaccgtgg acaagtccag gtggcaagag     1560
ggcaacgtgt tctcctgctc cgtgatgcac gaggccctgc acaatcacta cacccagaag     1620
tccctgtctc tgtccctggg caaatga                                         1647
```

<210> SEQ ID NO 42
<211> LENGTH: 1677
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
gctcaggaga tcaccgccag aatcggcgag cccctggtgc tgaaatgtaa aggcgcccct       60
aagaagcctc ctcagcggct ggaatggaag ctgaacaccg gcagaaccga ggcctggaaa      120
gtgctgtctc ctcaaggcgg aggccccttgg gattctgtgg ctagagtgct gcctaactcc      180
tccctgtttc tgcctgctgt gggcatccag gacgagggca tcttcaggtg tcaggccatg      240
aaccggaacg gcaaagagac aaagtccaac taccgcgtca gagtgtatca gatccccggc      300
aagcctgaga tcgtggactc tgcctctgaa ctgacagccg cgtgcccaa caaagtgggc      360 acttgtgtgt ccgagggcag ctatcctgct ggcaccctgt cttggcatct ggatggaaag      420
cctctggtgc ccaacgagaa aggcgtgtcc gtgaaagagc agaccagacg gcatcctgag      480
actggcctgt tcaccctgca gtccgagctg atggttaccc ctgctagagg cggcgatccc      540
agacctacct tcagctgctc cttctctcct ggcctgcctc gacatagagc cctgagaacc      600
gctcctatcc agcctagagt gtgggagcct gtgcctctgg aagaggtgca gctggtggtt      660
gaacctgaag gcggagctgt tgctcctggc ggaacagtga ccctgacctg tgaagttccc      720
```

```
gctcagccct ctccacagat ccactggatg aaggatggcg tgccactgcc tctgcctcca      780
tctcctgttc tgatcctgcc agagatcggc cctcaggacc agggcaccta ttcttgtgtg      840
gctacccact cctctcacgg ccctcaagag tctagagccg tgtccatctc catcatcgag      900
cctggcgagg aaggccctac agctggttct gttggaggct ctggactggg cactggcc       960 ctggctattg agggcagaat gcccaagtcc tgcgacaaga cccacacctg tcctccatgt     1020
cctgctccag aactgctcgg cggaccttcc gtgttcctgt ttcctccaaa gcctaaggac     1080
accctgatga tctctcggac ccctgaagtg acctgcgtgg tggtggatgt gtctcacgag     1140
gatcccgaag tgaagttcaa ttggtacgtg acggcgtgg aagtgcacaa cgccaagacc      1200
aagcctagag aggaacagta caactccacc tacagagtgg tgtccgtgct gaccgtgctg     1260
caccaggatt ggctgaatgg caaagagtat aagtgcaagg tgtccaacaa ggccctgcct     1320
gctcctatcg aaaagaccat ctccaaggcc aagggccagc ctagggaacc ccaggtttac     1380
accttgccac cttctcggga cgagctgacc aagaaccagg tgtccctgac atgcctggtc     1440
aagggcttct acccctccga tatcgccgtg gaatgggagt ctaatggcca gcctgagaac     1500
aactacaaga caaccctcc tgtgctggac tccgacggct cattcttcct gtactccaag      1560
ctgacagtgg acaagtccag atggcagcag ggcaacgtgt tctcctgctc cgtgatgcac     1620
gaggccctgc acaatcacta cacccagaag tccctgtctc tgtccctgg caaatga         1677
```

<210> SEQ ID NO 43
<211> LENGTH: 1647
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
gctcagaata tcaccgccag aatcggcgag cccctggtgc tgaaatgtaa aggcgcccct       60
aagaagcctc ctcagcggct ggaatggaag ctgaacaccg gcagaaccga ggcctggaaa      120
gtgctgtctc ctcaaggcgg aggccttgg gattctgtgg ctagagtgct gcctaacggc      180
tccctgtttc tgcctgctgt gggcatccag gacgagggca tcttcaggtg tcaggccatg      240
aaccggaacg gcaaagagac aaagtccaac taccgcgtca gagtgtatca gatccccggc      300
aagcctgaga tcgtggactc tgcctctgaa ctgacagccg gcgtgcccaa caaagtgggc      360
acttgtgtgt ccgagggcag ctatcctgct ggcacccgt cttggcatct ggatggaaag      420
cctctggtgc ccaacgagaa aggcgtgtcc gtgaaagagc agaccagacg gcatcctgag      480
actggcctgt tcaccctgca gtccgagctg atggttaccc ctgctagagg cggcgatccc      540
agacctacct tcagctgctc cttctctcct ggcctgcctc gacatagagc cctgagaacc      600
gctcctatcc agcctagagt gtgggagcct gtgcctctgg aagaggtgca gctggtggtt     660
gaacctgaag gcggagctgt tgctcctggc ggaacagtga ccctgacctg tgaagttccc     720
gctcagccct ctccacagat ccactggatg aaggatggcg tgccactgcc tctgcctcca     780
tctcctgttc tgatcctgcc agagatcggc cctcaggacc agggcaccta ttcttgtgtg     840
gctacccact cctctcacgg ccctcaagag tctagagccg tgtccatctc catcatcgag     900
cctggcgagg aaggacctac agctggcgag ggctttgaca agtgcgcga ggctgaggac     960 tctcctcagc acgctgttga gtgccctcca tgtgctcctc agttgctgg tggcccttcc     1020 gtgttcctgt ttcctccaaa gcctaaggac accctgtaca tcacccgcga gctgaagtg     1080
```

```
acctgcgtgg tggtggatgt gtcccaagag gatcccgagg tgcagttcaa ttggtacgtg    1140
gacggcgtgg aagtgcacaa cgccaagacc aagcctagag aggaacagtt caactccacc    1200
tacagagtgg tgtccgtgct gaccgtgctg caccaggatt ggctgaatgg caaagagtat    1260
aagtgcaagg tgtccaacaa gggcctgcct tccagcatcg aaaagaccat ctccaaggcc    1320
aagggccagc ctagggaacc ccaggtttac accctgcctc caagccaaga ggaaatgacc    1380
aagaaccagg tgtccctgac atgcctggtc aagggcttct acccctccga tatcgccgtg    1440
gaatgggagt ctaatggcca gcctgagaac aactacaaga ccacacctcc tgtgctggac    1500
tccgacggca gcttctttct gtactcccgc ctgaccgtgg acaagtccag gtggcaagag    1560
ggcaacgtgt tctcctgctc cgtgatgcac gaggccctgc acaatcacta cacccagaag    1620
tccctgtctc tgtccctggg caaatga                                        1647

<210> SEQ ID NO 44
<211> LENGTH: 1647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gctcaggaaa tcaccgccag aatcggcgag cccctggtgc tgaaatgtaa aggcgcccct      60
aagaagcctc ctcagcggct ggaatggaag ctgaacaccg gcagaaccga ggcctggaaa     120
gtgctgtctc tcaaggcgg aggcccttgg gattctgtgg ctagagtgct gcctaacggc     180
tccctgtttc tgcctgctgt gggcatccag gacgagggca tcttcaggtg tcaggccatg     240
aaccggaacg gcaaagagac aaagtccaac taccgcgtca gagtgtatca gatccccggc     300
aagcctgaga tcgtggactc tgcctctgaa ctgacagccg gcgtgcccaa caaagtgggc     360
acttgtgtgt ccgagggcag ctatcctgct ggcaccctgt cttggcatct ggatggaaag     420
cctctggtgc ccaacgagaa aggcgtgtcc gtgaaagagc agaccagacg gcatcctgag     480
actggcctgt tcaccctgca gtccgagctg atggttaccc ctgctagagg cggcgatccc     540
agacctacct tcagctgctc cttctctcct ggcctgcctc gacatagagc cctgagaacc     600
gctcctatcc agcctagagt gtgggagcct gtgcctctgg aagaggtgca gctggtggtt     660
gaacctgaag gcggagctgt tgctcctggc ggaacagtga ccctgacctg tgaagttccc    720
gctcagccct ctccacagat ccactggatg aaggatggcg tgccactgcc tctgcctcca    780
tctcctgttc tgatcctgcc agagatcggc cctcaggacc agggcaccta ttcttgtgtg    840
gctacccact cctctcacgg ccctcaagag tctagagccg tgtccatctc catcatcgag    900
cctggcgagg aaggacctac agctggcgag ggctttgaca agtgcgcga ggctgaggac     960 tctcctcagc acgctgttga gtgccctcca tgtgctcctc agttgctgg tggcccttcc    1020 gtgttcctgt ttcctccaaa gcctaaggac acctgatga tctctcgcac ccctgaagtg    1080
acctgcgtgg tggtggatgt gtcccaagag gatcccgagg tgcagttcaa ttggtacgtg    1140
gacggcgtgg aagtgcacaa cgccaagacc aagcctagag aggaacagtt caactccacc    1200
tacagagtgg tgtccgtgct gaccgtgctg caccaggatt ggctgaatgg caaagagtat    1260
aagtgcaagg tgtccaacaa gggcctgcct tccagcatcg aaaagaccat ctccaaggcc    1320
aagggccagc ctagggaacc ccaggtttac accctgcctc caagccaaga ggaaatgacc    1380
aagaaccagg tgtccctgac atgcctggtc aagggcttct acccctccga tatcgccgtg    1440
```

```
gaatgggagt ctaatggcca gcctgagaac aactacaaga ccacacctcc tgtgctggac    1500
tccgacggca gcttctttct gtactcccgc ctgaccgtgg acaagtccag gtggcaagag    1560
ggcaacgtgt tctcctgctc cgtgatgcac gaggccctgc acaatcacta cacccagaag    1620
tccctgtctc tgtccctggg caaatga                                        1647
```

<210> SEQ ID NO 45
<211> LENGTH: 1647
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gctcagcaga tcaccgccag aatcggcgag cccctggtgc tgaaatgtaa aggcgcccct     60
aagaagcctc ctcagcggct ggaatggaag ctgaacaccg gcagaaccga ggcctggaaa    120
gtgctgtctc tcaaggcgg aggcccttgg gattctgtgg ctagagtgct gcctaacggc    180
tccctgtttc tgcctgctgt gggcatccag gacgagggca tcttcaggtg tcaggccatg    240
aaccggaacg gcaaagagac aaagtccaac taccgcgtca gagtgtatca gatccccggc    300
aagcctgaga tcgtggactc tgcctctgaa ctgacagccg gcgtgcccaa caaagtgggc    360
acttgtgtgt ccgagggcag ctatcctgct ggcaccctgt cttggcatct ggatggaaag    420
cctctggtgc ccaacgagaa aggcgtgtcc gtgaaagagc agaccagacg gcatcctgag    480
actggcctgt tcaccctgca gtccgagctg atggttaccc ctgctagagg cggcgatccc    540
agacctacct tcagctgctc cttctctcct ggcctgcctc gacatagagc cctgagaacc    600
gctcctatcc agcctagagt gtgggagcct gtgcctctgg aagaggtgca gctggtggtt    660
gaacctgaag gcggagctgt tgctcctggc ggaacagtga ccctgacctg tgaagttccc    720
gctcagcccc tccacagat ccactggatg aaggatggcg tgccactgcc tctgcctcca    780
tctcctgttc tgatcctgcc agagatcggc cctcaggacc agggcaccta ttcttgtgtg    840
gctacccact cctctcacgg ccctcaagag tctagagccg tgtccatctc catcatcgag    900
cctggcgagg aaggacctac agctggcgag ggctttgaca aagtgcgcga ggctgaggac    960
tctcctcagc acgctgttga gtgccctcca tgtgctcctc cagttgctgg tggccctcc    1020 gtgttcctgt ttcctccaaa gcctaaggac accctgatga tctctcgcac ccctgaagtg    1080
acctgcgtgg tggtggatgt gtcccaagag gatcccgagg tgcagttcaa ttggtacgtg    1140
gacggcgtgg aagtgcacaa cgccaagacc aagcctagag aggaacagtt caactccacc    1200
tacagagtgg tgtccgtgct gaccgtgctg caccaggatt ggctgaatgg caaagagtat    1260
aagtgcaagg tgtccaacaa gggcctgcct tccagcatcg aaaagaccat ctccaaggcc    1320
aagggccagc ctagggaacc ccaggtttac accctgcctc caagccaaga ggaaatgacc    1380
aagaaccagg tgtccctgac atgcctggtc aagggcttct accctccga tatcgccgtg    1440 gaatgggagt ctaatggcca gcctgagaac aactacaaga ccacacctcc tgtgctggac    1500
tccgacggca gcttctttct gtactcccgc ctgaccgtgg acaagtccag gtggcaagag    1560
ggcaacgtgt tctcctgctc cgtgatgcac gaggccctgc acaatcacta cacccagaag    1620
tccctgtctc tgtccctggg caaatga                                        1647
```

<210> SEQ ID NO 46
<211> LENGTH: 1647

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gctcagaaca tcaccgccag aatcggcgag ccctggtgc tgaaatgtaa aggcgcccct      60
aagaagcctc ctcagcggct ggaatggaag ctgaacaccg gcagaaccga ggcctggaaa    120
gtgctgtctc ctcaaggcgg aggcccttgg gattctgtgg ctagagtgct gcctaactct    180
tccctgtttc tgcctgctgt gggcatccag gacgagggca tcttcaggtg tcaggccatg    240
aaccggaacg gcaaagagac aaagtccaac taccgcgtca gagtgtatca gatccccggc    300
aagcctgaga tcgtggactc tgcctctgaa ctgacagccg gcgtgcccaa caaagtgggc    360
acttgtgtgt ccgagggcag ctatcctgct ggcaccctgt cttggcatct ggatggaaag    420
cctctggtgc ccaacgagaa aggcgtgtcc gtgaaagagc agaccagacg gcatcctgag    480
actggcctgt tcaccctgca gtccgagctg atggttaccc ctgctagagg cggcgatccc    540
agacctacct tcagctgctc cttctctcct ggcctgcctc gacatagagc cctgagaacc    600
gctcctatcc agcctagagt gtgggagcct gtgcctctgg aagaggtgca gctggtggtt    660
gaacctgaag gcggagctgt tgctcctggc ggaacagtga ccctgacctg tgaagttccc    720
gctcagccct ctccacagat ccactggatg aaggatggcg tgccactgcc tctgcctcca    780
tctcctgttc tgatcctgcc agagatcggc cctcaggacc agggcaccta ttcttgtgtg    840
gctacccact cctctcacgg ccctcaagag tctagagccg tgtccatctc catcatcgag    900
cctggcgagg aaggacctac agctggcgag ggctttgaca agtgcgcga ggctgaggac    960 tctcctcagc acgctgttga gtgccctcca tgtgctcctc cagttgctgg tggcccttcc   1020
gtgttcctgt ttcctccaaa gcctaaggac acctgatga tctctcgcac ccctgaagtg   1080
acctgcgtga tggtggatgt gtcccaagag gatcccgagg tgcagttcaa ttggtacgtg   1140
gacggcgtgg aagtgcacaa cgccaagacc aagcctagag aggaacagtt caactccacc   1200
tacagagtgg tgtccgtgct gaccgtgctg caccaggatt ggctgaatgg caaagagtat   1260
aagtgcaagg tgtccaacaa gggcctgcct tccagcatcg aaaagaccat ctccaaggcc   1320
aagggccagc ctagggaacc ccaggtttac accctgcctc caagccaaga ggaaatgacc   1380
aagaaccagg tgtccctgac atgcctggtc aagggcttct acccctccga tatcgccgtg   1440
gaatgggagt ctaatggcca gcctgagaac aactacaaga ccacacctcc tgtgctggac   1500
tccgacggca gcttctttct gtactcccgc ctgaccgtgg acaagtccag gtggcaagag   1560
ggcaacgtgt tctcctgctc cgtgatgcac gaggccctgc acaatcacta cacccagaag   1620
tccctgtctc tgtccctggg caaatga                                       1647

<210> SEQ ID NO 47
<211> LENGTH: 1647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gctcaggaaa tcaccgccag aatcggcgag ccctggtgc tgaaatgtaa aggcgcccct      60
aagaagcctc ctcagcggct ggaatggaag ctgaacaccg gcagaaccga ggcctggaaa    120
```

| | |
|---|---|
| gtgctgtctc ctcaaggcgg aggcccttgg gattctgtgg ctagagtgct gcctaactct | 180 |
| tccctgtttc tgcctgctgt gggcatccag gacgagggca tcttcaggtg tcaggccatg | 240 |
| aaccggaacg gcaaagagac aaagtccaac taccgcgtca gagtgtatca gatccccggc | 300 |
| aagcctgaga tcgtggactc tgcctctgaa ctgacagccg gcgtgcccaa caaagtgggc | 360 |
| acttgtgtgt ccgagggcag ctatcctgct ggcaccctgt cttggcatct ggatggaaag | 420 |
| cctctggtgc ccaacgagaa aggcgtgtcc gtgaaagagc agaccagacg gcatcctgag | 480 |
| actggcctgt tcaccctgca gtccgagctg atggttaccc ctgctagagg cggcgatccc | 540 |
| agacctacct tcagctgctc cttctctcct ggcctgcctc gacatagagc cctgagaacc | 600 |
| gctcctatcc agcctagagt gtgggagcct gtgcctctgg aagaggtgca gctggtggtt | 660 |
| gaacctgaag gcggagctgt tgctcctggc ggaacagtga ccctgacctg tgaagttccc | 720 |
| gctcagccct ctccacagat ccactggatg aaggatggcg tgccactgcc tctgcctcca | 780 |
| tctcctgttc tgatcctgcc agagatcggc cctcaggacc agggcaccta ttcttgtgtg | 840 |
| gctacccact cctctcacgg ccctcaagag tctagagccg tgtccatctc catcatcgag | 900 |
| cctggcgagg aaggacctac agctggcgag ggctttgaca aagtgcgcga ggctgaggac | 960 |
| tctcctcagc acgctgttga gtgccctcca tgtgctcctc cagttgctgg tggcccttcc | 1020 |
| gtgttcctgt ttcctccaaa gcctaaggac accctgatga tctctcgcac ccctgaagtg | 1080 |
| acctgcgtgg tggtggatgt gtcccaagag gatcccgagg tgcagttcaa ttggtacgtg | 1140 |
| gacggcgtgg aagtgcacaa cgccaagacc aagcctagag aggaacagtt caactccacc | 1200 |
| tacagagtgg tgtccgtgct gaccgtgctg caccaggatt ggctgaatgg caaagagtat | 1260 |
| aagtgcaagg tgtccaacaa gggcctgcct tccagcatcg aaaagaccat ctccaaggcc | 1320 |
| aagggccagc ctagggaacc ccaggtttac accctgcctc caagccaaga ggaaatgacc | 1380 |
| aagaaccagg tgtccctgac atgcctggtc aagggcttct acccctccga tatcgccgtg | 1440 |
| gaatgggagt ctaatggcca gcctgagaac aactacaaga ccacacctcc tgtgctggac | 1500 |
| tccgacggca gcttctttct gtactcccgc ctgaccgtgg acaagtccag gtggcaagag | 1560 |
| ggcaacgtgt tctcctgctc cgtgatgcac gaggccctgc acaatcacta cacccagaag | 1620 |
| tccctgtctc tgtccctggg caaatga | 1647 |

<210> SEQ ID NO 48
<211> LENGTH: 1647
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48

| | |
|---|---|
| gctcagcaga tcaccgccag aatcggcgag ccctggtgc tgaaatgtaa aggcgcccct | 60 |
| aagaagcctc ctcagcggct ggaatggaag ctgaacaccg gcagaaccga ggcctggaaa | 120 |
| gtgctgtctc ctcaaggcgg aggcccttgg gattctgtgg ctagagtgct gcctaactct | 180 |
| tccctgtttc tgcctgctgt gggcatccag gacgagggca tcttcaggtg tcaggccatg | 240 |
| aaccggaacg gcaaagagac aaagtccaac taccgcgtca gagtgtatca gatccccggc | 300 |
| aagcctgaga tcgtggactc tgcctctgaa ctgacagccg gcgtgcccaa caaagtgggc | 360 |
| acttgtgtgt ccgagggcag ctatcctgct ggcaccctgt cttggcatct ggatggaaag | 420 |
| cctctggtgc ccaacgagaa aggcgtgtcc gtgaaagagc agaccagacg gcatcctgag | 480 |

```
actggcctgt tcaccctgca gtccgagctg atggttaccc ctgctagagg cggcgatccc    540
agacctacct tcagctgctc cttctctcct ggcctgcctc gacatagagc cctgagaacc    600
gctcctatcc agcctagagt gtgggagcct gtgcctctgg aagaggtgca gctggtggtt    660
gaacctgaag gcggagctgt tgctcctggc ggaacagtga ccctgacctg tgaagttccc    720
gctcagccct ctccacagat ccactggatg aaggatggcg tgccactgcc tctgcctcca    780
tctcctgttc tgatcctgcc agagatcggc cctcaggacc agggcaccta ttcttgtgtg    840
gctacccact cctctcacgg ccctcaagag tctagagccg tgtccatctc catcatcgag    900
cctggcgagg aaggacctac agctggcgag ggctttgaca aagtgcgcga ggctgaggac    960
tctcctcagc acgctgttga gtgccctcca tgtgctcctc cagttgctgg tggcccttcc   1020
gtgttcctgt ttcctccaaa gcctaaggac accctgatga tctctcgcac ccctgaagtg   1080
acctgcgtgg tggtggatgt gtcccaagag gatcccgagg tgcagttcaa ttggtacgtg   1140
gacggcgtgg aagtgcacaa cgccaagacc aagcctagag aggaacagtt caactccacc   1200
tacagagtgg tgtccgtgct gaccgtgctg caccaggatt ggctgaatgg caaagagtat   1260
aagtgcaagg tgtccaacaa gggcctgcct tccagcatcg aaaagaccat ctccaaggcc   1320
aagggccagc ctagggaacc ccaggtttac accctgcctc caagccaaga ggaaatgacc   1380
aagaaccagg tgtccctgac atgcctggtc aagggcttct accctccga tatcgccgtg   1440 gaatgggagt ctaatggcca gcctgagaac aactacaaga ccacacctcc tgtgctggac   1500
tccgacggca gcttctttct gtactcccgc ctgaccgtgg acaagtccag gtggcaagag   1560
ggcaacgtgt tctcctgctc cgtgatgcac gaggccctgc acaatcacta cacccagaag   1620
tccctgtctc tgtccctggg caaatga                                       1647
```

<210> SEQ ID NO 49
<211> LENGTH: 1647
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 49

```
gctcagaaca tcaccgccag aatcggcgag cccctggtgc tgaaatgtaa aggcgcccct     60
aagaagcctc ctcagcggct ggaatggaag ctgaacaccg gcagaaccga ggcctggaaa    120
gtgctgtctc ctcaaggcgg aggcccttgg gattctgtgg ctagagtgct gcctgctggc    180
tccctgtttc tgcctgctgt gggcatccag gacgagggca tcttcaggtg tcaggccatg    240
aaccggaacg gcaaagagac aaagtccaac taccgcgtca gagtgtatca gatccccggc    300
aagcctgaga tcgtggactc tgcctctgaa ctgacagccg gcgtgcccaa caaagtgggc    360
acttgtgtgt ccgagggcag ctatcctgct ggcacctgt cttggcatct ggatggaaag    420
cctctggtgc ccaacgagaa aggcgtgtcc gtgaaagagc agaccagacg gcatcctgag    480
actggcctgt tcaccctgca gtccgagctg atggttaccc ctgctagagg cggcgatccc    540
agacctacct tcagctgctc cttctctcct ggcctgcctc gacatagagc cctgagaacc    600
gctcctatcc agcctagagt gtgggagcct gtgcctctgg aagaggtgca gctggtggtt    660
gaacctgaag gcggagctgt tgctcctggc ggaacagtga ccctgacctg tgaagttccc    720
gctcagccct ctccacagat ccactggatg aaggatggcg tgccactgcc tctgcctcca    780
tctcctgttc tgatcctgcc agagatcggc cctcaggacc agggcaccta ttcttgtgtg    840
```

| | |
|---|---|
| gctacccact cctctcacgg ccctcaagag tctagagccg tgtccatctc catcatcgag | 900 |
| cctggcgagg aaggacctac agctggcgag ggctttgaca aagtgcgcga ggctgaggac | 960 |
| tctcctcagc acgctgttga gtgccctcca tgtgctcctc cagttgctgg tggcccttcc | 1020 |
| gtgttcctgt ttcctccaaa gcctaaggac accctgatga tctctcgcac ccctgaagtg | 1080 |
| acctgcgtgg tggtggatgt gtcccaagag gatcccgagg tgcagttcaa ttggtacgtg | 1140 |
| gacggcgtgg aagtgcacaa cgccaagacc aagcctagag aggaacagtt caactccacc | 1200 |
| tacagagtgg tgtccgtgct gaccgtgctg caccaggatt ggctgaatgg caaagagtat | 1260 |
| aagtgcaagg tgtccaacaa gggcctgcct tccagcatcg aaaagaccat ctccaaggcc | 1320 |
| aagggccagc ctagggaacc ccaggtttac accctgcctc caagccaaga ggaaatgacc | 1380 |
| aagaaccagg tgtccctgac atgcctggtc aagggcttct accctccga tatcgccgtg | 1440 |
| gaatgggagt ctaatggcca gcctgagaac aactacaaga ccacacctcc tgtgctggac | 1500 |
| tccgacggca gcttctttct gtactcccgc ctgaccgtgg acaagtccag gtggcaagag | 1560 |
| ggcaacgtgt tctcctgctc cgtgatgcac gaggccctgc acaatcacta cacccagaag | 1620 |
| tccctgtctc tgtccctggg caaatga | 1647 |

<210> SEQ ID NO 50
<211> LENGTH: 1647
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

| | |
|---|---|
| gctcaggaaa tcaccgccag aatcggcgag cccctggtgc tgaaatgtaa aggcgcccct | 60 |
| aagaagcctc ctcagcggct ggaatggaag ctgaacaccg gcagaaccga ggcctggaaa | 120 |
| gtgctgtctc ctcaaggcgg aggccccttgg gattctgtgg ctagagtgct gcctgctggc | 180 |
| tccctgtttc tgcctgctgt gggcatccag gacgagggca tcttcaggtg tcaggccatg | 240 |
| aaccggaacg gcaaagagac aaagtccaac taccgcgtca gagtgtatca gatccccggc | 300 |
| aagcctgaga tcgtggactc tgcctctgaa ctgacagccg gcgtgccaa caaagtgggc | 360 |
| acttgtgtgt ccgagggcag ctatcctgct ggcaccctgt cttggcatct ggatggaaag | 420 |
| cctctggtgc caacgagaa aggcgtgtcc gtgaaagagc agaccagacg gcatcctgag | 480 |
| actggcctgt tcaccctgca gtccgagctg atggttaccc tgctagagg cggcgatccc | 540 |
| agacctacct tcagctgctc cttctctcct ggcctgcctc gacatagagc cctgagaacc | 600 |
| gctcctatcc agcctagagt gtgggagcct gtgcctctgg aagaggtgca gctggtggtt | 660 |
| gaacctgaag gcgagctgt tgctcctggc ggaacagtga ccctgacctg tgaagttccc | 720 |
| gctcagccct ctccacagat ccactggatg aaggatggcg tgccactgcc tctgcctcca | 780 |
| tctcctgttc tgatcctgcc agagatcggc cctcaggacc agggcaccta ttcttgtgtg | 840 |
| gctacccact cctctcacgg ccctcaagag tctagagccg tgtccatctc catcatcgag | 900 |
| cctggcgagg aaggacctac agctggcgag ggctttgaca aagtgcgcga ggctgaggac | 960 |
| tctcctcagc acgctgttga gtgccctcca tgtgctcctc cagttgctgg tggcccttcc | 1020 |
| gtgttcctgt ttcctccaaa gcctaaggac accctgatga tctctcgcac ccctgaagtg | 1080 |
| acctgcgtgg tggtggatgt gtcccaagag gatcccgagg tgcagttcaa ttggtacgtg | 1140 |
| gacggcgtgg aagtgcacaa cgccaagacc aagcctagag aggaacagtt caactccacc | 1200 |

| | |
|---|---|
| tacagagtgg tgtccgtgct gaccgtgctg caccaggatt ggctgaatgg caaagagtat | 1260 |
| aagtgcaagg tgtccaacaa gggcctgcct tccagcatcg aaaagaccat ctccaaggcc | 1320 |
| aagggccagc taggggaacc ccaggtttac accctgcctc aagccaaga ggaaatgacc | 1380 |
| aagaaccagg tgtccctgac atgcctggtc aagggcttct accctccga tatcgccgtg | 1440 |
| gaatgggagt ctaatggcca gcctgagaac aactacaaga ccacacctcc tgtgctggac | 1500 |
| tccgacggca gcttctttct gtactcccgc ctgaccgtgg acaagtccag gtggcaagag | 1560 |
| ggcaacgtgt tctcctgctc cgtgatgcac gaggccctgc acaatcacta cacccagaag | 1620 |
| tccctgtctc tgtccctggg caaatga | 1647 |

<210> SEQ ID NO 51
<211> LENGTH: 1647
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| | |
|---|---|
| gctcagcaga tcaccgccag aatcggcgag cccctggtgc tgaaatgtaa aggcgcccct | 60 |
| aagaagcctc ctcagcggct ggaatggaag ctgaacaccg gcagaaccga ggcctggaaa | 120 |
| gtgctgtctc tcaaggcgg aggcccttgg gattctgtgg ctagagtgct gcctgctggc | 180 |
| tccctgtttc tgcctgctgt gggcatccag gacgagggca tcttcaggtg tcaggccatg | 240 |
| aaccggaacg gcaaagagac aaagtccaac taccgcgtca gagtgtatca gatccccggc | 300 |
| aagcctgaga tcgtggactc tgcctctgaa ctgacagccg gcgtgccaa caaagtgggc | 360 |
| acttgtgtgt ccgagggcag ctatcctgct ggcaccctgt cttggcatct ggatggaaag | 420 |
| cctctggtgc ccaacgagaa aggcgtgtcc gtgaaagagc agaccagacg gcatcctgag | 480 |
| actggcctgt tcaccctgca gtccgagctg atggttaccc ctgctagagg cggcgatccc | 540 |
| agacctacct tcagctgctc cttctctcct ggcctgcctc acatagagc cctgagaacc | 600 |
| gctcctatcc agcctagagt gtgggagcct gtgcctctgg aagaggtgca gctggtggtt | 660 |
| gaacctgaag gcggagctgt tgctcctggc ggaacagtga ccctgacctg tgaagttccc | 720 |
| gctcagccct ctccacagat ccactggatg aaggatggcg tgccactgcc tctgcctcca | 780 |
| tctcctgttc tgatcctgcc agagatcggc cctcaggacc agggcaccta ttcttgtgtg | 840 |
| gctaccccact cctctcacgg ccctcaagag tctagagccg tgtccatctc catcatcgag | 900 |
| cctggcgagg aaggacctac agctggcgag ggctttgaca aagtgcgcga ggctgaggac | 960 |
| tctcctcagc acgctgttga gtgccctcca tgtgctcctc cagttgctgg tggcccttcc | 1020 |
| gtgttcctgt ttcctccaaa gcctaaggac accctgatga tctctcgcac ccctgaagtg | 1080 |
| acctgcgtgg tggtggatgt gtcccaagag gatcccgagg tgcagttcaa ttggtacgtg | 1140 |
| gacggcgtgg aagtgcacaa cgccaagacc aagcctagag gaacagtt caactccacc | 1200 |
| tacagagtgg tgtccgtgct gaccgtgctg caccaggatt ggctgaatgg caaagagtat | 1260 |
| aagtgcaagg tgtccaacaa gggcctgcct tccagcatcg aaaagaccat ctccaaggcc | 1320 |
| aagggccagc taggggaacc ccaggtttac accctgcctc aagccaaga ggaaatgacc | 1380 |
| aagaaccagg tgtccctgac atgcctggtc aagggcttct accctccga tatcgccgtg | 1440 |
| gaatgggagt ctaatggcca gcctgagaac aactacaaga ccacacctcc tgtgctggac | 1500 |
| tccgacggca gcttctttct gtactcccgc ctgaccgtgg acaagtccag gtggcaagag | 1560 |

```
ggcaacgtgt tctcctgctc cgtgatgcac gaggccctgc acaatcacta cacccagaag    1620
tccctgtctc tgtccctggg caaatga                                        1647
```

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Glu Gly Phe Asp Lys Val Arg Glu Ala Glu Asp Ser Pro Gln His Met
1               5                   10                  15
```

<210> SEQ ID NO 53
<211> LENGTH: 546
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270
```

Asp Gln Gly Thr Tyr Ser Cys Val Ala Thr His Ser His Gly Pro
                275                 280                 285

Gln Glu Ser Arg Ala Val Ser Ile Ser Ile Ile Glu Pro Gly Glu Glu
            290                 295                 300

Gly Pro Thr Ala Gly Gly Thr Leu Val Thr Val Ser Ser Glu Ser Lys
305                 310                 315                 320

Tyr Gly Pro Pro Cys Pro Pro Cys Pro Ala Pro Glu Ala Ala Gly Gly
                325                 330                 335

Pro Ser Val Phe Leu Phe Pro Pro Lys Pro Lys Asp Thr Leu Met Ile
            340                 345                 350

Ser Arg Thr Pro Glu Val Thr Cys Val Val Val Asp Val Ser Gln Glu
            355                 360                 365

Asp Pro Glu Val Gln Phe Asn Trp Tyr Val Asp Gly Val Glu Val His
        370                 375                 380

Asn Ala Lys Thr Lys Pro Arg Glu Glu Gln Phe Asn Ser Thr Tyr Arg
385                 390                 395                 400

Val Val Ser Val Leu Thr Val Leu His Gln Asp Trp Leu Asn Gly Lys
                405                 410                 415

Glu Tyr Lys Cys Lys Val Ser Asn Lys Gly Leu Pro Ser Ser Ile Glu
            420                 425                 430

Lys Thr Ile Ser Lys Ala Lys Gly Gln Pro Arg Glu Pro Gln Val Tyr
        435                 440                 445

Thr Leu Pro Pro Ser Gln Glu Glu Met Thr Lys Asn Gln Val Ser Leu
    450                 455                 460

Thr Cys Leu Val Lys Gly Phe Tyr Pro Ser Asp Ile Ala Val Glu Trp
465                 470                 475                 480

Glu Ser Asn Gly Gln Pro Glu Asn Asn Tyr Lys Thr Thr Pro Pro Val
                485                 490                 495

Leu Asp Ser Asp Gly Ser Phe Phe Leu Tyr Ser Arg Leu Thr Val Asp
            500                 505                 510

Lys Ser Arg Trp Gln Glu Gly Asn Val Phe Ser Cys Ser Val Met His
        515                 520                 525

Glu Ala Leu His Asn His Tyr Thr Gln Lys Ser Leu Ser Leu Ser Leu
    530                 535                 540

Gly Lys
545

<210> SEQ ID NO 54
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met

-continued

```
                65                  70                  75                  80
Asn Arg Asn Gly Lys Glu Thr Lys Ser Asn Tyr Arg Val Arg Val Tyr
                    85                  90                  95
Gln Ile Pro Gly Lys Pro Glu Ile Val Asp Ser Ala Ser Glu Leu Thr
                    100                 105                 110
Ala Gly Val Pro Asn Lys Val Gly Thr Cys Val Ser Glu Gly Ser Tyr
                    115                 120                 125
Pro Ala Gly Thr Leu Ser Trp His Leu Asp Gly Lys Pro Leu Val Pro
                    130                 135                 140
Asn Glu Lys Gly Val Ser Val Lys Glu Gln Thr Arg Arg His Pro Glu
145                 150                 155                 160
Thr Gly Leu Phe Thr Leu Gln Ser Glu Leu Met Val Thr Pro Ala Arg
                    165                 170                 175
Gly Gly Asp Pro Arg Pro Thr Phe Ser Cys Ser Phe Ser Pro Gly Leu
                    180                 185                 190
Pro Arg His Arg Ala Leu Arg Thr Ala Pro Ile Gln Pro Arg Val Trp
                    195                 200                 205
Glu Pro Val Pro Leu Glu Glu Val Gln Leu Val Val Glu Pro Glu Gly
                    210                 215                 220
Gly Ala Val Ala Pro Gly Gly Thr Val Thr Leu Thr Cys Glu Val Pro
225                 230                 235                 240
Ala Gln Pro Ser Pro Gln Ile His Trp Met Lys Asp Gly Val Pro Leu
                    245                 250                 255
Pro Leu Pro Pro Ser Pro Val Leu Ile Leu Pro Glu Ile Gly Pro Gln
                    260                 265                 270
Asp Gln Gly Thr Tyr Ser Cys Val Ala Thr His Ser Ser His Gly Pro
                    275                 280                 285
Gln Glu Ser Arg Ala Val Ser Ile Ser Ile Ile Glu Pro Gly Glu Glu
                    290                 295                 300
Gly Pro Thr Ala Gly Gly Phe Asp Lys Val Arg Glu Ala Glu Asp
305                 310                 315                 320
Ser Pro Gln His Ala Val Glu Cys Pro Pro Cys Ala Pro Pro Val Ala
                    325                 330                 335
Gly Gly Pro Ser Val Phe Leu Phe Pro Pro Lys Pro Lys Asp Thr Leu
                    340                 345                 350
Tyr Ile Thr Arg Glu Pro Glu Val Thr Cys Val Val Val Asp Val Ser
                    355                 360                 365
Gln Glu Asp Pro Glu Val Gln Phe Asn Trp Tyr Val Asp Gly Val Glu
                    370                 375                 380
Val His Asn Ala Lys Thr Lys Pro Arg Glu Glu Gln Phe Asn Ser Thr
385                 390                 395                 400
Tyr Arg Val Val Ser Val Leu Thr Val Leu His Gln Asp Trp Leu Asn
                    405                 410                 415
Gly Lys Glu Tyr Lys Cys Lys Val Ser Asn Lys Gly Leu Pro Ser Ser
                    420                 425                 430
Ile Glu Lys Thr Ile Ser Lys Ala Lys Gly Gln Pro Arg Glu Pro Gln
                    435                 440                 445
Val Tyr Thr Leu Pro Pro Ser Gln Glu Glu Met Thr Lys Asn Gln Val
                    450                 455                 460
Ser Leu Thr Cys Leu Val Lys Gly Phe Tyr Pro Ser Asp Ile Ala Val
465                 470                 475                 480
Glu Trp Glu Ser Asn Gly Gln Pro Glu Asn Asn Tyr Lys Thr Thr Pro
                    485                 490                 495
```

```
Pro Val Leu Asp Ser Asp Gly Ser Phe Phe Leu Tyr Ser Arg Leu Thr
            500                 505                 510

Val Asp Lys Ser Arg Trp Gln Glu Gly Asn Val Phe Ser Cys Ser Val
    515                 520                 525

Met His Glu Ala Leu His Asn His Tyr Thr Gln Lys Ser Leu Ser Leu
530                 535                 540

Ser Leu Gly
545

<210> SEQ ID NO 55
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
```

```
Gly Pro Thr Ala Gly Glu Gly Phe Asp Lys Val Arg Glu Ala Glu Asp
305                 310                 315                 320

Ser Pro Gln His Ala Val Glu Cys Pro Pro Cys Ala Pro Pro Val Ala
                325                 330                 335

Gly Gly Pro Ser Val Phe Leu Phe Pro Pro Lys Pro Lys Asp Thr Leu
            340                 345                 350

Met Ile Ser Arg Thr Pro Glu Val Thr Cys Val Val Asp Val Ser
        355                 360                 365

Gln Glu Asp Pro Glu Val Gln Phe Asn Trp Tyr Val Asp Gly Val Glu
    370                 375                 380

Val His Asn Ala Lys Thr Lys Pro Arg Glu Glu Gln Phe Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Gly Leu Pro Ser Ser
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Gln Glu Glu Met Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Arg Leu Thr
            500                 505                 510

Val Asp Lys Ser Arg Trp Gln Glu Gly Asn Val Phe Ser Cys Ser Val
        515                 520                 525

Met His Glu Ala Leu His Asn His Tyr Thr Gln Lys Ser Leu Ser Leu
    530                 535                 540

Ser Leu Gly
545

<210> SEQ ID NO 56
<211> LENGTH: 1641
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gctcagaata tcaccgccag aatcggcgag ccctggtgc tgaaatgtaa aggcgcccct     60
aagaagcctc ctcagcggct ggaatggaag ctgaacaccg gcagaaccga ggcctggaaa    120
gtgctgtctc ctcaaggcgg aggccttgg gattctgtgg ctagagtgct gcctaacggc    180
tccctgtttc tgcctgctgt gggcatccag gacgagggca tcttcaggtg tcaggccatg    240
aaccggaacg gcaaagagac aaagtccaac taccgcgtca gagtgtatca gatccccggc    300
aagcctgaga tcgtggactc tgcctctgaa ctgacagccg gcgtgcccaa caaagtgggc    360
acttgtgtgt ccgagggcag ctatcctgct ggcaccctgt cttggcatct ggatggaaag    420
cctctggtgc ccaacgagaa aggcgtgtcc gtgaaagagc agaccagacg gcatcctgag    480
actggcctgt tcaccctgca gtccgagctg atggttaccc ctgctagagg cggcgatccc    540
```

| | | |
|---|---|---|
| agacctacct tcagctgctc cttctctcct ggcctgcctc gacatagagc cctgagaacc | 600 | |
| gctcctatcc agcctagagt gtgggagcct gtgcctctgg aagaggtgca gctggtggtt | 660 | |
| gaacctgaag gcggagctgt tgctcctggc ggaacagtga ccctgacctg tgaagttccc | 720 | |
| gctcagccct ctccacagat ccactggatg aaggatggcg tgccactgcc tctgcctcca | 780 | |
| tctcctgttc tgatcctgcc agagatcggc cctcaggacc agggcaccta ttcttgtgtg | 840 | |
| gctacccact cctctcacgg ccctcaagag tctagagccg tgtccatctc catcatcgag | 900 | |
| cctggcgagg aaggacctac agctggcgga acactggtca ccgtgtcctc cgagtctaag | 960 | |
| tacggccctc cttgtcctcc atgtcctgct ccagaagctg ctggcggccc ttccgtgttt | 1020 | |
| ctgttccctc caaagcctaa ggacaccctg atgatctctc ggaccctga agtgacctgc | 1080 | |
| gtggtggtgg atgtgtccca agaggatccc gaggtgcagt tcaattggta cgtggacggc | 1140 | |
| gtggaagtgc acaacgccaa gaccaagcct agagaggaac agttcaactc cacctacaga | 1200 | |
| gtggtgtccg tgctgaccgt gctgcaccag gattggctga atggcaaaga gtataagtgc | 1260 | |
| aaggtgtcca acaagggcct gccttccagc atcgaaaaga ccatctccaa ggccaagggc | 1320 | |
| cagcctaggg aaccccaggt ttacaccctg cctccaagcc aagaggaaat gaccaagaac | 1380 | |
| caggtgtccc tgacatgcct ggtcaagggc ttctacccct ccgatatcgc cgtggaatgg | 1440 | |
| gagtctaatg ccagcctga aacaactac aagaccacac ctcctgtgct ggactccgac | 1500 | |
| ggcagcttct ttctgtactc ccgcctgacc gtggacaagt ccaggtggca agagggcaac | 1560 | |
| gtgttctcct gctccgtgat gcacgaggcc ctgcacaatc actacaccca gaagtccctg | 1620 | |
| tctctgtccc tgggcaaatg a | 1641 | |

<210> SEQ ID NO 57
<211> LENGTH: 1634
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 57

| | | |
|---|---|---|
| gctcaggaga tcaccgccag aatcggcgag cccctggtgc tgaaatgtaa agggcccta | 60 | |
| agaagcctcc tcagcggctg gaatggaagc tgaacaccgg cagaaccgag gcctggaaag | 120 | |
| tgctgtctcc tcaaggcgga ggcccttggg attctgtggc tagagtgctg cctaacggct | 180 | |
| cctgtttctg cctgctgtgg gcatccagga cgagggcatc ttcaggtgtc aggccatgaa | 240 | |
| ccggaacggc aaagagacaa agtccaacta ccgcgtcaga gtgtatcaga tccccggcaa | 300 | |
| gcctgagtcg tggactctgc ctctgaactg acagccggcg tgcccaacaa agtgggcact | 360 | |
| tgtgtgtccg agggcagcta tcctgctggc accctgtctt ggcatctgga tggaaagcct | 420 | |
| ctggtgccca acgaaaaggc gtgtccgtga agagcagac cagacggcat cctgagactg | 480 | |
| gcctgttcac cctgcagtcc gagctgatgg ttacccctgc tagaggcggc gatcccagac | 540 | |
| ctaccttcag ctgctccttc ttcctggcct gcctcgacat agagccctga gaaccgctcc | 600 | |
| tatccagcct agagtgtggg agcctgtgcc tctggaagag gtgcagctgg tggttgaacc | 660 | |
| tgaaggcgga gctgttgctc ctggcggaca gtgaccctga cctgtgaagt tcccgctcag | 720 | |
| ccctctccac agatccactg gatgaaggat ggcgtgccac tgcctctgcc tccatctcct | 780 | |
| gttctgatcc tgccagagat cggccctcag gaccaggcac ctattcttgt gtggctaccc | 840 | |
| actcctctca cggccctcaa gagtctagag ccgtgtccat ctccatcatc gagcctggcg | 900 | |

```
aggaaggacc tacagctggc gagggctttg acaaagtgcg cgggctgagg actctcctca    960
gcacgctgtt gagtgccctc catgtgctcc tccagttgct ggtggccctt ccgtgttcct   1020
gtttcctcca aagcctaagg acaccctgta catcacccgc gagcctgaat gacctgcgtg   1080
gtggtggatg tgtcccaaga ggatcccgag gtgcagttca attggtacgt ggacggcgtg   1140
gaagtgcaca acgccaagac caagcctaga gaggaacagt tcaactccac ctacaggtgg   1200
tgtccgtgct gaccgtgctg caccaggatt ggctgaatgg caaagagtat aagtgcaagg   1260
tgtccaacaa gggcctgcct tccagcatcg aaaagaccat ctccaaggcc aagggccagc   1320
ctaggaaccc caggtttaca ccctgcctcc aagccaagag gaaatgacca agaaccaggt   1380
gtccctgaca tgcctggtca agggcttcta ccctccgat atcgccgtgg aatgggagtc   1440
taatggccag ctgagaacaa ctacaagacc acacctcctg tgctggactc cgacggcagc   1500
ttctttctgt actcccgcct gaccgtggac aagtccaggt ggcaagaggg caacgtgttc   1560
tcctgctccg tgatgcagag gccctgcaca atcactacac ccagaagtcc ctgtctctgt   1620
ccctgggcaa atga                                                    1634

<210> SEQ ID NO 58
<211> LENGTH: 1634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gctcagcaga tcaccgccag aatcggcgag cccctggtgc tgaaatgtaa agggccccta     60
agaagcctcc tcagcggctg gaatggaagc tgaacaccgg cagaaccgag gcctggaaag    120
tgctgtctcc tcaaggcgga ggcccttggg attctgtggc tagagtgctg cctaacggct    180
cctgtttctg cctgctgtgg gcatccagga cgagggcatc ttcaggtgtc aggccatgaa    240
ccggaacggc aaagagacaa agtccaacta ccgcgtcaga gtgtatcaga tccccggcaa    300
gcctgagtcg tggactctgc ctctgaactg acagccggcg tgcccaacaa agtgggcact    360
tgtgtgtccg agggcagcta tcctgctggc accctgtctt ggcatctgga tggaaagcct    420
ctggtgccca acgaaaaggc gtgtccgtga agagcagac cagacggcat cctgagactg    480
gcctgttcac cctgcagtcc gagctgatgg ttaccctgc tagaggcggc gatcccagac    540
ctaccttcag ctgctccttc ttcctggcct gcctcgacat agagccctga gaaccgctcc    600
tatccagcct agagtgtggg agcctgtgcc tctggaagag gtgcagctgg tggttgaacc    660
tgaaggcgga gctgttgctc ctggcggaca gtgaccctga cctgtgaagt tcccgctcag    720
ccctctccac agatccactg gatgaaggat ggcgtgccac tgcctctgcc tccatctcct    780
gttctgatcc tgccagagat cggccctcag gaccaggcac ctattcttgt gtggctaccc    840
actcctctca cggccctcaa gagtctagag ccgtgtccat ctccatcatc gagcctggcg    900
aggaaggacc tacagctggc gagggctttg acaaagtgcg cgggctgagg actctcctca    960
gcacgctgtt gagtgccctc catgtgctcc tccagttgct ggtggccctt ccgtgttcct   1020
gtttcctcca aagcctaagg acaccctgta catcacccgc gagcctgaat gacctgcgtg   1080
gtggtggatg tgtcccaaga ggatcccgag gtgcagttca attggtacgt ggacggcgtg   1140
gaagtgcaca acgccaagac caagcctaga gaggaacagt tcaactccac ctacaggtgg   1200
tgtccgtgct gaccgtgctg caccaggatt ggctgaatgg caaagagtat aagtgcaagg   1260
```

| | | |
|---|---|---|
| tgtccaacaa gggcctgcct tccagcatcg aaaagaccat ctccaaggcc aagggccagc | 1320 | |
| ctaggaaccc caggtttaca ccctgcctcc aagccaagag gaaatgacca agaaccaggt | 1380 | |
| gtccctgaca tgcctggtca agggcttcta ccctccgat atcgccgtgg aatgggagtc | 1440 | |
| taatggccag ctgagaacaa ctacaagacc acacctcctg tgctggactc cgacggcagc | 1500 | |
| ttctttctgt actcccgcct gaccgtggac aagtccaggt ggcaagaggg caacgtgttc | 1560 | |
| tcctgctccg tgatgcagag gccctgcaca atcactacac ccagaagtcc ctgtctctgt | 1620 | |
| ccctgggcaa atga | 1634 | |

<210> SEQ ID NO 59
<211> LENGTH: 1634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

| | | |
|---|---|---|
| gctcagaata tcaccgccag aatcggcgag ccctggtgc tgaaatgtaa agggcccta | 60 | |
| agaagcctcc tcagcggctg gaatggaagc tgaacaccgg cagaaccgag gcctggaaag | 120 | |
| tgctgtctcc tcaaggcgga ggccttgggg attctgtggc tagagtgctg cctaactctt | 180 | |
| cctgtttctg cctgctgtgg gcatccagga cgagggcatc ttcaggtgtc aggccatgaa | 240 | |
| ccggaacggc aaagagacaa agtccaacta ccgcgtcaga gtgtatcaga tccccggcaa | 300 | |
| gcctgagtcg tggactctgc ctctgaactg acagccggcg tgcccaacaa agtgggcact | 360 | |
| tgtgtgtccg agggcagcta tcctgctggc accctgtctt ggcatctgga tggaaagcct | 420 | |
| ctggtgccca cgaaaaggc gtgtccgtga aagagcagac cagacggcat cctgagactg | 480 | |
| gcctgttcac cctgcagtcc gagctgatgg ttacccctgc tagaggcggc gatcccagac | 540 | |
| ctaccttcag ctgctccttc ttcctggcct gcctcgacat agagccctga gaaccgctcc | 600 | |
| tatccagcct agagtgtggg agcctgtgcc tctggaagag gtgcagctgg tggttgaacc | 660 | |
| tgaaggcgga gctgttgctc ctggcggaca gtgaccctga cctgtgaagt tcccgctcag | 720 | |
| ccctctccac agatccactg gatgaaggat ggcgtgccac tgcctctgcc tccatctcct | 780 | |
| gttctgatcc tgccagagat cggccctcag gaccaggcac ctattcttgt gtggctaccc | 840 | |
| actcctctca cggccctcaa gagtctagag ccgtgtccat ctccatcatc gagcctggcg | 900 | |
| aggaaggacc tacagctggc gagggctttg acaaagtgcg cgggctgagg actctcctca | 960 | |
| gcacgctgtt gagtgccctc catgtgctcc tccagttgct ggtggccctt ccgtgttcct | 1020 | |
| gtttcctcca aagcctaagg acaccctgta catcacccgc gagcctgaat gacctgcgtg | 1080 | |
| gtggtggatg tgtcccaaga ggatcccgag gtgcagttca attggtacgt ggacggcgtg | 1140 | |
| gaagtgcaca cgccaagac caagcctaga gaggaacagt tcaactccac ctacaggtgg | 1200 | |
| tgtccgtgct gaccgtgctg caccaggatt ggctgaatgg caaagagtat aagtgcaagg | 1260 | |
| tgtccaacaa gggcctgcct tccagcatcg aaaagaccat ctccaaggcc aagggccagc | 1320 | |
| ctaggaaccc caggtttaca ccctgcctcc aagccaagag gaaatgacca agaaccaggt | 1380 | |
| gtccctgaca tgcctggtca agggcttcta ccctccgat atcgccgtgg aatgggagtc | 1440 | |
| taatggccag ctgagaacaa ctacaagacc acacctcctg tgctggactc cgacggcagc | 1500 | |
| ttctttctgt actcccgcct gaccgtggac aagtccaggt ggcaagaggg caacgtgttc | 1560 | |
| tcctgctccg tgatgcagag gccctgcaca atcactacac ccagaagtcc ctgtctctgt | 1620 | |

```
ccctgggcaa atga                                                    1634

<210> SEQ ID NO 60
<211> LENGTH: 1634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gctcaggaga tcaccgccag aatcggcgag cccctggtgc tgaaatgtaa agggccccta    60
agaagcctcc tcagcggctg gaatggaagc tgaacaccgg cagaaccgag gcctggaaag   120
tgctgtctcc tcaaggcgga ggccttgggg attctgtggc tagagtgctg cctaactcct   180
cctgtttctg cctgctgtgg gcatccagga cgagggcatc ttcaggtgtc aggccatgaa   240
ccggaacggc aaagagacaa agtccaacta ccgcgtcaga gtgtatcaga tccccggcaa   300
gcctgagtcg tggactctgc ctctgaactg acagccggcg tgcccaacaa agtgggcact   360
tgtgtgtccg agggcagcta tcctgctggc accctgtctt ggcatctgga tggaaagcct   420
ctggtgccca acgaaaaggc gtgtccgtga aagagcagac cagacggcat cctgagactg   480
gcctgttcac cctgcagtcc gagctgatgg ttaccctgc tagaggcggc gatcccagac   540
ctaccttcag ctgctccttc ttcctggcct gcctcgacat agagccctga gaaccgctcc   600
tatccagcct agagtgtggg agcctgtgcc tctggaagag gtgcagctgg tggttgaacc   660
tgaaggcgga gctgttgctc ctggcggaca gtgaccctga cctgtgaagt tcccgctcag   720
ccctctccac agatccactg gatgaaggat ggcgtgccac tgcctctgcc tccatctcct   780
gttctgatcc tgccagagat cggccctcag gaccaggcac ctattcttgt gtggctaccc   840
actcctctca cggccctcaa gagtctagag ccgtgtccat ctccatcatc gagcctggcg   900
aggaaggacc tacagctggc gagggctttg acaaagtgcg cgggctgagg actctcctca   960
gcacgctgtt gagtgccctc catgtgctcc tccagttgct ggtggccctt ccgtgttcct  1020
gtttcctcca aagcctaagg acaccctgta catcacccgc gagcctgaat gacctgcgtg  1080
gtggtggatg tgtcccaaga ggatcccgag gtgcagttca attggtacgt ggacggcgtg  1140
gaagtgcaca acgccaagac caagcctaga gaggaacagt tcaactccac ctacaggtgg  1200
tgtccgtgct gaccgtgctg caccaggatt ggctgaatgg caaagagtat aagtgcaagg  1260
tgtccaacaa gggcctgcct tccagcatcg aaaagaccat ctccaaggcc aagggccagc  1320
ctaggaaccc caggtttaca ccctgcctcc aagccaagag gaaatgacca agaaccaggt  1380
gtccctgaca tgcctggtca agggcttcta cccctccgat atcgccgtgg aatgggagtc  1440
taatggccag ctgagaacaa ctacaagacc acacctcctg tgctggactc cgacggcagc  1500
ttctttctgt actcccgcct gaccgtggac aagtccaggt ggcaagaggg caacgtgttc  1560
tcctgctccg tgatgcagag gccctgcaca atcactacac ccagaagtcc ctgtctctgt  1620
ccctgggcaa atga                                                    1634

<210> SEQ ID NO 61
<211> LENGTH: 1634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
```

```
gctcagcaga tcaccgccag aatcggcgag ccectggtgc tgaaatgtaa agggccccta      60
agaagcctcc tcagcggctg gaatggaagc tgaacaccgg cagaaccgag gcctggaaag     120
tgctgtctcc tcaaggcgga ggcccttggg attctgtggc tagagtgctg cctaactctt     180
cctgtttctg cctgctgtgg gcatccagga cgagggcatc ttcaggtgtc aggccatgaa     240
ccggaacggc aaagagacaa agtccaacta ccgcgtcaga gtgtatcaga tccccggcaa     300
gcctgagtcg tggactctgc ctctgaactg acagccggcg tgcccaacaa agtgggcact     360
tgtgtgtccg agggcagcta tcctgctggc accctgtctt ggcatctgga tggaaagcct     420
ctggtgccca cgaaaaggc gtgtccgtga aagagcagac cagacggcat cctgagactg      480
gcctgttcac cctgcagtcc gagctgatgg ttaccctgc tagaggcggc gatcccagac      540
ctaccttcag ctgctccttc ttcctggcct gcctcgacat agagccctga gaaccgctcc     600
tatccagcct agagtgtggg agcctgtgcc tctggaagag gtgcagctgg tggttgaacc     660
tgaaggcgga gctgttgctc ctggcggaca gtgaccctga cctgtgaagt tcccgctcag     720
ccctctccac agatccactg gatgaaggat ggcgtgccac tgcctctgcc tccatctcct     780
gttctgatcc tgccagagat cggccctcag gaccaggcac ctattcttgt gtggctaccc     840
actcctctca cggccctcaa gagtctagag ccgtgtccat ctccatcatc gagcctggcg     900
aggaaggacc tacagctggc gagggctttg acaaagtgcg cgggctgagg actctcctca     960
gcacgctgtt gagtgccctc catgtgctcc tccagttgct ggtggcccct ccgtgttcct    1020
gtttcctcca aagcctaagg acaccctgta catcacccgc gagcctgaat gacctgcgtg    1080
gtggtggatg tgtcccaaga ggatcccgag gtgcagttca attggtacgt ggacggcgtg    1140
gaagtgcaca cgccaagac caagcctaga gaggaacagt tcaactccac ctacaggtgg    1200
tgtccgtgct gaccgtgctg caccaggatt ggctgaatgg caaagagtat aagtgcaagg    1260
tgtccaacaa gggcctgcct tccagcatcg aaaagaccat ctccaaggcc aagggccagc    1320
ctaggaaccc caggtttaca ccctgcctcc aagccaagag gaaatgacca agaaccaggt    1380
gtccctgaca tgcctggtca agggcttcta ccectccgat atcgccgtgg aatgggagtc    1440
taatggccag ctgagaacaa ctacaagacc acacctcctg tgctggactc cgacggcagc    1500
ttctttctgt actcccgcct gaccgtggac aagtccaggt ggcaagaggg caacgtgttc    1560
tcctgctccg tgatgcagag gccctgcaca atcactacac ccagaagtcc ctgtctctgt    1620
ccctgggcaa atga                                                      1634

<210> SEQ ID NO 62
<211> LENGTH: 1649
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
gctcagaata tcaccgccag aatcggcgag ccectggtgc tgaaatgtaa agggccccta      60
agaagcctcc tcagcggctg gaatggaagc tgaacaccgg cagaaccgag gcctggaaag    120
tgctgtctcc tcaaggcgga ggcccttggg attctgtggc tagagtgctg cctaacggct    180
cctgtttctg cctgctgtgg gcatccagga cgagggcatc ttcaggtgtc aggccatgaa    240
ccggaacggc aaagagacaa agtccaacta ccgcgtcaga gtgtatcaga tccccggcaa    300
gcctgagtcg tggactctgc ctctgaactg acagccggcg tgcccaacaa agtgggcact    360
```

```
tgtgtgtccg agggcagcta tcctgctggc accctgtctt ggcatctgga tggaaagcct      420
ctggtgccca acgaaaaggc gtgtccgtga aagagcagac cagacggcat cctgagactg      480
gcctgttcac cctgcagtcc gagctgatgg ttacccctgc tagaggcggc gatcccagac      540
ctaccttcag ctgctccttc ttcctggcct gcctcgacat agagccctga gaaccgctcc      600
tatccagcct agagtgtggg agcctgtgcc tctggaagag gtgcagctgg tggttgaacc      660
tgaaggcgga gctgttgctc ctggcggaca gtgaccctga cctgtgaagt tcccgctcag      720
ccctctccac agatccactg gatgaaggat ggcgtgccac tgcctctgcc tccatctcct      780
gttctgatcc tgccagagat cggccctcag gaccaggcac ctattcttgt gtggctaccc      840
actcctctca cggccctcaa gagtctagag ccgtgtccat ctccatcatc gagcctggcg      900
aggaaggacc tacagctggc gagggctttg acaaagtgcg cgggctgagg actctcctca      960
gcacgctgag agaaagtgct gcgttgagtg ccctccatgt gctcctccag ttgctggtgg     1020
cccttccgtg ttcctgtttc ctccaaagcc taaggacacc ctgtacatcc ccgcgagcct     1080
gaagtgacct gcgtggtggt ggatgtgtcc aagaggatc ccgaggtgca gttcaattgg      1140
tacgtggacg gcgtggaagt gcacaacgcc aagaccaagc ctagagagga acagttaact     1200
ccacctacag agtggtgtcc gtgctgaccg tgctgcacca ggattggctg aatggcaaag     1260
agtataagtg caaggtgtcc aacaagggcc tgccttccag catcgaaaag accatctcca     1320
aggcaagggc cagcctaggg aaccccaggt ttacaccctg cctccaagcc aagaggaaat     1380
gaccaagaac caggtgtccc tgacatgcct ggtcaagggc ttctacccct ccgatatcgc     1440
cgtggaatgg agtctaatgg ccagcctgag aacaactaca agaccacacc tcctgtgctg     1500
gactccgacg gcagcttctt tctgtactcc cgcctgaccg tggacaagtc caggtggcaa     1560
gagggcaacg tgttctctgc tccgtgatgc acgaggccct gcacaatcac tacacccaga     1620
agtccctgtc tctgtccctg ggcaaatga                                         1649
```

<210> SEQ ID NO 63
<211> LENGTH: 1631
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gctcagaata tcaccgccag aatcggcgag ccctggtgc tgaaatgtaa agggccccta       60
agaagcctcc tcagcggctg gaatggaagc tgaacaccgg cagaaccgag gcctggaaag     120
tgctgtctcc tcaaggcgga ggcccttggg attctgtggc tagagtgctg cctaacggct     180
cctgtttctg cctgctgtgg gcatccagga cgagggcatc ttcaggtgtc aggccatgaa     240
ccggaacggc aaagagacaa agtccaacta ccgcgtcaga gtgtatcaga tccccggcaa     300
gcctgagtcg tggactctgc ctctgaactg acagccggcg tgcccaacaa agtgggcact     360
tgtgtgtccg agggcagcta tcctgctggc accctgtctt ggcatctgga tggaaagcct     420
ctggtgccca acgaaaaggc gtgtccgtga aagagcagac cagacggcat cctgagactg     480
gcctgttcac cctgcagtcc gagctgatgg ttacccctgc tagaggcggc gatcccagac     540
ctaccttcag ctgctccttc ttcctggcct gcctcgacat agagccctga gaaccgctcc     600
tatccagcct agagtgtggg agcctgtgcc tctggaagag gtgcagctgg tggttgaacc     660
tgaaggcgga gctgttgctc ctggcggaca gtgaccctga cctgtgaagt tcccgctcag     720
```

```
ccctctccac agatccactg gatgaaggat ggcgtgccac tgcctctgcc tccatctcct    780
gttctgatcc tgccagagat cggccctcag gaccaggcac ctattcttgt gtggctaccc    840
actcctctca cggccctcaa gagtctagag ccgtgtccat ctccatcatc gagcctggcg    900
aggaaggacc tacagctggc gagggctttg acaaagtgcg cgggctgagg actctcctca    960
gcacgctgtt gagtgccctc catgtgctcc tccagtggct ggcccttccg tgttcctgtt   1020
tcctccaaag cctaaggaca ccctgtacat cacccgcgag cctgaagtgc ctgcgtggtg   1080
gtggatgtgt ctcacgagga tcccgaggtg cagttcaatt ggtacgtgga cggcgtggaa   1140
gtgcacaacg ccaagaccaa gcctagagag gaacagttca actccacctt cagagtgtgt   1200
ccgtgctgac cgtggtgcat caggattggc tgaatgggaa agagtacaag tgcaaggtgt   1260
ccaacaaggg cctgcctgct cctatcgaaa agaccatctc taagaccaag ggacagcccc   1320
gggacctcag gtgtacacac tgccacctag ccgggaagag atgaccaaga accaggtgtc   1380
cctgacatgc ctggtcaagg gcttctaccc ctccgatatc gccgtggaat gggagtctaa   1440
tggccagcct agaacaacta caagaccaca cctcctatgc tggactccga cggctcattc   1500
ttcctgtact ccaagctgac agtggacaag tccagatggc agcagggcaa cgtgttctcc   1560
tgctccgtga tgcacgagcc ctgcacaatc actacaccca gaagtccctg tctctgtccc   1620
ctggcaaatg a                                                        1631

<210> SEQ ID NO 64
<211> LENGTH: 1634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gctcagaata tcaccgccag aatcggcgag cccctggtgc tgaaatgtaa agggccccta     60
agaagcctcc tcagcggctg gaatggaagc tgaacaccgg cagaaccgag gcctggaaag    120
tgctgtctcc tcaaggcgga ggccttggga ttctgtggc tagagtgctg cctaacggct    180
cctgtttctg cctgctgtgg gcatccagga cgagggcatc ttcaggtgtc aggccatgaa    240
ccggaacggc aaagagacaa agtccaacta ccgcgtcaga gtgtatcaga tccccggcaa    300
gcctgagtcg tggactctgc ctctgaactg acagccggcg tgcccaacaa agtgggcact    360
tgtgtgtccg agggcagcta tcctgctggc accctgtctt ggcatctgga tggaaagcct    420
ctggtgccca acgaaaaggc gtgtccgtga agagcagac cagacggcat cctgagactg    480
gcctgttcac cctgcagtcc gagctgatgg ttaccctgc tagaggcggc gatcccagac    540
ctaccttcag ctgctccttc ttcctggcct gcctcgacat agagccctga gaaccgctcc    600
tatccagcct agagtgtggg agcctgtgcc tctggaagag gtgcagctgg tggttgaacc    660
tgaaggcgga gctgttgctc ctggcggaca gtgaccctga cctgtgaagt tcccgctcag    720
ccctctccac agatccactg gatgaaggat ggcgtgccac tgcctctgcc tccatctcct    780
gttctgatcc tgccagagat cggccctcag gaccaggcac ctattcttgt gtggctaccc    840
actcctctca cggccctcaa gagtctagag ccgtgtccat ctccatcatc gagcctggcg    900
aggaaggacc tacagctggc gagggctttg acaaagtgcg cgggctgagg actctcctca    960
gcacgctgtt gagtgccctc catgtgctcc tccagttgct ggtggccctt ccgtgttcct   1020
gtttcctcca aagcctaagg acaccctgta catcacccgc gagcctgaat gacctgcgtg   1080
```

```
gtggtggatg tgtctcacga ggaccccgaa gtgaagttca attggtacgt ggacggcgtg    1140
gaagtgcaca acgccaagac caagcctaga gaggaacagt acaactccac ctacaggtgg    1200
tgtccgtgct gaccgtgctg caccaggatt ggctgaatgg caaagagtat aagtgcaagg    1260
tgtccaacaa ggccctgcct gctcctatcg aaaagaccat ctccaaggcc aagggccagc    1320
ctaggaaccc caggtttaca ccttgccacc ttctcgggac gagctgacca agaaccaggt    1380
gtccctgaca tgcctggtca agggcttcta ccccctccgat atcgccgtgg aatgggagtc    1440
taatggccag ctgagaacaa ctacaagacc acacctcctg tgctggactc cgacggctca    1500
ttcttcctgt actccaagct gacagtggac aagtccagat ggcagcaggg caacgtgttc    1560
tcctgctccg tgatgcagag ggccctgcaca atcactacac ccagaagtcc ctgtctctgt    1620
cccctggcaa atga                                                      1634
```

<210> SEQ ID NO 65
<211> LENGTH: 1652
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 65

```
gctcagaata tcaccgccag aatcggcgag ccctggtgc tgaaatgtaa agggccccta      60
agaagcctcc tcagcggctg aatggaagc tgaacaccgg cagaaccgag gcctggaaag     120
tgctgtctcc tcaaggcgga ggcccttggg attctgtggc tagagtgctg cctaacggct     180
cctgtttctg cctgctgtgg gcatccagga cgagggcatc ttcaggtgtc aggccatgaa     240
ccggaacggc aaagagacaa agtccaacta ccgcgtcaga gtgtatcaga tccccggcaa     300
gcctgagtcg tggactctgc ctctgaactg acagccggcg tgcccaacaa agtgggcact     360
tgtgtgtccg agggcagcta tcctgctggc accctgtctt ggcatctgga tggaaagcct     420
ctggtgccca acgaaaaggc gtgtccgtga agagcagac cagacggcat cctgagactg     480
gcctgttcac cctgcagtcc gagctgatgg ttacccctgc tagaggcggc gatcccagac     540
ctaccttcag ctgctccttc ttcctggcct gcctcgacat agagccctga aaccgctcc     600 tatccagcct agagtgtggg agcctgtgcc tctggaagag gtgcagctgg tggttgaacc     660
tgaaggcgga gctgttgctc ctggcggaca gtgaccctga cctgtgaagt tcccgctcag     720
ccctctccac agatccactg gatgaaggat ggcgtgccac tgcctctgcc tccatctcct     780
gttctgatcc tgccagagat cggccctcag gaccaggcac ctattcttgt gtggctaccc     840
actcctctca cggccctcaa gagtctagag ccgtgtccat ctccatcatc gagcctggcg     900
aggaaggacc tacagctggc gagggctttg acaaagtgcg cgggctgagg actctcctca     960
gcacgctgag tctaagtacg gccctccttg tcctccatgt cctgctccag aagctgctgg    1020
tggcccttcc gtgttcctgt ttcctccaaa gcctaaggac accctgtact cacccgcgag    1080
cctgaagtga cctgcgtggt ggtggatgtg tctcacgagg accccgaagt gaagttcaat    1140
tggtacgtgg acggcgtgga agtgcacaac gccaagacca agcctagaga ggaacataca    1200
actccaccta cagagtggtg tccgtgctga ccgtgctgca ccaggattgg ctgaatggca    1260
aagagtataa gtgcaaggtg tccaacaagg ccctgcctgc tcctatcgaa aagaccatct    1320
ccaggccaag ggccagccta gggaacccca ggtttacacc ttgccacctt ctcgggacga    1380
gctgaccaag aaccaggtgt ccctgacatg cctggtcaag ggcttctacc cctccgatat    1440
```

```
cgccgtggaa gggagtctaa tggccagcct gagaacaact acaagaccac acctcctgtg    1500
ctggactccg acggctcatt cttcctgtac tccaagctga cagtggacaa gtccagatgg    1560
cagcagggca acgtgtttcc tgctccgtga tgcacgaggc cctgcacaat cactacaccc    1620
agaagtccct gtctctgtcc cctggcaaat ga                                  1652

<210> SEQ ID NO 66
<211> LENGTH: 1661
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gctcagaata tcaccgccag aatcggcgag cccctggtgc tgaaatgtaa agggccccta      60
agaagcctcc tcagcggctg gaatggaagc tgaacaccgg cagaaccgag gcctggaaag     120
tgctgtctcc tcaaggcgga ggcccttggg attctgtggc tagagtgctg cctaacggct     180
cctgtttctg cctgctgtgg gcatccagga cgagggcatc ttcaggtgtc aggccatgaa     240
ccggaacggc aaagagacaa agtccaacta ccgcgtcaga gtgtatcaga tccccggcaa     300
gcctgagtcg tggactctgc ctctgaactg acagccggcg tgcccaacaa agtgggcact     360
tgtgtgtccg agggcagcta tcctgctggc accctgtctt ggcatctgga tggaaagcct     420
ctggtgccca acgaaaaggc gtgtccgtga agagcagaca cagacggcat cctgagactg     480
gcctgttcac cctgcagtcc gagctgatgg ttaccctgc tagaggcggc gatcccagac      540
ctaccttcag ctgctccttc ttcctggcct gcctcgacat agagccctga gaaccgctcc     600
tatccagcct agagtgtggg agcctgtgcc tctggaagag gtgcagctgg tggttgaacc     660
tgaaggcgga gctgttgctc ctggcggaca gtgaccctga cctgtgaagt tcccgctcag     720
ccctctccac agatccactg gatgaaggat ggcgtgccac tgcctctgcc tccatctcct     780
gttctgatcc tgccagagat cggccctcag gaccaggcac ctattcttgt gtggctaccc     840
actcctctca cggccctcaa gagtctagag ccgtgtccat ctccatcatc gagcctggcg     900
aggaaggacc tacagctggc gagggctttg acaaagtgcg cgggctgagg actctcctca     960
gcacgctgag cctaagtcct gcgacaagac ccacacctgt cctccatgtc ctgctccaga    1020
agctgctggt ggcccttccg tgttcctgtt tcctccaaag cctaaggacc cctgtacatc    1080
acccgcgagc ctgaagtgac ctgcgtggtg gtggatgtgt tcacgagga ccccgaagtg     1140 aagttcaatt ggtacgtgga cggcgtggaa gtgcacaacg ccaagaccaa gcctaggagg    1200
aacagtacaa ctccacctac agagtggtgt ccgtgctgac cgtgctgcac caggattggc    1260
tgaatggcaa agagtataag tgcaaggtgt ccaacaaggc cctgcctgct cctatcgaaa    1320
agacatctcc aaggccaagg ccagcctag ggaaccccag gtttacacct tgccaccttc      1380
tcgggacgag ctgaccaaga accaggtgtc cctgacatgc ctggtcaagg gcttctaccc    1440
ctccgatatc ccgtggaatg ggagtctaat ggccagcctg agaacaacta caagaccaca    1500
cctcctgtgc tggactccga cggctcattc ttcctgtact ccaagctgac agtggacaag    1560
tccagatggc agcagggaac gtgttctcct gctccgtgat gcacgaggcc ctgcacaatc    1620
actacaccca gaagtccctg tctctgtccc ctggcaaatg a                        1661

<210> SEQ ID NO 67
<211> LENGTH: 1665
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
gctcagaata tcaccgccag aatcggcgag ccctggtgc tgaaatgtaa aggcgcccct      60
aagaagcctc ctcagcggct ggaatggaag ctgaacaccg gcagaaccga ggcctggaaa    120
gtgctgtctc ctcaaggcgg aggcccttgg gattctgtgg ctagagtgct gcctaacggc    180
tccctgtttc tgcctgctgt gggcatccag gacgagggca tcttcaggtg tcaggccatg    240
aaccggaacg gcaaagagac aaagtccaac taccgcgtca gagtgtatca gatccccggc    300
aagcctgaga tcgtggactc tgcctctgaa ctgacagccg gcgtgcccaa caaagtgggc    360
acttgtgtgt ccgagggcag ctatcctgct ggcaccctgt cttggcatct ggatggaaag    420
cctctggtgc ccaacgagaa aggcgtgtcc gtgaaagagc agaccagacg gcatcctgag    480
actggcctgt tcaccctgca gtccgagctg atggttaccc ctgctagagg cggcgatccc    540
agacctacct tcagctgctc cttctctcct ggcctgcctc gacatagagc cctgagaacc    600
gctcctatcc agcctagagt gtgggagcct gtgcctctgg aagaggtgca gctggtggtt    660
gaacctgaag gcggagctgt tgctcctggc ggaacagtga ccctgacctg tgaagttccc    720
gctcagccct ctccacagat ccactggatg aaggatggcg tgccactgcc tctgcctcca    780
tctcctgttc tgatcctgcc agagatcggc cctcaggacc agggcaccta ttcttgtgtg    840
gctacccact cctctcacgg ccctcaagag tctagaccgg tgtccatctc catcatcgag    900
cctggcgagg aaggacctac agctggcgag ggctttgaca agtgcgcga ggccgaggat    960
tctcctcagc atgctgagtc taagtacggc cctccttgtc ctccatgtcc tgctccagaa   1020
gctgctggcg gcccttccgt gtttctgttc cctccaaagc ctaaggacac cctgtacatc   1080
acccgggagc tgaagtgac ctgcgtggtg gtggatgtgt cccaagagga tcccgaggtg   1140
cagttcaatt ggtacgtgga cggcgtggaa gtgcacaacg ccaagaccaa gcctagagag   1200
gaacagttca actccaccta cagagtggtg tccgtgctga ccgtgctgca ccaggattgg   1260
ctgaatggca agagtataa gtgcaaggtg tccaacaagg gcctgccttc cagcatcgaa   1320
aagaccatct ccaaggccaa gggccagcct agggaacccc aggtttacac cctgcctcca   1380
agccaagagg aaatgaccaa gaaccaggtg tccctgacat gcctggtcaa gggcttctac   1440
ccctccgata tcgccgtgga atgggagtct aatggccagc tgagaacaa ctacaagacc   1500
acacctcctg tgctggactc cgacggcagc ttcttctgt actcccgcct gaccgtggac   1560
aagtccaggt ggcaagaggg caacgtgttc tcctgctccg tgatgcacga ggccctgcac   1620
aatcactaca cccagaagtc cctgtctctg tccctgggca atga                    1665
```

<210> SEQ ID NO 68
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gctcagaata tcaccgccag aatcggcgag ccctggtgc tgaaatgtaa aggcgcccct      60
aagaagcctc ctcagcggct ggaatggaag ctgaacaccg gcagaaccga ggcctggaaa    120
```

```
gtgctgtctc ctcaaggcgg aggcccttgg gattctgtgg ctagagtgct gcctaacggc      180
tccctgtttc tgcctgctgt gggcatccag gacgagggca tcttcaggtg tcaggccatg      240
aaccggaacg gcaaagagac aaagtccaac taccgcgtca gagtgtatca gatccccggc      300
aagcctgaga tcgtggactc tgcctctgaa ctgacagccg gcgtgcccaa caaagtgggc      360
acttgtgtgt ccgagggcag ctatcctgct ggcaccctgt cttggcatct ggatggaaag      420
cctctggtgc ccaacgagaa aggcgtgtcc gtgaaagagc agaccagacg gcatcctgag      480
actggcctgt tcaccctgca gtccgagctg atggttaccc ctgctagagg cggcgatccc      540
agacctacct tcagctgctc cttctctcct ggcctgcctc gacatagagc cctgagaacc      600
gctcctatcc agcctagagt gtgggagcct gtgcctctgg aagaggtgca gctggtggtt      660
gaacctgaag gcggagctgt tgctcctggc ggaacagtga ccctgacctg tgaagttccc      720
gctcagccct ctccacagat ccactggatg aaggatggcg tgccactgcc tctgcctcca      780
tctcctgttc tgatcctgcc agagatcggc cctcaggacc agggcaccta ttcttgtgtg      840
gctacccact cctctcacgg ccctcaagag tctagagccg tgtccatctc catcatcgag      900
cctggcgagg aaggacctac agctggcgag ggctttgaca aagtgcgcga ggctgaggac      960
tctcctcagc atgccggaac actggtcacc gtgtcctccg agtctaagta cggccctcct     1020
tgtcctccat gtcctgctcc agaagctgct ggcggccctt ccgtgtttct gttccctcca     1080
aagcctaagg acaccctgta catcacccgg gagcctgaag tgacctgcgt ggtggtggat     1140
gtgtcccaag aggatcccga ggtgcagttc aattggtacg tggacggcgt ggaagtgcac     1200
aacgccaaga ccaagcctag agaggaacag ttcaactcca cctacagagt ggtgtccgtg     1260
ctgaccgtgc tgcaccagga ttggctgaat ggcaaagagt ataagtgcaa ggtgtccaac     1320
aagggcctgc cttccagcat cgaaaagacc atctccaagg ccaagggcca gcctagggaa     1380
ccccaggttt acaccctgcc tccaagccaa gaggaaatga ccaagaacca ggtgtccctg     1440
acatgcctgg tcaagggctt ctaccccctcc gatatcgccg tggaatggga gtctaatggc     1500
cagcctgaga caaactacaa gaccacacct cctgtgctgg actccgacgg cagcttcttt     1560
ctgtactccc gcctgaccgt ggacaagtcc aggtggcaag agggcaacgt gttctcctgc     1620
tccgtgatgc acgaggccct gcacaatcac tacacccaga agtccctgtc tctgtccctg     1680
ggcaaatga                                                            1689
```

<210> SEQ ID NO 69
<211> LENGTH: 1631
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
gctcagaata tcaccgccag aatcggcgag cccctggtgc tgaaatgtaa agggccccta       60
agaagcctcc tcagcggctg gaatggaagc tgaacaccgg cagaaccgag gcctggaaag      120
tgctgtctcc tcaaggcgga ggcccttggg attctgtggc tagagtgctg cctaacggct      180
cctgtttctg cctgctgtgg gcatccagga cgagggcatc ttcaggtgtc aggccatgaa      240
ccggaacggc aaagagacaa agtccaacta ccgcgtcaga gtgtatcaga tccccggcaa      300
gcctgagtcg tggactctgc ctctgaactg acagccggcg tgcccaacaa agtgggcact      360
tgtgtgtccg agggcagcta tcctgctggc accctgtctt ggcatctgga tggaaagcct      420
```

```
ctggtgccca acgaaaaggc gtgtccgtga aagagcagac cagacggcat cctgagactg    480
gcctgttcac cctgcagtcc gagctgatgg ttacccctgc tagaggcggc gatcccagac    540
ctaccttcag ctgctccttc ttcctggcct gcctcgacat agagccctga gaaccgctcc    600
tatccagcct agagtgtggg agcctgtgcc tctggaagag gtgcagctgg tggttgaacc    660
tgaaggcgga gctgttgctc ctggcggaca gtgaccctga cctgtgaagt tcccgctcag    720
ccctctccac agatccactg gatgaaggat ggcgtgccac tgcctctgcc tccatctcct    780
gttctgatcc tgccagagat cggccctcag gaccaggcac ctattcttgt gtggctaccc    840
actcctctca cggccctcaa gagtctagag ccgtgtccat ctccatcatc gagcctggcg    900
aggaaggacc tacagctggc gagggctttg acaaagtgcg cgggctgagg actctcctca    960
gcacgctgtt gagtgccctc catgtgctcc tccagttgct ggtggccctt ccgtgttcct   1020
gtttcctcca aagcctaagg acaccctgta catcacccgc gagcctgaat gacctgcgtg   1080
gtggtggatg tgtcccaaga ggatcccgag gtgcagttca attggtacgt ggacggcgtg   1140
gaagtgcaca acgccaagac caagcctaga gaggaacagt tcaactccac ctacaggtgg   1200
tgtccgtgct gaccgtgctg caccaggatt ggctgaatgg caaagagtat aagtgcaagg   1260
tgtccaacaa gggcctgcct tccagcatcg aaaagaccat ctccaaggcc aagggccagc   1320
ctaggaaccc caggtttaca ccctgcctcc aagccaagag gaaatgacca agaaccaggt   1380
gtccctgaca tgcctggtca agggcttcta cccctccgat atcgccgtgg aatgggagtc   1440
taatggccag ctgagaacaa ctacaagacc acacctcctg tgctggactc cgacggcagc   1500
ttctttctgt actcccgcct gaccgtggac aagtccaggt ggcaagaggg caacgtgttc   1560
tcctgctccg tgatgcagag gccctgcaca atcactacac ccagaagtcc ctgtctctgt   1620
ccctgggctg a                                                       1631

<210> SEQ ID NO 70
<211> LENGTH: 1644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gctcagaata tcaccgccag aatcggcgag cccctggtgc tgaaatgtaa aggcgcccct     60
aagaagcctc ctcagcggct ggaatggaag ctgaacaccg gcagaaccga ggcctggaaa    120
gtgctgtctc tcaaggcgg aggccccttgg gattctgtgg ctagagtgct gcctaacggc    180
tccctgtttc tgcctgctgt gggcatccag gacgagggca tcttcaggtg tcaggccatg    240
aaccggaacg gcaaagagac aaagtccaac taccgcgtca gagtgtatca gatccccggc    300
aagcctgaga tcgtggactc tgcctctgaa ctgacagccg gcgtgcccaa caaagtgggc    360
acttgtgtgt ccgagggcag ctatcctgct ggcaccctgt cttggcatct ggatggaaag    420
cctctggtgc ccaacgagaa aggcgtgtcc gtgaaagagc agaccagacg gcatcctgag    480
actggcctgt tcaccctgca gtccgagctg atggttaccc tgctagaggc ggcgatcccc    540
agacctacct tcagctgctc cttctctcct ggcctgcctc gacatagagc cctgagaacc    600
gctcctatcc agcctagagt gtgggagcct gtgcctctgg aagaggtgca gctggtggtt    660
gaacctgaag gcgagctgt tgctcctggc ggaacagtga ccctgacctg tgaagttccc    720
gctcagccct ctccacagat ccactggatg aaggatggcg tgccactgcc tctgcctcca    780
```

```
tctcctgttc tgatcctgcc agagatcggc cctcaggacc agggcaccta ttcttgtgtg    840
gctacccact cctctcacgg ccctcaagag tctagagccg tgtccatctc catcatcgag    900
cctggcgagg aaggacctac agctggcgag ggctttgaca aagtgcgcga ggctgaggac    960
tctcctcagc atgccgtgga atgccctcct tgtgctcctc ctgtggctgg cggcccttcc   1020
gtgtttctgt tccctccaaa gcctaaggac accctgatga tctctcggac ccctgaagtg   1080
acctgcgtgg tggtggatgt gtcccaagag gatcccgagg tgcagttcaa ttggtacgtg   1140
gacggcgtgg aagtgcacaa cgccaagacc aagcctagag aggaacagtt caactccacc   1200
tacagagtgg tgtccgtgct gaccgtgctg caccaggatt ggctgaatgg caaagagtat   1260
aagtgcaagg tgtccaacaa gggcctgcct tccagcatcg aaaagaccat ctccaaggcc   1320
aagggccagc ctagggaacc ccaggtttac accctgcctc caagccaaga ggaaatgacc   1380
aagaaccagg tgtccctgac atgcctggtc aagggcttct accctccgga tatcgccgtg   1440
gaatgggagt ctaatggcca gcctgagaac aactacaaga ccacacctcc tgtgctggac   1500
tccgacggca gcttctttct gtactcccgc ctgaccgtgg acaagtccag gtggcaagag   1560
ggcaacgtgt ctcctgctc cgtgatgcac gaggccctgc acaatcacta cacccagaag   1620
tccctgtctc tgtccctggg ctga                                         1644
```

<210> SEQ ID NO 71
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

His Ser Ser His Gly Pro Gln Glu Ser Arg Ala Val Ser Ile Ser Ile
1               5                   10                  15

Ile Glu Pro Gly Glu Glu Gly Pro Thr Ala Gly
            20                  25

<210> SEQ ID NO 72
<211> LENGTH: 43
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

His Ser Ser His Gly Pro Gln Glu Ser Arg Ala Val Ser Ile Ser Ile
1               5                   10                  15

Ile Glu Pro Gly Glu Glu Gly Pro Thr Ala Gly Glu Gly Phe Asp Lys
            20                  25                  30

Val Arg Glu Ala Glu Asp Ser Pro Gln His Ala
        35                  40

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Ser Val Gly Gly Ser Gly Leu Gly Thr Leu Ala Leu Ala

<210> SEQ ID NO 74
<211> LENGTH: 325
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
        115                 120                 125

Pro Ala Gly Thr Leu Ser Trp His Leu Asp Gly Lys Pro Leu Val Pro
    130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly Glu Gly Phe Asp Lys Val Arg Glu Ala Glu Asp
305                 310                 315                 320

Ser Pro Gln His Met
                325
```

<210> SEQ ID NO 75
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N-3-(2, 4-Dinitrophenyl)-L-2,3-diaminopropionyl

<400> SEQUENCE: 75

Lys Pro Leu Gly Leu Xaa Ala Arg
1               5
```

RAGE FUSION PROTEINS WITH IMPROVED STABILITY AND LIGAND BINDING AFFINITY AND USES THEREOF

CROSS REFERENCE TO RELATED APPLICATIONS

This application claims priority to U.S. Provisional Application No. 62/731,663, filed Sep. 14, 2018, which is hereby incorporated by reference in its entirety.

SEQUENCE LISTING

The instant application contains a Sequence Listing which has been submitted via EFS-Web and is hereby incorporated by reference in its entirety. Said ASCII copy, created on Oct. 11, 2019, is named 44263US_CRF_sequencelisting.txt and is 228,990 bytes in size.

BACKGROUND

The genes encoding both the bovine and human forms of receptor for advanced glycation end-products (RAGE) were reported in 1992. The open reading frame (ORF) consisted of 404 amino acid residues organized into (from N to C terminus) a projected signal sequence of 22 amino acid residues, an N-terminal exodomain of ~321 residues, a transmembrane domain of 19 residues, and an intracellular domain of 41 residues. The exodomain was shown to have three immunoglobulin (Ig)-like domains, including a variable domain and two constant regions. The signal sequence is thought to be residues 1-22, followed by the variable domain at residues 23-116, followed by a very short intervening sequence of about 6-8 residues leading to the C1 domain at residues 124-221. The C1 and C2 domains are separated by a longer ~18 residue linker. C2 spans residues 239-304, followed by a highly flexible stem of ~38 residues that allows for significant range of motion of the receptor on the surface of the cell. The transmembrane domain is ca. 19 residues and the C-terminal intracellular portion of the protein spans residues 264-404, with a serine phosphorylation site at S391.

Multiple RAGE receptors may interact and form clusters, which may aid in the binding of certain ligands, such as advanced glycation end products (AGEs), and result in intracellular signaling. Binding of a RAGE ligand to cell bound RAGE can trigger a series of downstream signaling events. Specific signaling profiles can differ, depending on the nature of ligand interaction, RAGE density, and other factors. Signaling may involve phosphorylation of RAGE at amino acid residue S391 by protein kinase C-zeta (PKCζ).

Nonenzymatic glycation and oxidation of proteins, lipids, and nucleic acids generates advanced glycation endproducts (AGEs), which are canonical RAGE ligands.

In addition to AGE, RAGE binds multiple ligands including amyloid-beta, S100B, S100A1, S100A2, S100A7 (psoriasin), S100A11, S100A12, HMGB1 (amphoterin), lipopolysaccharide (LPS), oxidized low-density lipoprotein (oxLDL), CD11b (MAC1), phosphatidyl serine, C3a, S100P, S100G, S100Z, carbonylated proteins, malondialdehyde (MDA), laminin, type I Collagen, type IV Collagen, CAPZA1, CAPZA2, DDOST, LGALS3, MAPK1, MAPK3, PRKCSH, S100A4, S100A5, S100A6, S100A8, S100A9, S100P, and SAA1.

Accumulation of AGE leading to activation of RAGE has been implicated in a variety of diseases and disorders, including diabetes and its microvascular complications, macrovascular complications, and other complications. AGEs and other RAGE ligands have been implicated in aging as well in a number of other diseases, including neurodegenerative disease, diabetic complications, ischemia-reperfusion injury in multiple organs, renal disease, etc. Soluble forms of RAGE (sRAGE and esRAGE) that include the extracellular ligand binding domain but lack the transmembrane and cytoplasmic domains of the endogenous protein may be useful for binding RAGE ligands, thereby impeding RAGE activation and downstream signaling cascades. Thus, there exists a need for drug-like soluble RAGE molecules with enhanced binding affinity to RAGE ligands and an extended half-life suitable for therapeutic applications. Production of therapeutic proteins on a commercial scale requires proteins that can be efficiently expressed and purified without disrupting protein function. Manufacturability can be described as the ability to express and purify a protein in a sufficiently efficient manner and with sufficient stability and structural integrity to allow for cost-effective production of the protein. For commercial purposes, manufacturability must be determined for each potential therapeutic protein. Although protein expression and purification processes can be optimized for a protein, manufacturability may be a function of intrinsic properties of the protein.

SUMMARY OF THE INVENTION

The present disclosure provides biologically active therapeutic proteins based on RAGE having improved manufacturability properties capable of efficient production as well as enhanced ligand binding properties and enhanced stability in vivo.

Disclosed here are compositions comprising RAGE fusion and methods of use thereof. Accordingly, one embodiment of the disclosure is an isolated polypeptide comprising a first domain and a second domain. In some embodiments the first domain is at least 97% identical to the sequence of SEQ ID NO: 74. In some embodiments the second domain comprises an Fc region of an immunoglobulin. In some embodiments the carboxy terminus of the first domain is coupled to the amino terminus of the second domain by a peptide linkage.

In some embodiments the polypeptide is resistant to cleavage by a disintegrin and metalloproteinase 10 (ADAM10). In some embodiments the polypeptide is at least 15% more resistant to cleavage by at least one of ADAM10, matrix metalloproteinase 9 (MMP9), and trypsin as compared to a polypeptide comprising the sequence set forth in SEQ ID NO: 5. In some embodiments the percent resistance equals the difference between the fraction of polypeptide that remains full length following incubation with at least one of ADAM10, MMP9, and trypsin for a defined time period compared to a control polypeptide treated for the same time and under the same conditions.

In some embodiments the polypeptide is resistant to degradation in human serum. In some embodiments the polypeptide is at least 15% more resistant to degradation in human serum as compared to a polypeptide comprising the sequence set forth in SEQ ID NO: 5. In some embodiments the percent resistance equals the difference between the fraction of polypeptide that remains full length following incubation in human serum for a defined time period as compared to a control polypeptide treated for the same time and under the same conditions.

In some embodiments the polypeptide has improved resistance to thermal denaturation. In some embodiments the polypeptide has a higher onset of thermal denaturation ($T_{agg}$) of at least 5° C. as compared to a polypeptide comprising the sequence set forth in SEQ ID NO: 5. In some embodiments the change in onset of thermal denaturation ($T_{agg}$) equals the temperature at which the polypeptide transitions from a compact folded monomeric state to an unfolded state as analyzed in a defined temperature gradient as compared to a control polypeptide treated in the same temperature gradient and under the same conditions.

In some embodiments the polypeptide specifically binds at least one of: an advanced glycation endproduct (AGE), CML-HSA (carboxymethylated human serum albumin), HMGB1 (amphoterin), amyloid-beta, S100A1, S100A2, S100A4 (metastasin), S100A5, S100A6, S100A7 (psoriasin), S100A8/9, S100A11, S100A12, S100B, S100P, lipopolysaccharide (LPS), oxidized low-density lipoprotein (oxLDL), CD11b (MAC1), phosphatidyl serine, C3a, S100P, S100G, S100Z, carbonylated proteins, malondialdehyde (MDA), laminin, type I Collagen, type IV Collagen, CAPZA1, CAPZA2, DDOST, LGALS3, MAPK1, MAPK3, PRKCSH, S100A4, S100A5, S100A6, S100A8, S100A9, S100P, and SAA1.

In some embodiments the polypeptide comprises a polypeptide dimer.

In some embodiments the first domain comprises at least one asparagine residue linked to a glycan. In some embodiments the first domain an amino acid substitution at one or more of amino acid residues 3 or 59, wherein said amino acid residues 3 or 59 correspond to an amino acid at position 3 or 59 of said first domain. In a preferred embodiment the amino acid at position 3 of the domain is substituted with glutamic acid or glutamine. In another preferred embodiment the amino acid at position 59 of the first domain is substituted with alanine, glutamic acid, or glutamine. In one embodiment the amino acid residue at position 60 of the first domain is substituted with serine. In some embodiments the first domain comprises the sequence set forth in SEQ ID NO: 74.

In some embodiments the heavy chain of the polypeptide comprises CH2 and CH3 domains of a human IgG. In one embodiment the CH2 and CH3 domains comprise the amino acid sequence set forth in SEQ ID NO: 4.

In some embodiments the immunoglobulin Fc of the polypeptide comprises one or more amino acid substitutions at one or more of amino acid residues 252, 254, or 256, numbered according to the EU numbering. In some embodiments amino acid residue 252 is substituted with tyrosine. In some embodiments amino acid residue 254 is substituted with threonine. In some embodiments amino acid residue 256 is substituted with glutamine or glutamic acid.

In some embodiments of the present disclosure the polypeptide may comprise a Fc region of an IgG1, IgG2, or IgG4 immunoglobulin. In some embodiments the polypeptide may comprise a peptide linkage that comprises at least a portion of an immunoglobulin hinge region. In some embodiments the peptide linkage may comprise at least a portion of the hinge region of IgG1, IgG2, or IgG4. In some embodiments the peptide linkage may comprise an amino acid sequence having at least 95% sequence identity to the sequence set forth in SEQ ID NO: 11, SEQ ID NO: 10, or SEQ ID NO: 8.

In some embodiments the carboxy terminal lysine of the IgG4 CH2-CH3 immunoglobulin domain is deleted comprising the sequences set forth in SEQ ID NO: 54 and SEQ ID NO: 55.

In some embodiments the polypeptide has a higher apparent binding affinity to a receptor for advanced glycation endproducts (RAGE) ligand compared to a polypeptide comprising the sequence of SEQ ID NO: 5. In some embodiments the apparent equilibrium dissociation constant (Kd) of the interaction between the polypeptide and its ligand may be 20 nanomolar (nM) or less.

Exemplary embodiments include a polypeptide that is expressed a greater amount in CHO-3E7 cells than a polypeptide comprising the sequence set forth in SEQ ID NO: 5 when CHO-3E7 cells are transfected under otherwise identical defined conditions with nucleic acid plasmid encoding either polypeptide. In a preferred embodiment the greater amount is at least 5%. In another preferred embodiment the nucleic acid plasmid comprises the nucleic acid vector pTT5.

One embodiment of the disclosure is an isolated polypeptide comprising a RAGE polypeptide coupled to an Fc region of an immunoglobulin. In some embodiments the carboxy terminus of the RAGE polypeptide is coupled to the amino terminus of the immunoglobulin Fc region by a peptide linkage. In some embodiments the peptide linkages comprise novel stem and hinge regions. In some embodiments the RAGE polypeptide comprises the amino acid sequence set forth in SEQ ID NO: 2.

In some embodiments the polypeptide has the amino acid sequence of SEQ ID NO: 53. In some embodiments the polypeptide has the amino acid sequence of SEQ ID NO: 12. In some embodiments the polypeptide has the amino acid sequence of SEQ ID NO: 15. In some embodiments the polypeptide has the amino acid sequence of SEQ ID NO: 16.

Some embodiments of the disclosure comprise an isolated nucleic acid molecule comprising a polynucleotide encoding a polypeptide comprising a RAGE polypeptide coupled to a heavy chain fragment of an Fc region of an immunoglobulin. In some embodiments the polynucleotide encodes a polypeptide comprising a first amino acid sequence and a second amino acid sequence. In some embodiments the sequence of the first domain is at least 97% identical to the sequence set forth in SEQ ID NO: 74. In some embodiments the second amino acid sequence comprises an Fc region of an immunoglobulin. In some embodiments the carboxy terminus of the first amino acid sequence is coupled to the amino terminus of the second amino acid sequence by a peptide linkage. In some embodiments the polynucleotide is operably linked to a transcriptional or translational regulatory sequence.

A further embodiment comprises a vector comprising an isolated nucleic acid molecule comprising a polynucleotide encoding a polypeptide comprising a RAGE polypeptide coupled to a heavy chain fragment of an Fc region of an immunoglobulin. Some embodiments of the present disclosure comprise a host cell comprising a vector comprising an isolated nucleic acid molecule comprising a polynucleotide encoding a polypeptide comprising a RAGE polypeptide coupled to a heavy chain fragment of an Fc region of an immunoglobulin. In some embodiments the host cell is a mammalian cell.

An embodiment of the present disclosure comprises a therapeutic composition for treating a RAGE-mediated disorder wherein the composition comprises a first amino acid sequence and a second amino acid sequence. In some embodiments the first domain is at least 97% identical to the sequence set forth in SEQ ID NO: 74. In some embodiments the second amino acid sequence comprises a heavy chain fragment of an Fc region of an immunoglobulin. In some embodiments the carboxy terminus of the first amino acid sequence is coupled to the amino terminus of the second amino acid sequence by a peptide linkage. In some embodiments the peptide linkage linking the first amino acid sequence and the second amino acid sequence comprises a stem derived from a soluble splice variant and a silent antibody hinge region.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Figure 1:
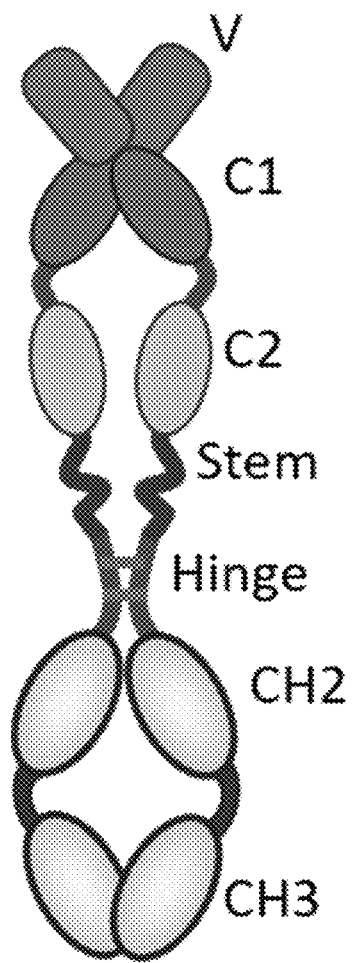
FIG. 1 is a schematic of a dimerized esRAGE-Fc fusion protein. The RAGE polypeptide comprises V, C1, C2, and the stem domains. The Fc polypeptide comprises the CH2 and CH3 domains. The linker between the two polypeptides is identified as the hinge.

The present disclosure describes fusion proteins comprising extracellular RAGE joined via a peptide linkage at the carboxyl terminus with an immunoglobulin Fc. The fusion proteins of the disclosure are characterized by their ability to bind to at least one RAGE ligand (e.g., advanced glycation end-product (AGE), HMGB1 (amphoterin), S100A11, S100A12) with high affinity, thereby disrupting endogenous RAGE-mediated signaling. The RAGE fusion proteins of the present disclosure are further characterized by enhanced stability, extended half-life, and improved manufacturability compared to other soluble RAGE proteins.

The stabilized RAGE-Fc fusion proteins are characterized by a RAGE protein that is different from the extracellular domain of the full-length RAGE polypeptide by the addition of 16 amino acids at the carboxyl terminus. The carboxyl terminus of the RAGE protein is joined to the amino terminus of a human immunoglobulin Fc via a peptide linkage comprised of at least part of an immunoglobulin hinge. In some embodiments a short peptide linker may be inserted between the RAGE protein and the immunoglobulin hinge.

Definitions

Terms used in the claims and specification are defined as set forth below unless otherwise specified.

The term "ameliorating" refers to any therapeutically beneficial result in the treatment of a disease state (e.g., a RAGE-mediated disease).

The term "isolated" refers to a protein or polypeptide molecule purified to some degree from endogenous material.

The term "RAGE" as used herein refers to the polypeptide sequence encoding Receptor for Advanced Glycation End-product (RAGE) or any variation thereof, including, but not limited to, isoforms that lack all or part of the N-terminal V-type immunoglobulin domain (N-truncated), isoforms that lack all or part of the transmembrane domain (C-truncated), and isoforms that comprise 1, 2, 3, 4 or more than 4 amino acid substitutions compared to wild-type RAGE.

The term "sRAGE" as used herein refers to soluble RAGE or RAGE lacking a transmembrane domain (C-truncated). As used herein, sRAGE refers to soluble RAGE that is generated as a result of protease cleavage that removes the transmembrane domain.

The term "esRAGE" (endogenous soluble RAGE) as used herein refers to soluble RAGE generated by an alternative splice site that results in a modified C-terminus comprising the following sequence at positions 332 to 347: EGFDKVREAEDSPQHM (the C-terminal portion of the V1 stem) (SEQ ID NO: 52). As used herein, "esRAGE" may comprise one or more amino acid substitutions, including point mutations within amino acid positions 332 to 347. The term percent "identity," in the context of two or more nucleic acid or polypeptide sequences, refer to two or more sequences or subsequences that have a specified percentage of nucleotides or amino acid residues that are identical, when compared and aligned for maximum correspondence using BLASTP and BLASTN algorithms, using the default parameters as publicly available through the National Center for Biotechnology Information (www.ncbi.nlm.nih.gov/).

Depending on the application, the percent "identity" can exist over a region of the sequence being compared, e.g., over a functional domain, or, alternatively, exist over the full length of the two sequences to be compared. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al.).

As used herein, the terms "treatment," "treating," and the like, refer to administering an agent, or carrying out a procedure for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of any pathological state in a mammal, particularly in a human, and includes: (a) inhibiting the disease, i.e., arresting its development; (b) relieving the disease, i.e., causing regression of the disease; (c) delaying onset of the disease; (d) decreasing the duration of the disease; (e) relieving or reducing the severity of any symptom of the disease; or (f) decreasing the risk or severity of any complication of the disease.

Treating may refer to any indicia of success in the treatment or amelioration or prevention of a pathologic state, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters, including the results of an examination by a physician. Accordingly, the term "treating" includes the administration of the compounds or agents of the present invention to delay, to alleviate, or to arrest or inhibit development of the symptoms or conditions associated with the pathologic state. The term "therapeutic effect" refers to the reduction, elimination, prevention, delayed onset, or accelerated resolution of the disease, symptoms of the disease, or side effects of the disease in the subject.

The term "prevent" as used herein refers to avoiding or averting the onset of a symptom or symptoms characteristic of one or more disease states.

The term "prophylaxis" as used herein refers to therapy given to prevent or ameliorate symptoms of one or more disease states.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

The term "subject" refers to any animal, such as mammals, including humans.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

The term "percent resistant" refers to the percent resistance equal to the difference between the fraction of peptide that remains full length following incubation with at least one of ADAM10, MMP9, and trypsin for a defined time period compared to a control peptide treated for the same time and under the same conditions.

The term "increased thermal stability" refers to the highest temperature which a polypeptide remains in a folded state following incubation in temperature gradient for a defined time period as compared to a control polypeptide treated with the same temperature gradient and under the same conditions.

The term "specific binding," as used herein, refers to an affinity between a receptor and its ligand in which the $K_d$ value is below $10^{-6}$M, $10^{-7}$M, $10^{-8}$M, $10^{-9}$M, or $10^{-10}$M.

Abbreviations used in this application include the following: Advanced Glycation Endproduct (AGE), Receptor for Advanced Glycation Endproduct (RAGE), soluble RAGE (sRAGE), endogenous secretory RAGE (esRAGE), immunoglobulin (Ig).

It must be noted that, as used in the specification and the appended claims, the singular forms "a," "an" and "the" include plural referents unless the context clearly dictates otherwise.

RAGE Fusion Proteins

The present disclosure provides RAGE fusion proteins, and methods of making and using such fusion proteins.

In a first aspect, isolated polypeptides are provided.

Embodiments of the isolated polypeptides are fusion proteins comprising four modules: an amino-terminus derived from a RAGE exodomain, a stem derived from a soluble splice variant (esRAGE) or a shortened portion of its stem region (lacking the C-terminal 13 amino acid residues of the stem containing the proteolytic cleavage site), a silent antibody hinge region, and an antibody Fc region. In some embodiments the fusion protein comprises an esRAGE polypeptide. The esRAGE polypeptide may be at least 90%, 91%, 92%, 93%, 94%, 95%, 96%, 97%, 98%, or 99% identical to SEQ ID NO: 74.

In typical embodiments, the isolated polypeptides comprise a first domain wherein said first domain has an amino acid sequence at least 97% identical to the sequence of SEQ ID NO:74; and a second domain comprising a fragment of a Fc region of an immunoglobulin, wherein the carboxy terminus of said first domain is coupled to the amino terminus of said second domain by a peptide linkage.

SEQ ID NO: 1 provides the sequence of esRAGE (including the N-terminal leader sequence) and SEQ ID NO:74 provides the sequence of mature esRAGE (lacking the N-terminal leader sequence). esRAGE is an endogenous soluble form of RAGE generated by an alternative splice site which results in the extracellular domain of full RAGE, modified at the carboxyl terminus by an additional 16 amino acids beginning at position 332 (SEQ ID NO: 1) or position 310 (SEQ ID NO: 74).

In various embodiments, the first domain has a sequence that differs from SEQ ID NO: 1 by 1, 2, 3, 4, 5, 6, 7, or more than 7 amino acids. In some embodiments, the first domain has a substitution of the asparagine at position 25 of SEQ ID NO: 1 (position 3 of SEQ ID NO: 74), wherein the substitution is a glutamic acid or glutamine. In some embodiments, the first domain has the asparagine at position 81 of SEQ ID NO: 1 (position 59 of SEQ ID NO: 74) substituted with alanine. In some embodiments, the first domain has the glycine at position 82 of SEQ ID NO: 1 (position 60 of SEQ ID NO: 74) substituted with serine. In some embodiments, the first domain has an amino acid inserted, deleted, or substituted in the amino acid sequence corresponding to positions 332-347 of SEQ ID NO: 1 (positions 310-325 of SEQ ID NO: 74).

In some embodiments the fusion protein comprises a full-length RAGE polypeptide.

In some embodiments the fusion protein comprises a RAGE polypeptide with a shortened stem region lacking the C-terminal 13 amino acid residues. The shortened stem RAGE polypeptide may be at least 90%, 91%, 92%, 93%, 94%, 95%, 96%, 97%, 98%, or 99% identical to SEQ ID NO: 74.

In some embodiments the amino-terminus module may comprise a signal sequence. The signal sequence may comprise the amino acid residues at positions 1-22 of the amino acid sequence set forth in SEQ ID NO: 1. In some embodiments the signal sequence may be at least 50%, 60%, 70%, 80%, 90%, 91%, 92%, 93%, 94%, 95%, 96%, 97%, 98%, or 99% identical to the amino acid sequence at positions 1-22 of the sequence set forth in SEQ ID NO: 1. In still other embodiments the amino-terminus module may comprise any signal sequence useful for expressing RAGE fusion proteins.

In some embodiments, the amino-terminus module comprising a RAGE polypeptide of the present disclosure may be glycosylated on at least one of the asparagine residues at positions 25 and 81 (SEQ ID NO: 1) or positions 3 and 59 (SEQ ID NO: 74). In some embodiments glycosylation at either position may be required for optimal ligand binding. In some embodiments glycosylation of the asparagine residues at both position 25 and 81 (SEQ ID NO: 1) or position 3 and 59 (SEQ ID NO: 74) may impair ligand binding.

In some embodiments of the present disclosure the RAGE polypeptide may dimerize. In some embodiments the RAGE polypeptide may dimerize upon binding a RAGE ligand. In some cases the V domains of RAGE polypeptides may interact to form homodimers. In some cases dimerization may be mediated by the C1 or C2 domains.

In some embodiments, the RAGE polypeptide may be linked to a polypeptide comprising an immunoglobulin domain or a portion (e.g., a fragment thereof) of an immunoglobulin domain. In some cases the polypeptide comprising an immunoglobulin domain or a portion of an immunoglobulin domain may comprise a human IgG Fc region or a portion thereof. In some cases the human IgG Fc region comprises at least a portion of the CH2 and CH3 domains of a human IgG Fc region. The human IgG Fc region may be derived from any of the known IgG subtypes: IgG1, IgG2, IgG3, or IgG4.

In some cases the RAGE fusion protein may comprise the CH2 and CH3 domains of human IgG4. In some embodiments the fusion protein may comprise the sequence set forth in SEQ ID NO: 7. In other embodiments the fusion protein may comprise a polypeptide having at least 75%, 80%, 85%, 90%, 95%, 96%, 97%, 98%, or 99% sequence identity to SEQ ID NO: 7.

In some embodiments the Fc polypeptide of the fusion protein may be proinflammatory in vivo. In other embodiments, the Fc polypeptide may be silenced (e.g. comprise a peptide sequence that prevents formation of immune complexes that otherwise would form through productive engagement (i.e. engagement that results in an inflammatory response) of the Fc polypeptide to an Fc receptor) in vivo. In some embodiments the Fc polypeptide may be silenced with respect to binding Fc-gamma receptors by the nature of specific AA sequences in the hinge region.

The Fc polypeptide of the RAGE fusion protein may increase the stability of the fusion protein. For example, the Fc polypeptide of the fusion protein may contribute to stabilizing the RAGE fusion protein, thereby increasing the half-life of the RAGE fusion protein. In some cases the Fc polypeptide may significantly increase the serum half-life.

In some embodiments the RAGE fusion protein of the present disclosure may be more stable than RAGE fusion proteins in the prior art because the RAGE fusion protein of the disclosure lacks protease cleavage sites of RAGE fusion proteins of the prior art. For example, removal of the additional 16 amino acids in the esRAGE splice variant may result in the elimination of one or more protease cleavage sites. In some embodiments the RAGE fusion protein lacks the C-terminal 13 amino acids of the RAGE stem and thereby lacks a protease cleavage site of the prior art. In some embodiments the Fc polypeptide of the present disclosure may include fewer protease cleavage sites than the prior art. In other embodiments, the peptide linkage may include fewer protease cleavage sites than that in the prior art.

Protease cleavage sites are amino acid sequences recognized and cleaved by protease enzymes, resulting in a truncated polypeptide. Protease enzymes may include but are not limited to a disintegrin and metalloproteinase 10 (ADAM10), matrix metalloproteinase 9 (MMP9), and trypsin.

In one embodiment, the RAGE fusion protein of the present disclosure comprises an Fc polypeptide optimized to increase the in vivo serum half-life of the fusion protein. In one embodiment the Fc polypeptide is optimized by generating mutations (e.g., amino acid substitutions) that increase the half-life of the fusion protein. In one embodiment the Fc polypeptide comprises mutations comprising amino acid substitutions at residue positions 252, 254, and 256 (numbered according to the EU index as in Kabat). In a preferred embodiment the residue at position 252 is substituted with tyrosine, the residue at position 254 is substituted with threonine, and the residue at position 256 is substituted with glutamic acid (glutamate).

In some embodiments the serum half-life of the fusion protein is increased by 10%, 20%, 30%, 40%, 50%, 60%, 70%, 80%, 90%, 100%, 150%, or 200% as compared to a polypeptide comprising the sequence set forth in SEQ ID NO: 5.

The RAGE fusion protein of the present disclosure further comprises a peptide linkage (linker). Linkers serve primarily as a spacer between a polypeptide and a second heterologous polypeptide or other type of fusion. In one embodiment the linker is made up of amino acids linked together by peptide bonds, preferably from 1 to 20 amino acids linked by peptide bonds, wherein the amino acids are selected from the 20 naturally occurring amino acids. In one embodiment a linker is made up of a majority of amino acids that are sterically unhindered (e.g., glycine, alanine). In a further embodiment the linker may comprise the amino acid sequence of an IgG hinge region or partial IgG hinge region, as exemplified in SEQ ID NO: 8.

Expression of RAGE Fusion Proteins

RAGE fusion proteins of the present disclosure may be produced using a variety of expression-host systems. These systems include but are not limited to microorganisms such as bacteria transformed with recombinant bacteriophage, plasmid, or cosmid DNA expression vectors; yeast transformed with yeast expression vectors; and insect cell systems infected with virus expression vectors (e.g., baculovirus); and mammalian systems. Mammalian cells useful in recombinant protein production include but are not limited to VERO cells, HeLa cells, Chinese hamster ovary (CHO) cells (e.g., CHO-3E7 cells), COS cells, W138, BHK, HepG2, 3T3, RIN, MDCK, A549, PC12, K562, L cells, C127 cells, HEK 293, epidermal A431 cells, human Colo205 cells, HL-60, U937, HaK, and Jurkat cells. Mammalian expression allows for the production of secreted or soluble polypeptides which may be recovered from the growth medium.

Recombinant expression of a RAGE fusion protein of the present disclosure may require construction of a plasmid comprising a polynucleotide that encodes the fusion protein. The plasmid may be generated by sub-cloning the polynucleotide into an expression vector (e.g. pTT5, pcDNA3.1) using standard recombinant techniques, wherein the expression vector comprises regulatory signals for transcription and translation in mammalian systems.

In one embodiment a recombinant plasmid comprising a polynucleotide that encodes the fusion protein may be introduced into CHO cells by transfection such that the cells express the fusion protein. In one embodiment, cells expressing the fusion protein may be selected and cloned to generate cell lines that stably express the fusion protein. For example, cells expressing the recombinant construct may be selected for plasmid-encoded neomycin resistance by applying the antibiotic G418 to transfected cells. Individual clones may be selected and clones expressing high levels of the fusion protein as detected by Western Blot analysis of the cell supernatant may be expanded.

The RAGE fusion proteins of the present disclosure may be purified according to protein purification techniques known to those of skill in the art. For example, supernatant from a system which secretes recombinant protein into culture may be concentrated using a commercially available protein concentration filter. In one embodiment the supernatant may be applied directly to a suitable affinity purification matrix. For example, a suitable affinity purification matrix may comprise a molecule (e.g. Protein A, AGE) bound to a support. In one embodiment the supernatant may be applied to an anion exchange resin, for example, a matrix having pendant diethylaminoethyl (DEAE) groups. In another embodiment the supernatant may be applied to a cation exchange matrix. The matrices may include but are not limited to, acrylamide, agarose, dextran, and cellulose. After washing and eluting from the purification matrix, eluted fractions may be concentrated. In some embodiments the elution may be subjected to aqueous ion exchange or size exclusion chromatography. In some embodiments the elution may be subjected to high performance liquid chromatography (HPLC) for final purification.

Pharmaceutical Compositions

Methods for treatment of RAGE-mediated diseases are also encompassed by the present disclosure. Said methods of the disclosure include administering a therapeutically effective amount of esRAGE-Fc fusion protein. The fusion protein of the disclosure can be formulated in pharmaceutical compositions. These compositions can comprise, in addition to one or more of the esRAGE-Fc fusion proteins, a pharmaceutically acceptable excipient, carrier, buffer, stabilizer, or other materials well known to those skilled in the art. Such materials should be non-toxic and should not interfere with the efficacy of the active ingredient. The precise nature of the carrier or other material can depend on the route of administration, e.g. intravenous, cutaneous or subcutaneous, nasal, intramuscular, intraperitoneal routes.

For pharmaceutical compositions for intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

Administration of the pharmaceutically useful fusion protein of the present invention is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Uses of RAGE Fusion Proteins

The present disclosure provides methods and pharmaceutical compositions for binding RAGE ligands with high affinity, thereby inhibiting or reducing RAGE activation and thus RAGE-mediated signaling. In one aspect, the present disclosure provides methods and reagents for treating RAGE-mediated disorders (e.g., inflammation, nephropathy, arteriosclerosis, retinopathy, and other complications resulting from diabetes) in a subject in need thereof by administering a therapeutically effective amount of the fusion proteins of the disclosure to the subject. In one embodiment the fusion proteins of the present disclosure may bind one or more RAGE ligands in a subject and thereby decrease or inhibit RAGE-mediated signaling cascades. In some embodiments the fusion proteins may thereby reduce or inhibit an inflammatory response.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature.

Example 1: Expression and Purification of RAGE-IgG Fc Fusion Proteins

The following methods were used for expressing and purifying the RAGE-Fc fusion proteins.

The following method was used to produce the RAGE-Fc protein comprising the amino acid sequence set forth in SEQ ID NO: 16. Polynucleotides encoding esRAGE (SEQ ID NO: 1) were fused to polynucleotides encoding the human IgG4 Fc (amino acid residues 359-590 of the amino acid sequence set forth in SEQ ID NO: 17) via polynucleotides encoding a linker sequence derived from the IgG2 hinge (SEQ ID NO: 9) by PCR overlap extension. Primers used for PCR contained the mutation resulting in the amino acid substitutions of methionine to tyrosine at position 252, serine to threonine at position 254, and threonine to glutamic acid (glutamate) at position 256 of the Fc polypeptide wherein the numbering is according to the EU index as in Kabat. The full polynucleotide sequence is SEQ ID NO: 43 for the RAGE-Fc fusion protein having the amino acid sequence set forth in SEQ ID NO:16. Double stranded DNA fragments were subcloned into pTT5 vector.

Transient expression of RAGE-Fc fusion proteins was carried out as follows.

The RAGE-Fc polypeptide comprising the amino acid sequence set forth in SEQ ID NO: 16 was transiently expressed in CHO-3E7 cells grown in serum-free FreeStyle™ CHO Expression Medium (Thermo Fisher Scientific). The cells were maintained in Erlenmeyer Flasks (Corning Inc.) at 37° C. with 5% $CO_2$ on an orbital shaker (VWR Scientific). One day before transfection the cells were seeded at an appropriate density in Corning Erlenmeyer Flasks. On the day of transfection, DNA containing a polynucleotide encoding the esRAGE-Fc polypeptide and transfection reagent were mixed at an optimal ratio and then added into the flask containing cells previously seeded for transfection. The recombinant plasmid DNA encoding the esRAGE-Fc polypeptide was transiently transfected into suspension CHO-3E7 cell cultures. The cell culture supernatant collected on post-transfection day 6 was used for purification.

Purification of esRAGE-Fc fusion proteins was carried out as follows.

The cell culture broth was centrifuged and the resulting supernatant was loaded onto a Monofinity A Resin prepacked affinity purification column at an appropriate flow rate. After washing and elution with appropriate buffer, the eluted fractions were pooled and buffer exchanged to final formulation buffer.

Figure 2A:
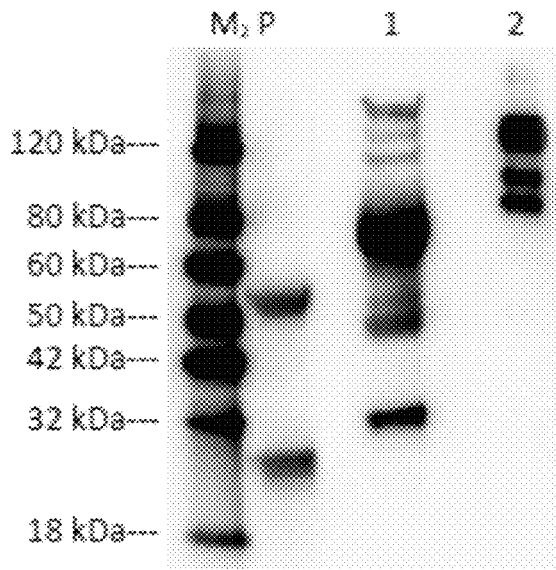
FIGS. 2A-2L show expression of RAGE-Fc fusion protein constructs assessed by Western blot: Construct #1 (FIG. 2A); Construct #9 (FIG. 2B); Construct #10 (FIG. 2C); Construct #11 (FIG. 2D); Construct #12 (FIG. 2E); Construct #13 (FIG. 2F); Construct #14 (FIG. 2G); Construct #15 (FIG. 2H); Construct #16 (FIG. 2I); Construct #17 (FIG. 2J); Construct #18 (FIG. 2K); and Construct #19 (FIG. 2L).
Figure 2B:
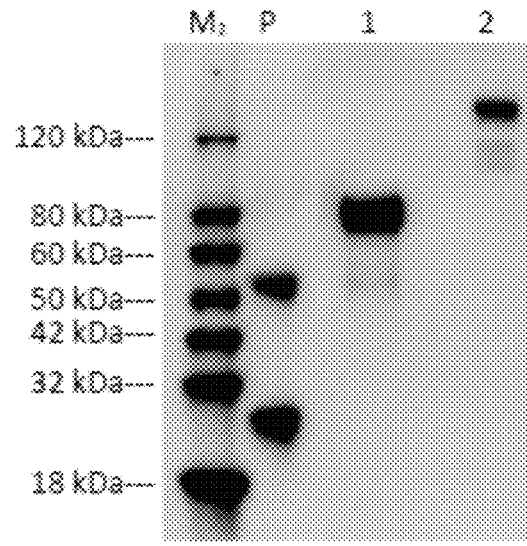
Figure 2C:
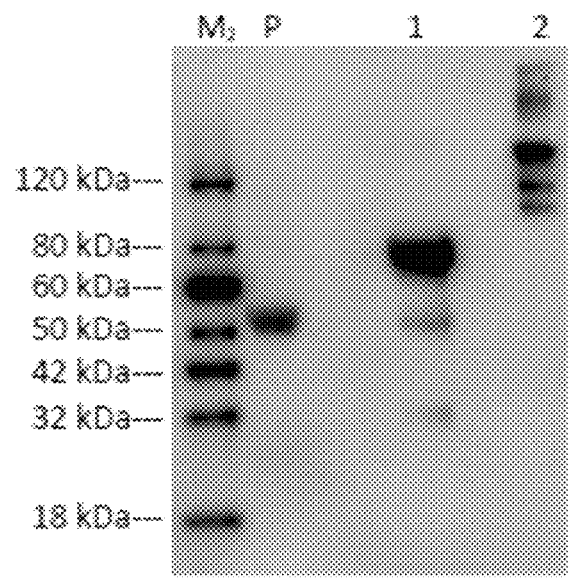
Figure 2D:
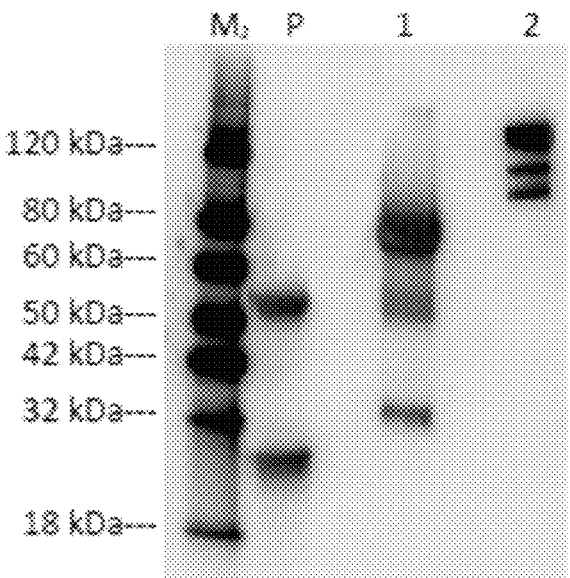
Figure 2E:
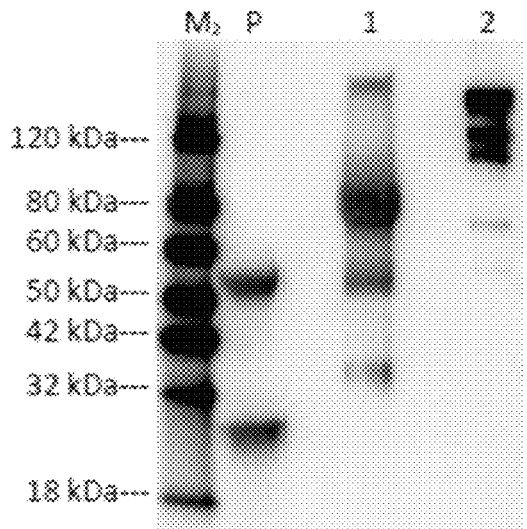
Figure 2F:
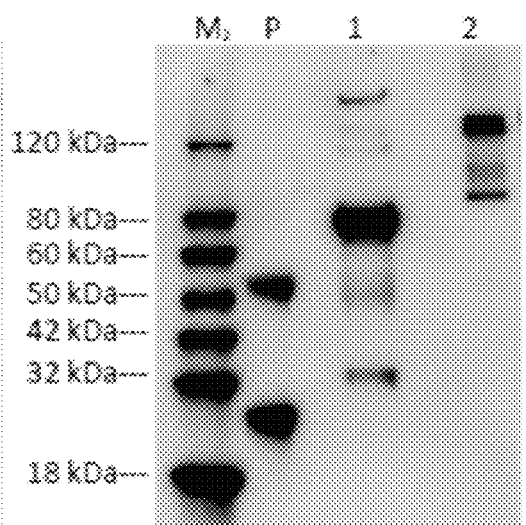
Figure 2G:
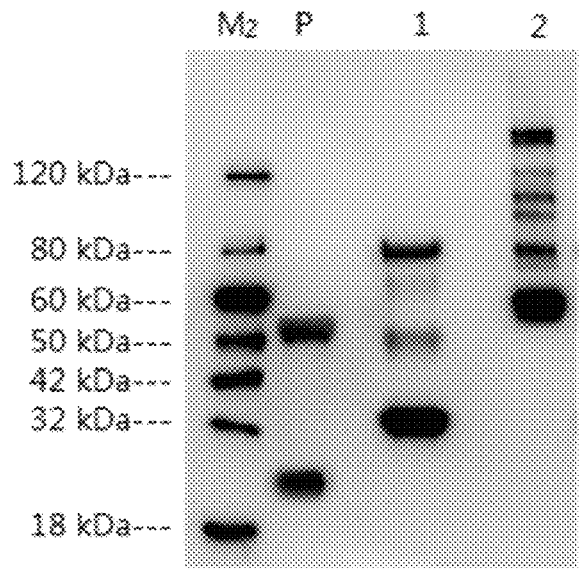
Figure 2H:
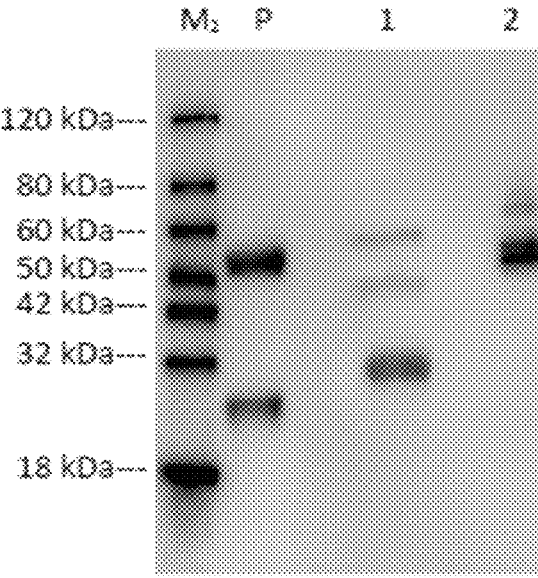
Figure 2I:
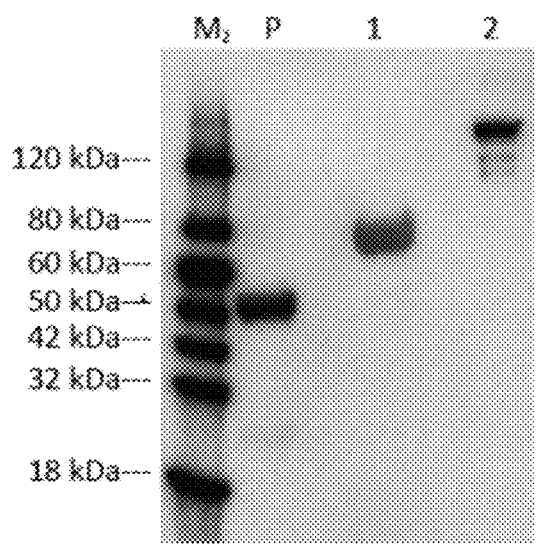
Figure 2J:
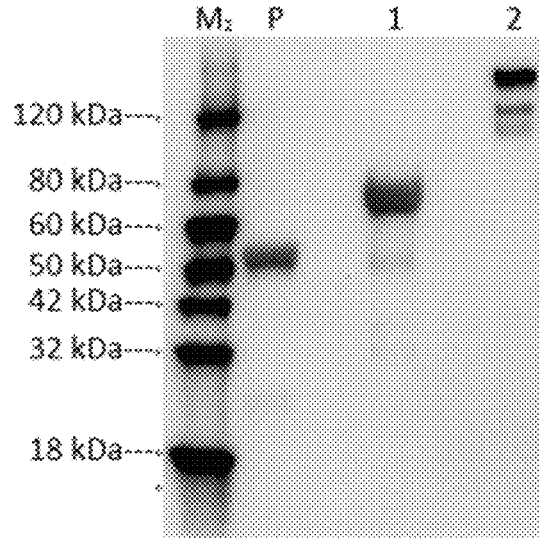
Figure 2K:
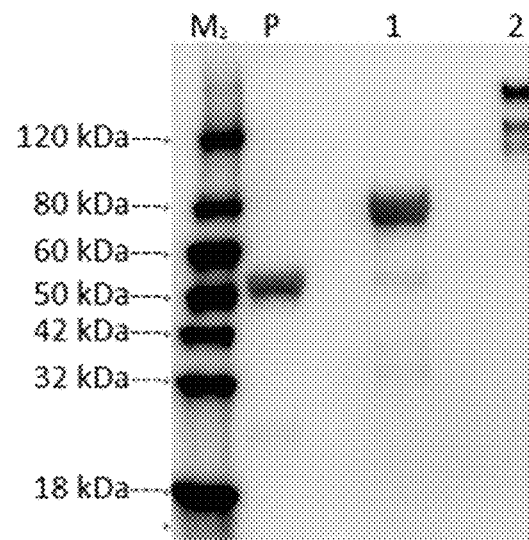
Figure 2L:
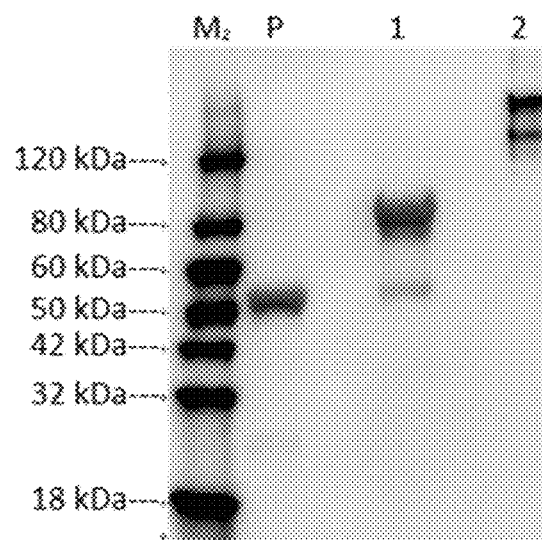
Figure 3A:
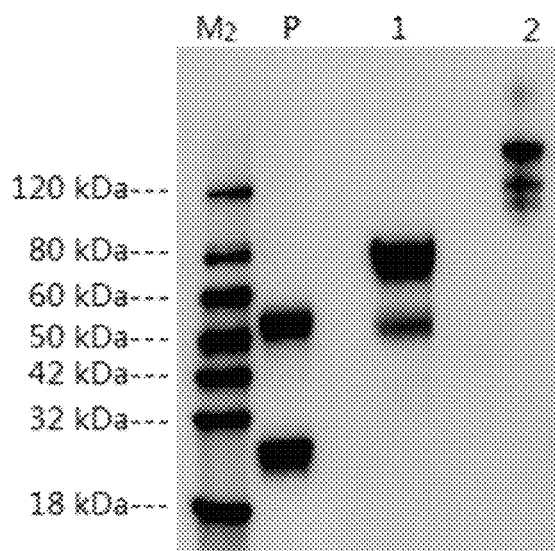
FIGS. 3A-3J show expression of RAGE-Fc fusion protein constructs assessed by Western blot: Construct #20 (FIG. 3A); Construct #21 (FIG. 3B); Construct #22 (FIG. 3C); Construct #23 (FIG. 3D); Construct #24 (FIG. 3E); Construct #25 (FIG. 3F); Construct #26 (FIG. 3G); Construct #27 (FIG. 3H); Construct #28 (FIG. 3I); and Construct #29 (FIG. 3J).
Figure 3B:
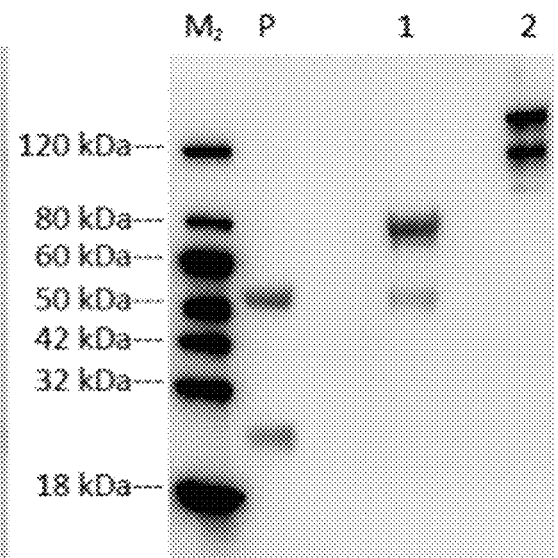
Figure 3C:
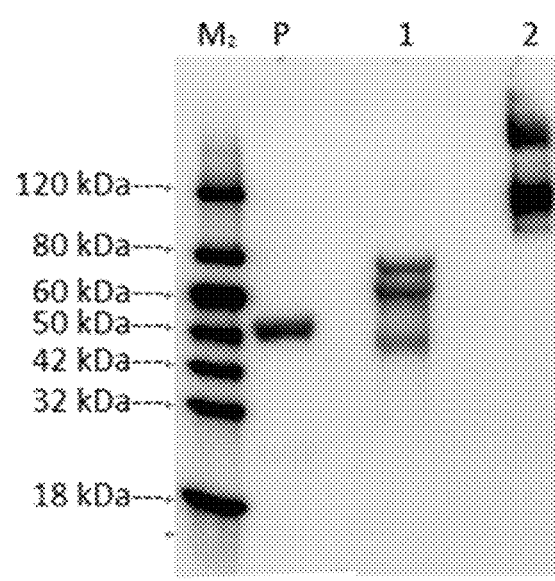
Figure 3D:
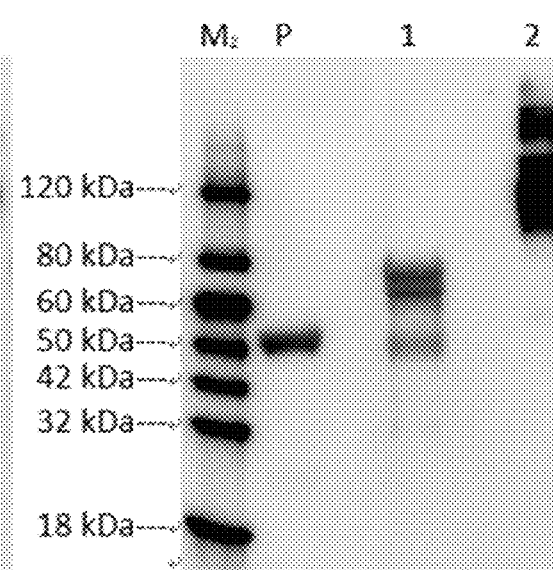
Figure 3E:
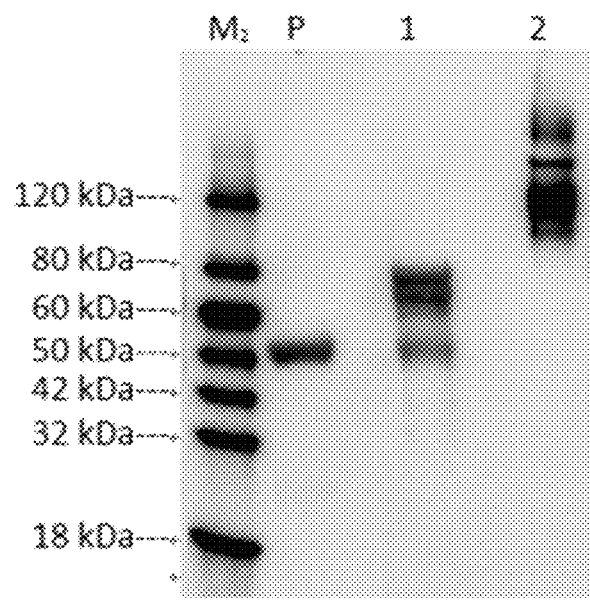
Figure 3F:
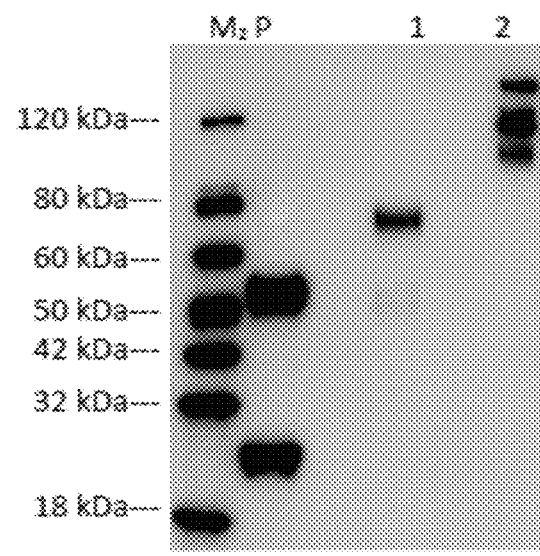
Figure 3G:
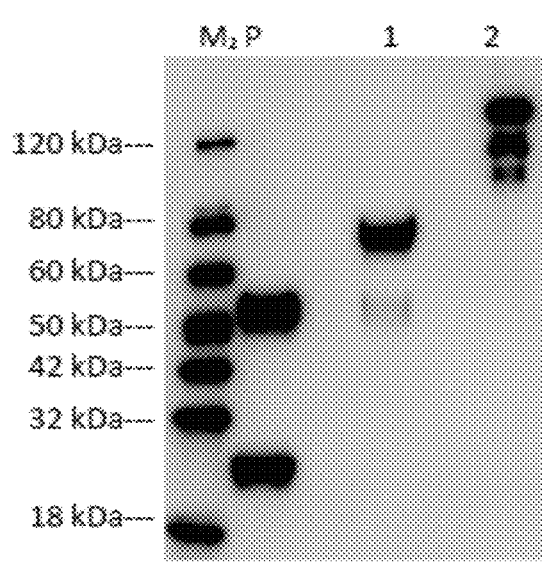
Figure 3H:
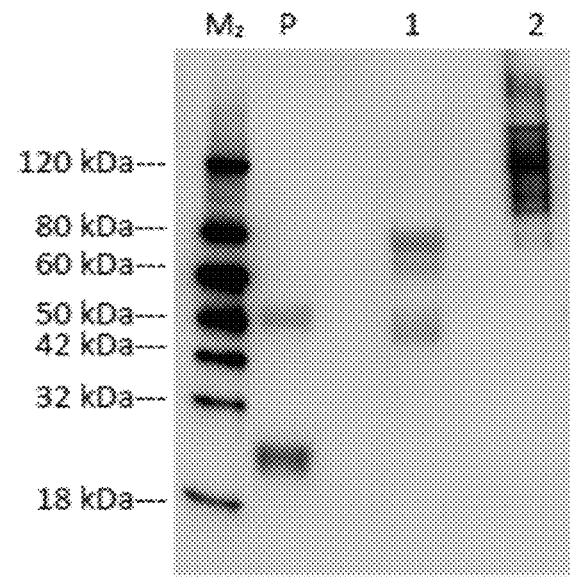
Figure 3I:
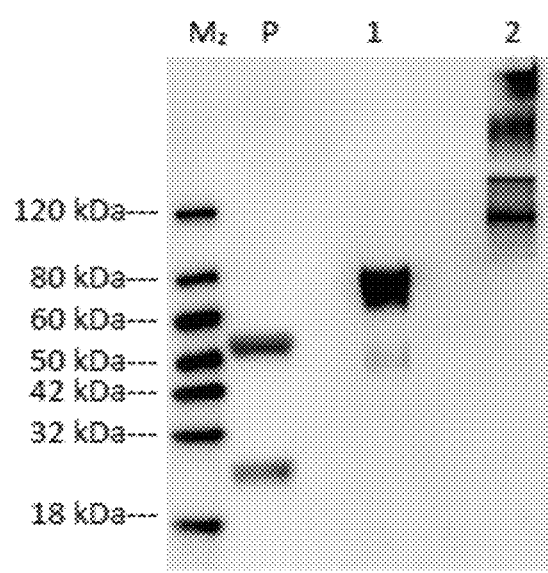
Figure 3J:
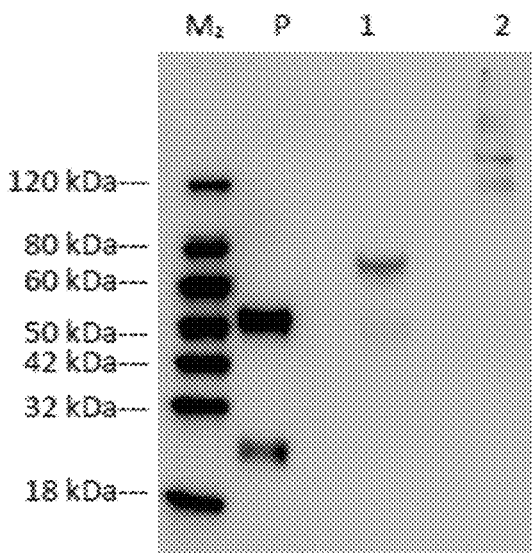
Figure 4A:
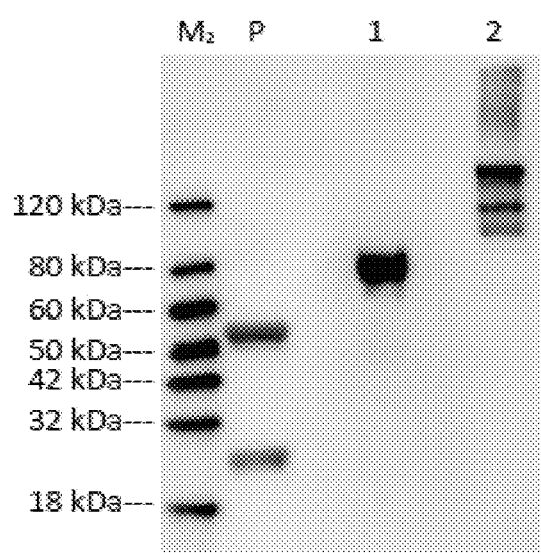
FIGS. 4A-4I show expression of RAGE-Fc fusion protein constructs assessed by Western blot: Construct #30 (FIG. 4A); Construct #31 (FIG. 4B); Construct #32 (FIG. 4C); Construct #33 (FIG. 4D); Construct #34 (FIG. 4E); Construct #35 (FIG. 4F); Construct #36 (FIG. 4G); Construct #16ΔK (FIG. 4H); Construct #12ΔK (FIG. 4I).
Figure 4B:
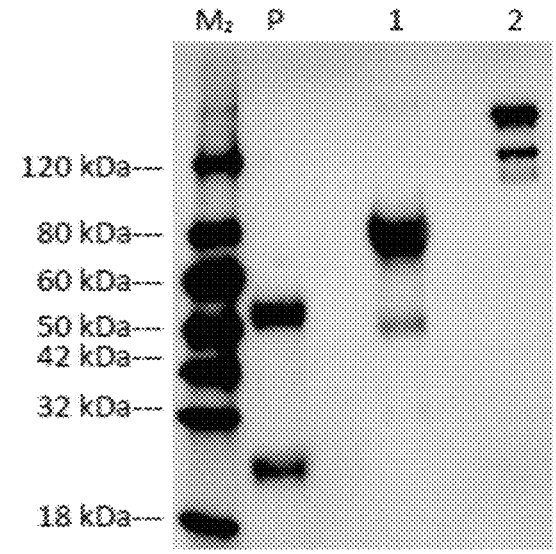
Figure 4C:
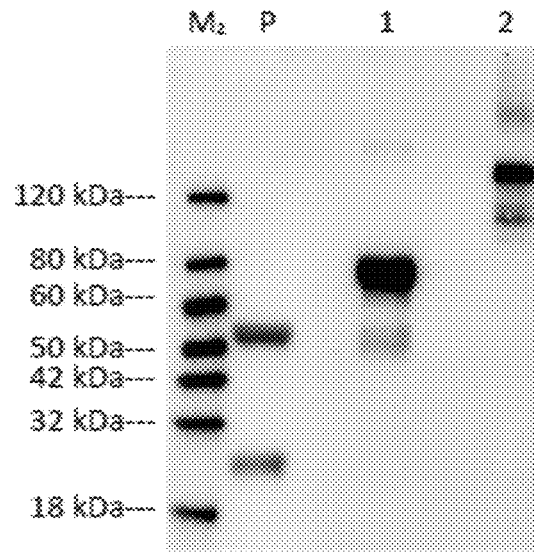
Figure 4D:
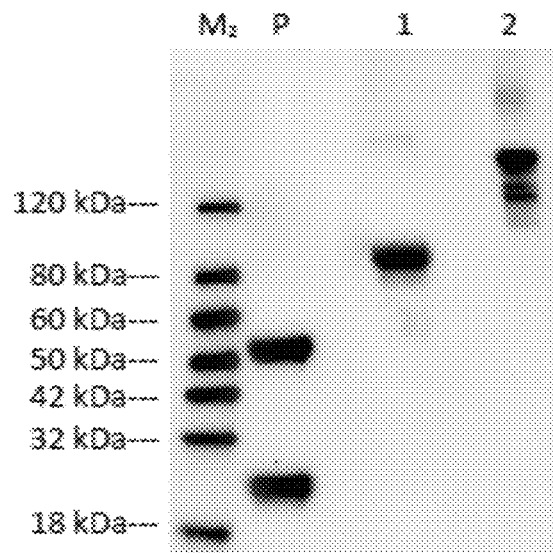
Figure 4E:
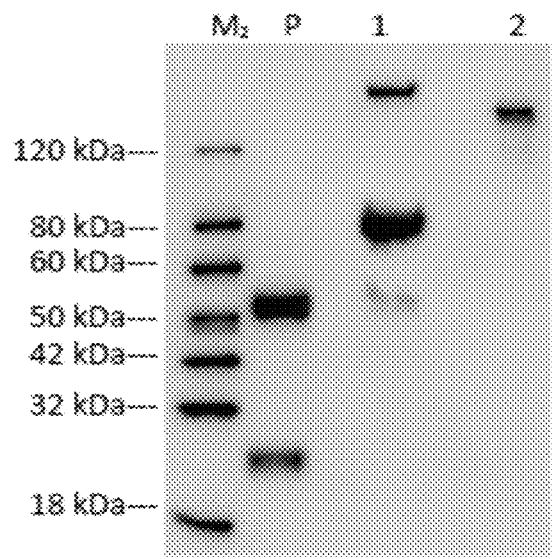
Figure 4F:
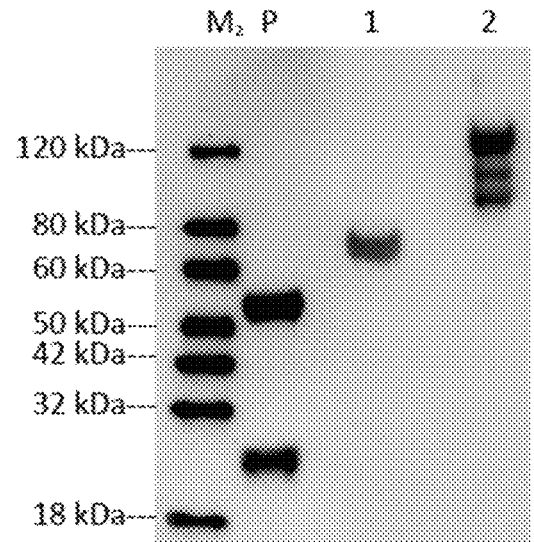
Figure 4G:
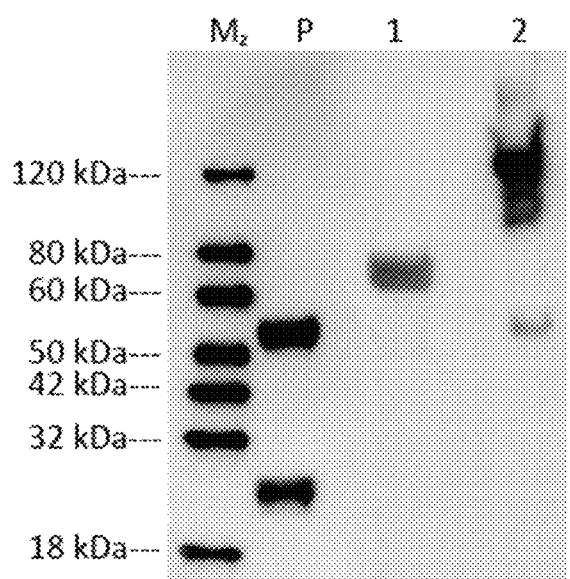
Figure 4H:
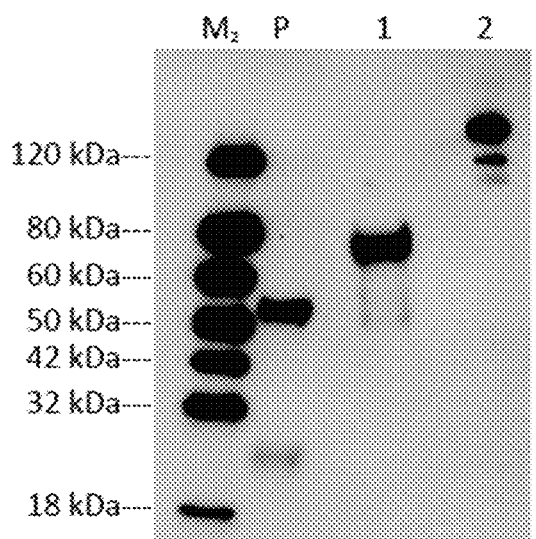
Figure 4I:
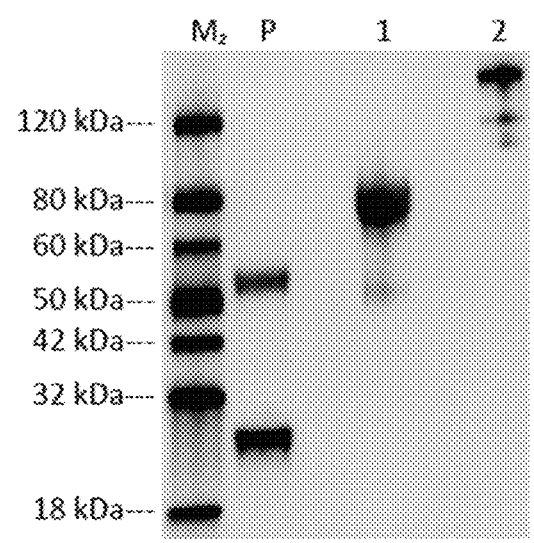

The purified protein was analyzed by SDS-PAGE and Western blotting for molecular weight and purity measurements. Results of Western blots of the fusion proteins are shown in FIGS. 2A-4I: Construct #1 (FIG. 2A); Construct #9 (FIG. 2B); Construct #10 (FIG. 2C); Construct #11 (FIG. 2D); Construct #12 (FIG. 2E); Construct #13 (FIG. 2F); Construct #14 (FIG. 2G); Construct #15 (FIG. 2H); Construct #16 (FIG. 2I); Construct #17 (FIG. 2J); Construct #18 (FIG. 2K); Construct #19 (FIG. 2L); Construct #20 (FIG. 3A); Construct #21 (FIG. 3B); Construct #22 (FIG. 3C); Construct #23 (FIG. 3D); Construct #24 (FIG. 3E); Construct #25 (FIG. 3F); Construct #26 (FIG. 3G); Construct #27 (FIG. 3H); Construct #28 (FIG. 3I); Construct #29 (FIG. 3J); Construct #30 (FIG. 4A); Construct #31 (FIG. 4B); Construct #32 (FIG. 4C); Construct #33 (FIG. 4D); Construct #34 (FIG. 4E); Construct #35 (FIG. 4F); Construct #36 (FIG. 4G); Construct #16ΔK (FIG. 4H); Construct #12ΔK (FIG. 24I).

Figure 5A:
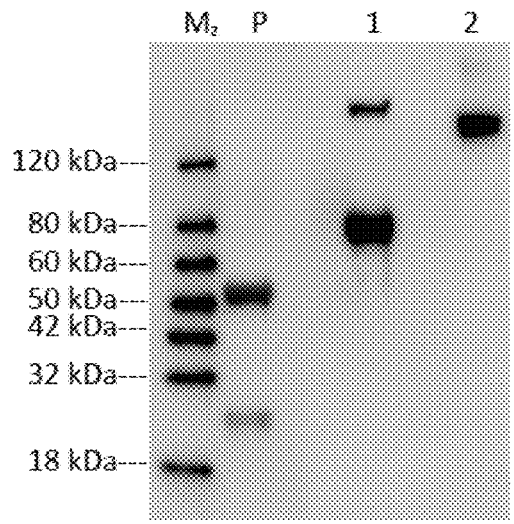
FIGS. 5A-5F show scaled-up expression of RAGE-Fc fusion protein constructs assessed by Western blot: Construct #1 (FIG. 5A); Construct #9 (FIG. 5B); Construct #10 (FIG. 5C); Construct #11 (FIG. 5D); Construct #12 (FIG. 5E); Construct #6 (FIG. 5F).
Figure 5B:
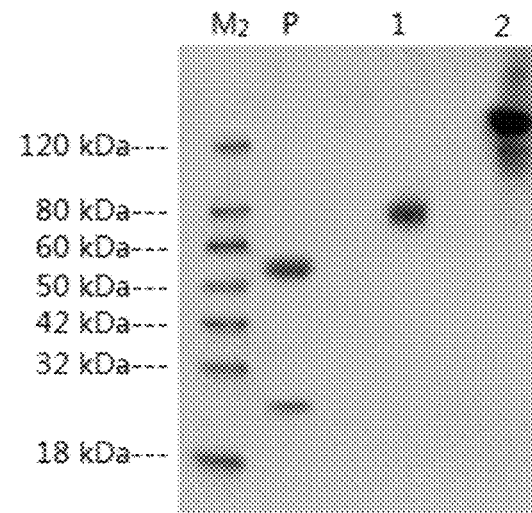
Figure 5C:
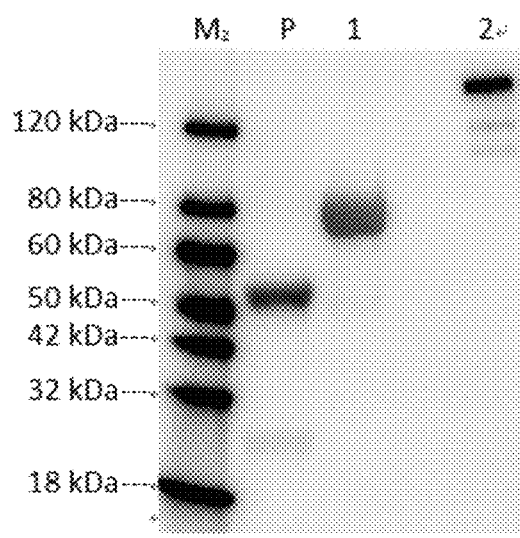
Figure 5D:
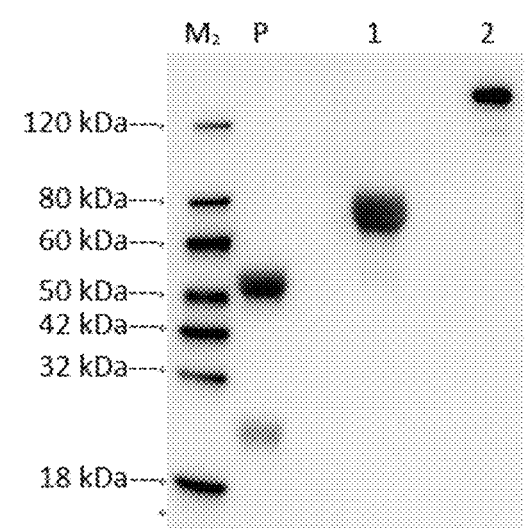
Figures 5E, 5F:
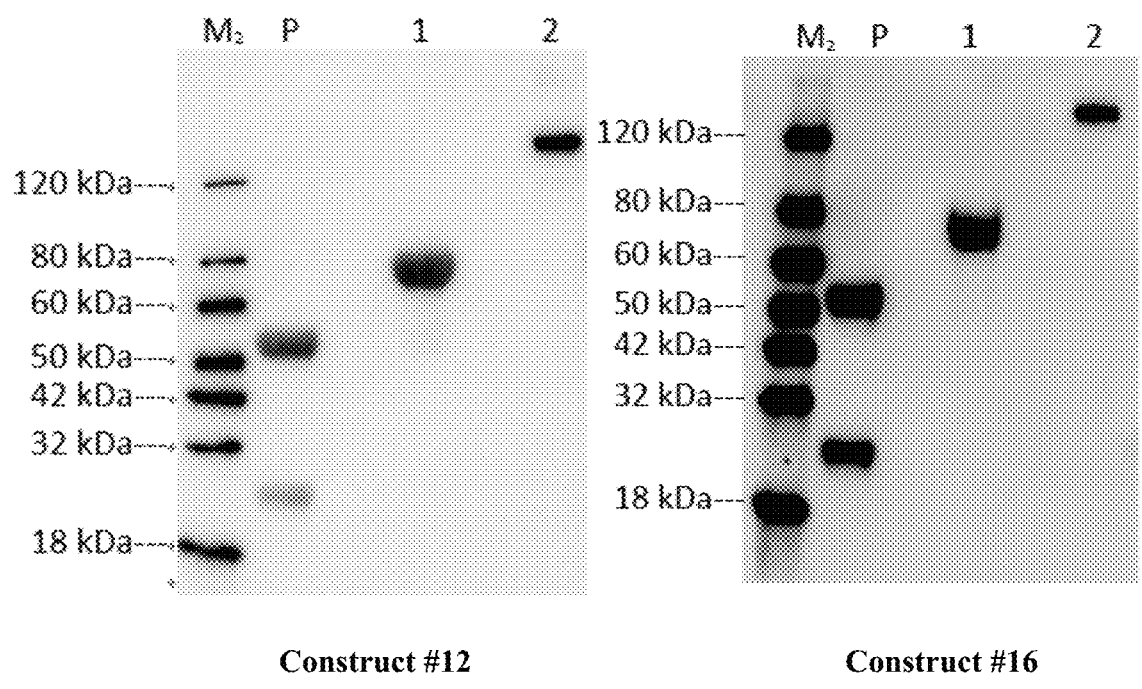

Expression of a number of fusion proteins was performed at 1 L scale and proteins were purified by Protein A affinity chromatography, followed by Superdex200 size exclusion chromatography. Purified protein was analyzed by SDS-PAGE and Western blotting for molecular weight and purity measurements. Results of Western blots of the fusion proteins are shown in FIG. 5: Construct #1 (FIG. 5A); Construct #9 (FIG. 5B); Construct #10 (FIG. 5C); Construct #11 (FIG. 5D); Construct #12 (FIG. 5E); Construct #6 (FIG. 5F)

The lanes of each blot in FIGS. 2A-2L, FIGS. 3A-3J, FIGS. 4A-4I, and FIGS. 5A-5F are labeled according to the contents of each as follows: $M_2$, protein marker (GenScript, Cat. No. M00521); P, Human IgG1, Kappa (as positive control) (Sigma, Cat. No. 15154); 1, RAGE-Fc fusion protein under reducing conditions (with DTT); 2, RAGE-Fc fusion protein under non-reducing conditions (no DTT). The primary antibody used for all blots was Goat Anti-Human IgG-HRP (GenScript, Cat. No. A00166).

The concentration of the purified protein was determined by Bradford assay using bovine serum albumin (BSA) as a standard. Quantified expression data is shown in Tables 9, 10 and 11.

Example 2: Assessing Binding Affinities of RAGE Fusion Proteins by ELISA

Functional ELISA assays were performed to assess the ligand binding characteristics of RAGE-Fc fusion proteins. Apparent binding affinities of RAGE-Fc fusion proteins to the RAGE ligands CML-HSA, HMGB1, S100A9 and S100A12 were measured for the following fusion proteins: Construct #1 (SEQ ID NO: 5), Construct #9 (SEQ ID NO: 53), Construct #10 (SEQ ID NO: 12), Construct #12 (SEQ ID NO: 15), and Construct #16 (SEQ ID NO: 16). Previous experiments were carried out to determine fundamental functionality of an ELISA, optimal coating concentrations and volumes, a dynamic range for the RAGE-Fc constructs, as well as optimized antibody dilutions and TMB development times.

RAGE ligands CML-HSA, HMGB1, S100A9 and S100A12 were separately coated onto a coated plate (MaxiSorp™) at a concentration of 50 nanomolar (nM), 100 microliters (μL) per well. RAGE ligand CML-HSA was separately coated onto a coated plate (MaxiSorp™) at a concentration of 100 nanograms (ng), 100 μL per well. The plates were then incubated overnight at 4° C. to allow the protein to bind to the plate coating. Following the coating step, the plates were washed once with 150 μL of wash solution (2.67 mM potassium chloride, 1.47 potassium phosphate monobasic, 136.9 mM sodium chloride, 8.10 mM sodium phosphate dibasic, 0.05% Tween-20). The plate was then aspirated and blocked for 90 minutes at 4° C. with 130 μL of a solution of 1% BSA (1 g/L) in DPBS (pH 7.4) with 0.03% sodium azide to prevent background binding to unfilled regions of the plate wells while blocking with a protein that does not interact with soluble RAGE constructs. After the blocking step, two washes were performed with the wash solution. The RAGE-Fc fusion protein was then incubated on the wells in log 10 dilution with each separate ligand for 120 minutes at 37° C. while shaking. After the RAGE-Fc binding step, three washes were performed with the wash solution. Binding of the RAGE-Fc fusion to CML-HSA, HMGB1, S100A9, and S100A12 was detected with a horseradish peroxidase (HRP) conjugated antibody with antigen specificity to IgG Fc (Abcam, Cat. No. ab99759). 100 μL of antibody diluted 1:5000 in DBPS was added to the assay wells, followed by 60 minutes of incubation at 37° C. while shaking. The wells were then washed four times with the wash solution. 100 μL of TMB (ThermoFisher Scientific, Cat. No. 34029) was then added to each well. After approximately one minute, the reaction was stopped by the addition of 50 μL of 1 M hydrochloric acid. Absorbance of the well contents was measured on a spectrophotometer at a wavelength of 450 nM.

Figure 6A:
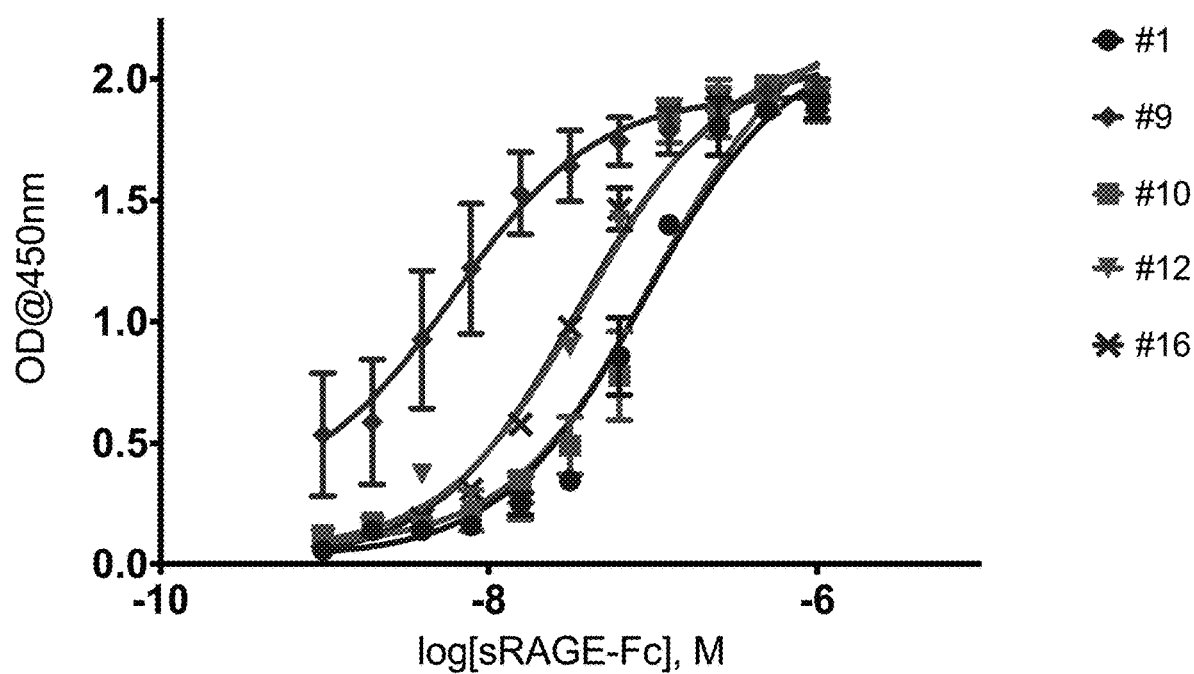
FIGS. 6A-6D show the concentration response curves generated by ELISA assays performed to assess ligand binding activities of RAGE-Fc fusion proteins: CML-HSA (FIG. 6A); HMGB1 (FIG. 6B); S100A9 (FIG. 6C); S100A12 (FIG. 6D).
Figure 6B:
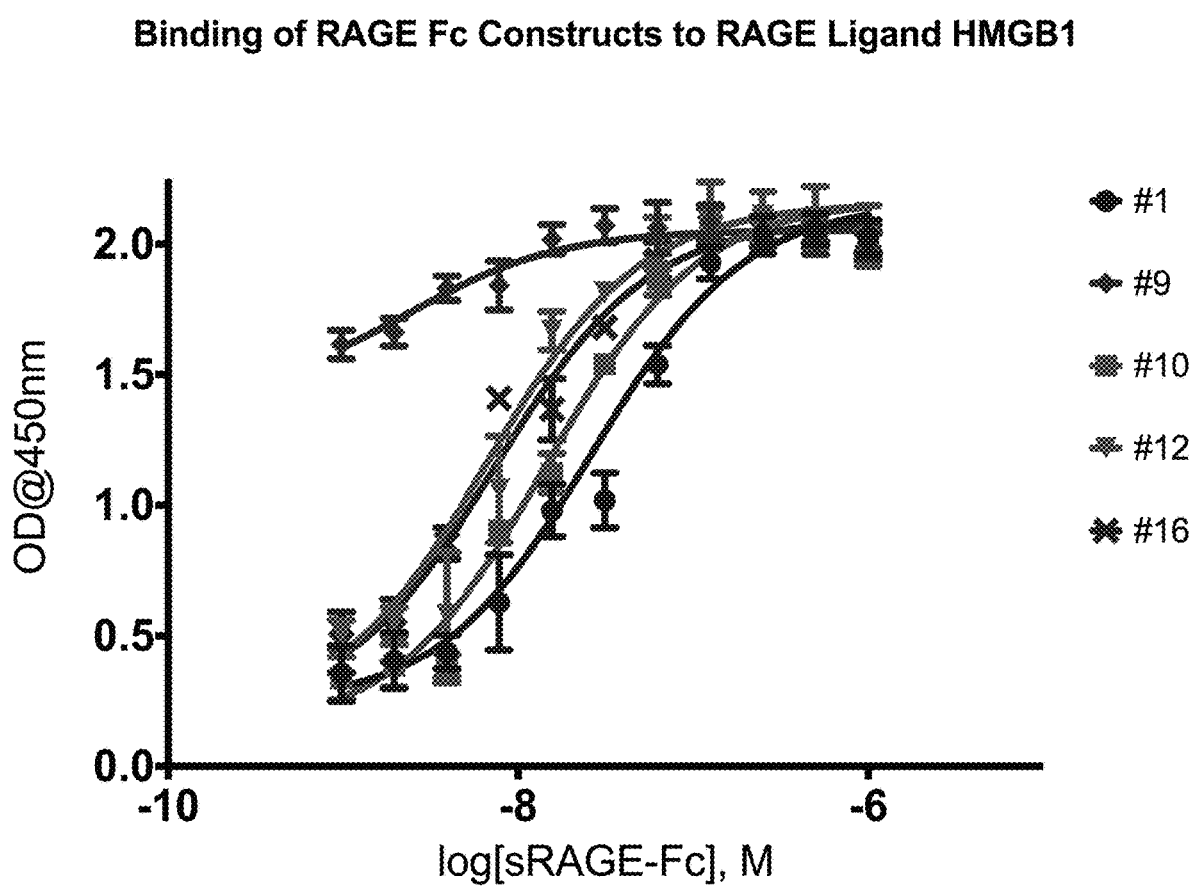
Figure 6C:
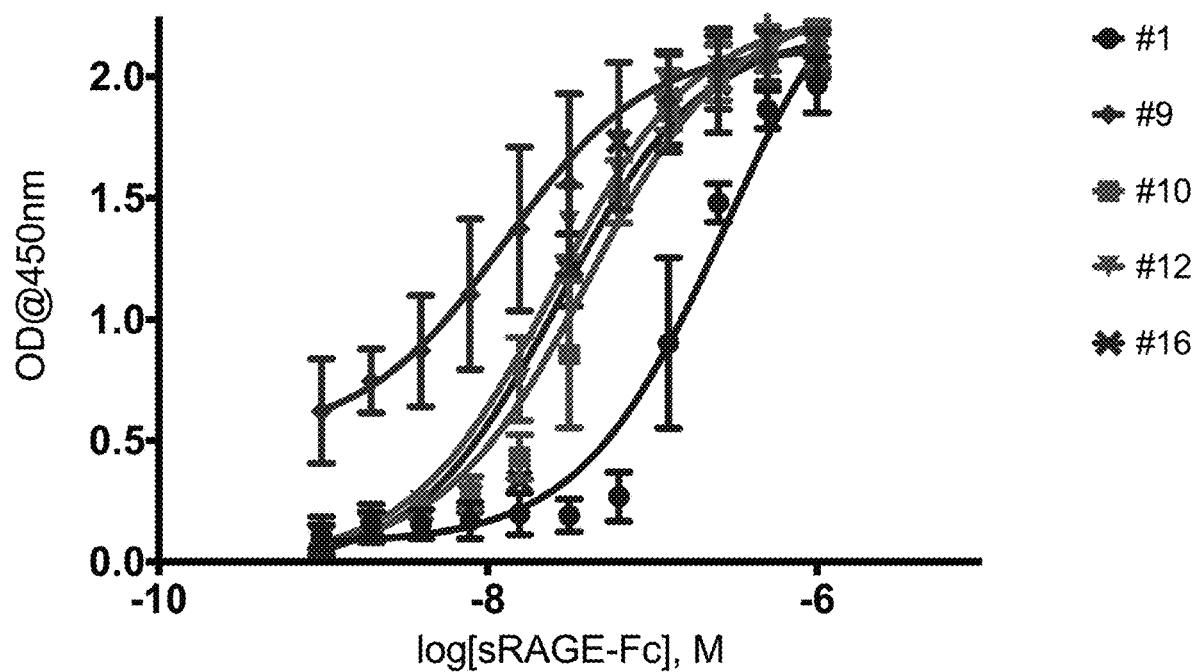
Figure 6D:
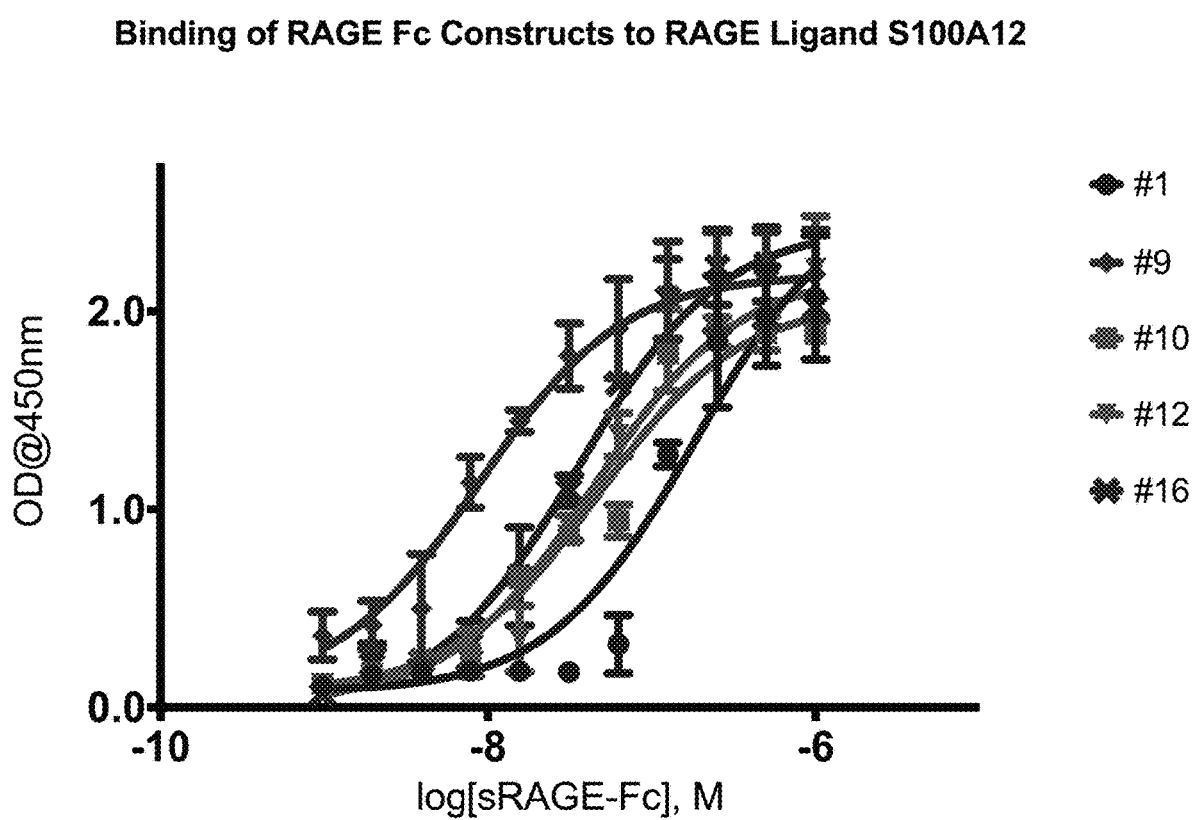
Figure 7A:
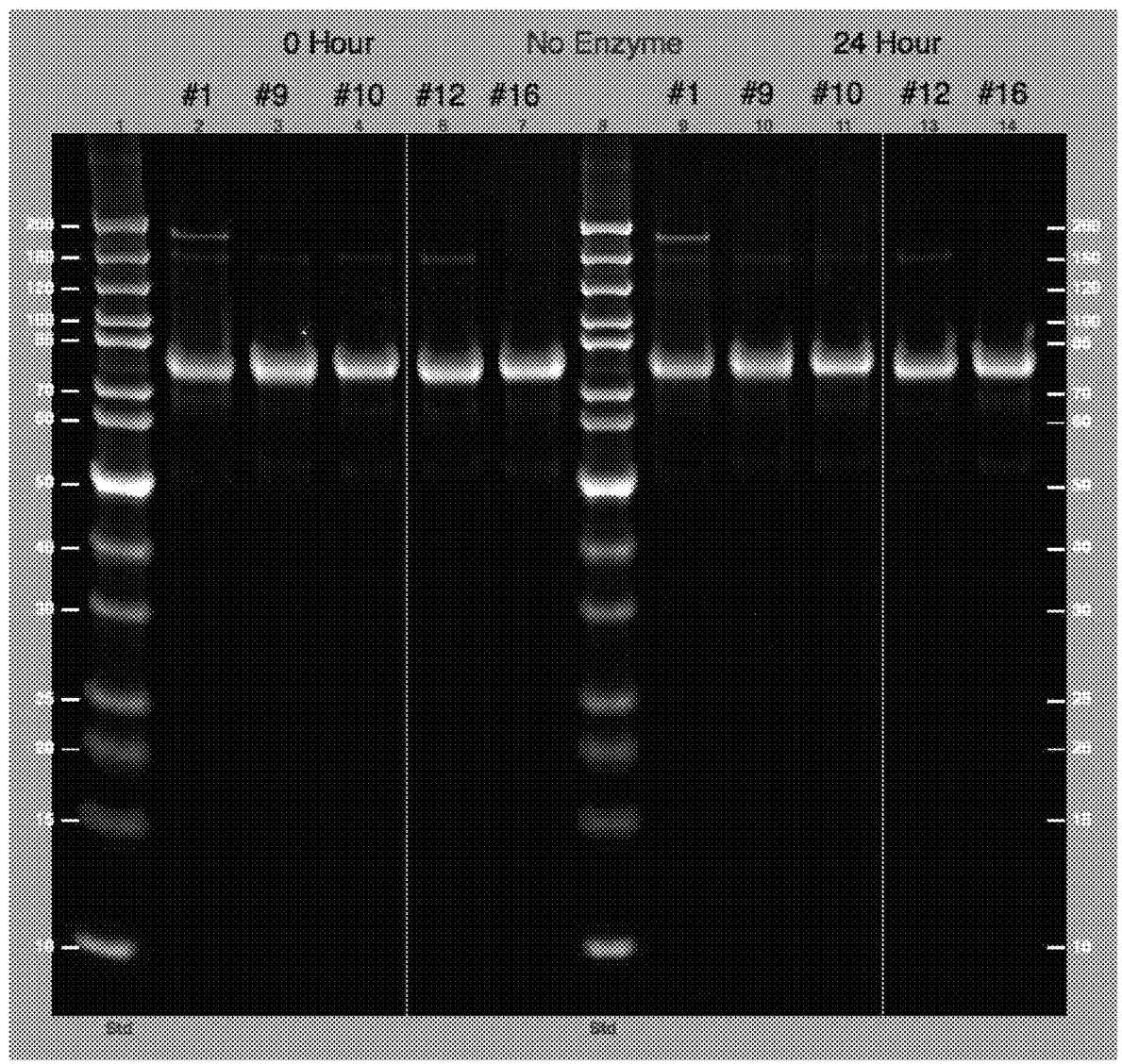
FIGS. 7A-7G show SDS-PAGE results of RAGE-Fc fusion proteins incubated with buffer alone for 0 and 24 hours (FIG. 7A); MMP9 for 0 and 24 hours (FIG. 7B); MMP9 for 15 and 24 hours (FIG. 7C); ADAM10 for 0 and 2 hours (FIG. 7D); ADAM10 for 15 and 24 hours (FIG. 7E); trypsin for 0 and 2 hours (FIG. 7F); and trypsin for 15 and 24 hours (FIG. 7G).
Figure 7B:
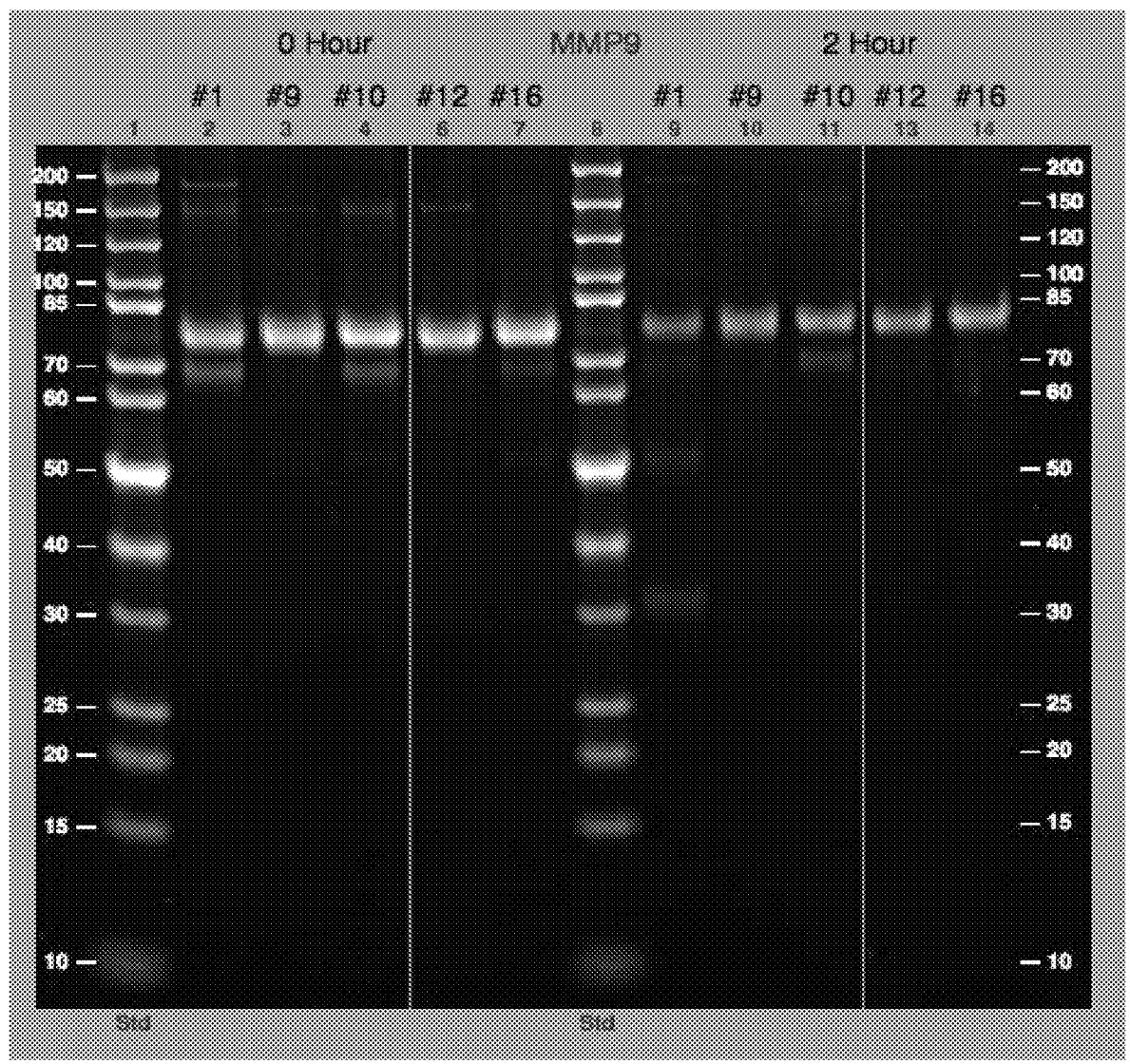
Figure 7C:
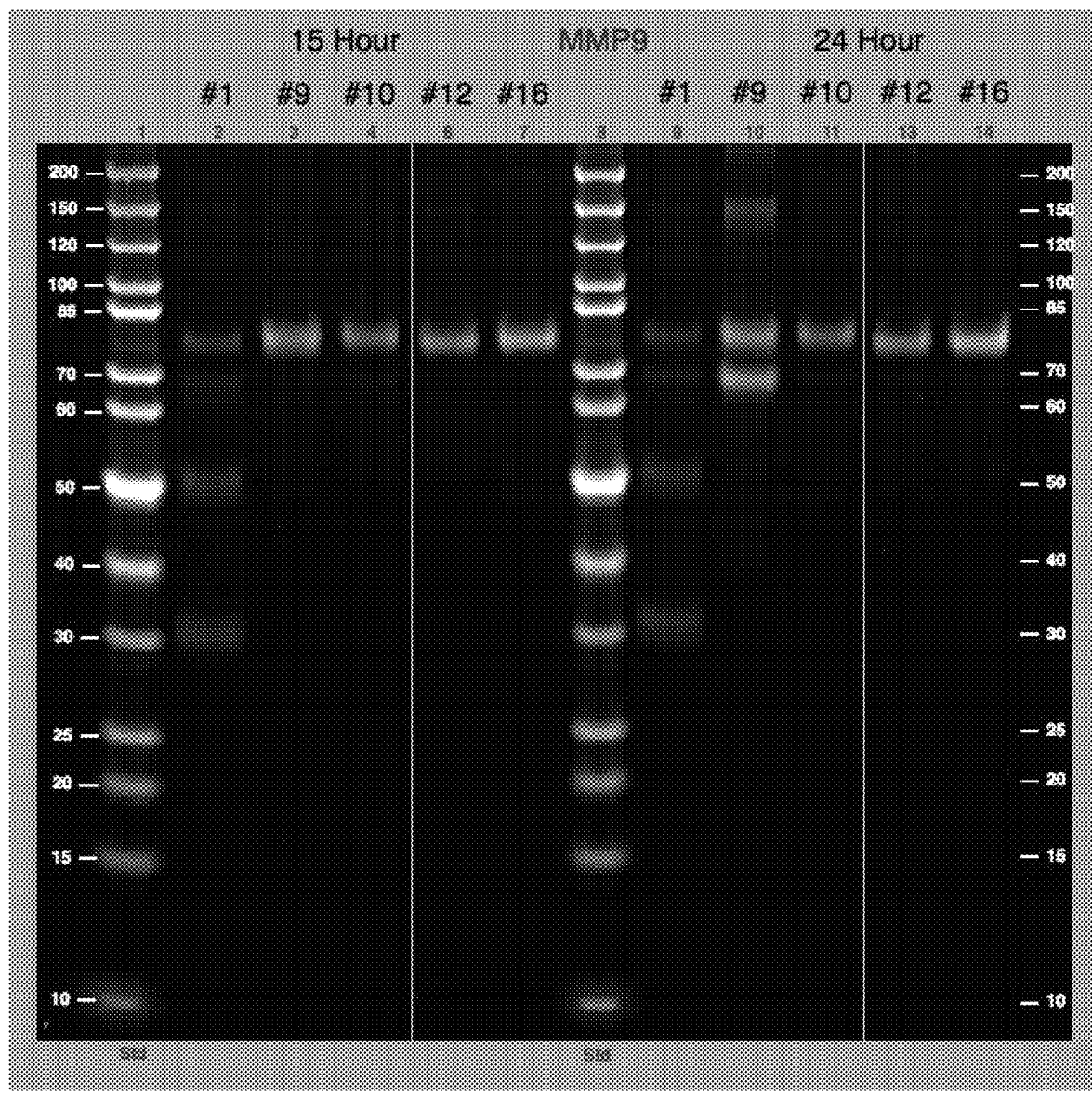
Figure 7D:
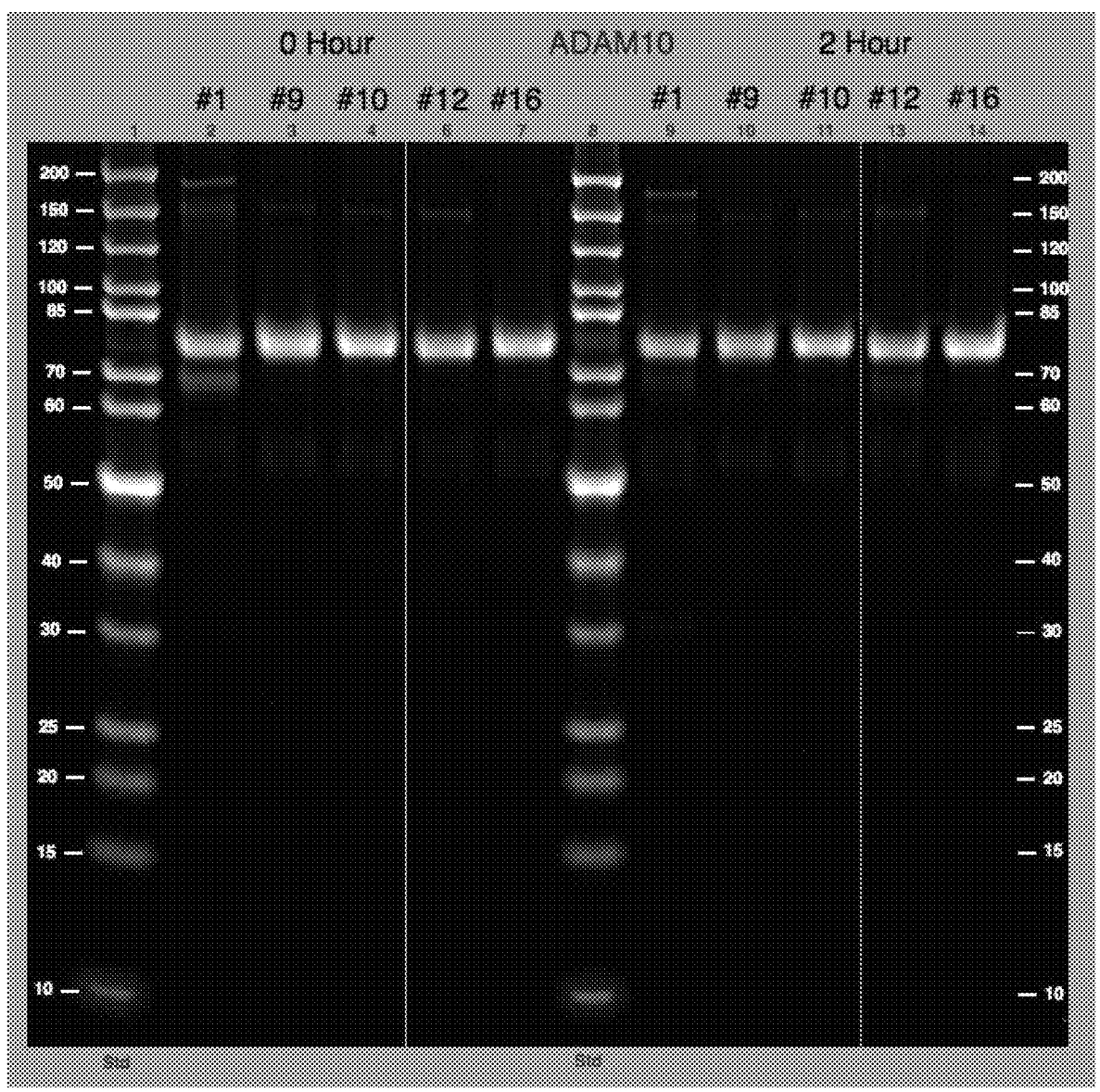
Figure 7E:
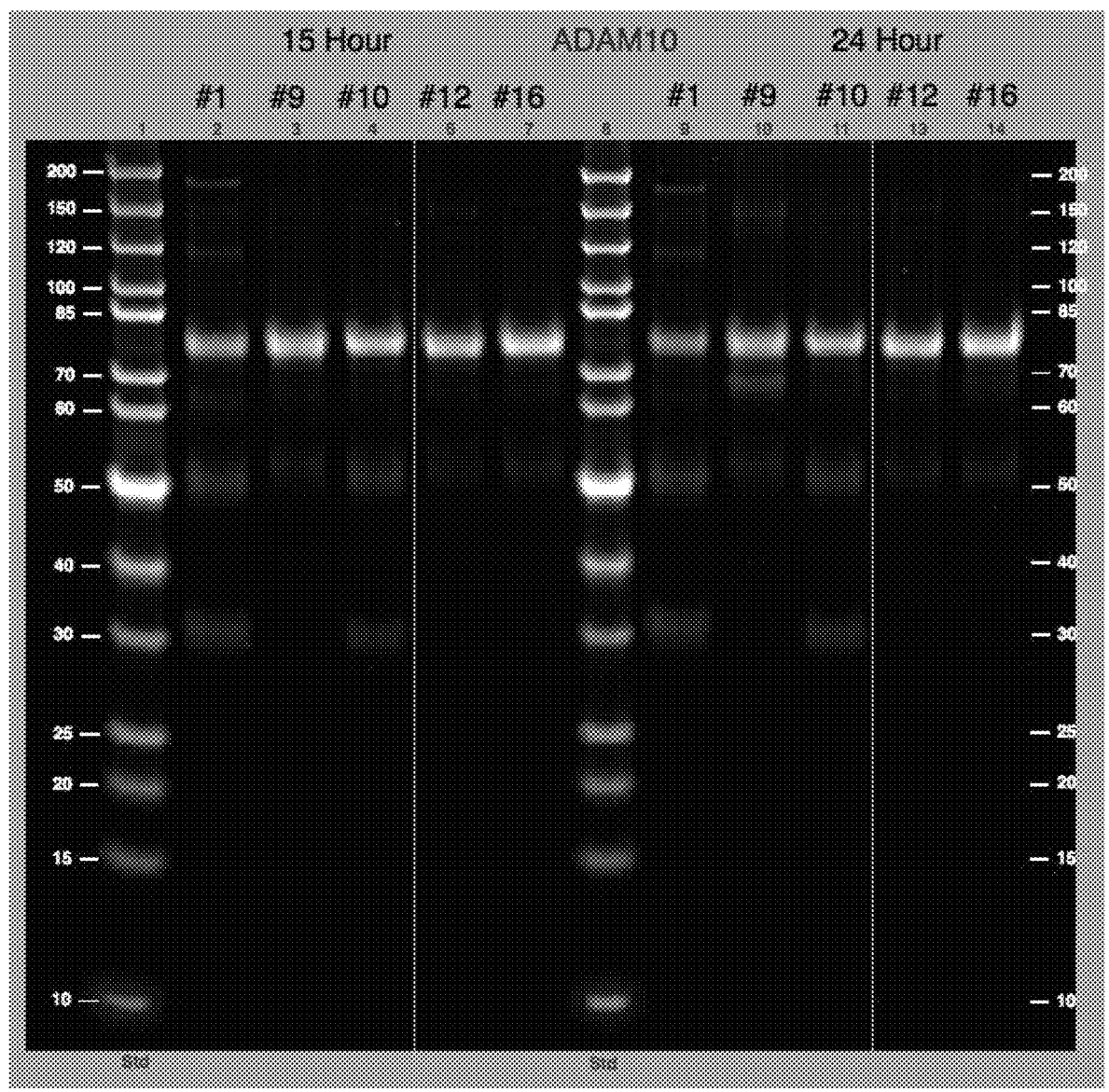
Figure 7F:
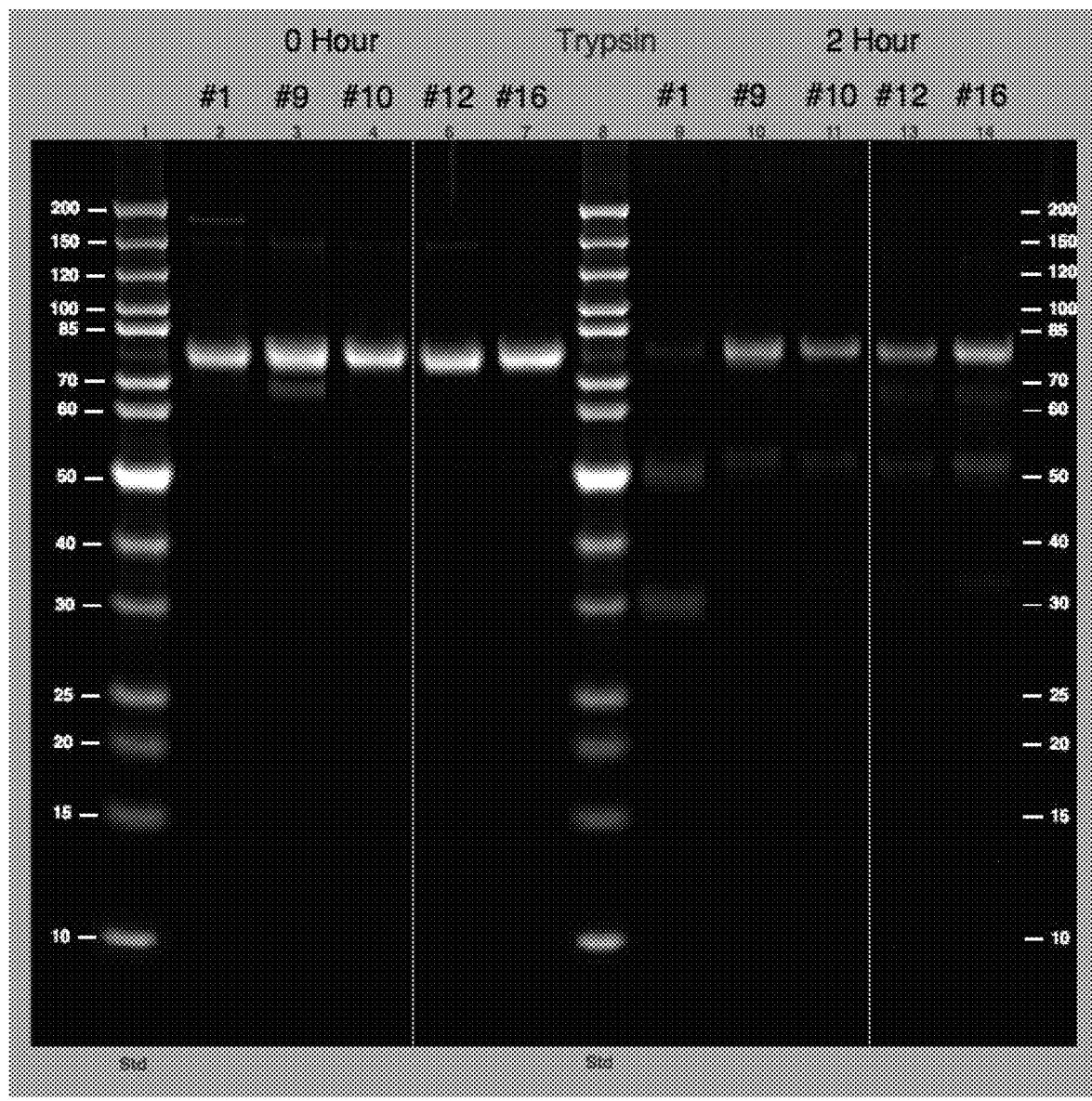
Figure 7G:
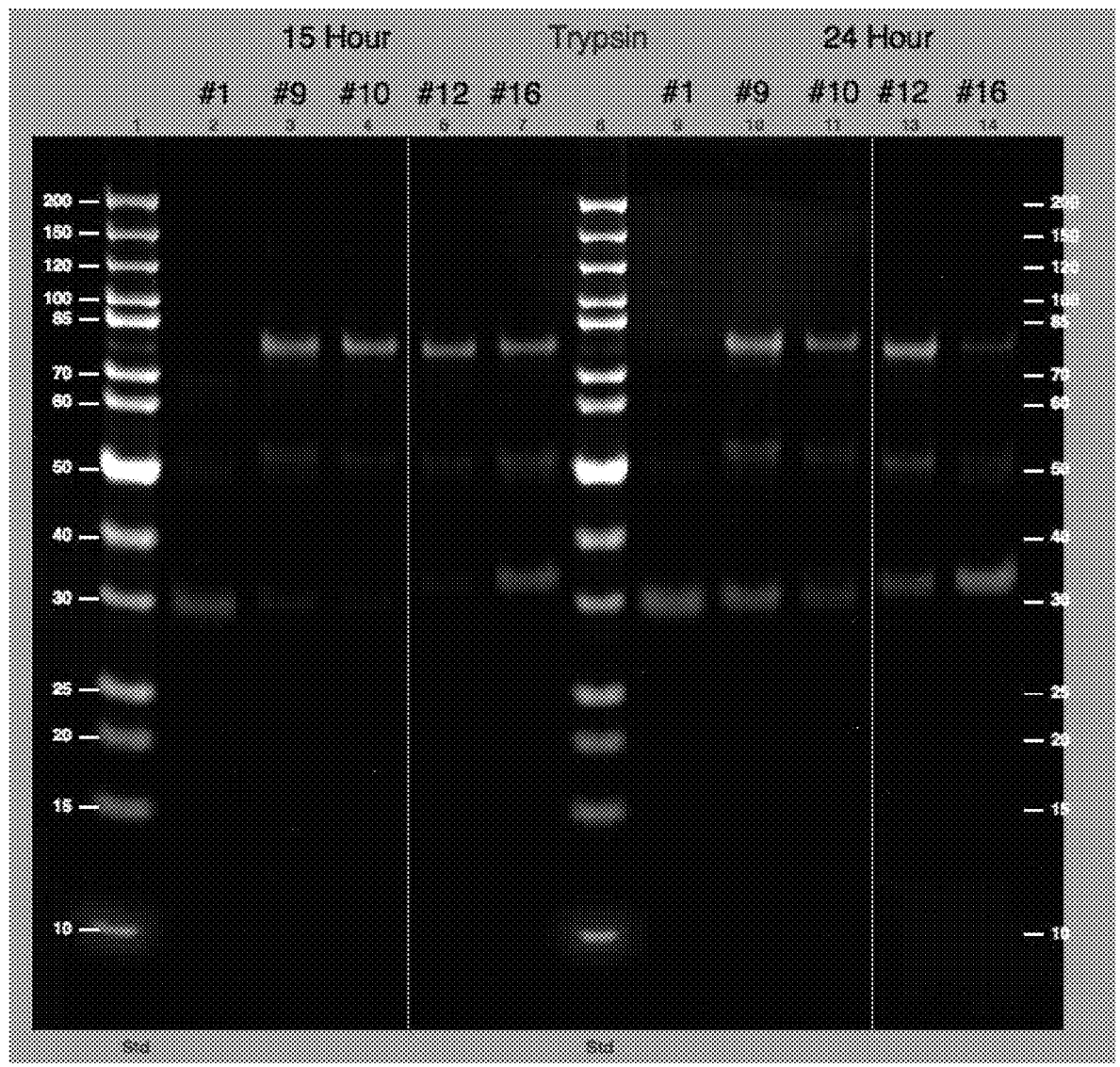
Figure 8A:
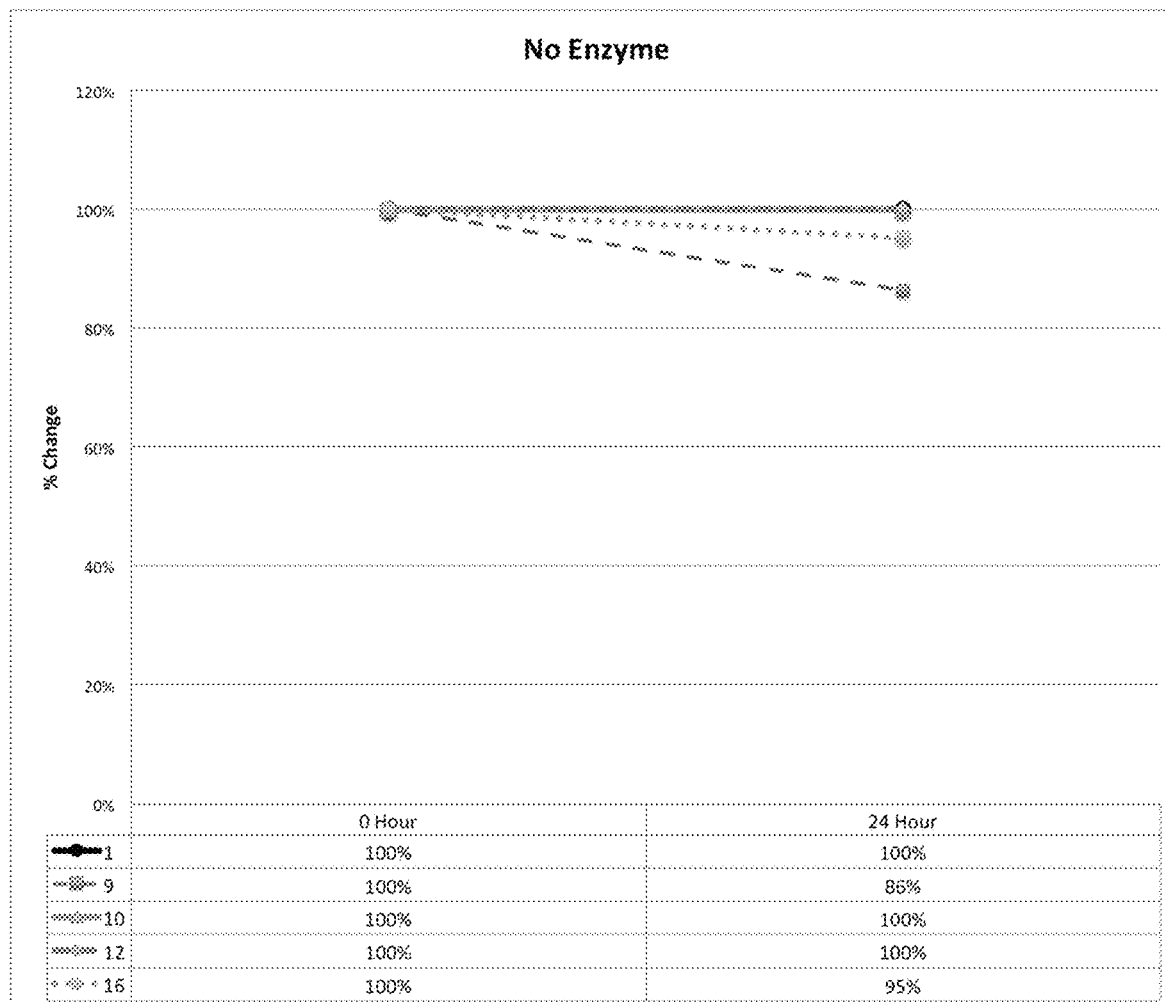
FIGS. 8A-8D show time course proteolysis data for fusion proteins incubated in the absence of protease (FIG. 8A); or in the presence of MMP9 (FIG. 8B); ADAM10 (FIG. 8C); or trypsin (FIG. 8D).
Figure 8B:
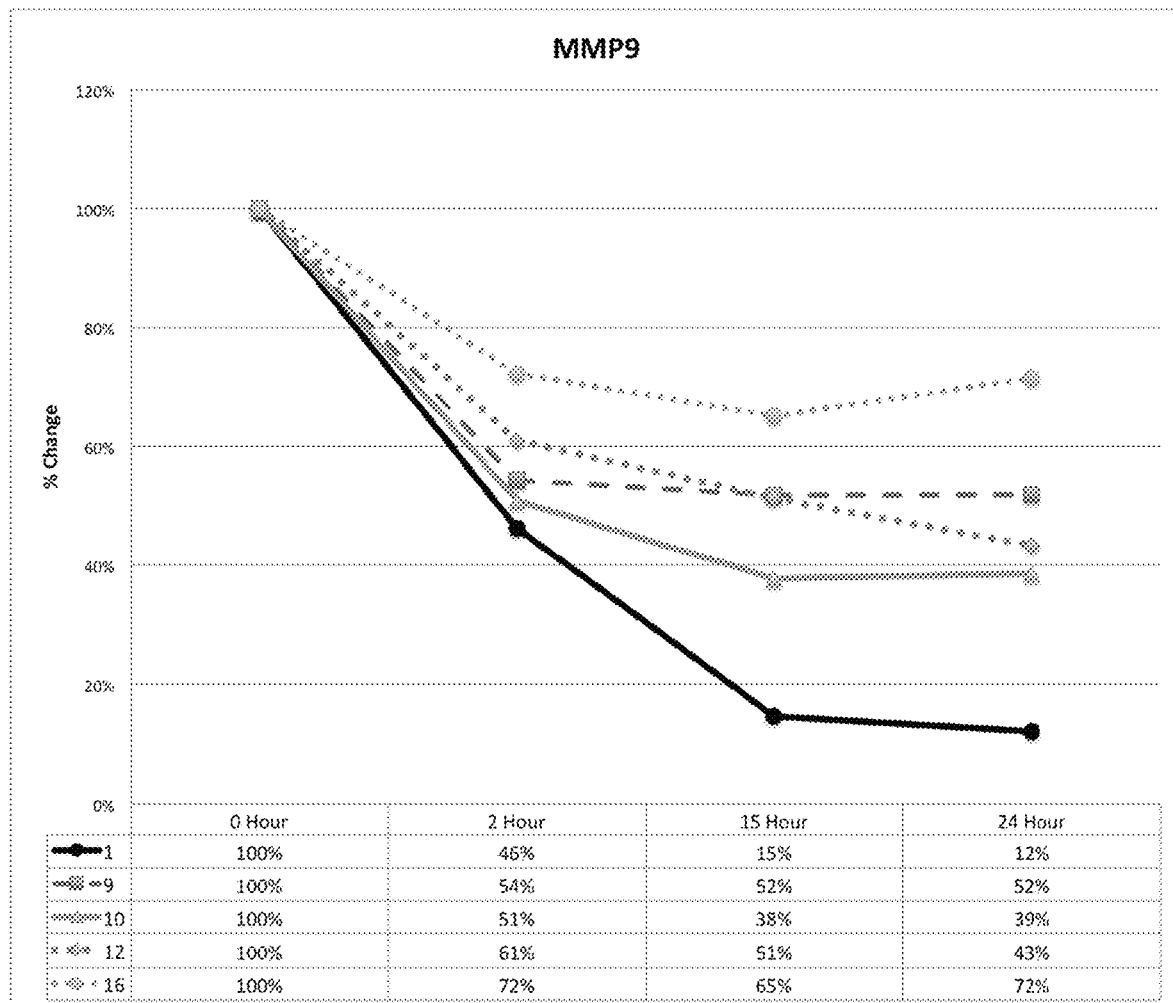
Figure 8C:
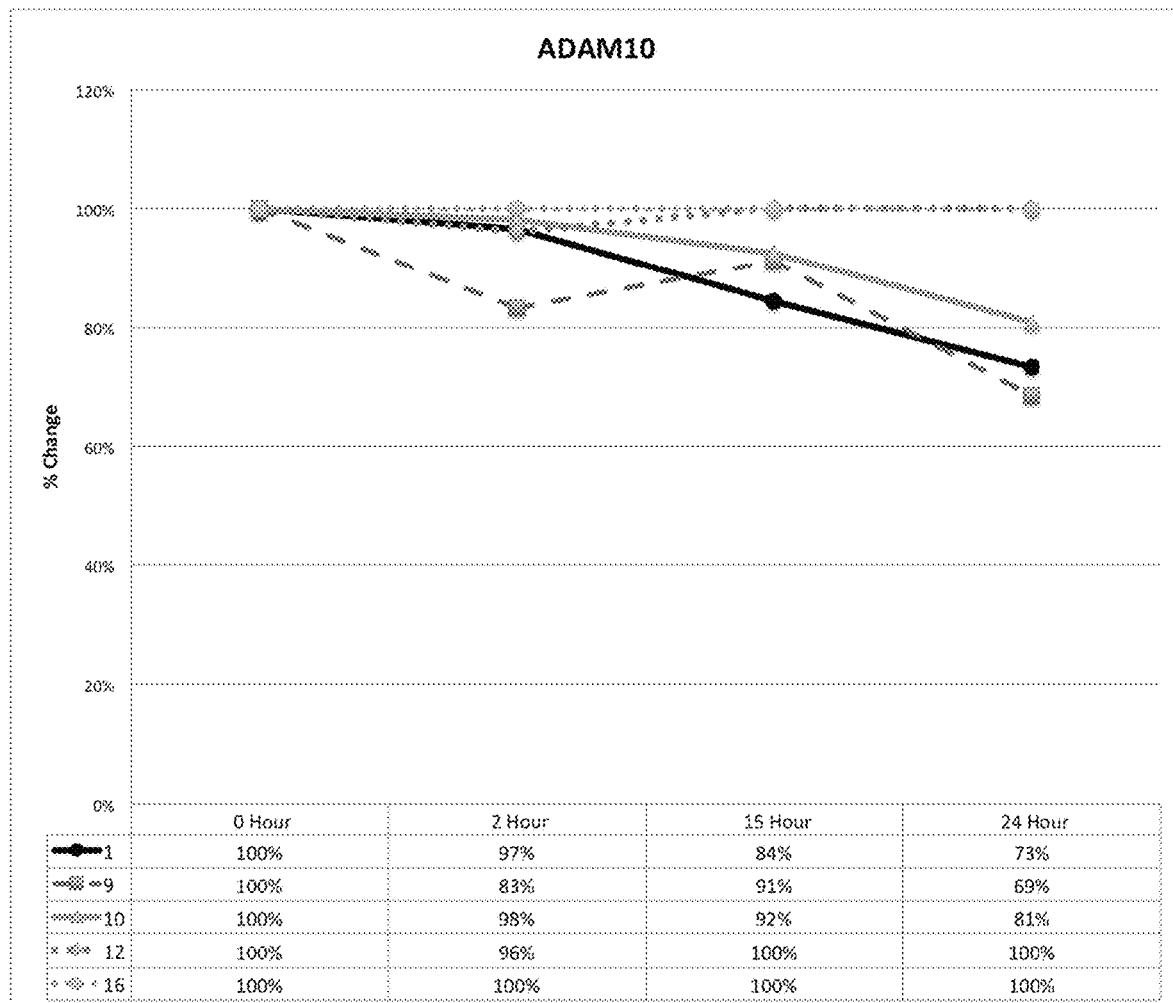
Figure 8D:
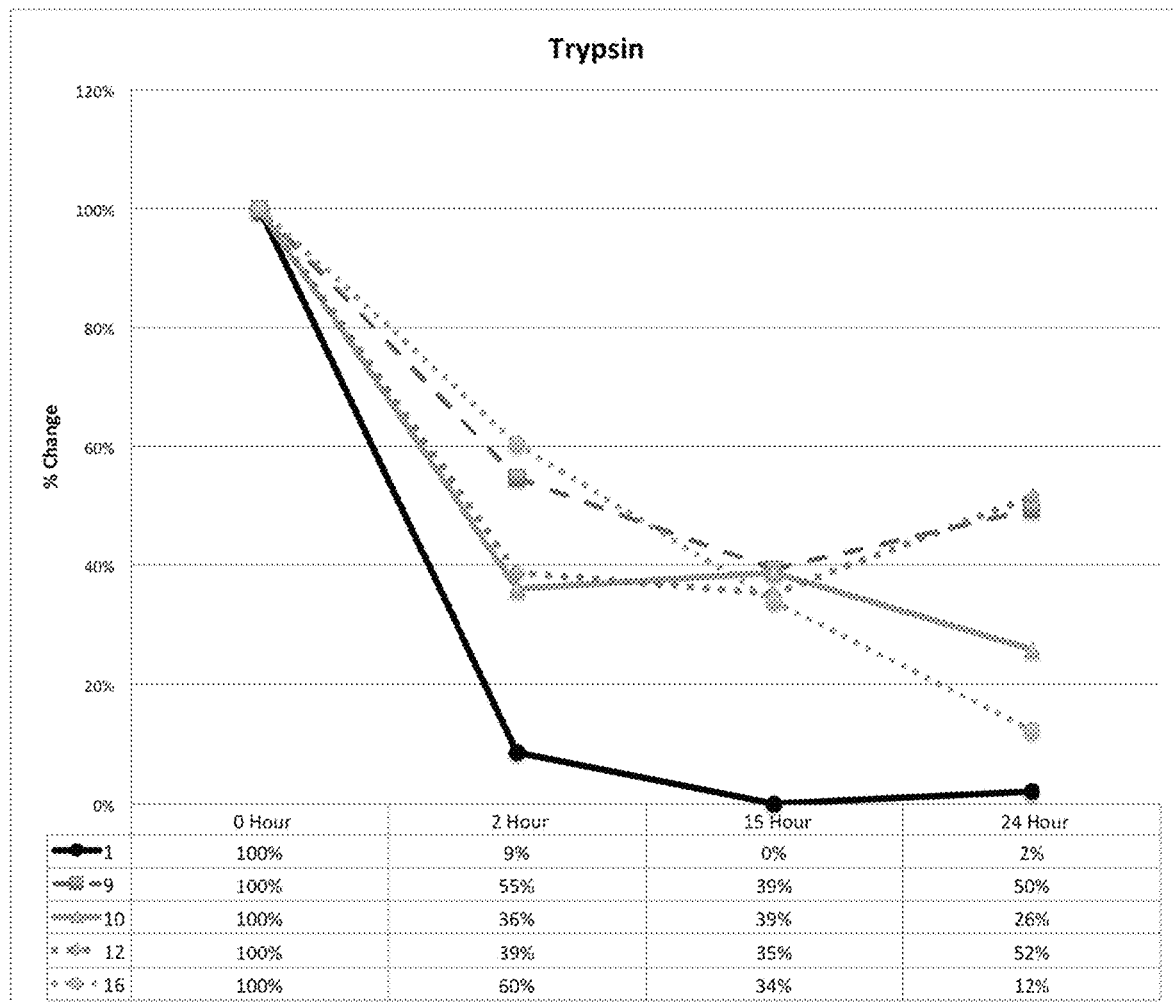
Figure 9A:
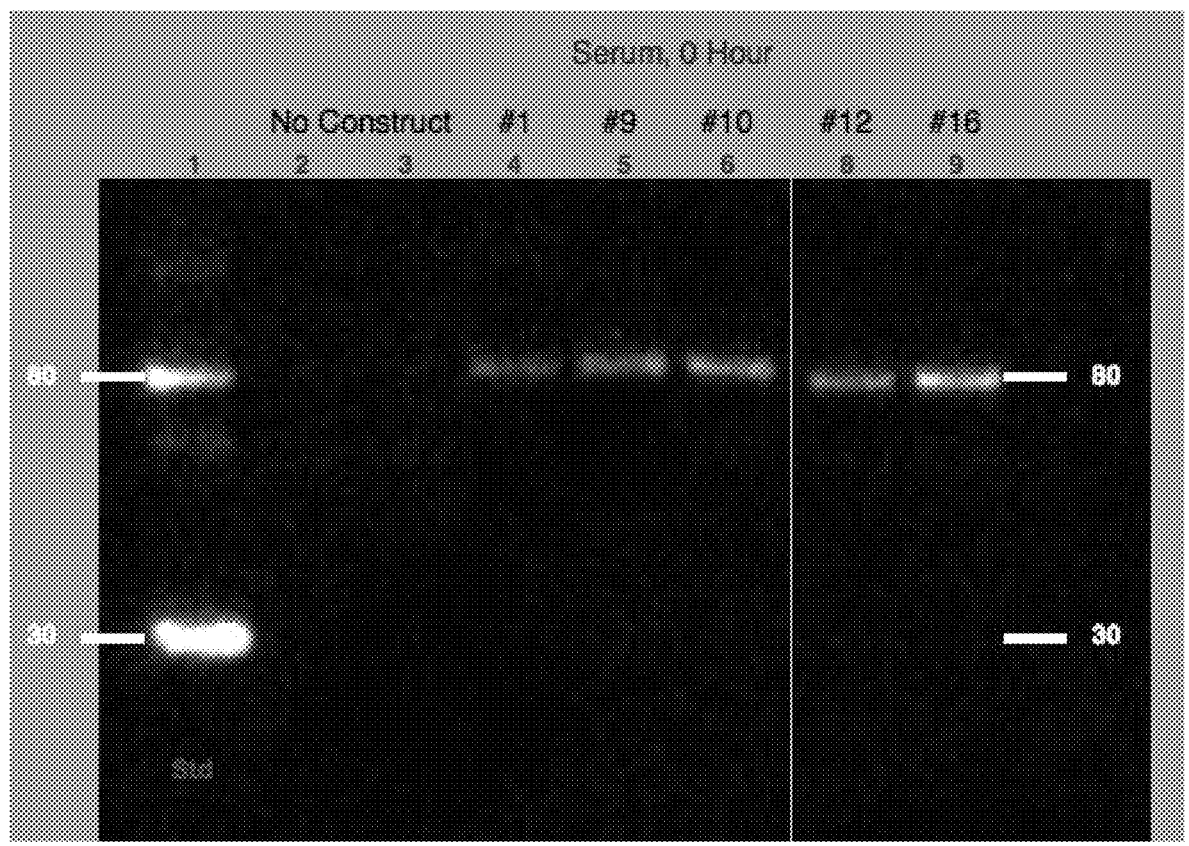
FIGS. 9A-9D show SDS-PAGE results of RAGE-Fc fusion proteins incubated with human serum for 0 hours (FIG. 9A); 17 hours (FIG. 9B); 49 hours (FIG. 9C); and 138 hours (FIG. 9D).
Figure 9B:
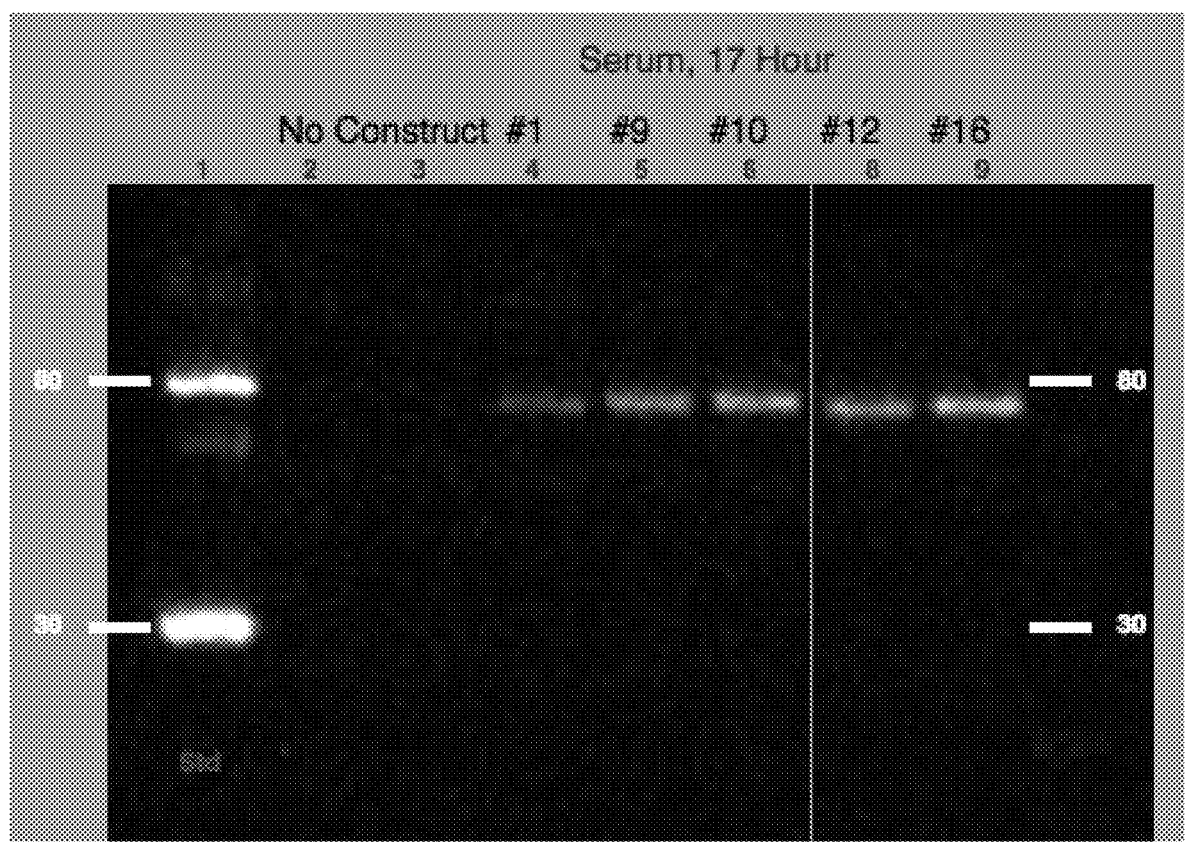
Figure 9C:
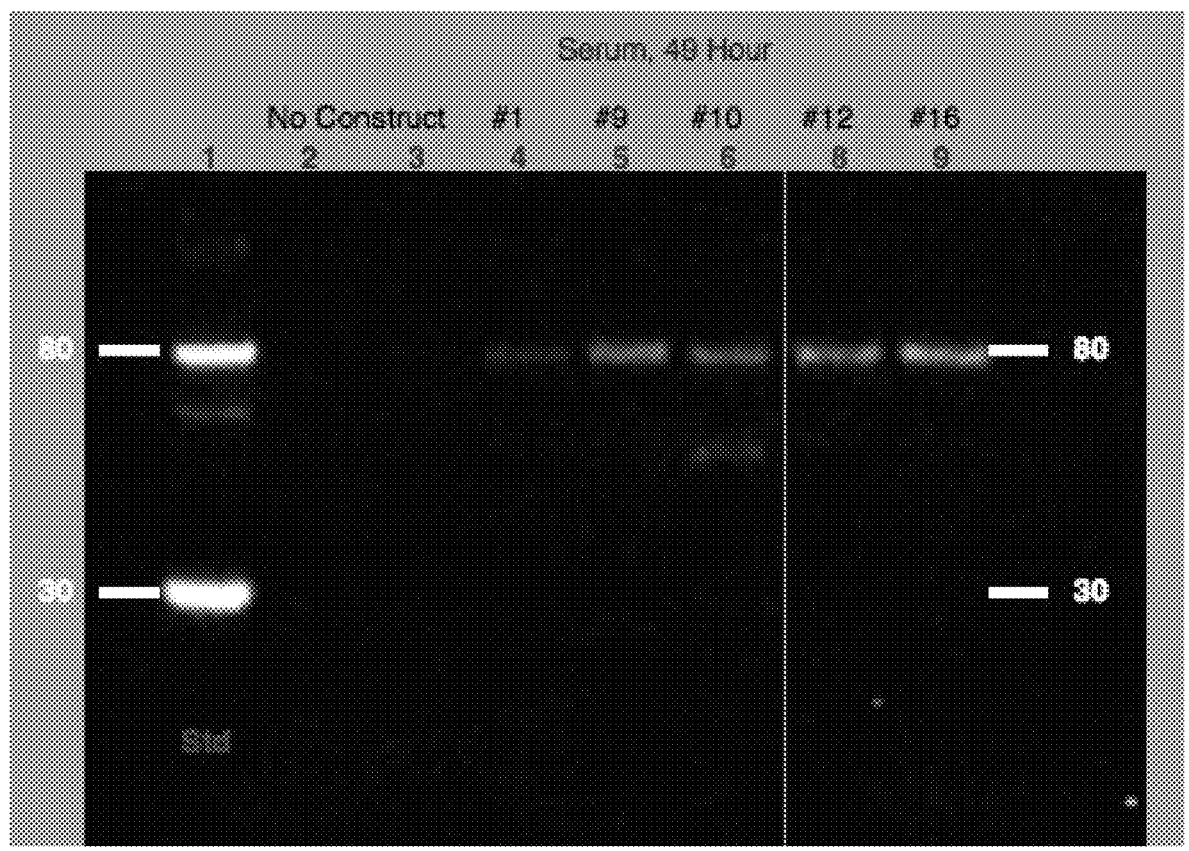
Figure 9D:
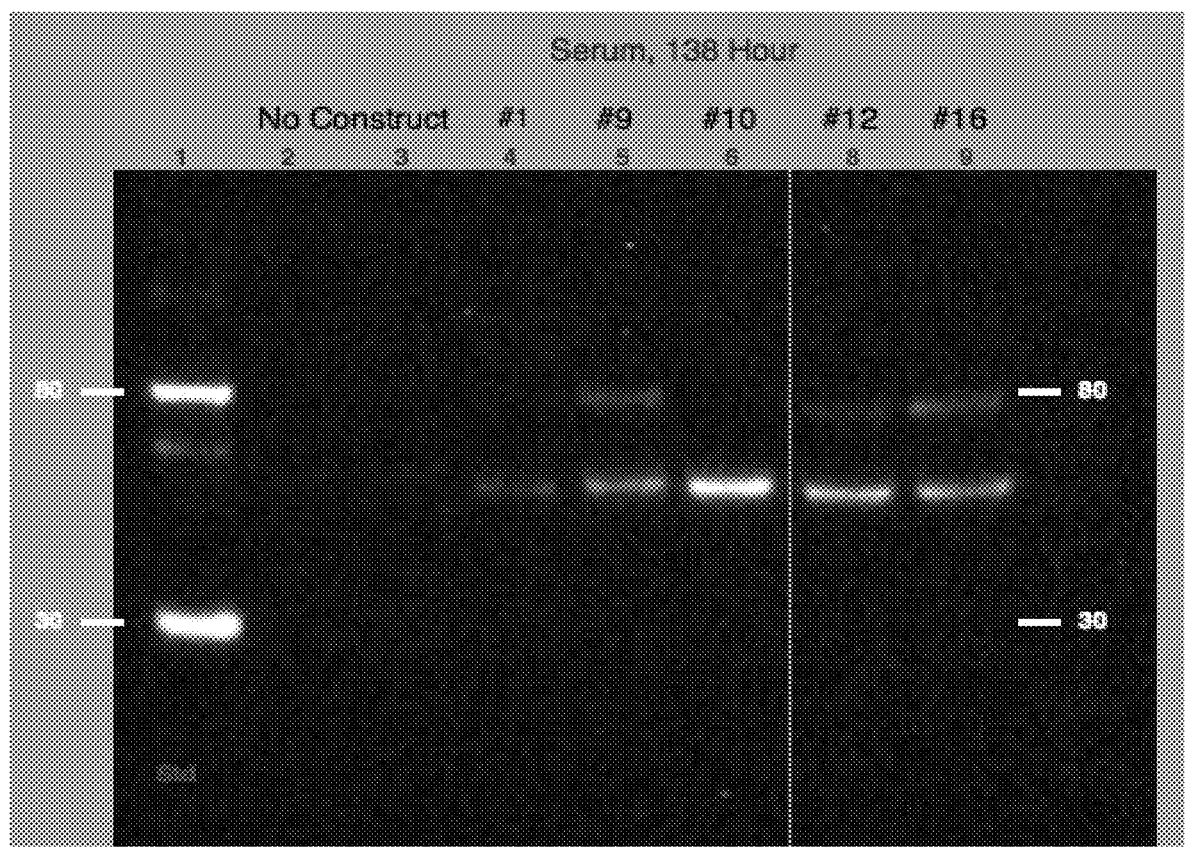
Figure 10:
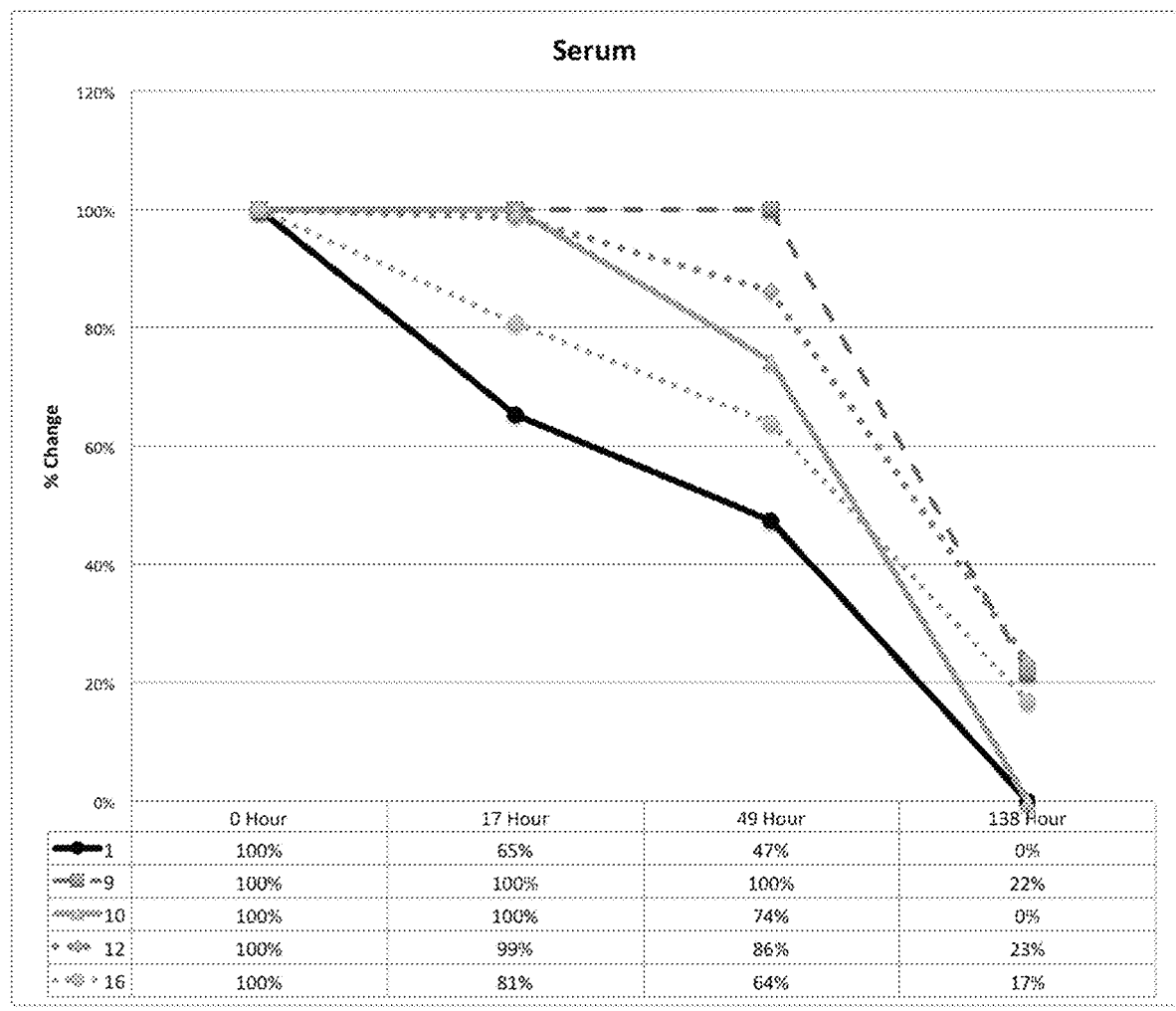
FIG. 10 shows time course proteolysis data for fusion proteins incubated in human serum over 138 hours.

Results of the ELISA assays (FIGS. 6A-6D) show that the RAGE-Fc fusion proteins of the disclosure (Constructs #9, 10, 12, 16) bind to the RAGE ligands CML-HSA (FIG. 6A), HMGB1 (FIG. 6B), S100A9 (FIG. 6C) and S100A12 (FIG. 6D) with greater apparent affinity than the RAGE-Fc fusion in the prior art (Construct #1). Apparent Kd values were calculated for each fusion protein-ligand interaction and are shown in Tables 1, 2, 3, and 4.

TABLE 1

Apparent binding affinity of RAGE-Fc constructs to CML-HSA

|  | Construct #1 | Construct #9 | Construct #10 | Construct #12 | Construct #16 |
|---|---|---|---|---|---|
| Apparent Kd | 88 nM | 6 nM | 99 nM | 39 nM | 35 nM |

TABLE 2

Apparent binding affinity of RAGE-Fc constructs to HMGB1

|  | Construct #1 | Construct #9 | Construct #10 | Construct #12 | Construct #16 |
|---|---|---|---|---|---|
| Apparent Kd | 26 nM | 2 nM | 15 nM | 7 nM | 7 nM |

TABLE 3

Apparent binding affinity of RAGE-Fc constructs to S100A9

|  | Construct #1 | Construct #9 | Construct #10 | Construct #12 | Construct #16 |
|---|---|---|---|---|---|
| Apparent Kd | 266 nM | 13 nM | 41 nM | 25 nM | 27 nM |

TABLE 4

Apparent binding affinity of RAGE-Fc constructs to S100A12

|  | Construct #1 | Construct #9 | Construct #10 | Construct #12 | Construct #16 |
|---|---|---|---|---|---|
| Apparent Kd | 180 nM | 9 nM | 46 nM | 44 nM | 36 nM |

Example 3: Assessing Susceptibility to Proteolytic Degradation

ADAM10 (a disintegrin and metalloproteinase 10) and MMP9 (matrix metalloproteinase 9) are enzymes that cleave full length RAGE. The enzymes were used to assess the vulnerability of RAGE-Fc fusion proteins to proteolytic cleavage by biologically relevant enzymes. In addition, trypsin was used as a non-specific enzyme to assess the general protease resistance of each fusion protein. For comparison, the esRAGE-Fc fusion proteins of the present disclosure were tested against a purified version identical to commercially available RAGE-Fc construct.

Each enzyme was verified to be functional under set assay conditions by demonstrating cleavage of a known peptide substrate. In brief, 0.06 μM of ADAM10 or 0.01 μM of MMP9 was incubated with 5 μM of fluorogenic peptide substrate [Mca-KPLGL-Dpa-AR-NH2 (SEQ ID NO: 75)]. The fluorescence was measured kinetically at 320 nm excitation and 405 nm emission via an automated fluorescence microplate reader. Trypsin at 0.002 μM was incubated with 766 μM of chromogenic substrate [Nα-Benzoyl-DL-arginine 4-nitroanilide hydrochloride]. The absorbance was measured kinetically at 405 nm via an automated microplate spectrophotometer. All the enzymes demonstrated proteolytic activity (data not shown).

Once the enzymes were verified to be functional they were incubated at 37° C. with the various RAGE-Fc fusion proteins for up to 24 hours. In brief, 0.06 μM of ADAM10 (Specific Activity: 1 μg of ADAM10 cleaves 20 pmol/min/μg of substrate; 50,000 μg=1 Unit), 0.01 μM of MMP9 (Specific Activity: 1 μg of MMP9 cleaves 1,300 pmol/min/μg of substrate; 769 μg=1 Unit), or 0.002 μM of trypsin (Specific Activity: 1 μg of Trypsin cleaves 2,500 pmol/min/μg of substrate; 400 μg=1 Unit) were incubated with 2.5 μM of RAGE-Fc fusion protein. The enzymatic reaction was stopped by adding an anionic detergent 1% lithium dodecyl sulfate (LDS), at the following time points: 0, 2, 15, 24 hours. As a control, the RAGE-Fc fusion proteins were incubated without enzyme to ensure that they were stable over the 24-hour time course of the experiment. The samples were then run on SDS-PAGE using SYPRO Ruby protein gel stain. Each sample was run under reducing (0.1 M DTT) conditions. The gels were imaged on Bio-Rad Molecular Imager and the bands were analyzed using Image Lab Software.

Results of the proteolytic stability experiments are shown in FIGS. 7A-7G, FIGS. 8A-8D, and Table 5. The results show that Constructs #9 (RAGE-Fc fusion lacking the C-terminal 13 amino acid RAGE stem), and 10, 12, and 16 (esRAGE-Fc fusions) were more resistant to proteolytic cleavage by MMP9 and trypsin and Constructs #12 and 16 were more resistant to proteolytic cleavage by ADAM10, as compared to Construct #1 (commercial RAGE-Fc fusion protein without the additional 16 amino acids at the carboxy terminus of the RAGE polypeptide) (SEQ ID NO: 5). All protease experiments were conducted under non-reducing conditions to preserve disulfide bonds in the Fc polypeptide during the stability time course. Reaction products were run on SDS-PAGE under reducing conditions in order to observe the reduced monomeric products (FIGS. 7A-7G). Examples of quantification data of the SDS-PAGE results at a specific time point are shown in Table 5. Data is presented as percent of full-length RAGE-Fc fusion protein (FL) remaining after the indicated treatment. The full-length proteins were quantified by fluorescent image intensities on the SDS-PAGE gel. Percentages are expressed as of function of the time zero band intensity for each condition. FIGS. 8A-8D show time course proteolysis data for the fusion proteins. Data shown is quantified from fluorescent bands of SDS-PAGE gels run under reducing conditions. Percent change is expressed as percent of the full length RAGE-Fc construct present at the indicated time point. Table 6 identifies the SEQ ID NO. of each construct tested.

TABLE 5

| Protease | Time (h) | Full Length Construct | | | | |
|---|---|---|---|---|---|---|
| | | #1 | #9 | #10 | #12 | #16 |
| ADAM10 | 15 | 84% | 91% | 92% | 100% | 100% |
| MMP9 | 15 | 15% | 52% | 38% | 51% | 65% |
| Trypsin | 15 | 0% | 39% | 39% | 35% | 34% |

TABLE 6

| RAGE Fc Construct | SEQ ID NO |
|---|---|
| #1 | 5 |
| #9 | 53 |
| #10 | 12 |
| #12 | 15 |
| #16 | 16 |

Example 4: Assessing Susceptibility to Degradation in Serum

The RAGE-Fc fusion proteins were assessed for their vulnerability to cleavage by enzymes found in normal human serum. For comparison, the esRAGE-Fc fusion proteins of the present disclosure were tested against a purified version identical to commercially available RAGE-Fc construct.

The serum was verified to contain active enzymes under set assay conditions by demonstrating cleavage of a fluorogenic peptide substrate. In brief, the serum was incubated with 10 µM of fluorogenic peptide substrate [Mca-KPLGL-Dpa-AR-NH2 (SEQ ID NO: 75)]. The fluorescence was measured kinetically at 320 nm excitation and 405 nm emission via an automated fluorescence microplate reader. The serum demonstrated proteolytic activity (data not shown).

Once the serum was verified to contain active enzymes it was incubated at 37° C. with the various RAGE-Fc fusion proteins for up to 138 hours. In brief, 75% (v/v) of serum was incubated with 25% (v/v) of 2 µM of RAGE-Fc fusion protein in PBS. The enzymatic reaction was stopped by adding an anionic detergent 1% lithium dodecyl sulfate (LDS), at the following time points: 0, 17, 49, 138 hours. As a control, the serum was tested without RAGE-Fc fusion protein to ensure no endogenous soluble RAGE was detected in the serum. The serum samples were tested with Western Blot to detect the presence of the constructs. In brief, the samples were run on SDS-PAGE under reducing conditions (0.1 M DTT), then transferred to PVDF membrane and stained with Ponceau to ensure the transfer was successful. The PVDF membrane was then blocked with 5% BSA in TBS-Tween for 1 hour at room temperature, then incubated with the primary antibody diluted 1:500 in TBS-Tween containing 5% BSA (Invitrogen, Cat. No. 701316) overnight at 4° C. The membrane was then washed five times with TBS-Tween for 5 min per wash and then incubated with the secondary antibody diluted 1:5000 in TBS-Tween containing 5% BSA (GenTex, Cat No. GTX213110-01) for 1 hour at room temperature. The membrane was again washed five times with TBS-Tween for 5 min per wash, and then detected using (ECL) chemiluminescence. The gels were imaged on Bio-Rad Molecular Imager and the bands were analyzed using Image Lab Software.

Results of the serum stability experiments are shown in FIGS. 9A-9D, FIG. 10, and Table 7. The results show that Constructs #9, 12, and 16 were more resistant to proteolytic cleavage by enzymes found in serum as compared to Constructs #1 and #10. All serum stability experiments were conducted under non-reducing conditions to preserve disulfide bonds in the Fc polypeptide during the stability time course. Reaction products were run on SDS-PAGE under reducing conditions in order to observe the reduced monomeric products as seen on the Western Blots (FIGS. 9A-9D). Quantification data of the Western Blot results are shown in Table 7. Data is presented as percent of full-length RAGE-Fc fusion protein (FL) remaining after the indicated time point. The full-length proteins were quantified by image intensities on the Western Blot membrane. Percentages are expressed as of function of the time zero band intensity for each condition. FIGS. 8A-8D show time course proteolysis data for the fusion proteins. Data shown is quantified from intensity bands of the Western Blot membranes run under reducing conditions. Percent change is expressed as percent of the full length RAGE-Fc construct present at the indicated time point. Table 4 identifies the SEQ ID NO. of each construct tested.

TABLE 7

| Time (h) | Full Length Construct | | | | |
|---|---|---|---|---|---|
| | #1 | #9 | #10 | #12 | #16 |
| 0 | 100% | 100% | 100% | 100% | 100% |
| 17 | 65% | 100% | 100% | 99% | 81% |
| 49 | 47% | 100% | 74% | 86% | 64% |
| 138 | 0% | 22% | 0% | 23% | 17% |

Example 5: Assessing Thermal Stability and Aggregation

Figure 11A:
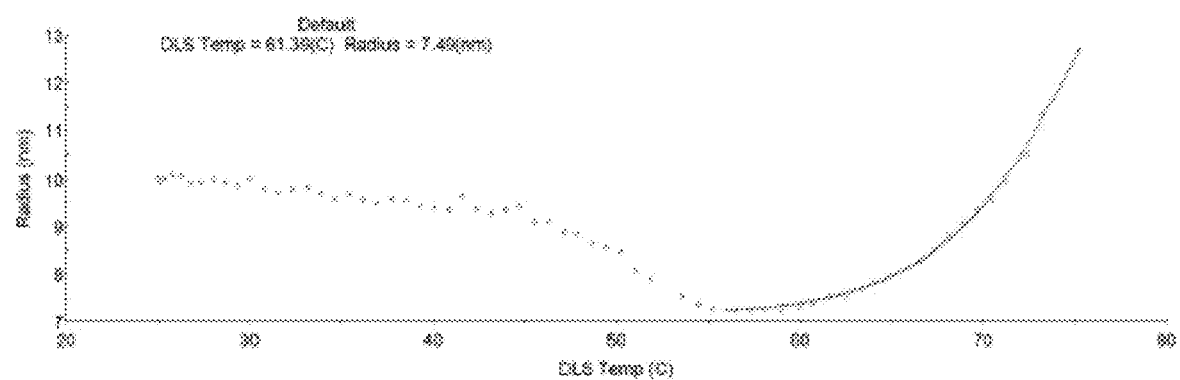
FIGS. 11A-11D show thermal denaturation curves of RAGE-Fc fusion proteins as measured by dynamic light scattering: Construct #1 (FIG. 11A); Construct #10 (FIG. 11B); Construct #12 (FIG. 11C); and Construct #16 (FIG. 11D).
Figure 11B:
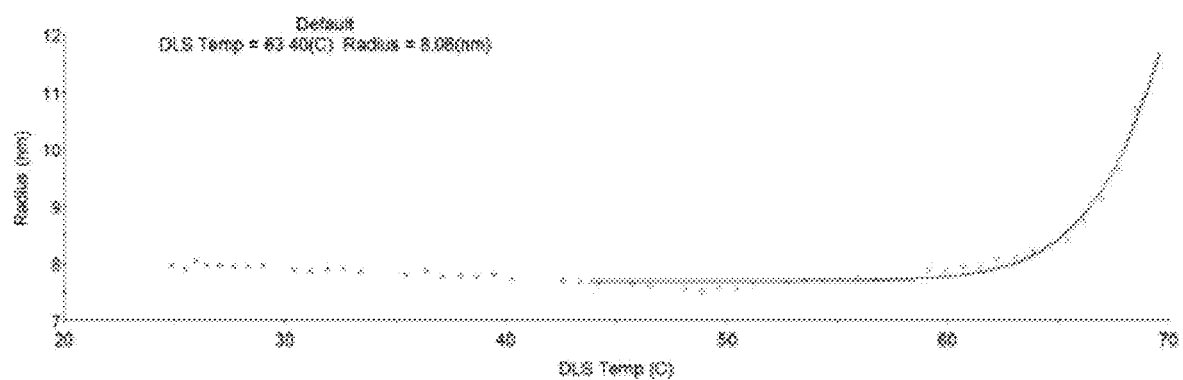
Figure 11C:
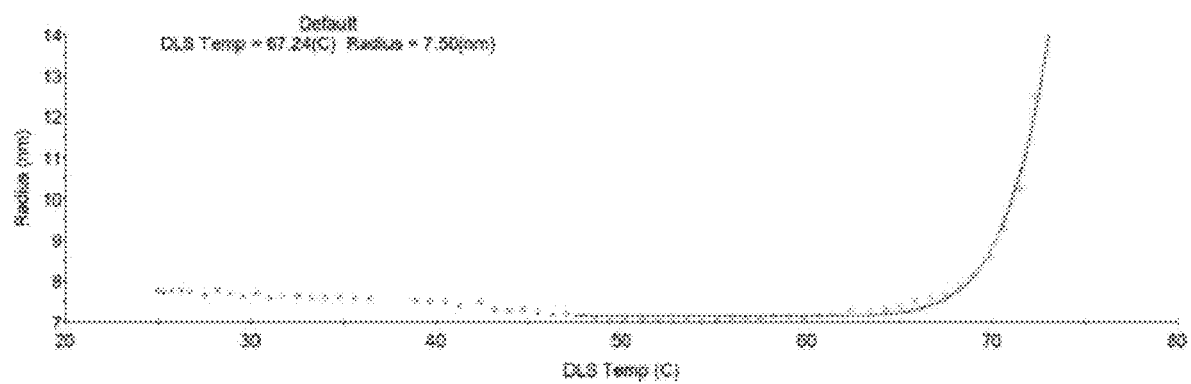
Figure 11D:
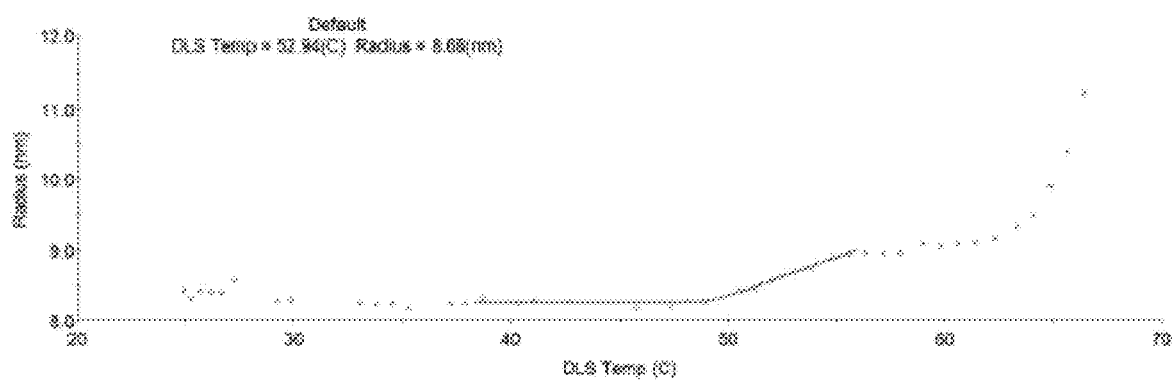

Dynamic light scattering (DLS) was used to analyze the aggregation temperature ($T_{agg}$) of RAGE-Fc fusion proteins in the same buffer solution. DLS was performed using the DynaPro® NanoStar® instrument to measure the effect of temperature on translational diffusion coefficients ($D_t$) of nanoparticles and colloids in solution by quantifying dynamic fluctuations in scattered light. Sizes and size distributions, in turn, are calculated from the diffusion coefficients in terms of hydrodynamic diameter ($d_h$). Results are shown in FIGS. 11A-11D: Construct #1 (FIG. 11A); Construct #10 (FIG. 11B); Construct #12 (FIG. 11C); Construct #16 (FIG. 11D). DLS profiles of fusion proteins were analyzed by the framework of Onset model, the dots indicate the raw data while the green solid line indicates the fitting curve by the model. The results show that Constructs #10 and #12 (esRAGE-Fc fusions) have enhanced thermal stability as compared to Construct #1. Results from this analysis including hydrodynamic radius (nm) and $T_{agg}$ (° C.) are shown in Table 8.

TABLE 8

| Construct | Concentration (mg/ml) | $T_{agg}$ (° C.) | Radius (nm) |
|---|---|---|---|
| #1 | 2.26 | 61.39 | 7.49 |
| #10 | 2.86 | 63.40 | 8.06 |
| #12 | 1.55 | 67.24 | 7.50 |
| #16 | 2.00 | 52.94 | 8.68 |

Example 6: Improved Manufacturability

Further modified RAGE-Fc fusion proteins were constructed to test for improvement of protein expression and manufacturability of the fusion protein. Improved manufacturability manifests in one or more of the following ways: higher expression, increased stability, or improved solubility. Solubility may be assessed by SDS-PAGE under reducing and non-reducing conditions, followed by Western blot. In contrast to the prior art, the improved molecules of the present disclosure demonstrate reduced tendency to aggregate as shown by distinct protein bands visible under reducing conditions compared to smeared bands visible under non-reducing conditions (see FIGS. 2A-2L, FIGS. 3A-3J, FIGS. 4A-4I, and FIGS. 5A-5F, comparing bands in lane 1 (reducing condition) with bands in lane 2 (non-reducing conditions)).

For example, esRAGE-Fc fusion proteins were constructed using at least a portion of the hinge region of alternative human IgG polypeptides as a linker between the C-terminus of esRAGE and the amino terminus of the Fc polypeptide of the fusion protein. A RAGE-Fc fusion protein was also constructed using a RAGE polypeptide with a shortened stem region lacking the C-terminal 13 amino acid residues, with a portion of the hinge region of alternative human IgG polypeptides as a linker between the C-terminus of RAGE and the amino terminus of the Fc polypeptide of the fusion protein. Additional modified fusion proteins were generated by introducing amino acid substitutions into the esRAGE polypeptide, and/or the Fc polypeptide of the fusion protein. Fusion proteins comprising alternative linkers and amino acid substitutions were generated using overlap PCR mutagenesis according to known methods.

Testing of esRAGE-Fc fusion proteins comprising linkers from alternative IgG hinge regions and esRAGE-Fc fusion proteins comprising amino acid substitutions was performed as follows. Polynucleotides encoding esRAGE-Fc fusion proteins comprising an IgG4 hinge linker (SEQ ID NO: 39), a RAGE polypeptide with a shortened stem region lacking the C-terminal 13-amino acid residues (SEQ ID NO: 54), or polynucleotides encoding fusion proteins comprising an IgG2 linker (SEQ ID NO: 41) were expressed in CHO-3E7 cells as described in Example 1. Further, polynucleotides encoding esRAGE-Fc fusion proteins comprising amino substitutions M252Y, S254T, and T256E in the Fc polypeptide (SEQ ID NO: 44) were also expressed in CHO-3E7 cells as described in Example 1. The cultures were grown for six days following transfection; on day 6 the cell culture supernatant was collected and used for purification as described in Example 1. Purified protein was analyzed by SDS-PAGE under reducing and non-reducing conditions and by Western blot using a primary Goat Anti-Human IgG-HRP antibody (GenScript, Cat. No. A00166). Protein concentration was determined by Bradford assay using BSA as a protein standard. Tables 5 and 6 show the concentration, purity, and total purified protein yield for each fusion protein.

The esRAGE-Fc fusion protein encoded by the amino acid sequence set forth in SEQ ID NO: 12 (nucleotide sequence set forth in SEQ ID NO: 39) differs from the fusion protein encoded by the amino acid sequence set forth in SEQ ID NO 15 (nucleotide sequence set forth in SEQ ID NO: 41) only by the IgG hinge from which the linker is derived. Further, the esRAGE-Fc fusion protein encoded by the amino acid sequence set forth in SEQ ID NO: 16 (nucleotide sequence set forth in SEQ ID NO: 43) differs from the fusion protein encoded by the amino acid sequence set forth in SEQ ID NO: 15 (nucleotide sequence set forth in SEQ ID NO: 41) only by the amino acid substitutions at positions 252, 254, and 256 (EU numbering) of the Fc polypeptide. The results shown in Table 9 demonstrate that the purity and yield, and thus the manufacturability of the fusion protein may be improved by replacing a linker from the IgG4 hinge with a linker from the IgG2 hinge. Similarly, the results shown in Table 9 demonstrate that manufacturability of the fusion protein is improved by incorporating amino acid substitutions M252Y, S254T, and T256E (EU numbering) in the Fc polypeptide of the fusion protein.

TABLE 9

| Amino acid sequence | Nucleotide sequence | Construct name | Concentration | Purity | Total protein |
|---|---|---|---|---|---|
| SEQ ID NO: 12 | SEQ ID NO: 39 | Construct #10: RAGEV-C1-C2-V1 stem (M/A)-IgG4-hinge(S/P-AA)-(IgG4CH2—CH3) | 0.29 mg/mL | 70% | 580 µg |
| SEQ ID NO: 14 | SEQ ID NO: 40 | Construct #11: RAGEV-C1-C2-V1 stem (M/A)-VH8aa-IgG4-hinge(S/P-AA)-(IgG4CH2—CH3) | 0.16 mg/mL | 80% | 640 µg |
| SEQ ID NO: 15 | SEQ ID NO: 41 | Construct #12: RAGEV-C1-C2-V1stem(M/A)-IgG2lowerhinge-(IgG4CH2—CH3) | 0.19 mg/mL | 80% | 760 µg |
| SEQ ID NO: 16 | SEQ ID NO: 43 | Construct #16: RAGE V-C1-C2-V1stem(M/A)-IgG2 lower hinge-(IgG4CH2—CH3)-YTE | 0.21 mg/mL | 90% | 1.68 mg |

Data showing the concentration, purity, and total purified protein yield for RAGE-Fc fusion proteins expressed at 1 L scale and purified using Monofinity A Resin affinity purification, followed by HiLoad26/600 Superdex200 pg size exclusion chromatography. The results shown in Table 10 demonstrate that the purity and yield, and thus the manufacturability of the fusion protein in scaled-up production may be improved by replacing a linker from the IgG4 hinge with a linker from the IgG2 hinge. Similarly, the results shown in Table 10 demonstrate that manufacturability of the fusion protein is improved by incorporating amino acid substitutions M252Y, S254T, and T256E (EU numbering) in the Fc polypeptide of the fusion protein.

TABLE 10

| Amino acid sequence | Nucleotide sequence | Construct name | Concentration | Purity | Total protein |
| --- | --- | --- | --- | --- | --- |
| SEQ ID NO: 5 | SEQ ED NO: 38 | Construct #1: RAGE V-C1-C2-Natural Stem-short linker-IgG1 hinge-(IgG1CH2—CH3) | 0.58 mg/mL | 90% | 18.27 mg |
| SEQ ID NO: 54 | SEQ ID NO: 57 | Construct #9: RAGE V-C1-C2-shortenedstem-VH8aa-IgG4-hinge(S/P-AA)—(IgG4CH2—CH3) | 0.48 mg/mL | 90% | 2.88 mg |
| SEQ ID NO: 12 | SEQ ID NO: 39 | Construct #10: RAGEV-C1-C2-V1 stem (M/A)-IgG4-hinge(S/P-AA)-(IgG4CH2—CH3) | 0.38 mg/mL | 90% | 4.94 mg |
| SEQ ID NO: 14 | SEQ ID NO: 40 | Construct #11: RAGEV-C1-C2-V1 stem (M/A)-VH8aa-IgG4-hinge(S/P-AA)-(IgG4CH2—CH3) | 0.43 mg/mL | 90% | 4.30 mg |
| SEQ ID NO: 15 | SEQ ID NO: 41 | Construct #12: RAGEV-C1-C2-V1stem(M/A)-IgG2lowerhinge-(IgG4CH2—CH3) | 0.66 mg/mL | 90% | 7.26 mg |
| SEQ ID NO: 16 | SEQ ID NO: 43 | Construct #16: RAGE V-C1-C2-V1stem(M/A)-IgG2 lower hinge-(IgG4CH2—CH3)-YTE | 0.43 mg/mL | 90% | 12.25 mg |

Data showing the concentration, purity, and total purified protein yield for additional RAGE-Fc fusion proteins is provided in Table 11.

TABLE 11

| Amino acid sequence | Nucleotide sequence | Construct name | Concentration | Purity | Total protein |
| --- | --- | --- | --- | --- | --- |
| SEQ ID NO: 5 | SEQ ID NO: 38 | Construct #1: RAGE V-C1-C2-Natural Stem-short linker-IgG1 hinge-(IgG1CH2—CH3) | 0.26 mg/mL | 80% | 1.56 mg |
| SEQ ID NO: 37 | SEQ ID NO: 42 | Construct #13: RAGEV-C1-C2 (N25E/G82S)-Natural Stem-short linker-IgG1 hinge-(IgG1CH2—CH3) | 0.15 mg/mL | 65% | 450 μg |
| SEQ ID NO: 17 | SEQ ID NO: 44 | Construct #17: RAGE V-C1-C2-V1stem(M/A)-(N25E)-IgG2 lower hinge-(IgG4CH2—CH3) | 0.21 mg/mL | 80% | 2.10 mg |
| SEQ ID NO: 18 | SEQ ID NO: 45 | Construct #18: RAGE V-C1-C2-V1stem(M/A)-(N25Q)-IgG2 lower hinge-(IgG4CH2—CH3) | 0.14 mg/mL | 75% | 1.40 mg |
| SEQ ID NO: 19 | SEQ ID NO: 46 | Construct #19: RAGE V-C1-C2-V1stem(M/A)-(G82S)-IgG2 lower hinge-(IgG4CH2—CH3) | 0.13 mg/mL | 85% | 780 μg |
| SEQ ID NO: 20 | SEQ ID NO: 47 | Construct #20: RAGE V-C1-C2-V1stem(M/A)-(N25E/G82S)-IgG2 lower hinge-(IgG4CH2—CH3) | 0.10 mg/mL | 70% | 1.05 mg |
| SEQ ID NO: 21 | SEQ ID NO: 48 | Construct #21: RAGE V-C1-C2-V1stem(M/A)-(N25Q/G82S)-IgG2 lower hinge-(IgG4CH2—CH3) | 0.12 mg/mL | 75% | 1.08 mg |
| SEQ ID NO: 22 | SEQ ID NO: 49 | Construct #22: RAGE V-C1-C2-V1stem(M/A)-(N81A)-IgG2 lower hinge-(IgG4CH2—CH3) | 0.13 mg/mL | N/A | 780 μg |
| SEQ ID NO: 23 | SEQ ID NO: 50 | Construct #23: RAGE V-C1-C2-V1stem(M/A)-(N25E/N81A)-IgG2 lower hinge—(IgG4CH2—CH3) | 52 μg/mL | 35% | 676 μg |
| SEQ ID NO: 24 | SEQ ID NO: 51 | Construct #24: RAGE V-C1-C2-V1stem(M/A)-(N25Q/N81A)-IgG2 lower hinge—(IgG4CH2—CH3) | 0.13 mg/mL | N/A | 1.69 mg |

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

| INFORMAL SEQUENCE LISTING | | |
| --- | --- | --- |
| SEQ ID NO | DESCRIPTION | SEQUENCE |
| SEQ ID NO: 1 | esRAGE including the natural leader sequence (natural leader sequence is underlined) | <u>MAAGTAVGAW VLVLSLWGAV VGAQ</u>NITARI GEPLVLKCKG APKKPPQRLE WKLNTGRTEA WKVLSPQGGG PWDSVARVLP NGSLFLPAVG IQDEGIFRCQ AMNRNGKETK SNYRVRVYQI |

INFORMAL SEQUENCE LISTING

| SEQ ID NO | DESCRIPTION | SEQUENCE |
|---|---|---|
| | | PGKPEIVDSA SELTAGVPNK VGTCVSEGSY<br>PAGTLSWHLD GKPLVPNEKG VSVKEQTRRH<br>PETGLFTLQS ELMVTPARGG DPRPTFSCSF<br>SPGLPRHRAL RTAPIQPRVW EPVPLEEVQL<br>VVEPEGGAVA PGGTVTLTCE VPAQPSPQIH<br>WMKDGVPLPL PPSPVLILPE IGPQDQGTYS<br>CVATHSSHGP QESRAVSISI IEPGEEGPTA<br>GEGFDKVREA EDSPQHM |
| SEQ ID NO: 2 | 15 of 16 AA of C-term. sequence unique to esRAGE | EGFDKVREA EDSPQH |
| SEQ ID NO: 3 | AA sequence of hRAGE-IgG4Fc fusion protein of US 9,399,668-SEQ ID NO: 6 in the '668 patent (includes the natural leader sequence, underlined) | <u>MAAGTAVGAW VLVLSLWGAV VGA</u>QNITARI<br>GEPLVLKCKG APKKPPQRLE WKLNTGRTEA<br>WKVLSPQGGG PWDSVARVLP NGSLFLPAVG<br>TQDEGIFRCQ AMNRNGKETK SNYRVRVYQI<br>PGKPEIVDSA SELTAGVPNK VGTCVSEGSY<br>PAGTLSWHLD GKPLVPNEKG VSVKEQTRRH<br>PETGLFTLQS ELMVTPARGG DPRPTFSCSP<br>SPGLPRRRAL HTAPIQPRVW EPVPLEEVQL<br>VVEPEGGAVA PGGTVTLTCE VPAQPSPQIH<br>WMKDGVPLPL PPSPVLILPE IGPQDQGTYS<br>CVATHSSHGP QESRAVSISI IEPGEEGPTA<br>GSVGGSGLGT LALAASTKGP SVFPLAPCSR<br>STSESTAALG CLVKDYFPEP VTVSWNSGAL<br>TSGVHTFPAV LQSSGLYSLS SVVTVPSSSL<br>GTKTYTCNVD HKPSNTKVDK RVESKYGPPC<br>PSCPAPEFLG GPSVFLFPPK PKDTLMISRT<br>PEVTCVVVDV SQEDPEVQFN WYVDGVEVHN<br>AKTKPREEQF NSTYRVVSVL TVLHQDWLNG<br>KEYKCKVSNK GLPSSTEKTI SKAKGQPREP<br>QVYTLPPSQE EMTKNQVSLT CLVKGFYPSD<br>IAVEWESNGQ PENNYKTTPP VLDSDGSFFL<br>YSRLTVDKSR WQEGNVFSCS VMHEALHNHY<br>TQKSLSLSLG K |
| SEQ ID NO: 4 | Sequence corresponding to M252Y/S254T/T256E mutation in CH2 domain of IgG Fc | xYxTxE |
| SEQ ID NO: 5 | Sequence corresponding to Construct #1 (mature protein; lacking the natural leader sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GSVGGSGLGT LALAIEGRMP<br>KSCDKTHTCP PCPAPELLGG PSVFLFPPKP<br>KDTLMISRTP EVTCVVVDVS HEDPEVKFNW<br>YVDGVEVHNA KTKPREEQYN STYRVVSVLT<br>VLHQDWLNGK EYKCKVSNKA LPAPIEKTIS<br>KAKGQPREPQ VYTLPPSRDE LTKNQVSLTC<br>LVKGFYPSDI AVEWESNGQP ENNYKTTPPV<br>LDSDGSFFLY SKLTVDKSRW QQGNVFSCSV<br>MHEALHNHYT QKSLSLSPGK |
| SEQ ID NO: 6 | Sequence of extracellular domain of WT hRAGE (not the splice variant) (mature protein; lacking the natural leader sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA G |

| SEQ ID NO | DESCRIPTION | SEQUENCE |
|---|---|---|
| SEQ ID NO: 7 | AA359-590 of construct #17 | GG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| SEQ ID NO: 8 | Modified IgG4 (S/P-AA) hinge that is present in esRAGE-Fc linker in constructs #10, 11, 33, 35, and 36 | ESKYGPPCPPCPAPEAA |
| SEQ ID NO: 9 | IgG2 lower hinge that is present in esRAGE-Fc linker in constructs #12, 16-29, 31-32 | VECPPCAPPVA |
| SEQ ID NO: 10 | IgG2 complete hinge that is present in esRAGE-Fc linker in construct #30 | ERKCCVECPPCAPPVA |
| SEQ ID NO: 11 | IgG1 hinge that is present in esRAGE-Fc linker in construct #34 | EPKSCDKTHTCPPCPAPEAA |
| SEQ ID NO: 12 | Construct #10 RAGE V-C1-C2-V1 stem(M/A)-IgG4-hinge (S/P-AA)-(IgG4CH2-CH3) (mature protein; lacking the natural leader sequence) | AQNITARIGE PLVLKCKGAP KKPPQRLE WKLNTGRTEA WKVLSPQGGG PWDSVARVLP NGSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAESK YGPPCPPCPA PEAAGGPSVF LFPPKPKDTL MISRTPEVTC VVVDVSQEDP EVQFNWYVDG VEVHNAKTKP REEQFNSTYR VVSVLTVLHQ DWLNGKEYKC KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVMHEA LHNHYTQKSL SLSLGK |
| SEQ ID NO: 13 | Shortened stem-VH8aa-IgG4-hinge(S/P-AA) | GTLVTVSS |
| SEQ ID NO: 14 | Construct #11 RAGE V-C1-C2-V1 stem(M/A)-VH8aa-IgG4-hinge (S/P-AA)-(IgG4CH2-CH3) (mature protein; lacking the natural leader sequence) | AQNITARIGE PLVLKCKGAP KKPPQRLE WKLNTGRTEA WKVLSPQGGG PWDSVARVLP NGSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAGTL VTVSSESKYG PPCPPCPAPE AAGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK |

INFORMAL SEQUENCE LISTING

| SEQ ID NO | DESCRIPTION | SEQUENCE |
|---|---|---|
| SEQ ID NO: 15 | Construct #12<br>RAGE V-C1-C2-<br>V1 stem(M/A)-IgG2 lower<br>hinge-(IgG4CH2-CH3)<br>(mature protein; lacking the<br>natural leader sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAVEC<br>PPCAPPVAGG PSVFLFPPKP KDTLMISRTP<br>EVTCVVVDVS QEDPEVQFNW YVDGVEVHNA<br>KTKPREEQFN STYRVVSVLT VLHQDWLNGK<br>EYKCKVSNKG LPSSIEKTIS KAKGQPREPQ<br>VYTLPPSQEE MTKNQVSLTC LVKGFYPSDI<br>AVEWESNGQP ENNYKTTPPV LDSDGSFFLY<br>SRLTVDKSRW QEGNVFSCSV MHEALHNHYT<br>QKSLSLSLGK |
| SEQ ID NO: 16 | Construct #16<br>(#12 + YTE)<br>RAGE V-C1-C2-<br>V1 stem(M/A)-IgG2 lower<br>hinge-(IgG4CH2-CH3)-<br>YTE (mature protein;<br>lacking the natural leader<br>sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAVEC<br>PPCAPPVAGG PSVFLFPPKP KDTLYITREP<br>EVTCVVVDVS QEDPEVQFNW YVDGVEVHNA<br>KTKPREEQFN STYRVVSVLT VLHQDWLNGK<br>EYKCKVSNKG LPSSIEKTIS KAKGQPREPQ<br>VYTLPPSQEE MTKNQVSLTC LVKGFYPSDI<br>AVEWESNGQP ENNYKTTPPV LDSDGSFFLY<br>SRLTVDKSRW QEGNVFSCSV MHEALHNHYT<br>QKSLSLSLGK |
| SEQ ID NO: 17 | Construct #17<br>RAGE V-C1-C2-<br>V1 stem(M/A)-(N25E)-IgG2<br>lower hinge-(IgG4CH2-<br>CH3) (mature protein;<br>lacking the natural leader<br>sequence) | AQEITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAVEC<br>PPCAPPVAGG PSVFLFPPKP KDTLMISRTP<br>EVTCVVVDVS QEDPEVQFNW YVDGVEVHNA<br>KTKPREEQFN STYRVVSVLT VLHQDWLNGK<br>EYKCKVSNKG LPSSIEKTIS KAKGQPREPQ<br>VYTLPPSQEE MTKNQVSLTC LVKGFYPSDI<br>AVEWESNGQP ENNYKTTPPV LDSDGSFFLY<br>SRLTVDKSRW QEGNVFSCSV MHEALHNHYT<br>QKSLSLSLGK |
| SEQ ID NO: 18 | Construct #18<br>RAGE V-C1-C2-<br>V1 stem(M/A)-(N25Q)-IgG2<br>lower hinge-(IgG4CH2-<br>CH3) (mature protein;<br>lacking the natural leader<br>sequence) | AQQITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAVEC<br>PPCAPPVAGG PSVFLFPPKP KDTLMISRTP<br>EVTCVVVDVS QEDPEVQFNW YVDGVEVHNA<br>KTKPREEQFN STYRVVSVLT VLHQDWLNGK |

| SEQ ID NO | DESCRIPTION | SEQUENCE |
|---|---|---|
| | | EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| SEQ ID NO: 19 | Construct #19 RAGE V-C1-C2-V1 stem(M/A)-(G82S)-IgG2 lower hinge-(IgG4CH2-CH3) (mature protein; lacking the natural leader sequence) | AQNITARIGE PLVLKCKGAP KKPPQRLE WKLNTGRTEA WKVLSPQGGG PWDSVARVLP NSSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| SEQ ID NO: 20 | Construct #20 RAGE V-C1-C2-V1 stem(M/A)-(N25E/G82S)-IgG2 lower hinge-(IgG4CH2-CH3) (mature protein; lacking the natural leader sequence) | AQEITARIGE PLVLKCKGAP KKPPQRLE WKLNTGRTEA WKVLSPQGGG PWDSVARVLP NSSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| SEQ ID NO: 21 | Construct #21 RAGE V-C1-C2-V1 stem(M/A)-(N25Q/G82S)-IgG2 lower hinge-(IgG4CH2-CH3) (mature protein; lacking the natural leader sequence) | AQQITARIGE PLVLKCKGAP KKPPQRLE WKLNTGRTEA WKVLSPQGGG PWDSVARVLP NSSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| SEQ ID NO: 22 | Construct #22 RAGE V-C1-C2-V1 stem(M/A)-(N81A)-IgG2 lower hinge-(IgG4CH2-CH3) (mature protein; lacking the natural leader sequence) | AQNITARIGE PLVLKCKGAP KKPPQRLE WKLNTGRTEA WKVLSPQGGG PWDSVARVLP AGSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE |

| SEQ ID NO | DESCRIPTION | SEQUENCE |
|---|---|---|
| | | IGPQDQGTYS CVATHSSHGP QESRAVSISI IEPGEEGPTA GEGFDKVREA EDSPQHAVEC PPCAPPVAGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNYT QKSLSLSLGK |
| SEQ ID NO: 23 | Construct #23 RAGE V-C1-C2-V1 stem(M/A)-(N25E/N81A)-IgG2 lower hinge-(IgG4CH2-CH3) (mature protein; lacking the natural leader sequence) | AQEITARIGE PLVLKCKGAP KKPPQRLE WKLNTGRTEA WKVLSPQGGG PWDSVARVLP AGSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNYT QKSLSLSLGK |
| SEQ ID NO: 24 | Construct #24 RAGE V-C1-C2-V1 stem(M/A)-(N25Q/N81A)-IgG2 lower hinge-(IgG4CH2-CH3) (mature protein; lacking the natural leader sequence) | AQQITARIGE PLVLKCKGAP KKPPQRLE WKLNTGRTEA WKVLSPQGGG PWDSVARVLP AGSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNYT QKSLSLSLGK |
| SEQ ID NO: 25 | Construct #25 RAGE V-C1-C2-V1 stem(M/A)-(N25E)-IgG2 lower hinge-(IgG4CH2-CH3)-YTE (mature protein; lacking the natural leader sequence) | AQEITARIGE PLVLKCKGAP KKPPQRLE WKLNTGRTEA WKVLSPQGGG PWDSVARVLP NGSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLYITREP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNYT QKSLSLSLGK |
| SEQ ID NO: 26 | Construct #26 RAGE V-C1-C2-V1 stem(M/A)-(N25Q)-IgG2 lower hinge-(IgG4CH2- | AQQITARIGE PLVLKCKGAP KKPPQRLE WKLNTGRTEA WKVLSPQGGG PWDSVARVLP NGSLFLPAVG IQDEGIFRCQ AMNRNGKETK SNYRVRVYQI PGKPEIVDSA SELTAGVPNK |

| SEQ ID NO | DESCRIPTION | SEQUENCE |
|---|---|---|
| | CH3)-YTE (mature protein; lacking the natural leader sequence) | VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLYITREP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| SEQ ID NO: 27 | Construct #27 RAGE V-C1-C2-V1 stem(M/A)-(G82S)-IgG2 lower hinge-(IgG4CH2-CH3)-YTE (mature protein; lacking the natural leader sequence) | AQNITARIGE PLVLKCKGAP KKPPQRLE WKLNTGRTEA WKVLSPQGGG PWDSVARVLP NSSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLYITREP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| SEQ ID NO: 28 | Construct #28 RAGE V-C1-C2-V1 stem(M/A)-(N25E/G82S)-IgG2 lower hinge-(IgG4CH2-CH3)-YTE (mature protein; lacking the natural leaders sequence) | AQEITARIGE PLVLKCKGAP KKPPQRLE WKLNTGRTEA WKVLSPQGGG PWDSVARVLP NSSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLYITREP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| SEQ ID NO: 29 | Construct #29 RAGE V-C1-C2-V1 stem(M/A)-(N25Q/G82S)-IgG2 lower hinge-(IgG4CH2-CH3)-YTE (mature protein; lacking the natural leaders sequence) | AQQITARIGE PLVLKCKGAP KKPPQRLE WKLNTGRTEA WKVLSPQGGG PWDSVARVLP NSSLFLPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEPGEEGPTA GEGFDKVREA EDSPQHAVEC PPCAPPVAGG PSVFLFPPKP KDTLYITREP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |

| INFORMAL SEQUENCE LISTING | | |
|---|---|---|
| SEQ ID NO | DESCRIPTION | SEQUENCE |
| SEQ ID NO: 30 | Construct #30<br>RAGE V-C1-C2-<br>V1 stem(M/A)-IgG2<br>complete hinge-(IgG4CH2-<br>CH3)-YTE (mature protein;<br>lacking the natural leader<br>sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAERK<br>CCVECPPCAP PVAGGPSVFL FPPKPKDTLY<br>ITREPEVTCV VVDVSQEDPE VQFNWYVDGV<br>EVHNAKTKPR EEQFNSTYRV VSVLTVLHQD<br>WLNGKEYKCK VSNKGLPSSI EKTISKAKGQ<br>PREPQVYTLP PSQEEMTKNQ VSLTCLVKGF<br>YPSDIAVEWE SNGQPENNYK TTPPVLDSDG<br>SFFLYSRLTV DKSRWQEGNV FSCSVMHEAL<br>HNHYTQKSLS LSLGK |
| SEQ ID NO: 31 | Construct #31<br>RAGE V-C1-C2-<br>V1 stem(M/A)-IgG2 lower<br>hinge-(IgG2CH2-CH3)-<br>YTE (mature protein;<br>lacking the natural leader<br>sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAVEC<br>PPCAPPVAGP SVFLFPPKPK DTLYITREPE<br>VTCVVVDVSH EDPEVQFNWY VDGVEVHNAK<br>TKPREEQFNS TFRVVSVLTV VHQDWLNGKE<br>YKCKVSNKGL PAPIEKTISK TKGQPREPQV<br>YTLPPSREEM TKNQVSLTCL VKGFYPSDIA<br>VEWESNGQPE NNYKTTPPML DSDGSFFLYS<br>KLTVDKSRWQ QGNVFSCSVM HEALHNHYTQ<br>KSLSLSPGK |
| SEQ ID NO: 32 | Construct #32<br>RAGE V-C1-C2-<br>V1 stem(M/A)-IgG2 lower<br>hinge-(IgG1CH2-CH3)-<br>YTE (mature protein;<br>lacking the natural leader<br>sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAVEC<br>PPCAPPVAGG PSVFLFPPKP KDTLYITREP<br>EVTCVVVDVS HEDPEVKFNW YVDGVEVHNA<br>KTKPREEQYN STYRVVSVLT VLHQDWLNGK<br>EYKCKVSNKA LPAPIEKTIS KAKGQPREPQ<br>VYTLPPSRDE LTKNQVSLTC LVKGFYPSDI<br>AVEWESNGQP ENNYKTTPPV LDSDGSFFLY<br>SKLTVDKSRW QQGNVFSCSV MHEALHNHYT<br>QKSLSLSPGK |
| SEQ ID NO: 33 | Construct #33<br>RAGE V-C1-C2-<br>V1 stem(M/A)-IgG4-hinge<br>(S/P-AA)-(IgG1CH2-<br>CH3)-YTE (mature protein;<br>lacking the natural leaders<br>sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAESK<br>YGPPCPPCPA PEAAGGPSVF LFPPKPKDTL<br>YITREPEVTC VVVDVSHEDP EVKFNWYVDG<br>VEVHNAKTKP REEQYNSTYR VVSVLTVLHQ |

-continued

INFORMAL SEQUENCE LISTING

| SEQ ID NO | DESCRIPTION | SEQUENCE |
|---|---|---|
| | | DWLNGKEYKC KVSNKALPAP IEKTISKAKG<br>QPREPQVYTL PPSRDELTKN QVSLTCLVKG<br>FYPSDIAVEW ESNGQPENNY KTTPPVLDSD<br>GSFFLYSKLT VDKSRWQQGN VFSCSVMHEA<br>LHNHYTQKSL SLSPGK |
| SEQ ID NO: 34 | Construct #34<br>RAGE V-C1-C2-<br>V1 stem(M/A)-IgG1 hinge<br>(AA)-(IgG1CH2-CH3)-<br>YTE (mature protein;<br>lacking the natural leaders<br>sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAEPK<br>SCDKTHTCPP CPAPEAAGGP SVFLFPPKPK<br>DTLYITREPE VTCVVVDVSH EDPEVKFNWY<br>VDGVEVHNAK TKPREEQYNS TYRVVSVLTV<br>LHQDWLNGKE YKCKVSNKAL PAPIEKTISK<br>AKGQPREPQV YTLPPSRDEL TKNQVSLTCL<br>VKGFYPSDIA VEWESNGQPE NNYKTTPPVL<br>DSDGSFFLYS KLTVDKSRWQ QGNVFSCSVM<br>HEALHNHYTQ KSLSLSPGK |
| SEQ ID NO: 35 | Construct #35<br>(#10 + YTE)<br>RAGE V-C1-C2-RAGE V-<br>C1-C2-V1stem(M/A)-IgG4-<br>hinge (S/P-AA)-<br>(IgG4CH2-CH3)-YTE<br>(mature protein; lacking the<br>natural leaders sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAESK<br>YGPPCPPCPA PEAAGGPSVF LFPPKPKDTL<br>YITREPEVTC VVVDVSQEDP EVQFNWYVDG<br>VEVHNAKTKP REEQFNSTYR VVSVLTVLHQ<br>DWLNGKEYKC KVSNKGLPSS IEKTISKAKG<br>QPREPQVYTL PPSQEEMTKN QVSLTCLVKG<br>FYPSDIAVEW ESNGQPENNY KTTPPVLDSD<br>GSFFLYSRLT VDKSRWQEGN VFSCSVMHEA<br>LHNHYTQKSL SLSLGK |
| SEQ ID NO: 36 | Construct #36<br>(#11 + YTE)<br>RAGE V-C1-C2-<br>V1 stem(M/A)-VH8aa-IgG4-<br>hinge (S/P-AA)-<br>(IgG4CH2-CH3)-YTE<br>(mature protein; lacking the<br>natural leaders sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAGTL<br>VTVSSESKYG PPCPPCPAPE AAGGPSVFLF<br>PPKPKDTLYI TREPEVTCVV VDVSQEDPEV<br>QFNWYVDGVE VHNAKTKPRE EQFNSTYRVV<br>SVLTVLHQDW LNGKEYKCKV SNKGLPSSIE<br>KTISKAKGQP REPQVYTLPP SQEEMTKNQV<br>SLTCLVKGFY PSDIAVEWES NGQPENNYKT<br>TPPVLDSDGS FFLYSRLTVD KSRWQEGNVF<br>SCSVMHEALH NHYTQKSLSL SLGK |
| SEQ ID NO: 37 | Construct #13<br>RAGEV-C1-C2 (N25E/G82S)-<br>Natural Stem-short linker-IgG1<br>hinge-(IgG1CH2-CH3)<br>(mature protein; lacking the<br>natural leaders sequence) | AQEITARIGE PLVLKCKGAP KKPPQRLEWK<br>LNTGRTEAWK VLSPQGGGPW DSVARVLPNS<br>TCVSEGSYPA GTLSWHLDGK PLVPNEKGVS<br>VKEQTRRHPE TGLFTLQSEL MVTPARGGDP<br>RPTFSCSFSP GLPRHRALRT APIQPRVWEP<br>VPLEEVQLVV EPEGGAVAPG GTVTLTCEVP<br>AQPSPQIHWM KDGVPLPLPP SPVLILPEIG<br>PQDQGTYSCV ATHSSHGPQE SRAVSISIIE<br>PGEEGPTAGS VGGSGLGTLA LAIEGRMPKS |

| INFORMAL SEQUENCE LISTING | | |
|---|---|---|
| SEQ ID NO | DESCRIPTION | SEQUENCE |
| | | CDKTHTCPPC PAPELLGGPS VFLFPPKPKD<br>TLMISRTPEV TCVVVDVSHE DPEVKFNWYV<br>DGVEVHNAKT KPREEQYNST YRVVSVLTVL<br>HQDWLNGKEY KCKVSNKALP APIEKTISKA<br>KGQPREPQVY TLPPSRDELT KNQVSLTCLV<br>KGFYPSDIAV EWESNGQPEN NYKTTPPVLD<br>SDGSFFLYSK LTVDKSRWQQ GNVFSCSVMH<br>EALHNHYTQK SLSLSPGK |
| SEQ ID NO: 38 | Nucleotide sequence of Construct #1 | GCTCAGAATATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGCCCTACAGCTGGTTCTGTTGGA<br>GGCTCTGGACTGGGCACACTGGCCCTGGCTATTGAGGGC<br>AGAATGCCCAAGTCCTGCGACAAGACCCACACCTGTCCT<br>CCATGTCCTGCTCCAGAACTGCTCGGCGGACCTTCCGTG<br>TTCCTGTTTCCTCCAAAGCCTAAGGACACCCTGATGATC<br>TCTCGGACCCCTGAAGTGACCTGCGTGGTGGTGGATGTG<br>TCTCACGAGGATCCCGAAGTGAAGTTCAATTGGTACGTG<br>GACGGCGTGGAAGTGCACAACGCCAAGACCAAGCCTAGA<br>GAGGAACAGTACAACTCCACCTACAGAGTGGTGTCCGTG<br>CTGACCGTGCTGCACCAGGATTGGCTGAATGGCAAAGAG<br>TATAAGTGCAAGGTGTCCAACAAGGCCCTGCCTGCTCCT<br>ATCGAAAAGACCATCTCCAAGGCCAAGGGCCAGCCTAGG<br>GAACCCCAGGTTTACACCTTGCCACCTTCTCGGGACGAG<br>CTGACCAAGAACCAGGTGTCCCTGACATGCCTGGTCAAG<br>GGCTTCTACCCCTCCGATATCGCCGTGGAATGGGAGTCT<br>AATGGCCAGCCTGAGAACAACTACAAGACAACCCCTCCT<br>GTGCTGGACTCCGACGGCTCATTCTTCCTGTACTCCAAG<br>CTGACAGTGGACAAGTCCAGATGGCAGCAGGGCAACGTG<br>TTCTCCTGCTCCGTGATGCACGAGGCCCTGCACAATCAC<br>TACACCCAGAAGTCCCTGTCTCTGTCCCCTGGCAAATGA |
| SEQ ID NO: 39 | Nucleotide sequence of Construct #10 | GCTCAGAATATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC |

| INFORMAL SEQUENCE LISTING | | |
|---|---|---|
| SEQ ID NO | DESCRIPTION | SEQUENCE |
| | | GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCCGAGGATTCTCCTCAGCATGCT<br>GAGTCTAAGTACGGCCCTCCTTGTCCTCCATGTCCTGCT<br>CCAGAAGCTGCTGGCGGCCCTTCCGTGTTTCTGTTCCCT<br>CCAAAGCCTAAGGACACCCTGATGATCTCTCGGACCCCT<br>GAAGTGACCTGCGTGGTGGTGGATGTGTCCCAAGAGGAT<br>CCCGAGGTGCAGTTCAATTGGTACGTGGACGGCGTGGAA<br>GTGCACAACGCCAAGACCAAGCCTAGAGAGGAACAGTTC<br>AACTCCACCTACAGAGTGGTGTCCGTGCTGACCGTGCTG<br>CACCAGGATTGGCTGAATGGCAAAGAGTATAAGTGCAAG<br>GTGTCCAACAAGGGCCTGCCTTCCAGCATCGAAAAGACC<br>ATCTCCAAGGCCAAGGGCCAGCCTAGGGAACCCCAGGTT<br>TACACCCTGCCTCCAAGCCAAGAGGAAATGACCAAGAAC<br>CAGGTGTCCCTGACATGCCTGGTCAAGGGCTTCTACCCC<br>TCCGATATCGCCGTGGAATGGGAGTCTAATGGCCAGCCT<br>GAGAACAACTACAAGACCACACCTCCTGTGCTGGACTCC<br>GACGGCAGCTTCTTTCTGTACTCCCGCCTGACCGTGGAC<br>AAGTCCAGGTGGCAAGAGGGCAACGTGTTCTCCTGCTCC<br>GTGATGCACGAGGCCCTGCACAATCACTACACCCAGAAG<br>TCCCTGTCTCTGTCCCTGGGCAAATGA |
| SEQ ID NO: 40 | Nucleotide sequence of<br>Construct #11 | GCTCAGAATATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACGGCTCCCGTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCTGAGGACTCTCCTCAGCATGCC<br>GGAACACTGGTCACCGTGTCCTCCGAGTCTAAGTACGGC<br>CCTCCTTGTCCTCCATGTCCTGCTCCAGAAGCTGCTGGC<br>GGCCCTTCCGTGTTTCTGTTCCCTCCAAAGCCTAAGGAC<br>ACCCTGATGATCTCTCGGACCCCTGAAGTGACCTGCGTG<br>GTGGTGGATGTGTCCCAAGAGGATCCCGAGGTGCAGTTC<br>AATTGGTACGTGGACGGCGTGGAAGTGCACAACGCCAAG<br>ACCAAGCCTAGAGAGGAACAGTTCAACTCCACCTACAGA<br>GTGGTGTCCGTGCTGACCGTGCTGCACCAGGATTGGCTG<br>AATGGCAAAGAGTATAAGTGCAAGGTGTCCAACAAGGGC<br>CTGCCTTCCAGCATCGAAAAGACCATCTCCAAGGCCAAG<br>GGCCAGCCTAGGGAACCCCAGGTTTACACCCTGCCTCCA<br>AGCCAAGAGGAAATGACCAAGAACCAGGTGTCCCTGACA<br>TGCCTGGTCAAGGGCTTCTACCCCTCCGATATCGCCGTG<br>GAATGGGAGTCTAATGGCCAGCCTGAGAACAACTACAAG<br>ACCACACCTCCTGTGCTGGACTCCGACGGCAGCTTCTTT<br>CTGTACTCCCGCCTGACCGTGGACAAGTCCAGGTGGCAA<br>GAGGGCAACGTGTTCTCCTGCTCCGTGATGCACGAGGCC<br>CTGCACAATCACTACACCCAGAAGTCCCTGTCTCTGTCC<br>CTGGGCAAATGA |
| SEQ ID NO: 41 | Nucleotide sequence of<br>Construct #12 | GCTCAGAATATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACGGCTCCCGTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC |

INFORMAL SEQUENCE LISTING

| SEQ ID NO | DESCRIPTION | SEQUENCE |
|---|---|---|
| | | GTGGACTCTGCCTCTGAACTGACAGCCGGCGTGCCCAAC AAAGTGGGCACTTGTGTGTCCGAGGGCAGCTATCCTGCT GGCACCCTGTCTTGGCATCTGGATGGAAAGCCTCTGGTG CCCAACGAGAAAGGCGTGTCCGTGAAAGAGCAGACCAGA CGGCATCCTGAGACTGGCCTGTTCACCCTGCAGTCCGAG CTGATGGTTACCCCTGCTAGAGGCGGCGATCCCAGACCT ACCTTCAGCTGCTCCTTCTCTCCTGGCCTGCCTCGACAT AGAGCCCTGAGAACCGCTCCTATCCAGCCTAGAGTGTGG GAGCCTGTGCCTCTGGAAGAGGTGCAGCTGGTGGTTGAA CCTGAAGGCGGAGCTGTTGCTCCTGGCGGAACAGTGACC CTGACCTGTGAAGTTCCCGCTCAGCCCTCTCCACAGATC CACTGGATGAAGGATGGCGTGCCACTGCCTCTGCCTCCA TCTCCTGTTCTGATCCTGCCAGAGATCGGCCCTCAGGAC CAGGGCACCTATTCTTGTGTGGCTACCCACTCCTCTCAC GGCCCTCAAGAGTCTAGAGCCGTGTCCATCTCCATCATC GAGCCTGGCGAGGAAGGACCTACAGCTGGCGAGGGCTTT GACAAAGTGCGCGAGGCTGAGGACTCTCCTCAGCATGCC GTGGAATGCCCTCCTTGTGCTCCTCCTGTGGCTGGCGGC CCTTCCGTGTTTCTGTTCCCTCCAAAGCCTAAGGACACC CTGATGATCTCTCGGACCCCTGAAGTGACCTGCGTGGTG GTGGATGTGTCCCAAGAGGATCCCGAGGTGCAGTTCAAT TGGTACGTGGACGGCGTGGAAGTGCACAACGCCAAGACC AAGCCTAGAGAGGAACAGTTCAACTCCACCTACAGAGTG GTGTCCGTGCTGACCGTGCTGCACCAGGATTGGCTGAAT GGCAAAGAGTATAAGTGCAAGGTGTCCAACAAGGGCCTG CCTTCCAGCATCGAAAAGACCATCTCCAAGGCCAAGGGC CAGCCTAGGGAACCCCAGGTTTACACCCTGCCTCCAAGC CAAGAGGAAATGACCAAGAACCAGGTGTCCCTGACATGC CTGGTCAAGGGCTTCTACCCCTCCGATATCGCCGTGGAA TGGGAGTCTAATGGCCAGCCTGAGAACAACTACAAGACC ACACCTCCTGTGCTGGACTCCGACGGCAGCTTCTTTCTG TACTCCCGCCTGACCGTGGACAAGTCCAGGTGGCAAGAG GGCAACGTGTTCTCCTGCTCCGTGATGCACGAGGCCCTG CACAATCACTACACCCAGAAGTCCCTGTCTCTGTCCCTG GGCAAATGA |
| SEQ ID NO: 42 | Nucleotide sequence of Construct #13 | GCTCAGGAGATCACCGCCAGAATCGGCGAGCCCCTGGTG CTGAAATGTAAAGGCGCCCCTAAGAAGCCTCCTCAGCGG CTGGAATGGAAGCTGAACACCGGCAGAACCGAGGCCTGG AAAGTGCTGTCTCCTCAAGGCGGAGGCCCTTGGGATTCT GTGGCTAGAGTGCTGCCTAACTCCTCCCTGTTTCTGCCT GCTGTGGGCATCCAGGACGAGGGCATCTTCAGGTGTCAG GCCATGAACCGGAACGGCAAAGAGACAAAGTCCAACTAC CGCGTCAGAGTGTATCAGATCCCCGGCAAGCCTGAGATC GTGGACTCTGCCTCTGAACTGACAGCCGGCGTGCCCAAC AAAGTGGGCACTTGTGTGTCCGAGGGCAGCTATCCTGCT GGCACCCTGTCTTGGCATCTGGATGGAAAGCCTCTGGTG CCCAACGAGAAAGGCGTGTCCGTGAAAGAGCAGACCAGA CGGCATCCTGAGACTGGCCTGTTCACCCTGCAGTCCGAG CTGATGGTTACCCCTGCTAGAGGCGGCGATCCCAGACCT ACCTTCAGCTGCTCCTTCTCTCCTGGCCTGCCTCGACAT AGAGCCCTGAGAACCGCTCCTATCCAGCCTAGAGTGTGG GAGCCTGTGCCTCTGGAAGAGGTGCAGCTGGTGGTTGAA CCTGAAGGCGGAGCTGTTGCTCCTGGCGGAACAGTGACC CTGACCTGTGAAGTTCCCGCTCAGCCCTCTCCACAGATC CACTGGATGAAGGATGGCGTGCCACTGCCTCTGCCTCCA TCTCCTGTTCTGATCCTGCCAGAGATCGGCCCTCAGGAC CAGGGCACCTATTCTTGTGTGGCTACCCACTCCTCTCAC GGCCCTCAAGAGTCTAGAGCCGTGTCCATCTCCATCATC GAGCCTGGCGAGGAAGGCCCTACAGCTGGTTCTGTTGGA GGCTCTGGACTGGGCACACTGGCCCTGGCTATTGAGGGC AGAATGCCCAAGTCCTGCGACAAGACCCACACCTGTCCT CCATGTCCTGCTCCAGAACTGCTCGGCGGACCTTCCGTG TTCCTGTTTCCTCCAAAGCCTAAGGACACCCTGATGATC TCTCGGACCCCTGAAGTGACCTGCGTGGTGGTGGATGTG TCTCACGAGGATCCCGAAGTGAAGTTCAATTGGTACGTG GACGGCGTGGAAGTGCACAACGCCAAGACCAAGCCTAGA GAGGAACAGTACAACTCCACCTACAGAGTGGTGTCCGTG CTGACCGTGCTGCACCAGGATTGGCTGAATGGCAAAGAG TATAAGTGCAAGGTGTCCAACAAGGGCCCTGCCTGCTCCT ATCGAAAAGACCATCTCCAAGGCCAAGGGCCAGCCTAGG GAACCCCAGGTTTACACCTTGCCACCTTCTCGGGACGAG CTGACCAAGAACCAGGTGTCCCTGACATGCCTGGTCAAG GGCTTCTACCCCTCCGATATCGCCGTGGAATGGGAGTCT AATGGCCAGCCTGAGAACAACTACAAGACAACCCCTCCT |

| SEQ ID NO | DESCRIPTION | SEQUENCE |
|---|---|---|
| | | GTGCTGGACTCCGACGGCTCATTCTTCCTGTACTCCAAG<br>CTGACAGTGGACAAGTCCAGATGGCAGCAGGGCAACGTG<br>TTCTCCTGCTCCGTGATGCACGAGGCCCTGCACAATCAC<br>TACACCCAGAAGTCCCTGTCTCTGTCCCCTGGCAAATGA |
| SEQ ID NO: 43 | Nucleotide sequence of Construct #16 | GCTCAGAATATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCTGAGGACTCTCCTCAGCACGCT<br>GTTGAGTGCCCTCCATGTGCTCCTCCAGTTGCTGGTGGC<br>CCTTCCGTGTTCCTGTTTCCTCCAAAGCCTAAGGACACC<br>CTGTACATCACCCGCGAGCCTGAAGTGACCTGCGTGGTG<br>GTGGATGTGTCCCAAGAGGATCCCGAGGTGCAGTTCAAT<br>TGGTACGTGGACGGCGTGGAAGTGCACAACGCCAAGACC<br>AAGCCTAGAGAGGAACAGTTCAACTCCACCTACAGAGTG<br>GTGTCCGTGCTGACCGTGCTGCACCAGGATTGGCTGAAT<br>GGCAAAGAGTATAAGTGCAAGGTGTCCAACAAGGGCCTG<br>CCTTCCAGCATCGAAAAGACCATCTCCAAGGCCAAGGGC<br>CAGCCTAGGGAACCCCAGGTTTACACCCTGCCTCCAAGC<br>CAAGAGGAAATGACCAAGAACCAGGTGTCCCTGACATGC<br>CTGGTCAAGGGCTTCTACCCCTCCGATATCGCCGTGGAA<br>TGGGAGTCTAATGGCCAGCCTGAGAACAACTACAAGACC<br>ACACCTCCTGTGCTGGACTCCGACGGCAGCTTCTTTCTG<br>TACTCCCGCCTGACCGTGGACAAGTCCAGGTGGCAAGAG<br>GGCAACGTGTTCTCCTGCTCCGTGATGCACGAGGCCCTG<br>CACAATCACTACACCCAGAAGTCCCTGTCTCTGTCCCTG<br>GGCAAATGA |
| SEQ ID NO: 44 | Nucleotide sequence of Construct #17 | GCTCAGGAAATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCTGAGGACTCTCCTCAGCACGCT<br>GTTGAGTGCCCTCCATGTGCTCCTCCAGTTGCTGGTGGC |

| INFORMAL SEQUENCE LISTING | | |
|---|---|---|
| SEQ ID NO | DESCRIPTION | SEQUENCE |
| | | CCTTCCGTGTTCCTGTTTCCTCCAAAGCCTAAGGACACC CTGATGATCTCTCGCACCCCTGAAGTGACCTGCGTGGTG GTGGATGTGTCCCAAGAGGATCCCGAGGTGCAGTTCAAT TGGTACGTGGACGGCGTGGAAGTGCACAACGCCAAGACC AAGCCTAGAGAGGAACAGTTCAACTCCACCTACAGAGTG GTGTCCGTGCTGACCGTGCTGCACCAGGATTGGCTGAAT GGCAAAGAGTATAAGTGCAAGGTGTCCAACAAGGGCCTG CCTTCCAGCATCGAAAAGACCATCTCCAAGGCCAAGGGC CAGCCTAGGGAACCCCAGGTTTACACCCTGCCTCCAAGC CAAGAGGAAATGACCAAGAACCAGGTGTCCCTGACATGC CTGGTCAAGGGCTTCTACCCCTCCGATATCGCCGTGGAA TGGGAGTCTAATGGCCAGCCTGAGAACAACTACAAGACC ACACCTCCTGTGCTGGACTCCGACGGCAGCTTCTTTCTG TACTCCCGCCTGACCGTGGACAAGTCCAGGTGGCAAGAG GGCAACGTGTTCTCCTGCTCCGTGATGCACGAGGCCCTG CACAATCACTACACCCAGAAGTCCCTGTCTCTGTCCCTG GGCAAATGA |
| SEQ ID NO: 45 | Nucleotide sequence of Construct #18 | GCTCAGCAGATCACCGCCAGAATCGGCGAGCCCCTGGTG CTGAAATGTAAAGGCGCCCCTAAGAAGCCTCCTCAGCGG CTGGAATGGAAGCTGAACACCGGCAGAACCGAGGCCTGG AAAGTGCTGTCTCCTCAAGGCGGAGGCCCTTGGGATTCT GTGGCTAGAGTGCTGCCTAACGGCTCCCGTGTTTCTGCCT GCTGTGGGCATCCAGGACGAGGGCATCTTCAGGTGTCAG GCCATGAACCGGAACGGCAAAGAGACAAAGTCCAACTAC CGCGTCAGAGTGTATCAGATCCCCGGCAAGCCTGAGATC GTGGACTCTGCCTCTGAACTGACAGCCGGCGTGCCCAAC AAAGTGGGCACTTGTGTGTCCGAGGGCAGCTATCCTGCT GGCACCCTGTCTTGGCATCTGGATGGAAAGCCTCTGGTG CCCAACGAGAAAGGCGTGTCCGTGAAGAGCAGACCAGA CGGCATCCTGAGACTGGCCTGTTCACCCTGCAGTCCGAG CTGATGGTTACCCCTGCTAGAGGCGGCGATCCCAGACCT ACCTTCAGCTGCTCCTTCTCTCCTGGCCTGCCTCGACAT AGAGCCCTGAGAACCGCTCCTATCCAGCCTAGAGTGTGG GAGCCTGTGCCTCTGGAAGAGGTGCAGCTGGTGGTTGAA CCTGAAGGCGGAGCTGTTGCTCCTGGCGGAACAGTGACC CTGACCTGTGAAGTTCCCGCTCAGCCCTCTCCACAGATC CACTGGATGAAGGATGGCGTGCCACTGCCTCTGCCTCCA TCTCCTGTTCTGATCCTGCCAGAGATCGGCCCTCAGGAC CAGGGCACCTATTCTTGTGTGGCTACCCACTCCTCTCAC GGCCCTCAAGAGTCTAGAGCCGTGTCCATCTCCATCATC GAGCCTGGCGAGGAAGGACCTACAGCTGGCGAGGGCTTT GACAAAGTGCGCGAGGCTGAGGACTCTCCTCAGCACGCT GTTGAGTGCCCTCCATGTGCTCCTCCAGTTGCTGGTGGC CCTTCCGTGTTCCTGTTTCCTCCAAAGCCTAAGGACACC CTGATGATCTCTCGCACCCCTGAAGTGACCTGCGTGGTG GTGGATGTGTCCCAAGAGGATCCCGAGGTGCAGTTCAAT TGGTACGTGGACGGCGTGGAAGTGCACAACGCCAAGACC AAGCCTAGAGAGGAACAGTTCAACTCCACCTACAGAGTG GTGTCCGTGCTGACCGTGCTGCACCAGGATTGGCTGAAT GGCAAAGAGTATAAGTGCAAGGTGTCCAACAAGGGCCTG CCTTCCAGCATCGAAAAGACCATCTCCAAGGCCAAGGGC CAGCCTAGGGAACCCCAGGTTTACACCCTGCCTCCAAGC CAAGAGGAAATGACCAAGAACCAGGTGTCCCTGACATGC CTGGTCAAGGGCTTCTACCCCTCCGATATCGCCGTGGAA TGGGAGTCTAATGGCCAGCCTGAGAACAACTACAAGACC ACACCTCCTGTGCTGGACTCCGACGGCAGCTTCTTTCTG TACTCCCGCCTGACCGTGGACAAGTCCAGGTGGCAAGAG GGCAACGTGTTCTCCTGCTCCGTGATGCACGAGGCCCTG CACAATCACTACACCCAGAAGTCCCTGTCTCTGTCCCTG GGCAAATGA |
| SEQ ID NO: 46 | Nucleotide sequence of Construct #19 | GCTCAGAACATCACCGCCAGAATCGGCGAGCCCCTGGTG CTGAAATGTAAAGGCGCCCCTAAGAAGCCTCCTCAGCGG CTGGAATGGAAGCTGAACACCGGCAGAACCGAGGCCTGG AAAGTGCTGTCTCCTCAAGGCGGAGGCCCTTGGGATTCT GTGGCTAGAGTGCTGCCTAACTCTTCCCTGTTTCTGCCT GCTGTGGGCATCCAGGACGAGGGCATCTTCAGGTGTCAG GCCATGAACCGGAACGGCAAAGAGACAAAGTCCAACTAC CGCGTCAGAGTGTATCAGATCCCCGGCAAGCCTGAGATC GTGGACTCTGCCTCTGAACTGACAGCCGGCGTGCCCAAC AAAGTGGGCACTTGTGTGTCCGAGGGCAGCTATCCTGCT GGCACCCTGTCTTGGCATCTGGATGGAAAGCCTCTGGTG CCCAACGAGAAAGGCGTGTCCGTGAAGAGCAGACCAGA CGGCATCCTGAGACTGGCCTGTTCACCCTGCAGTCCGAG |

| SEQ ID NO | DESCRIPTION | SEQUENCE |
|---|---|---|
| | | CTGATGGTTACCCCTGCTAGAGGCGGCGATCCCAGACCT |
| | | ACCTTCAGCTGCTCCTTCTCTCCTGGCCTGCCTCGACAT |
| | | AGAGCCCTGAGAACCGCTCCTATCCAGCTAGAGTGTGG |
| | | GAGCCTGTGCCTCTGGAAGAGGTGCAGCTGGTGGTTGAA |
| | | CCTGAAGGCGGAGCTGTTGCTCCTGGCGGAACAGTGACC |
| | | CTGACCTGTGAAGTTCCCGCTCAGCCCTCTCCACAGATC |
| | | CACTGGATGAAGGATGGCGTGCCACTGCCTCTGCCTCCA |
| | | TCTCCTGTTCTGATCCTGCCAGAGATCGGCCCTCAGGAC |
| | | CAGGGCACCTATTCTTGTGTGGCTACCCACTCCTCTCAC |
| | | GGCCCTCAAGAGTCTAGAGCCGTGTCCATCTCCATCATC |
| | | GAGCCTGGCGAGGAAGGACCTACAGCTGGCGAGGGCTTT |
| | | GACAAAGTGCGCGAGGCTGAGGACTCTCCTCAGCACGCT |
| | | GTTGAGTGCCCTCCATGTGCTCCTCCAGTTGCTGGTGGC |
| | | CCTTCCGTGTTCCTGTTTCCTCCAAAGCCTAAGGACACC |
| | | CTGATGATCTCTCGCACCCCTGAAGTGACCTGCGTGGTG |
| | | GTGGATGTGTCCCAAGAGGATCCCGAGGTGCAGTTCAAT |
| | | TGGTACGTGGACGGCGTGGAAGTGCACAACGCCAAGACC |
| | | AAGCCTAGAGAGGAACAGTTCAACTCCACCTACAGAGTG |
| | | GTGTCCGTGCTGACCGTGCTGCACCAGGATTGGCTGAAT |
| | | GGCAAAGAGTATAAGTGCAAGGTGTCCAACAAGGGCCTG |
| | | CCTTCCAGCATCGAAAAGACCATCTCCAAGGCCAAGGGC |
| | | CAGCCTAGGGAACCCCAGGTTTACACCCTGCCTCCAAGC |
| | | CAAGAGGAAATGACCAAGAACCAGGTGTCCCTGACATGC |
| | | CTGGTCAAGGGCTTCTACCCCTCCGATATCGCCGTGGAA |
| | | TGGGAGTCTAATGGCCAGCCTGAGAACAACTACAAGACC |
| | | ACACCTCCTGTGCTGGACTCCGACGCCAGCTTCTTTCTG |
| | | TACTCCCGCCTGACCGTGGACAAGTCCAGGTGGCAAGAG |
| | | GGCAACGTGTTCTCCTGCTCCGTGATGCACGAGGCCCTG |
| | | CACAATCACTACACCCAGAAGTCCCTGTCTCTGTCCCTG |
| | | GGCAAATGA |
| SEQ ID NO: 47 | Nucleotide sequence of Construct #20 | GCTCAGGAAATCACCGCCAGAATCGGCGAGCCCCTGGTG |
| | | CTGAAATGTAAAGGCGCCCCTAAGAAGCCTCCTCAGCGG |
| | | CTGGAATGGAAGCTGAACACCGGCAGAACCGAGGCCTGG |
| | | AAAGTGCTGTCTCCTCAAGGCGGAGGCCCTTGGGATTCT |
| | | GTGGCTAGAGTGCTGCCTAACTCTTCCCTGTTTCTGCCT |
| | | GCTGTGGGCATCCAGGACGAGGGCATCTTCAGGTGTCAG |
| | | GCCATGAACCGGAACGGCAAAGAGACAAAGTCCAACTAC |
| | | CGCGTCAGAGTGTATCAGATCCCCGGCAAGCCTGAGATC |
| | | GTGGACTCTGCCTCTGAACTGACAGCCGGCGTGCCCAAC |
| | | AAAGTGGGCACTTGTGTGTCCGAGGGCAGCTATCCTGCT |
| | | GGCACCCTGTCTTGGCATCTGGATGGAAAGCCTCTGGTG |
| | | CCCAACGAGAAAGGCGTGTCCGTGAAAGAGCAGACCAGA |
| | | CGGCATCCTGAGACTGGCCTGTTCACCCTGCAGTCCGAG |
| | | CTGATGGTTACCCCTGCTAGAGGCGGCGATCCCAGACCT |
| | | ACCTTCAGCTGCTCCTTCTCTCCTGGCCTGCCTCGACAT |
| | | AGAGCCCTGAGAACCGCTCCTATCCAGCTAGAGTGTGG |
| | | GAGCCTGTGCCTCTGGAAGAGGTGCAGCTGGTGGTTGAA |
| | | CCTGAAGGCGGAGCTGTTGCTCCTGGCGGAACAGTGACC |
| | | CTGACCTGTGAAGTTCCCGCTCAGCCCTCTCCACAGATC |
| | | CACTGGATGAAGGATGGCGTGCCACTGCCTCTGCCTCCA |
| | | TCTCCTGTTCTGATCCTGCCAGAGATCGGCCCTCAGGAC |
| | | CAGGGCACCTATTCTTGTGTGGCTACCCACTCCTCTCAC |
| | | GGCCCTCAAGAGTCTAGAGCCGTGTCCATCTCCATCATC |
| | | GAGCCTGGCGAGGAAGGACCTACAGCTGGCGAGGGCTTT |
| | | GACAAAGTGCGCGAGGCTGAGGACTCTCCTCAGCACGCT |
| | | GTTGAGTGCCCTCCATGTGCTCCTCCAGTTGCTGGTGGC |
| | | CCTTCCGTGTTCCTGTTTCCTCCAAAGCCTAAGGACACC |
| | | CTGATGATCTCTCGCACCCCTGAAGTGACCTGCGTGGTG |
| | | GTGGATGTGTCCCAAGAGGATCCCGAGGTGCAGTTCAAT |
| | | TGGTACGTGGACGGCGTGGAAGTGCACAACGCCAAGACC |
| | | AAGCCTAGAGAGGAACAGTTCAACTCCACCTACAGAGTG |
| | | GTGTCCGTGCTGACCGTGCTGCACCAGGATTGGCTGAAT |
| | | GGCAAAGAGTATAAGTGCAAGGTGTCCAACAAGGGCCTG |
| | | CCTTCCAGCATCGAAAAGACCATCTCCAAGGCCAAGGGC |
| | | CAGCCTAGGGAACCCCAGGTTTACACCCTGCCTCCAAGC |
| | | CAAGAGGAAATGACCAAGAACCAGGTGTCCCTGACATGC |
| | | CTGGTCAAGGGCTTCTACCCCTCCGATATCGCCGTGGAA |
| | | TGGGAGTCTAATGGCCAGCCTGAGAACAACTACAAGACC |
| | | ACACCTCCTGTGCTGGACTCCGACGGCAGCTTCTTTCTG |
| | | TACTCCCGCCTGACCGTGGACAAGTCCAGGTGGCAAGAG |
| | | GGCAACGTGTTCTCCTGCTCCGTGATGCACGAGGCCCTG |
| | | CACAATCACTACACCCAGAAGTCCCTGTCTCTGTCCCTG |
| | | GGCAAATGA |

| INFORMAL SEQUENCE LISTING | | |
|---|---|---|
| SEQ ID NO | DESCRIPTION | SEQUENCE |
| SEQ ID NO: 48 | Nucleotide sequence of Construct #21 | GCTCAGCAGATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACTCTTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCTGAGGACTCTCCTCAGCACGCT<br>GTTGAGTGCCCTCCATGTGCTCCTCCAGTTGCTGGTGGC<br>CCTTCCGTGTTCCTGTTTCCTCCAAAGCCTAAGGACACC<br>CTGATGATCTCTCGCACCCCTGAAGTGACCTGCGTGGTG<br>GTGGATGTGTCCCAAGAGGATCCCGAGGTGCAGTTCAAT<br>TGGTACGTGGACGGCGTGGAAGTGCACAACGCCAAGACC<br>AAGCCTAGAGAGGAACAGTTCAACTCCACCTACAGAGTG<br>GTGTCCGTGCTGACCGTGCTGCACCAGGATTGGCTGAAT<br>GGCAAAGAGTATAAGTGCAAGGTGTCCAACAAGGGCCTG<br>CCTTCCAGCATCGAAAAGACCATCTCCAAGGCCAAGGGC<br>CAGCCTAGGGAACCCCAGGTTTACACCCTGCCTCCAAGC<br>CAAGAGGAAATGACCAAGAACCAGGTGTCCCTGACATGC<br>CTGGTCAAGGGCTTCTACCCCTCCGATATCGCCGTGGAA<br>TGGGAGTCTAATGGCCAGCCTGAGAACAACTACAAGACC<br>ACACCTCCTGTGCTGGACTCCGACGGCAGCTTCTTTCTG<br>TACTCCCGCCTGACCGTGGACAAGTCCAGGTGGCAAGAG<br>GGCAACGTGTTCTCCTGCTCCGTGATGCACGAGGCCCTG<br>CACAATCACTACACCCAGAAGTCCCTGTCTCTGTCCCTG<br>GGCAAATGA |
| SEQ ID NO: 49 | Nucleotide sequence of Construct #22 | GCTCAGAACATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTGCTGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCTGAGGACTCTCCTCAGCACGCT<br>GTTGAGTGCCCTCCATGTGCTCCTCCAGTTGCTGGTGGC<br>CCTTCCGTGTTCCTGTTTCCTCCAAAGCCTAAGGACACC<br>CTGATGATCTCTCGCACCCCTGAAGTGACCTGCGTGGTG<br>GTGGATGTGTCCCAAGAGGATCCCGAGGTGCAGTTCAAT<br>TGGTACGTGGACGGCGTGGAAGTGCACAACGCCAAGACC<br>AAGCCTAGAGAGGAACAGTTCAACTCCACCTACAGAGTG |

| INFORMAL SEQUENCE LISTING | | |
|---|---|---|
| SEQ ID NO | DESCRIPTION | SEQUENCE |
| | | GTGTCCGTGCTGACCGTGCTGCACCAGGATTGGCTGAAT<br>GGCAAAGAGTATAAGTGCAAGGTGTCCAACAAGGGCCTG<br>CCTTCCAGCATCGAAAAGACCATCTCCAAGGCCAAGGGC<br>CAGCCTAGGGAACCCCAGGTTTACACCCTGCCTCCAAGC<br>CAAGAGGAAATGACCAAGAACCAGGTGTCCCTGACATGC<br>CTGGTCAAGGGCTTCTACCCCTCCGATATCGCCGTGGAA<br>TGGGAGTCTAATGGCCAGCCTGAGAACAACTACAAGACC<br>ACACCTCCTGTGCTGGACTCCGACGGCAGCTTCTTTCTG<br>TACTCCCGCCTGACCGTGGACAAGTCCAGGTGGCAAGAG<br>GGCAACGTGTTCTCCTGCTCCGTGATGCACGAGGCCCTG<br>CACAATCACTACACCCAGAAGTCCCTGTCTCTGTCCCTG<br>GGCAAATGA |
| SEQ ID NO: 50 | Nucleotide sequence of Construct #23 | GCTCAGGAAATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTGCTGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCTGAGGACTCTCCTCAGCACGCT<br>GTTGAGTGCCCTCCATGTGCTCCTCCAGTTGCTGGTGGC<br>CCTTCCGTGTTCCTGTTTCCTCCAAAGCCTAAGGACACC<br>CTGATGATCTCTCGCACCCCTGAAGTGACCTGCGTGGTG<br>GTGGATGTGTCCCAAGAGGATCCCGAGGTGCAGTTCAAT<br>TGGTACGTGGACGGCGTGGAAGTGCACAACGCCAAGACC<br>AAGCCTAGAGAGGAACAGTTCAACTCCACCTACAGAGTG<br>GTGTCCGTGCTGACCGTGCTGCACCAGGATTGGCTGAAT<br>GGCAAAGAGTATAAGTGCAAGGTGTCCAACAAGGGCCTG<br>CCTTCCAGCATCGAAAAGACCATCTCCAAGGCCAAGGGC<br>CAGCCTAGGGAACCCCAGGTTTACACCCTGCCTCCAAGC<br>CAAGAGGAAATGACCAAGAACCAGGTGTCCCTGACATGC<br>CTGGTCAAGGGCTTCTACCCCTCCGATATCGCCGTGGAA<br>TCCCACTCTAATCCCAGCCTCACAACAACTACAACACC<br>ACACCTCCTGTGCTGGACTCCGACGGCAGCTTCTTTCTG<br>TACTCCCGCCTGACCGTGGACAAGTCCAGGTGGCAAGAG<br>GGCAACGTGTTCTCCTGCTCCGTGATGCACGAGGCCCTG<br>CACAATCACTACACCCAGAAGTCCCTGTCTCTGTCCCTG<br>GGCAAATGA |
| SEQ ID NO: 51 | Nucleotide sequence of Construct #24 | GCTCAGCAGATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTGCTGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC |

| SEQ ID NO | DESCRIPTION | SEQUENCE |
|---|---|---|
| | | CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCTGAGGACTCTCCTCAGCACGCT<br>GTTGAGTGCCCTCCATGTGCTCCTCCAGTTGCTGGTGGC<br>CCTTCCGTGTTCCTGTTTCCTCCAAAGCCTAAGGACACC<br>CTGATGATCTCTCGCACCCCTGAAGTGACCTGCGTGGTG<br>GTGGATGTGTCCCAAGAGGATCCCGAGGTGCAGTTCAAT<br>TGGTACGTGGACGGCGTGGAAGTGCACAACGCCAAGACC<br>AAGCCTAGAGAGGAACAGTTCAACTCCACCTACAGAGTG<br>GTGTCCGTGCTGACCGTGCTGCACCAGGATTGGCTGAAT<br>GGCAAAGAGTATAAGTGCAAGGTGTCCAACAAGGGCCTG<br>CCTTCCAGCATCGAAAAGACCATCTCCAAGGCCAAGGGC<br>CAGCCTAGGGAACCCCAGGTTTACACCCTGCCTCCAAGC<br>CAAGAGGAAATGACCAAGAACCAGGTGTCCCTGACATGC<br>CTGGTCAAGGGCTTCTACCCCTCCGATATCGCCGTGGAA<br>TGGGAGTCTAATGGCCAGCCTGAGAACAACTACAAGACC<br>ACACCTCCTGTGCTGGACTCCGACGGCAGCTTCTTTCTG<br>TACTCCCGCCTGACCGTGGACAAGTCCAGGTGGCAAGAG<br>GGCAACGTGTTCTCCTGCTCCGTGATGCACGAGGCCCTG<br>CACAATCACTACACCCAGAAGTCCCTGTCTCTGTCCCTG<br>GGCAAATGA |
| SEQ ID NO: 52 | 16 AA C-terminal sequence unique to esRAGE | EGFDKVREAEDSPQHM |
| SEQ ID NO: 53 | Construct #9<br>RAGE V-C1-C2-shortened stem-VH8aa-IgG4-hinge(S/P-AA)-(IgG4CH2-CH3) (mature protein; lacking the natural leaders sequence) | AQNITARIGEPLVLKCKGAPKKPPQRLEWKLNTGRTEAW<br>KVLSPQGGGPWDSVARVLPNGSLFLPAVGIQDEGIFRCQ<br>AMNRNGKETKSNYRVRVYQIPGKPEIVDSASELTAGVPN<br>KVGTCVSEGSYPAGTLSWHLDGKPLVPNEKGVSVKEQTR<br>RHPETGLFTLQSELMVTPARGGDPRPTFSCSFSPGLPRH<br>RALRTAPIQPRVWEPVPLEEVQLVVEPEGGAVAPGGTVT<br>LTCEVPAQPSPQIHWMKDGVPLPLPPSPVLILPEIGPQD<br>QGTYSCVATHSSHGPQESRAVSISIIEPGEEGPTAGGTL<br>VTVSSESKYGPPCPPCPAPEAAGGPSVFLFPPKPKDTLM<br>ISRTPEVTCVVVDVSQEDPEVQFNWYVDGVEVHNAKTKP<br>REEQFNSTYRVVSVLTVLHQDWLNGKEYKCKVSNKGLPS<br>SIEKTISKAKGQPREPQVYTLPPSQEEMTKNQVSLTCLV<br>KGFYPSDIAVEWESNGQPENNYKTTPPVLDSDGSFFLYS<br>RLTVDKSRWQEGNVFSCSVMHEALHNHYTQKSLSLSLGK |
| SEQ ID NO: 54 | Construct #16ΔK<br>RAGEV-C1-C2-V1 stem (M/A)-IgG2 lower hinge-(IgG4CH2-CH3)-YTE-ΔK (mature protein; lacking the natural leaders sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAVEC<br>PPCAPPVAGG PSVFLFPPKP KDTLYITREP<br>EVTCVVVDVS QEDPEVQFNW YVDGVEVHNA<br>KTKPREEQFN STYRVVSVLT VLHQDWLNGK<br>EYKCKVSNKG LPSSIEKTIS KAKGQPREPQ<br>VYTLPPSQEE MTKNQVSLTC LVKGFYPSDI<br>AVEWESNGQP ENNYKTTPPV LDSDGSFFLY<br>SRLTVDKSRW QEGNVFSCSV MHEALHNHYT<br>QKSLSLSLG* |
| SEQ ID NO: 55 | Construct #12ΔK<br>RAGE V-C1-C2-V1 stem (M/A)-IgG2 lower hinge-(IgG4CH2-CH3)-ΔK (mature protein; lacking the natural leaders sequence) | AQNITARIGE PLVLKCKGAP KKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG<br>VSVKEQTRRH PETGLFTLQS ELMVTPARGG<br>DPRPTFSCSF SPGLPRHRAL RTAPIQPRVW<br>EPVPLEEVQL VVEPEGGAVA PGGTVTLTCE<br>VPAQPSPQIH WMKDGVPLPL PPSPVLILPE<br>IGPQDQGTYS CVATHSSHGP QESRAVSISI<br>IEPGEEGPTA GEGFDKVREA EDSPQHAVEC |

INFORMAL SEQUENCE LISTING

| SEQ ID NO | DESCRIPTION | SEQUENCE |
|---|---|---|
| | | PPCAPPVAGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLG* |
| SEQ ID NO: 56 | Nucleotide sequence of Construct #9 | GCTCAGAATATCACCGCCAGAATCGGCGAGCCCCTGGTG CTGAAATGTAAAGGCGCCCCTAAGAAGCCTCCTCAGCGG CTGGAATGGAAGCTGAACACCGGCAGAACCGAGGCCTGG AAAGTGCTGTCTCCTCAAGGCGGAGGCCCTTGGGATTCT GTGGCTAGAGTGCTGCCTAACGGCTCCCTGTTTCTGCCT GCTGTGGGCATCCAGGACGAGGGCATCTTCAGGTGTCAG GCCATGAACCGGAACGGCAAAGAGACAAAGTCCAACTAC CGCGTCAGAGTGTATCAGATCCCCGGCAAGCCTGAGATC GTGGACTCTGCCTCTGAACTGACAGCCGGCGTGCCCAAC AAAGTGGGCACTTGTGTGTCCGAGGGCAGCTATCCTGCT GGCACCCTGTCTTGGCATCTGGATGGAAAGCCTCTGGTG CCCAACGAGAAAGGCGTGTCCGTGAAAGAGCAGACCAGA CGGCATCCTGAGACTGGCCTGTTCACCCTGCAGTCCGAG CTGATGGTTACCCCTGCTAGAGGCGGCGATCCCAGACCT ACCTTCAGCTGCTCCTTCTCTCCTGGCCTGCCTCGACAT AGAGCCCTGAGAACCGCTCCTATCCAGCCTAGAGTGTGG GAGCCTGTGCCTCTGGAAGAGGTGCAGCTGGTGGTTGAA CCTGAAGGCGGAGCTGTTGCTCCTGGCGGAACAGTGACC CTGACCTGTGAAGTTCCCGCTCAGCCCTCTCCACAGATC CACTGGATGAAGGATGGCGTGCCACTGCCTCTGCCTCCA TCTCCTGTTCTGATCCTGCCAGAGATCGGCCCTCAGGAC CAGGGCACCTATTCTTGTGTGGCTACCCACTCCTCTCAC GGCCCTCAAGAGTCTAGAGCCGTGTCCATCTCCATCATC GAGCCTGGCGAGGAAGGACCTACAGCTGGCGGAACACTG GTCACCGTGTCCTCCGAGTCTAAGTACGGCCCTCCTTGT CCTCCATGTCCTGCTCCAGAAGCTGCTGGCGGCCCTTCC GTGTTTCTGTTCCCTCCAAAGCCTAAGGACACCCTGATG ATCTCTCGGACCCCTGAAGTGACCTGCGTGGTGGTGGAT GTGTCCCAAGAGGATCCCGAGGTGCAGTTCAATTGGTAC GTGGACGGCGTGGAAGTGCACAACGCCAAGACCAAGCCT AGAGAGGAACAGTTCAACTCCACCTACAGAGTGGTGTCC GTGCTGACCGTGCTGCACCAGGATTGGCTGAATGGCAAA GAGTATAAGTGCAAGGTGTCCAACAAGGGCCTGCCTTCC AGCATCGAAAAGACCATCTCCAAGGCCAAGGGCCAGCCT AGGGAACCCCAGGTTTACACCCTGCCTCCAAGCCAAGAG GAAATGACCAAGAACCAGGTGTCCCTGACATGCCTGGTC AAGGGCTTCTACCCCTCCGATATCGCCGTGGAATGGGAG TCTAATGGCCAGCCTGAGAACAACTACAAGACCACACCT CCTGTGCTGGACTCCGACGGCAGCTTCTTTCTGTACTCC CGCCTGACCGTGGACAAGTCCAGGTGGCAAGAGGGCAAC GTGTTCTCCTGCTCCGTGATGCACGAGGCCCTGCACAAT CACTACACCCAGAAGTCCCTGTCTCTGTCCCTGGGCAAA TGA |
| SEQ ID NO: 57 | Nucleotide sequence of Construct #25 | GCTCAGGAGATCACCGCCAGAATCGGCGAGCCCCTGGTG CTGAAATGTAAAGGGCCCCTAAGAAGCCTCCTCAGCGGC TGGAATGGAAGCTGAACACCGGCAGAACCGAGGCCTGGA AAGTGCTGTCTCCTCAAGGCGGAGGCCCTTGGGATTCTG TGGCTAGAGTGCTGCCTAACGGCTCCTGTTTCTGCCTGC TGTGGGCATCCAGGACGAGGGCATCTTCAGGTGTCAGGC CATGAACCGGAACGGCAAAGAGACAAAGTCCAACTACCG CGTCAGAGTGTATCAGATCCCCGGCAAGCCTGAGTCGTG GACTCTGCCTCTGAACTGACAGCCGGCGTGCCCAACAAA GTGGGCACTTGTGTGTCCGAGGGCAGCTATCCTGCTGGC ACCCTGTCTTGGCATCTGGATGGAAAGCCTCTGGTGCCC AACGAAAAGGCGTGTCCGTGAAAGAGCAGACCAGACGGC ATCCTGAGACTGGCCTGTTCACCCTGCAGTCCGAGCTGA TGGTTACCCCTGCTAGAGGCGGCGATCCCAGACCTACCT TCAGCTGCTCCTTCTTCCTGGCCTGCCTCGACATAGAGC CCTGAGAACCGCTCCTATCCAGCCTAGAGTGTGGGAGCC TGTGCCTCTGGAAGAGGTGCAGCTGGTGGTTGAACCTGA AGGCGGAGCTGTTGCTCCTGGCGGACAGTGACCCTGACC TGTGAAGTTCCCGCTCAGCCCTCTCCACAGATCCACTGG ATGAAGGATGGCGTGCCACTGCCTCTGCCTCCATCTCCT GTTCTGATCCTGCCAGAGATCGGCCCTCAGGACCAGGCA CCTATTCTTGTGTGGCTACCCACTCCTCTCACGGCCCTC |

| INFORMAL SEQUENCE LISTING | | |
|---|---|---|
| SEQ ID NO | DESCRIPTION | SEQUENCE |
| | | AAGAGTCTAGAGCCGTGTCCATCTCCATCATCGAGCCTG<br>GCGAGGAAGGACCTACAGCTGGCGAGGGCTTTGACAAAG<br>TGCGCGGGCTGAGGACTCTCCTCAGCACGCTGTTGAGTG<br>CCCTCCATGTGCTCCTCCAGTTGCTGGTGGCCCTTCCGT<br>GTTCCTGTTTCCTCCAAAGCCTAAGGACACCCTGTACAT<br>CACCCGCGAGCCTGAATGACCTGCGTGGTGGTGGATGTG<br>TCCCAAGAGGATCCCGAGGTGCAGTTCAATTGGTACGTG<br>GACGGCGTGGAAGTGCACAACGCCAAGACCAAGCCTAGA<br>GAGGAACAGTTCAACTCCACCTACAGGTGGTGTCCGTGC<br>TGACCGTGCTGCACCAGGATTGGCTGAATGGCAAAGAGT<br>ATAAGTGCAAGGTGTCCAACAAGGGCCTGCCTTCCAGCA<br>TCGAAAAGACCATCTCCAAGGCCAAGGGCCAGCCTAGGA<br>ACCCCAGGTTTACACCCTGCCTCCAAGCCAAGAGGAAAT<br>GACCAAGAACCAGGTGTCCCTGACATGCCTGGTCAAGGG<br>CTTCTACCCCTCCGATATCGCCGTGGAATGGGAGTCTAA<br>TGGCCAGCTGAGAACAACTACAAGACCACACCTCCTGTG<br>CTGGACTCCGACGGCAGCTTCTTTCTGTACTCCCGCCTG<br>ACCGTGGACAAGTCCAGGTGGCAAGAGGGCAACGTGTTC<br>TCCTGCTCCGTGATGCAGAGGCCCTGCACAATCACTACA<br>CCCAGAAGTCCCTGTCTCTGTCCCTGGGCAAATGA |
| SEQ ID NO: 58 | Nucleotide sequence of<br>Construct #26 | GCTCAGCAGATCACCGCCAGAATCGGCGAGCCCCTGGTG<br>CTGAAATGTAAAGGGCCCCTAAGAAGCCTCCTCAGCGGC<br>TGGAATGGAAGCTGAACACCGGCAGAACCGAGGCCTGGA<br>AAGTGCTGTCTCCTCAAGGCGGAGGCCCTTGGGATTCTG<br>TGGCTAGAGTGCTGCCTAACGGCTCCTGTTTCTGCCTGC<br>TGTGGGCATCCAGGACGAGGGCATCTTCAGGTGTCAGGC<br>CATGAACCGGAACGGCAAAGAGACAAAGTCCAACTACCG<br>CGTCAGAGTGTATCAGATCCCCGGCAAGCCTGAGTCGTG<br>GACTCTGCCTCTGAACTGACAGCCGGCGTGCCCAACAAA<br>GTGGGCACTTGTGTGTCCGAGGGCAGCTATCCTGCTGGC<br>ACCCTGTCTTGGCATCTGGATGGAAAGCCTCTGGTGCCC<br>AACGAAAAGGCGTGTCCGTGAAAGAGCAGACCAGACGGC<br>ATCCTGAGACTGGCCTGTTCACCCTGCAGTCCGAGCTGA<br>TGGTTACCCCTGCTAGAGGCGGCGATCCCAGACCTACCT<br>TCAGCTGCTCCTTCTTCCTGGCCTGCCTCGACATAGAGC<br>CCTGAGAACCGCTCCTATCCAGCTAGAGTGTGGGAGCC<br>TGTGCCTCTGGAAGAGGTGCAGCTGGTGGTTGAACCTGA<br>AGGCGGAGCTGTTGCTCCTGGCGGACAGTGACCCTGACC<br>TGTGAAGTTCCCGCTCAGCCCTCTCCACAGATCCACTGG<br>ATGAAGGATGGCGTGCCACTGCCTCTGCCTCCATCTCCT<br>GTTCTGATCCTGCCAGAGATCGGCCCTCAGGACCAGGCA<br>CCTATTCTTGTGTGGCTACCCACTCCTCTCACGGCCCTC<br>AAGAGTCTAGAGCCGTGTCCATCTCCATCATCGAGCCTG<br>GCGAGGAAGGACCTACAGCTGGCGAGGGCTTTGACAAAG<br>TGCGCGGGCTGAGGACTCTCCTCAGCACGCTGTTGAGTG<br>CCCTCCATGTGCTCCTCCAGTTGCTGGTGGCCCTTCCGT<br>GTTCCTGTTTCCTCCAAAGCCTAAGGACACCCTGTACAT<br>CACCCGCGAGCCTGAATGACCTGCGTGGTGGTGGATGTG<br>TCCCAAGAGGATCCCGAGGTGCAGTTCAATTGGTACGTG<br>GACGGCGTGGAAGTGCACAACGCCAAGACCAAGCCTAGA<br>GAGGAACAGTTCAACTCCACCTACAGGTGGTGTCCGTGC<br>TGACCGTGCTGCACCAGGATTGGCTGAATGGCAAAGAGT<br>ATAAGTGCAAGGTGTCCAACAAGGGCCTGCCTTCCAGCA<br>TCGAAAAGACCATCTCCAAGGCCAAGGGCCAGCCTAGGA<br>ACCCCAGGTTTACACCCTGCCTCCAAGCCAAGAGGAAAT<br>GACCAAGAACCAGGTGTCCCTGACATGCCTGGTCAAGGG<br>CTTCTACCCCTCCGATATCGCCGTGGAATGGGAGTCTAA<br>TGGCCAGCTGAGAACAACTACAAGACCACACCTCCTGTG<br>CTGGACTCCGACGGCAGCTTCTTTCTGTACTCCCGCCTG<br>ACCGTGGACAAGTCCAGGTGGCAAGAGGGCAACGTGTTC<br>TCCTGCTCCGTGATGCAGAGGCCCTGCACAATCACTACA<br>CCCAGAAGTCCCTGTCTCTGTCCCTGGGCAAATGA |
| SEQ ID NO: 59 | Nucleotide sequence of<br>Construct #27 | GCTCAGAATATCACCGCCAGAATCGGCGAGCCCCTGGTG<br>CTGAAATGTAAAGGGCCCCTAAGAAGCCTCCTCAGCGGC<br>TGGAATGGAAGCTGAACACCGGCAGAACCGAGGCCTGGA<br>AAGTGCTGTCTCCTCAAGGCGGAGGCCCTTGGGATTCTG<br>TGGCTAGAGTGCTGCCTAACTCTTCCTGTTTCTGCCTGC<br>TGTGGGCATCCAGGACGAGGGCATCTTCAGGTGTCAGGC<br>CATGAACCGGAACGGCAAAGAGACAAAGTCCAACTACCG<br>CGTCAGAGTGTATCAGATCCCCGGCAAGCCTGAGTCGTG<br>GACTCTGCCTCTGAACTGACAGCCGGCGTGCCCAACAAA<br>GTGGGCACTTGTGTGTCCGAGGGCAGCTATCCTGCTGGC<br>ACCCTGTCTTGGCATCTGGATGGAAAGCCTCTGGTGCCC |

INFORMAL SEQUENCE LISTING

| SEQ ID NO | DESCRIPTION | SEQUENCE |
|---|---|---|
| | | AACGAAAAGGCGTGTCCGTGAAAGAGCAGACCAGACGGC |
| | | ATCCTGAGACTGGCCTGTTCACCCTGCAGTCCGAGCTGA |
| | | TGGTTACCCCTGCTAGAGGCGGCGATCCCAGACCTACCT |
| | | TCAGCTGCTCCTTCTTCCTGGCCTGCCTCGACATAGAGC |
| | | CCTGAGAACCGCTCCTATCCAGCCTAGAGTGTGGGAGCC |
| | | TGTGCCTCTGGAAGAGGTGCAGCTGGTGGTTGAACCTGA |
| | | AGGCGGAGCTGTTGCTCCTGGCGGACAGTGACCCTGACC |
| | | TGTGAAGTTCCCGCTCAGCCCTCTCCACAGATCCACTGG |
| | | ATGAAGGATGGCGTGCCACTGCCTCTGCCTCCATCTCCT |
| | | GTTCTGATCCTGCCAGAGATCGGCCCTCAGGACCAGGCA |
| | | CCTATTCTTGTGTGGCTACCCACTCCTCTCACGGCCCTC |
| | | AAGAGTCTAGAGCCGTGTCCATCTCCATCATCGAGCCTG |
| | | GCGAGGAAGGACCTACAGCTGGCGAGGGCTTTGACAAAG |
| | | TGCGCGGGCTGAGGACTCTCCTCAGCACGCTGTTGAGTG |
| | | CCCTCCATGTGCTCCTCCAGTTGCTGGTGGCCCTTCCGT |
| | | GTTCCTGTTTCCTCCAAAGCCTAAGGACACCCTGTACAT |
| | | CACCCGCGAGCCTGAATGACCTGCGTGGTGGTGGATGTG |
| | | TCCCAAGAGGATCCCGAGGTGCAGTTCAATTGGTACGTG |
| | | GACGGCGTGGAAGTGCACAACGCCAAGACCAAGCCTAGA |
| | | GAGGAACAGTTCAACTCCACCTACAGGTGGTGTCCGTGC |
| | | TGACCGTGCTGCACCAGGATTGGCTGAATGGCAAAGAGT |
| | | ATAAGTGCAAGGTGTCCAACAAGGGCCTGCCTTCCAGCA |
| | | TCGAAAAGACCATCTCCAAGGCCAAGGGCCAGCCTAGGA |
| | | ACCCCAGGTTTACACCCTGCCTCAAGCCAAGAGGAAAT |
| | | GACCAAGAACCAGGTGTCCCTGACATGCCTGGTCAAGGG |
| | | CTTCTACCCCTCCGATATCGCCGTGGAATGGGAGTCTAA |
| | | TGGCCAGCTGAGAACAACTACAAGACCACACCTCCTGTG |
| | | CTGGACTCCGACGGCAGCTTCTTTCTGTACTCCCGCCTG |
| | | ACCGTGGACAAGTCCAGGTGGCAAGAGGGCAACGTGTTC |
| | | TCCTGCTCCGTGATGCAGAGGCCCTGCACAATCACTACA |
| | | CCCAGAAGTCCCTGTCTCTGTCCCTGGGCAAATGA |
| SEQ ID NO: 60 | Nucleotide sequence of Construct #28 | GCTCAGGAGATCACCGCCAGAATCGGCGAGCCCCTGGTG |
| | | CTGAAATGTAAAGGGCCCCTAAGAAGCCTCCTCAGCGGC |
| | | TGGAATGGAAGCTGAACACCGGCAGAACCGAGGCCTGGA |
| | | AAGTGCTGTCTCCTCAAGGCGGAGGCCCTTGGGATTCTG |
| | | TGGCTAGAGTGCTGCCTAACTCCTCCGTTTCTGCCTGC |
| | | TGTGGGCATCCAGGACGAGGGCATCTTCAGGTGTCAGGC |
| | | CATGAACCGGAACGGCAAAGAGACAAAGTCCAACTACCG |
| | | CGTCAGAGTGTATCAGATCCCCGGCAAGCCTGAGTCGTG |
| | | GACTCTGCCTCTGAACTGACAGCCGGCGTGCCCAACAAA |
| | | GTGGGCACTTGTGTGTCCGAGGGCAGCTATCCTGCTGGC |
| | | ACCCTGTCTTGGCATCTGGATGGAAAGCCTCTGGTGCCC |
| | | AACGAAAAGGCGTGTCCGTGAAAGAGCAGACCAGACGGC |
| | | ATCCTGAGACTGGCCTGTTCACCCTGCAGTCCGAGCTGA |
| | | TGGTTACCCCTGCTAGAGGCGGCGATCCCAGACCTACCT |
| | | TCAGCTGCTCCTTCTTCCTGGCCTGCCTCGACATAGAGC |
| | | CCTGAGAACCGCTCCTATCCAGCCTAGAGTGTGGGAGCC |
| | | TGTGCCTCTGGAAGAGGTGCAGCTGGTGGTTGAACCTGA |
| | | AGGCGGAGCTGTTGCTCCTGGCGGACAGTGACCCTGACC |
| | | TGTGAAGTTCCCGCTCAGCCCTCTCCACAGATCCACTGG |
| | | ATGAAGGATGGCGTGCCACTGCCTCTGCCTCCATCTCCT |
| | | GTTCTGATCCTGCCAGAGATCGGCCCTCAGGACCAGGCA |
| | | CCTATTCTTGTGTGGCTACCCACTCCTCTCACGGCCCTC |
| | | AAGAGTCTAGAGCCGTGTCCATCTCCATCATCGAGCCTG |
| | | GCGAGGAAGGACCTACAGCTGGCGAGGGCTTTGACAAAG |
| | | TGCGCGGGCTGAGGACTCTCCTCAGCACGCTGTTGAGTG |
| | | CCCTCCATGTGCTCCTCCAGTTGCTGGTGGCCCTTCCGT |
| | | GTTCCTGTTTCCTCCAAAGCCTAAGGACACCCTGTACAT |
| | | CACCCGCGAGCCTGAATGACCTGCGTGGTGGTGGATGTG |
| | | TCCCAAGAGGATCCCGAGGTGCAGTTCAATTGGTACGTG |
| | | GACGGCGTGGAAGTGCACAACGCCAAGACCAAGCCTAGA |
| | | GAGGAACAGTTCAACTCCACCTACAGGTGGTGTCCGTGC |
| | | TGACCGTGCTGCACCAGGATTGGCTGAATGGCAAAGAGT |
| | | ATAAGTGCAAGGTGTCCAACAAGGGCCTGCCTTCCAGCA |
| | | TCGAAAAGACCATCTCCAAGGCCAAGGGCCAGCCTAGGA |
| | | ACCCCAGGTTTACACCCTGCCTCAAGCCAAGAGGAAAT |
| | | GACCAAGAACCAGGTGTCCCTGACATGCCTGGTCAAGGG |
| | | CTTCTACCCCTCCGATATCGCCGTGGAATGGGAGTCTAA |
| | | TGGCCAGCTGAGAACAACTACAAGACCACACCTCCTGTG |
| | | CTGGACTCCGACGGCAGCTTCTTTCTGTACTCCCGCCTG |
| | | ACCGTGGACAAGTCCAGGTGGCAAGAGGGCAACGTGTTC |
| | | TCCTGCTCCGTGATGCAGAGGCCCTGCACAATCACTACA |
| | | CCCAGAAGTCCCTGTCTCTGTCCCTGGGCAAATGA |

INFORMAL SEQUENCE LISTING

| SEQ ID NO | DESCRIPTION | SEQUENCE |
| --- | --- | --- |
| SEQ ID NO: 61 | Nucleotide sequence of Construct #29 | GCTCAGCAGATCACCGCCAGAATCGGCGAGCCCCTGGTG<br>CTGAAATGTAAAGGGCCCCTAAGAAGCCTCCTCAGCGGC<br>TGGAATGGAAGCTGAACACCGGCAGAACCGAGGCCTGGA<br>AAGTGCTGTCTCCTCAAGGCGGAGGCCCTTGGGATTCTG<br>TGGCTAGAGTGCTGCCTAACTCTTCCTGTTTCTGCCTGC<br>TGTGGGCATCCAGGACGAGGGCATCTTCAGGTGTCAGGC<br>CATGAACCGGAACGGCAAAGAGACAAAGTCCAACTACCG<br>CGTCAGAGTGTATCAGATCCCCGGCAAGCCTGAGTCGTG<br>GACTCTGCCTCTGAACTGACAGCCGGCGTGCCCAACAAA<br>GTGGGCACTTGTGTGTCCGAGGGCAGCTATCCTGCTGGC<br>ACCCTGTCTTGGCATCTGGATGGAAAGCCTCTGGTGCCC<br>AACGAAAAGGCGTGTCCGTGAAAGAGCAGACCAGACGGC<br>ATCCTGAGACTGGCCTGTTCACCCTGCAGTCCGAGCTGA<br>TGGTTACCCCTGCTAGAGGCGGCGATCCCAGACCTACCT<br>TCAGCTGCTCCTTCTTCCTGGCCTGCCTCGACATAGAGC<br>CCTGAGAACCGCTCCTATCCAGCCTAGAGTGTGGGAGCC<br>TGTGCCTCTGGAAGAGGTGCAGCTGGTGGTTGAACCTGA<br>AGGCGGAGCTGTTGCTCCTGGCGGACAGTGACCCTGACC<br>TGTGAAGTTCCCGCTCAGCCCTCTCCACAGATCCACTGG<br>ATGAAGGATGGCGTGCCACTGCCTCTGCCTCCATCTCCT<br>GTTCTGATCCTGCCAGAGATCGGCCCTCAGGACCAGGCA<br>CCTATTCTTGTGTGGCTACCCACTCCTCTCACGGCCCTC<br>AAGAGTCTAGAGCCGTGTCCATCTCCATCATCGAGCCTG<br>GCGAGGAAGGACCTACAGCTGGCGAGGGCTTTGACAAAG<br>TGCGCGGGCTGAGGACTCTCCTCAGCACGCTGTTGAGTG<br>CCCTCCATGTGCTCCTCCAGTTGCTGGTGGCCCTTCCGT<br>GTTCCTGTTTCCTCCAAAGCCTAAGGACACCCTGTACAT<br>CACCCCGCGAGCCTGAATGACCTGCGTGGTGGTGGATGTG<br>TCCCAAGAGGATCCCGAGGTGCAGTTCAATTGGTACGTG<br>GACGGCGTGGAAGTGCACAACGCCAAGACCAAGCCTAGA<br>GAGGAACAGTTCAACTCCACCTACAGGTGGTGTCCGTGC<br>TGACCGTGCTGCACCAGGATTGGCTGAATGGCAAAGAGT<br>ATAAGTGCAAGGTGTCCAACAAGGGCCTGCCTTCCAGCA<br>TCGAAAAGACCATCTCCAAGGCCAAGGGCCAGCCTAGGA<br>ACCCCAGGTTTACACCCTGCCTCCAAGCCAAGAGGAAAT<br>GACCAAGAACCAGGTGTCCCTGACATGCCTGGTCAAGGG<br>CTTCTACCCCTCCGATATCGCCGTGGAATGGGAGTCTAA<br>TGGCCAGCTGAGAACAACTACAAGACCACACCTCCTGTG<br>CTGGACTCCGACGGCAGCTTCTTTCTGTACTCCCGCCTG<br>ACCGTGGACAAGTCCAGGTGGCAAGAGGGCAACGTGTTC<br>TCCTGCTCCGTGATGCAGAGGCCCTGCACAATCACTACA<br>CCCAGAAGTCCCTGTCTCTGTCCCTGGGCAAATGA |
| SEQ ID NO: 62 | Nucleotide sequence of Construct #30 | GCTCAGAATATCACCGCCAGAATCGGCGAGCCCCTGGTG<br>CTGAAATGTAAAGGGCCCCTAAGAAGCCTCCTCAGCGGC<br>TGGAATGGAAGCTGAACACCGGCAGAACCGAGGCCTGGA<br>AAGTGCTGTCTCCTCAAGGCGGAGGCCCTTGGGATTCTG<br>TGGCTAGAGTGCTGCCTAACGGCTCCTGTTTCTGCCTGC<br>TGTGGGCATCCAGGACGAGGGCATCTTCAGGTGTCAGGC<br>CATGAACCGGAACGGCAAAGAGACAAAGTCCAACTACCG<br>CGTCAGAGTGTATCAGATCCCCGGCAAGCCTGAGTCGTG<br>GACTCTGCCTCTGAACTGACAGCCGGCGTGCCCAACAAA<br>GTGGGCACTTGTGTGTCCGAGGGCAGCTATCCTGCTGGC<br>ACCCTGTCTTGGCATCTGGATGGAAAGCCTCTGGTGCCC<br>AACGAAAAGGCGTGTCCGTGAAAGAGCAGACCAGACGGC<br>ATCCTGAGACTGGCCTGTTCACCCTGCAGTCCGAGCTGA<br>TGGTTACCCCTGCTAGAGGCGGCGATCCCAGACCTACCT<br>TCAGCTGCTCCTTCTTCCTGGCCTGCCTCGACATAGAGC<br>CCTGAGAACCGCTCCTATCCAGCCTAGAGTGTGGGAGCC<br>TGTGCCTCTGGAAGAGGTGCAGCTGGTGGTTGAACCTGA<br>AGGCGGAGCTGTTGCTCCTGGCGGACAGTGACCCTGACC<br>TGTGAAGTTCCCGCTCAGCCCTCTCCACAGATCCACTGG<br>ATGAAGGATGGCGTGCCACTGCCTCTGCCTCCATCTCCT<br>GTTCTGATCCTGCCAGAGATCGGCCCTCAGGACCAGGCA<br>CCTATTCTTGTGTGGCTACCCACTCCTCTCACGGCCCTC<br>AAGAGTCTAGAGCCGTGTCCATCTCCATCATCGAGCCTG<br>GCGAGGAAGGACCTACAGCTGGCGAGGGCTTTGACAAAG<br>TGCGCGGGCTGAGGACTCTCCTCAGCACGCTGAGAGAAA<br>GTGCTGCGTTGAGTGCCCTCCATGTGCTCCTCCAGTTGC<br>TGGTGGCCCTTCCGTGTTCCTGTTTCCTCCAAAGCCTAA<br>GGACACCCTGTACATCCCCGCGAGCCTGAAGTGACCTGC<br>GTGGTGGTGGATGTGTCCCAAGAGGATCCCGAGGTGCAG<br>TTCAATTGGTACGTGGACGGCGTGGAAGTGCACAACGCC<br>AAGACCAAGCCTAGAGAGGAACAGTTAACTCCACCTACA<br>GAGTGGTGTCCGTGCTGACCGTGCTGCACCAGGATTGGC |

| INFORMAL SEQUENCE LISTING | | |
|---|---|---|
| SEQ ID NO | DESCRIPTION | SEQUENCE |
| | | TGAATGGCAAAGAGTATAAGTGCAAGGTGTCCAACAAGG<br>GCCTGCCTTCCAGCATCGAAAAGACCATCTCCAAGGCAA<br>GGGCCAGCCTAGGGAACCCCAGGTTTACACCCTGCCTCC<br>AAGCCAAGAGGAAATGACCAAGAACCAGGTGTCCCTGAC<br>ATGCCTGGTCAAGGGCTTCTACCCCTCCGATATCGCCGT<br>GGAATGGAGTCTAATGGCCAGCCTGAGAACAACTACAAG<br>ACCACACCTCCTGTGCTGGACTCCGACGGCAGCTTCTTT<br>CTGTACTCCCGCCTGACCGTGGACAAGTCCAGGTGGCAA<br>GAGGGCAACGTGTTCTCTGCTCCGTGATGCACGAGGCCC<br>TGCACAATCACTACACCCAGAAGTCCCTGTCTCTGTCCC<br>TGGGCAAATGA |
| SEQ ID NO: 63 | Nucleotide sequence of<br>Construct #31 | GCTCAGAATATCACCGCCAGAATCGGCGAGCCCCTGGTG<br>CTGAAATGTAAAGGGCCCCTAAGAAGCCTCCTCAGCGGC<br>TGGAATGGAAGCTGAACACCGGCAGAACCGAGGCCTGGA<br>AAGTGCTGTCTCCTCAAGGCGGAGGCCCTTGGGATTCTG<br>TGGCTAGAGTGCTGCCTAACGGCTCCTGTTTCTGCCTGC<br>TGTGGGCATCCAGGACGAGGGCATCTTCAGGTGTCAGGC<br>CATGAACCGGAACGGCAAAGAGACAAAGTCCAACTACCG<br>CGTCAGAGTGTATCAGATCCCCGGCAAGCCTGAGTCGTG<br>GACTCTGCCTCTGAACTGACAGCCGGCGTGCCCAACAAA<br>GTGGGCACTTGTGTGTCCGAGGGCAGCTATCCTGCTGGC<br>ACCCTGTCTTGGCATCTGGATGGAAAGCCTCTGGTGCCC<br>AACGAAAAGGCGTGTCCGTGAAAGAGCAGACCAGACGGC<br>ATCCTGAGACTGGCCTGTTCACCCTGCAGTCCGAGCTGA<br>TGGTTACCCCTGCTAGAGGCGGCGATCCCAGACCTACCT<br>TCAGCTGCTCCTTCTTCCTGGCCTGCCTCGACATAGAGC<br>CCTGAGAACCGCTCCTATCCAGCCTAGAGTGTGGGAGCC<br>TGTGCCTCTGGAAGAGGTGCAGCTGGTGGTTGAACCTGA<br>AGGCGGAGCTGTTGCTCCTGGCGGACAGTGACCCTGACC<br>TGTGAAGTTCCCGCTCAGCCCTCTCCACAGATCCACTGG<br>ATGAAGGATGGCGTGCCACTGCCTCTGCCTCCATCTCCT<br>GTTCTGATCCTGCCAGAGATCGGCCCTCAGGACCAGGCA<br>CCTATTCTTGTGTGGCTACCCACTCCTCTCACGGCCCTC<br>AAGAGTCTAGAGCCGTGTCCATCTCCATCATCGAGCCTG<br>GCGAGGAAGGACCTACAGCTGGCGAGGGCTTTGACAAAG<br>TGCGCGGGCTGAGGACTCTCCTCAGCACGCTGTTGAGTG<br>CCCTCCATGTGCTCCTCCAGTGGCTGGCCCTTCCGTGTT<br>CCTGTTTCCTCCAAAGCCTAAGGACACCCTGTACATCAC<br>CCGCGAGCCTGAAGTGCCTGCGTGGTGGTGGATGTGTCT<br>CACGAGGATCCCGAGGTGCAGTTCAATTGGTACGTGGAC<br>GGCGTGGAAGTGCACAACGCCAAGACCAAGCCTAGAGAG<br>GAACAGTTCAACTCCACCTTCAGAGTGTGTCCGTGCTGA<br>CCGTGGTGCATCAGGATTGGCTGAATGGGAAAGAGTACA<br>AGTGCAAGGTGTCCAACAAGGGCCTGCCTGCTCCTATCG<br>AAAAGACCATCTCTAAGACCAAGGGACAGCCCCGGGACC<br>TCAGGTGTACACACTGCCACCTAGCCGGGAAGAGATGAC<br>CAAGAACCAGGTGTCCCTGACATGCCTGGTCAAGGGCTT<br>CTACCCCTCCGATATCGCCGTGGAATGGGAGTCTAATGG<br>CCAGCCTAGAACAACTACAAGACCACACCTCCTATGCTG<br>GACTCCGACGGCTCATTCTTCCTGTACTCCAAGCTGACA<br>GTGGACAAGTCCAGATGGCAGCAGGGCAACGTGTTCTCC<br>TGCTCCGTGATGCACGAGCCCTGCACAATCACTACACCC<br>AGAAGTCCCTGTCTCTGTCCCTGGCAAATGA |
| SEQ ID NO: 64 | Nucleotide sequence of<br>Construct #32 | GCTCAGAATATCACCGCCAGAATCGGCGAGCCCCTGGTG<br>CTGAAATGTAAAGGGCCCCTAAGAAGCCTCCTCAGCGGC<br>TGGAATGGAAGCTGAACACCGGCAGAACCGAGGCCTGGA<br>AAGTGCTGTCTCCTCAAGGCGGAGGCCCTTGGGATTCTG<br>TGGCTAGAGTGCTGCCTAACGGCTCCTGTTTCTGCCTGC<br>TGTGGGCATCCAGGACGAGGGCATCTTCAGGTGTCAGGC<br>CATGAACCGGAACGGCAAAGAGACAAAGTCCAACTACCG<br>CGTCAGAGTGTATCAGATCCCCGGCAAGCCTGAGTCGTG<br>GACTCTGCCTCTGAACTGACAGCCGGCGTGCCCAACAAA<br>GTGGGCACTTGTGTGTCCGAGGGCAGCTATCCTGCTGGC<br>ACCCTGTCTTGGCATCTGGATGGAAAGCCTCTGGTGCCC<br>AACGAAAAGGCGTGTCCGTGAAAGAGCAGACCAGACGGC<br>ATCCTGAGACTGGCCTGTTCACCCTGCAGTCCGAGCTGA<br>TGGTTACCCCTGCTAGAGGCGGCGATCCCAGACCTACCT<br>TCAGCTGCTCCTTCTTCCTGGCCTGCCTCGACATAGAGC<br>CCTGAGAACCGCTCCTATCCAGCCTAGAGTGTGGGAGCC<br>TGTGCCTCTGGAAGAGGTGCAGCTGGTGGTTGAACCTGA<br>AGGCGGAGCTGTTGCTCCTGGCGGACAGTGACCCTGACC<br>TGTGAAGTTCCCGCTCAGCCCTCTCCACAGATCCACTGG<br>ATGAAGGATGGCGTGCCACTGCCTCTGCCTCCATCTCCT |

| SEQ ID NO | DESCRIPTION | SEQUENCE |
|---|---|---|
| | | GTTCTGATCCTGCCAGAGATCGGCCCTCAGGACCAGGCA<br>CCTATTCTTGTGTGGCTACCCACTCCTCTCACGGCCCTC<br>AAGAGTCTAGAGCCGTGTCCATCTCCATCATCGAGCCTG<br>GCGAGGAAGGACCTACAGCTGGCGAGGGCTTTGACAAAG<br>TGCGCGGGCTGAGGACTCTCCTCAGCACGCTGTTGAGTG<br>CCCTCCATGTGCTCCTCCAGTTGCTGGTGGCCCTTCCGT<br>GTTCCTGTTTCCTCCAAAGCCTAAGGACACCCTGTACAT<br>CACCCGCGAGCCTGAATGACCTGCGTGGTGGTGGATGTG<br>TCTCACGAGGACCCCGAAGTGAAGTTCAATTGGTACGTG<br>GACGGCGTGGAAGTGCACAACGCCAAGACCAAGCCTAGA<br>GAGGAACAGTACAACTCCACCTACAGGTGGTGTCCGTGC<br>TGACCGTGCTGCACCAGGATTGGCTGAATGGCAAAGAGT<br>ATAAGTGCAAGGTGTCCAACAAGGCCCTGCCTGCTCCTA<br>TCGAAAAGACCATCTCCAAGGCCAAGGGCCAGCCTAGGA<br>ACCCCAGGTTTACACCTTGCCACCTTCTCGGGACGAGCT<br>GACCAAGAACCAGGTGTCCCTGACATGCCTGGTCAAGGG<br>CTTCTACCCCTCCGATATCGCCGTGGAATGGGAGTCTAA<br>TGGCCAGCTGAGAACAACTACAAGACCACACCTCCTGTG<br>CTGGACTCCGACGGCTCATTCTTCCTGTACTCCAAGCTG<br>ACAGTGGACAAGTCCAGATGGCAGCAGGGCAACGTGTTC<br>TCCTGCTCCGTGATGCAGAGGCCCTGCACAATCACTACA<br>CCCAGAAGTCCCTGTCTCTGTCCCCTGGCAAATGA |
| SEQ ID NO: 65 | Nucleotide sequence of Construct #33 | GCTCAGAATATCACCGCCAGAATCGGCGAGCCCCTGGTG<br>CTGAAATGTAAAGGGCCCCTAAGAAGCCTCCTCAGCGGC<br>TGGAATGGAAGCTGAACACCGGCAGAACCGAGGCCTGGA<br>AAGTGCTGTCTCCTCAAGGCGGAGGCCCTTGGGATTCTG<br>TGGCTAGAGTGCTGCCTAACGGCTCCTGTTTCTGCCTGC<br>TGTGGGCATCCAGGACGAGGGCATCTTCAGGTGTCAGGC<br>CATGAACCGGAACGGCAAAGACAAAGTCCAACTACCG<br>CGTCAGAGTGTATCAGATCCCCGGCAAGCCTGAGTCGTG<br>GACTCTGCCTCTGAACTGACAGCCGGCGTGCCCAACAAA<br>GTGGGCACTTGTGTGTCCGAGGGCAGCTATCCTGCTGGC<br>ACCCTGTCTTGGCATCTGGATGGAAAGCCTCTGGTGCCC<br>AACGAAAAGGCGTGTCCGTGAAAGAGCAGACCAGACGGC<br>ATCCTGAGACTGGCCTGTTCACCCTGCAGTCCGAGCTGA<br>TGGTTACCCCTGCTAGAGGCGGCGATCCCAGACCTACCT<br>TCAGCTGCTCCTTCTTCCTGGCCTGCCTCGACATAGAGC<br>CTGAGAACCGCTCCTATCCAGCCTAGAGTGTGGGAGCC<br>TGTGCCTCTGGAAGAGGTGCAGCTGGTGGTTGAACCTGA<br>AGGCGGAGCTGTTGCTCCTGGCGGACAGTGACCCTGACC<br>TGTGAAGTTCCCGCTCAGCCCTCTCCACAGATCCACTGG<br>ATGAAGGATGGCGTGCCACTGCCTCTGCCTCCATCTCCT<br>GTTCTGATCCTGCCAGAGATCGGCCCTCAGGACCAGGCA<br>CCTATTCTTGTGTGGCTACCCACTCCTCTCACGGCCCTC<br>AAGAGTCTAGAGCCGTGTCCATCTCCATCATCGAGCCTG<br>GCGAGGAAGGACCTACAGCTGGCGAGGGCTTTGACAAAG<br>TGCGCGGGCTGAGGACTCTCCTCAGCACGCTGAGTCTAA<br>GTACGGCCCTCCTTGTCCTCCATGTCCTGCTCCAGAAGC<br>TGCTGGTGGCCCTTCCGTGTTCCTGTTTCCTCCAAAGCC<br>TAAGGACACCCTGTACTCACCCGCGAGCCTGAAGTGACC<br>TGCGTGGTGGTGGATGTGTCTCACGAGGACCCCGAAGTG<br>AAGTTCAATTGGTACGTGGACGGCGTGGAAGTGCACAAC<br>GCCAAGACCAAGCCTAGAGAGGAACATACAACTCCACCT<br>ACAGAGTGGTGTCCGTGCTGACCGTGCTGCACCAGGATT<br>GGCTGAATGGCAAAGAGTATAAGTGCAAGGTGTCCAACA<br>AGGCCCTGCCTGCTCCTATCGAAAAGACCATCTCCAGGC<br>CAAGGGCCAGCCTAGGGAACCCCAGGTTTACACCTTGCC<br>ACCTTCTCGGGACGAGCTGACCAAGAACCAGGTGTCCCT<br>GACATGCCTGGTCAAGGGCTTCTACCCCTCCGATATCGC<br>CGTGGAAGGGAGTCTAATGGCCAGCTGAGAACAACTAC<br>AAGACCACACCTCCTGTGCTGGACTCCGACGGCTCATTC<br>TTCCTGTACTCCAAGCTGACAGTGGACAAGTCCAGATGG<br>CAGCAGGGCAACGTGTTTCCTGCTCCGTGATGCACGAGG<br>CCCTGCACAATCACTACACCCAGAAGTCCCTGTCTCTGT<br>CCCCTGGCAAATGA |
| SEQ ID NO: 66 | Nucleotide sequence of Construct #34 | GCTCAGAATATCACCGCCAGAATCGGCGAGCCCCTGGTG<br>CTGAAATGTAAAGGGCCCCTAAGAAGCCTCCTCAGCGGC<br>TGGAATGGAAGCTGAACACCGGCAGAACCGAGGCCTGAA<br>AAGTGCTGTCTCCTCAAGGCGGAGGCCCTTGGGATTCTG<br>TGGCTAGAGTGCTGCCTAACGGCTCCTGTTTCTGCCTGC<br>TGTGGGCATCCAGGACGAGGGCATCTTCAGGTGTCAGGC<br>CATGAACCGGAACGGCAAAGACAAAGTCCAACTACCG<br>CGTCAGAGTGTATCAGATCCCCGGCAAGCCTGAGTCGTG |

| SEQ ID NO | DESCRIPTION | SEQUENCE |
|---|---|---|
| | | GACTCTGCCTCTGAACTGACAGCCGGCGTGCCCAACAAA<br>GTGGGCACTTGTGTGTCCGAGGGCAGCTATCCTGCTGGC<br>ACCCTGTCTTGGCATCTGGATGGAAAGCCTCTGGTGCCC<br>AACGAAAAGGCGTGTCCGTGAAAGAGCAGACCAGACGGC<br>ATCCTGAGACTGGCCTGTTCACCCTGCAGTCCGAGCTGA<br>TGGTTACCCCTGCTAGAGGCGGCGATCCCAGACCTACCT<br>TCAGCTGCTCCTTCTTCCTGGCCTGCCTCGACATAGAGC<br>CCTGAGAACCGCTCCTATCCAGCCTAGAGTGTGGGAGCC<br>TGTGCCTCTGGAAGAGGTGCAGCTGGTGGTTGAACCTGA<br>AGGCGGAGCTGTTGCTCCTGGCGGACAGTGACCCTGACC<br>TGTGAAGTTCCCGCTCAGCCCTCTCCACAGATCCACTGG<br>ATGAAGGATGGCGTGCCACTGCCTCTGCCTCCATCTCCT<br>GTTCTGATCCTGCCAGAGATCGGCCCTCAGGACCAGGCA<br>CCTATTCTTGTGTGGCTACCCACTCCTCTCACGGCCCTC<br>AAGAGTCTAGAGCCGTGTCCATCTCCATCATCGAGCCTG<br>GCGAGGAAGGACCTACAGCTGGCGAGGGCTTTGACAAAG<br>TGCGCGGGCTGAGGACTCTCCTCAGCACGCTGAGCCTAA<br>GTCCTGCGACAAGACCCACACCTGTCCTCCATGTCCTGC<br>TCCAGAAGCTGCTGGTGGCCCTTCCGTGTTCCTGTTTCC<br>TCCAAAGCCTAAGGACCCCTGTACATCACCCGCGAGCCT<br>GAAGTGACCTGCGTGGTGGTGGATGTGTCTCACGAGGAC<br>CCCGAAGTGAAGTTCAATTGGTACGTGGACGGCGTGGAA<br>GTGCACAACGCCAAGACCAAGCCTAGGAGGAACAGTACA<br>ACTCCACCTACAGAGTGGTGTCCGTGCTGACCGTGCTGC<br>ACCAGGATTGGCTGAATGGCAAAGAGTATAAGTGCAAGG<br>TGTCCAACAAGGCCCTGCCTGCTCCTATCGAAAAGACAT<br>CTCCAAGGCCAAGGGCCAGCCTAGGGAACCCCAGGTTTA<br>CACCTTGCCACCTTCTCGGGACGAGCTGACCAAGAACCA<br>GGTGTCCCTGACATGCCTGGTCAAGGGCTTCTACCCCTC<br>CGATATCCCGTGGAATGGGAGTCTAATGGCCAGCCTGAG<br>AACAACTACAAGACCACACCTCCTGTGCTGGACTCCGAC<br>GGCTCATTCTTCCTGTACTCCAAGCTGACAGTGGACAAG<br>TCCAGATGGCAGCAGGGAACGTGTTCTCCTGCTCCGTGA<br>TGCACGAGGCCCTGCACAATCACTACACCCAGAAGTCCC<br>TGTCTCTGTCCCCTGGCAAATGA |
| SEQ ID NO: 67 | Nucleotide sequence of Construct #35 | GCTCAGAATATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCCGAGGATTCTCCTCAGCATGCT<br>GAGTCTAAGTACGGCCCTCCTTGTCCTCCATGTCCTGCT<br>CCAGAAGCTGCTGGCGGCCCTTCCGTGTTTCTGTTCCCT<br>CCAAAGCCTAAGGACACCCTGTACATCACCCGGGAGCCT<br>GAAGTGACCTGCGTGGTGGTGGATGTGTCCCAAGAGGAT<br>CCCGAGGTGCAGTTCAATTGGTACGTGGACGGCGTGGAA<br>GTGCACAACGCCAAGACCAAGCCTAGAGAGGAACAGTTC<br>AACTCCACCTACAGAGTGGTGTCCGTGCTGACCGTGCTG<br>CACCAGGATTGGCTGAATGGCAAAGAGTATAAGTGCAAG<br>GTGTCCAACAAGGGCCTGCCTTCCAGCATCGAAAAGACC<br>ATCTCCAAGGCCAAGGGCCAGCCTAGGGAACCCCAGGTT<br>TACACCCTGCCTCCAAGCCAAGAGGAAATGACCAAGAAC<br>CAGGTGTCCCTGACATGCCTGGTCAAGGGCTTCTACCCC<br>TCCGATATCGCCGTGGAATGGGAGTCTAATGGCCAGCCT<br>GAGAACAACTACAAGACCACACCTCCTGTGCTGGACTCC |

| SEQ ID NO | DESCRIPTION | SEQUENCE |
|---|---|---|
| | | GACGGCAGCTTCTTTCTGTACTCCCGCCTGACCGTGGAC AAGTCCAGGTGGCAAGAGGGCAACGTGTTCTCCTGCTCC GTGATGCACGAGGCCCTGCACAATCACTACACCCAGAAG TCCCTGTCTCTGTCCCTGGGCAAATGA |
| SEQ ID NO: 68 | Nucleotide sequence of Construct #36 | GCTCAGAATATCACCGCCAGAATCGGCGAGCCCCTGGTG CTGAAATGTAAAGGCGCCCCTAAGAAGCCTCCTCAGCGG CTGGAATGGAAGCTGAACACCGGCAGAACCGAGGCCTGG AAAGTGCTGTCTCCTCAAGGCGGAGGCCCTTGGGATTCT GTGGCTAGAGTGCTGCCTAACGGCTCCCTGTTTCTGCCT GCTGTGGGCATCCAGGACGAGGGCATCTTCAGGTGTCAG GCCATGAACCGGAACGGCAAAGAGACAAAGTCCAACTAC CGCGTCAGAGTGTATCAGATCCCCGGCAAGCCTGAGATC GTGGACTCTGCCTCTGAACTGACAGCCGGCGTGCCCAAC AAAGTGGGCACTTGTGTGTCCGAGGGCAGCTATCCTGCT GGCACCCTGTCTTGGCATCTGGATGGAAAGCCTCTGGTG CCCAACGAGAAAGGCGTGTCCGTGAAAGAGCAGACCAGA CGGCATCCTGAGACTGGCCTGTTCACCCTGCAGTCCGAG CTGATGGTTACCCCTGCTAGAGGCGGCGATCCCAGACCT ACCTTCAGCTGCTCCTTCTCTCCTGGCCTGCCTCGACAT AGAGCCCTGAGAACCGCTCCTATCCAGCCTAGAGTGTGG GAGCCTGTGCCTCTGGAAGAGGTGCAGCTGGTGGTTGAA CCTGAAGGCGGAGCTGTTGCTCCTGGCGGAACAGTGACC CTGACCTGTGAAGTTCCCGCTCAGCCCTCTCCACAGATC CACTGGATGAAGGATGGCGTGCCACTGCCTCTGCCTCCA TCTCCTGTTCTGATCCTGCCAGAGATCGGCCCTCAGGAC CAGGGCACCTATTCTTGTGTGGCTACCCACTCCTCTCAC GGCCCTCAAGAGTCTAGAGCCGTGTCCATCTCCATCATC GAGCCTGGCGAGGAAGGACCTACAGCTGGCGAGGGCTTT GACAAAGTGCGCGAGGCTGAGGACTCTCCTCAGCATGCC GGAACACTGGTCACCGTGTCCTCCGAGTCTAAGTACGGC CCTCCTTGTCCTCCATGTCCTGCTCCAGAAGCTGCTGGC GGCCCTTCCGTGTTTCTGTTCCCTCCAAAGCCTAAGGAC ACCCTGTACATCACCCGGGAGCCTGAAGTGACCTGCGTG GTGGTGGATGTGTCCCAAGAGGATCCCGAGGTGCAGTTC AATTGGTACGTGGACGGCGTGGAAGTGCACAACGCCAAG ACCAAGCCTAGAGAGGAACAGTTCAACTCCACCTACAGA GTGGTGTCCGTGCTGACCGTGCTGCACCAGGATTGGCTG AATGGCAAAGAGTATAAGTGCAAGGTGTCCAACAAGGGC CTGCCTTCCAGCATCGAAAAGACCATCTCCAAGGCCAAG GGCCAGCCTAGGGAACCCCAGGTTTACACCCTGCCTCCA AGCCAAGAGGAAATGACCAAGAACCAGGTGTCCCTGACA TGCCTGGTCAAGGGCTTCTACCCCCTCCGATATCGCCGTG GAATGGGAGTCTAATGGCCAGCCTGAGAACAACTACAAG ACCACACCTCCTGTGCTGGACTCCGACGGCAGCTTCTTT CTGTACTCCCGCCTGACCGTGGACAAGTCCAGGTGGCAA GAGGGCAACGTGTTCTCCTGCTCCGTGATGCACGAGGCC CTGCACAATCACTACACCCAGAAGTCCCTGTCTCTGTCC CTGGGCAAATGA |
| SEQ ID NO: 69 | Nucleotide sequence of Construct #16ΔK | GCTCAGAATATCACCGCCAGAATCGGCGAGCCCCTGGTG CTGAAATGTAAAGGGCCCCTAAGAAGCCTCCTCAGCGGC TGGAATGGAAGCTGAACACCGGCAGAACCGAGGCCTGGA AAGTGCTGTCTCCTCAAGGCGGAGGCCCTTGGGATTCTG TGGCTAGAGTGCTGCCTAACGGCTCCTGTTTCTGCCTGC TGTGGGCATCCAGGACGAGGGCATCTTCAGGTGTCAGGC CATGAACCGGAACGGCAAAGAGACAAAGTCCAACTACCG CGTCAGAGTGTATCAGATCCCCGGCAAGCCTGAGTCGTG GACTCTGCCTCTGAACTGACAGCCGGCGTGCCCAACAAA GTGGGCACTTGTGTGTCCGAGGGCAGCTATCCTGCTGGC ACCCTGTCTTGGCATCTGGATGGAAAGCCTCTGGTGCCC AACGAAAAGGCGTGTCCGTGAAAGAGCAGACCAGACGGC ATCCTGAGACTGGCCTGTTCACCCTGCAGTCCGAGCTGA TGGTTACCCCTGCTAGAGGCGGCGATCCCAGACCTACCT TCAGCTGCTCCTTCTTCCTGGCCTGCCTCGACATAGAGC CCTGAGAACCGCTCCTATCCAGCCTAGAGTGTGGGAGCC TGTGCCTCTGGAAGAGGTGCAGCTGGTGGTTGAACCTGA AGGCGGAGCTGTTGCTCCTGGCGGACAGTGACCCTGACC TGTGAAGTTCCCGCTCAGCCCTCTCCACAGATCCACTGG ATGAAGGATGGCGTGCCACTGCCTCTGCCTCCATCTCCT GTTCTGATCCTGCCAGAGATCGGCCCTCAGGACCAGGCA CCTATTCTTGTGTGGCTACCCACTCCTCTCACGGCCCTC AAGAGTCTAGAGCCGTGTCCATCTCCATCATCGAGCCTG GCGAGGAAGGACCTACAGCTGGCGAGGGCTTTGACAAAG TGCGCGGGCTGAGGACTCTCCTCAGCACGCTGTTGAGTG |

| INFORMAL SEQUENCE LISTING | | |
|---|---|---|
| SEQ ID NO | DESCRIPTION | SEQUENCE |
| | | CCCTCCATGTGCTCCTCCAGTTGCTGGTGGCCCTTCCGT<br>GTTCCTGTTTCCTCCAAAGCCTAAGGACACCCTGTACAT<br>CACCCGCGAGCCTGAATGACCTGCGTGGTGGTGGATGTG<br>TCCCAAGAGGATCCCGAGGTGCAGTTCAATTGGTACGTG<br>GACGGCGTGGAAGTGCACAACGCCAAGACCAAGCCTAGA<br>GAGGAACAGTTCAACTCCACCTACAGGTGGTGTCCGTGC<br>TGACCGTGCTGCACCAGGATTGGCTGAATGGCAAAGAGT<br>ATAAGTGCAAGGTGTCCAACAAGGGCCTGCCTTCCAGCA<br>TCGAAAAGACCATCTCCAAGGCCAAGGGCCAGCCTAGGA<br>ACCCCAGGTTTACACCCTGCCTCCAAGCCAAGAGGAAAT<br>GACCAAGAACCAGGTGTCCCTGACATGCCTGGTCAAGGG<br>CTTCTACCCCTCCGATATCGCCGTGGAATGGGAGTCTAA<br>TGGCCAGCTGAGAACAACTACAAGACCACACCTCCTGTG<br>CTGGACTCCGACGGCAGCTTCTTTCTGTACTCCCGCCTG<br>ACCGTGGACAAGTCCAGGTGGCAAGAGGGCAACGTGTTC<br>TCCTGCTCCGTGATGCAGAGGCCCTGCACAATCACTACA<br>CCCAGAAGTCCCTGTCTCTGTCCCTGGGCTGA |
| SEQ ID NO: 70 | Nucleotide sequence of Construct #12ΔK | GCTCAGAATATCACCGCCAGAATCGGCGAGCCCCTGGTG<br>CTGAAATGTAAAGGCGCCCCTAAGAAGCCTCCTCAGCGG<br>CTGGAATGGAAGCTGAACACCGGCAGAACCGAGGCCTGG<br>AAAGTGCTGTCTCCTCAAGGCGGAGGCCCTTGGGATTCT<br>GTGGCTAGAGTGCTGCCTAACGGCTCCCTGTTTCTGCCT<br>GCTGTGGGCATCCAGGACGAGGGCATCTTCAGGTGTCAG<br>GCCATGAACCGGAACGGCAAAGAGACAAAGTCCAACTAC<br>CGCGTCAGAGTGTATCAGATCCCCGGCAAGCCTGAGATC<br>GTGGACTCTGCCTCTGAACTGACAGCCGGCGTGCCCAAC<br>AAAGTGGGCACTTGTGTGTCCGAGGGCAGCTATCCTGCT<br>GGCACCCTGTCTTGGCATCTGGATGGAAAGCCTCTGGTG<br>CCCAACGAGAAAGGCGTGTCCGTGAAAGAGCAGACCAGA<br>CGGCATCCTGAGACTGGCCTGTTCACCCTGCAGTCCGAG<br>CTGATGGTTACCCCTGCTAGAGGCGGCGATCCCAGACCT<br>ACCTTCAGCTGCTCCTTCTCTCCTGGCCTGCCTCGACAT<br>AGAGCCCTGAGAACCGCTCCTATCCAGCCTAGAGTGTGG<br>GAGCCTGTGCCTCTGGAAGAGGTGCAGCTGGTGGTTGAA<br>CCTGAAGGCGGAGCTGTTGCTCCTGGCGGAACAGTGACC<br>CTGACCTGTGAAGTTCCCGCTCAGCCCTCTCCACAGATC<br>CACTGGATGAAGGATGGCGTGCCACTGCCTCTGCCTCCA<br>TCTCCTGTTCTGATCCTGCCAGAGATCGGCCCTCAGGAC<br>CAGGGCACCTATTCTTGTGTGGCTACCCACTCCTCTCAC<br>GGCCCTCAAGAGTCTAGAGCCGTGTCCATCTCCATCATC<br>GAGCCTGGCGAGGAAGGACCTACAGCTGGCGAGGGCTTT<br>GACAAAGTGCGCGAGGCTGAGGACTCTCCTCAGCATGCC<br>GTGGAATGCCCTCCTTGTGCTCCTCCTGTGGCTGGCGGC<br>CCTTCCGTGTTTCTGTTCCCTCCAAAGCCTAAGGACACC<br>CTGATGATCTCTCGGACCCCTGAAGTGACCTGCGTGGTG<br>GTGGATGTGTCCCAAGAGGATCCCGAGGTGCAGTTCAAT<br>TGGTACGTGGACGGCGTGGAAGTGCACAACGCCAAGACC<br>AAGCCTAGAGAGGAACAGTTCAACTCCACCTACAGAGTG<br>GTGTCCGTGCTGACCGTGCTGCACCAGGATTGGCTGAAT<br>GGCAAAGAGTATAAGTGCAAGGTGTCCAACAAGGGCCTG<br>CCTTCCAGCATCGAAAAGACCATCTCCAAGGCCAAGGGC<br>CAGCCTAGGGAACCCCAGGTTTACACCCTGCCTCCAAGC<br>CAAGAGGAAATGACCAAGAACCAGGTGTCCCTGACATGC<br>CTGGTCAAGGGCTTCTACCCCTCCGATATCGCCGTGGAA<br>TGGGAGTCTAATGGCCAGCCTGAGAACAACTACAAGACC<br>ACACCTCCTGTGCTGGACTCCGACGGCAGCTTCTTTCTG<br>TACTCCCGCCTGACCGTGGACAAGTCCAGGTGGCAAGAG<br>GGCAACGTGTTCTCCTGCTCCGTGATGCACGAGGCCCTG<br>CACAATCACTACACCCAGAAGTCCCTGTCTCTGTCCCTG<br>GGCTGA |
| SEQ ID NO: 71 | Short Stem sequence (#9) | HSSHGPQESRAVSISIIEPGEEGPTAG |
| SEQ ID NO: 72 | V1 stem sequence | HSSHGPQESRAVSISIIEPGEEGPTAGEGFDKVREAEDS<br>PQHA |
| SEQ ID NO: 73 | C-terminal 13 amino acids of RAGE stem | SVGGSGLGTLALA |
| SEQ ID NO: 74 | esRAGE (sequence of the mature protein; lacking the natural leader sequence) | AQNITARI GEPLVLKCKG APKKPPQRLE<br>WKLNTGRTEA WKVLSPQGGG PWDSVARVLP<br>NGSLFLPAVG IQDEGIFRCQ AMNRNGKETK<br>SNYRVRVYQI PGKPEIVDSA SELTAGVPNK<br>VGTCVSEGSY PAGTLSWHLD GKPLVPNEKG |

| INFORMAL SEQUENCE LISTING | | |
|---|---|---|
| SEQ ID NO | DESCRIPTION | SEQUENCE |
| | | VSVKEQTRRH PETGLFTLQS ELMVTPARGG |
| | | DPRPTFSCSF SPGLPRHRAL RTAPIQPRVW |
| | | EPVPLEEVQL VVEPEGGAVA PGGTVTLTCE |
| | | VPAQPSPQIH WMKDGVPLPL PPSPVLILPE |
| | | IGPQDQGTYS CVATHSSHGP QESRAVSISI |
| | | IEPGEEGPTA GEGFDKVREA EDSPQHM |

The invention claimed is:

1. An isolated polypeptide comprising:
   (a) a first domain wherein said first domain has an amino acid sequence at least 97% identical to the sequence of SEQ ID NO:74; and
   (b) a second domain comprising a fragment of a Fc region of an immunoglobulin,
      wherein the carboxy terminus of said first domain is coupled to the amino terminus of said second domain by a peptide linkage,
      wherein the polypeptide comprising the first domain and the second domain has an amino acid sequence selected from: SEQ ID NO: 12, SEQ ID NO:15, SEQ ID NO: 16, and SEQ ID NO: 53.

2. The isolated polypeptide of claim 1, wherein said first domain has the sequence set forth in SEQ ID NO: 74.

3. The isolated polypeptide of claim 1, wherein the polypeptide has the sequence of SEQ ID NO: 15.

4. The isolated polypeptide of claim 1, wherein said polypeptide is resistant to cleavage by a disintegrin and metalloproteinase 10 (ADAM10).

5. The isolated polypeptide of claim 1, wherein said polypeptide is at least 15% more resistant to cleavage by at least one of ADAM10, matrix metalloproteinase 9 (MMP9), and trypsin as compared to a polypeptide having the sequence of SEQ ID NO: 5.

6. The isolated polypeptide of claim 1, wherein said polypeptide is at least 15% more resistant to degradation in human serum as compared to a polypeptide comprising the sequence of SEQ ID NO: 5, wherein the percent resistance equals the difference between the fraction of peptide that remains full length following incubation in human serum for a defined time period compared to a control peptide treated for the same time and under the same conditions.

7. The isolated polypeptide of claim 1, wherein said polypeptide has increased thermal stability of at least 5° C. as compared to a polypeptide having the sequence of SEQ ID NO: 5.

8. The isolated polypeptide of claim 1, wherein said polypeptide specifically binds an advanced glycation end product (AGE).

9. The isolated polypeptide of claim 1, wherein said polypeptide specifically binds HMGB1 (Amphoterin).

10. The isolated polypeptide of claim 1, wherein said polypeptide specifically binds at least one of the group consisting of: S100A1, S100A2, S100A4 (metastasin), S100A5, S100A6, S100A7 (psoriasin), S100A8/9, S100A11, S100A12, S100B, S100P, lipopolysaccharide (LPS), oxidized low-density lipoprotein (oxLDL), CD11b (MAC1), phosphatidyl serine, C3a, S100P, S100G, S100Z, carbonylated proteins, malondialdehyde (MDA), laminin, type I Collagen, type IV Collagen, CAPZA1, CAPZA2, DDOST, LGALS3, MAPK1, MAPK3, PRKCSH, S100A4, S100A5, S100A6, S100A8, S100A9, S100P, and SAA1.

11. The isolated polypeptide of claim 1, wherein said polypeptide specifically binds amyloid-beta.

12. The isolated polypeptide of claim 1, wherein said first domain comprises at least one asparagine residue linked to a glycan.

13. The isolated polypeptide of claim 1, wherein said Fc fragment comprises CH2 and CH3 domains of a human IgG.

14. An isolated polypeptide comprising a RAGE polypeptide coupled to a Fc region of an immunoglobulin, wherein the carboxy terminus of said RAGE polypeptide is coupled to the amino terminus of said immunoglobulin Fc region by a peptide linkage and wherein said RAGE polypeptide has the sequence of SEQ ID NO: 2.

15. A pharmaceutical composition for treating a RAGE-mediated disorder comprising the isolated polypeptide of claim 1.

* * * * *